(12) United States Patent
Novak et al.

(10) Patent No.: US 10,226,484 B2
(45) Date of Patent: Mar. 12, 2019

(54) PHARMACEUTICAL COMPOSITION FOR IMPROVING HEALTH, CURE ABNORMALITIES AND DEGENERATIVE DISEASE, ACHIEVE ANTI-AGING EFFECT OF THERAPY AND THERAPEUTIC EFFECT ON MAMMALS AND METHOD THEREOF

(71) Applicants: Peter Y Novak, Sunny Isles Beach, FL (US); Maxim V Temnikov, Miami, FL (US); Oleksandr Balakin, Dnepropetrovsk (UA)

(72) Inventors: Peter Y Novak, Sunny Isles Beach, FL (US); Maxim V Temnikov, Miami, FL (US); Oleksandr Balakin, Dnepropetrovsk (UA)

( * ) Notice: Subject to any disclaimer, the term of this patent is extended or adjusted under 35 U.S.C. 154(b) by 0 days.

(21) Appl. No.: 15/613,109

(22) Filed: Jun. 2, 2017

(65) Prior Publication Data

US 2018/0055879 A1    Mar. 1, 2018

Related U.S. Application Data

(63) Continuation-in-part of application No. 14/833,114, filed on Aug. 23, 2015.

(60) Provisional application No. 62/123,900, filed on Dec. 1, 2014.

(51) Int. Cl.
| | |
|---|---|
| *A61K 33/30* | (2006.01) |
| *A61K 33/06* | (2006.01) |
| *A61K 33/00* | (2006.01) |
| *A61K 45/06* | (2006.01) |
| *A61K 31/704* | (2006.01) |
| *A23L 33/10* | (2016.01) |

(52) U.S. Cl.
CPC ............ *A61K 33/30* (2013.01); *A23L 33/10* (2016.08); *A61K 31/704* (2013.01); *A61K 33/00* (2013.01); *A61K 33/06* (2013.01); *A61K 45/06* (2013.01)

(58) Field of Classification Search
CPC ........................................................ A61K 33/30
See application file for complete search history.

(56) References Cited

U.S. PATENT DOCUMENTS

| | | | |
|---|---|---|---|
| 4,068,122 A | 1/1978 | Schmidt et al. | |
| 5,912,178 A | 6/1999 | Porter et al. | |
| 6,656,127 B1 | 12/2003 | Ben-oren | |
| 6,838,020 B2 | 1/2005 | Kelsey | |
| 7,473,892 B2 | 1/2009 | Sano | |
| 8,512,258 B2 | 8/2013 | Ben Oren | |
| 8,512,676 B1 | 8/2013 | Eghbalnia | |
| 8,753,889 B1 | 6/2014 | Roeder | |
| 9,518,972 B2 | 12/2016 | Joseph | |
| 9,861,659 B2 | 1/2018 | Novak et al. | |
| 2003/0068351 A1 | 4/2003 | Roig | |
| 2003/0118713 A1 | 6/2003 | Bjorkstrom | |
| 2004/0013732 A1 | 1/2004 | Farber | |
| 2004/0234450 A1* | 11/2004 | Howes | A61K 31/24 424/1.11 |
| 2007/0123791 A1 | 5/2007 | Assadi-Porter | |
| 2007/0207191 A1 | 9/2007 | Kanzer | |
| 2009/0042304 A1 | 2/2009 | Anderson | |
| 2010/0183736 A1 | 7/2010 | Hays | |
| 2010/0240089 A1 | 9/2010 | Inskip | |
| 2012/0021526 A1 | 1/2012 | Baer | |
| 2013/0115650 A1 | 5/2013 | Anbar | |
| 2014/0033795 A1 | 2/2014 | Guggenheim et al. | |
| 2014/0051116 A1 | 2/2014 | Tea | |
| 2014/0219961 A1 | 8/2014 | Jung | |
| 2016/0151415 A1 | 6/2016 | Novak | |
| 2016/0153957 A1 | 6/2016 | Novak | |

FOREIGN PATENT DOCUMENTS

| | | |
|---|---|---|
| CN | 106854147 A | 6/2017 |
| GB | 2531207 | 4/2016 |
| JP | S57156329 A | 9/1982 |
| JP | S6163619 | 4/1986 |
| RU | 2498807 | 11/2013 |
| UA | 83809 | 9/2013 |
| WO | 0182871 | 11/2001 |

(Continued)

OTHER PUBLICATIONS

IRMM-007/5 Certificate, 2 pages, 2007.*
F. Albarede et al., Medical applications of Cu, Zn, and S isotope effects, Metallomics 8: 1056 (Oct. 1, 2016).
CRC Handbook of Chemistry and Physics (49th ed. 1968), pp. B-171, B-263: Physical Constants of Inorganic Compounds.
Maria R. Florez et al., Isotope ratio mapping by means of laser ablation-single collector-ICP-mass spectrometry: Zn tracer studies in thin sections of Daphnia magna, J. Anal. At. Spectrom. 28: 1005 (2013).

(Continued)

*Primary Examiner* — Kyle A Purdy
(74) *Attorney, Agent, or Firm* — Lawrence H. Frank; Liang & Frank LLP

(57) ABSTRACT

A pharmaceutical composition of the present invention is used for improving health, cure abnormalities and degenerative disease; achieve anti-aging effect of therapy and therapeutic effect on mammals. The pharmaceutical composition includes a pharmaceutical carrier and an isotope selective ingredient including at least one of a chemical element and a chemical compound containing the chemical element whereby isotope distribution in the at least one of the chemical element and the chemical compound containing the chemical element is different from natural distribution of at least one of isotopes wherein the part of selected isotope of the chemical element ranges from 0 to 100%. A method of the present invention uses the inventive pharmaceutical composition to improve health, cure abnormalities and degenerative disease and achieve therapeutic effect on mammals.

10 Claims, 134 Drawing Sheets

(56) References Cited

FOREIGN PATENT DOCUMENTS

| WO | 2006072054 | 7/2006 |
| WO | 2010068130 | 6/2010 |

OTHER PUBLICATIONS

Jefferson Lab: "It's Elemental" (Zinc isotopes).
Yoshida, "Leaching of zinc oxide in acidic solution," Materials Trans. 44: 2489-2493 (2003).
U.S. Appl. No. 15/486,026 (filed Apr. 12, 2017) (Novak), Office Action dated Apr. 17, 2018.
U.S. Appl. No. 15/486,026 (Novak) Notice of Allowance (dated Sep. 18, 2018) incl. Examiner's Amendment.
U.S. Appl. No. 15/486,026 (Novak) Interview Summary & Refs. Cited (dated Sep. 18, 2018).
U.S. Appl. No. 15/486,026 (Novak) Terminal Disclaimer & Approval (dated Sep. 7, 2018).

* cited by examiner

FIG. 1B

Table of Concentration Characteristics of Components used

| Initial dose of components | 1<br>Dose of chloride in a well | 2<br>Dose of sulphate in a well | 3<br>Dose of sulphate in a well | 4<br>Dose of doxorubicin in a well | 5<br>Initial dose of doxorubicin in a well |
|---|---|---|---|---|---|
| A 20mg/ml | Cells + comp. $^{39}$K | 10 mg/ml | Cells + comp. $^{64}$Zn | 10 mg/ml | Cells + comp. $^{24}$Mg | 10 мг/мл 2 мг/мл | Cells + doxorubicin | 0,4 mg/ml | 0,8 mg/ml |
| B 4mg/ml | | 2 mg/ml | | 2 mg/ml | | 2 mg/ml | | 0,08 mg/ml | 0,16 mg/ml |
| C 0,8mg/ml | | 0,4 mg/ml | | 0,4 mg/ml | | 0,4 mg/ml | | 16 mcg/ml | 32 mcg/ml |
| D 0,16mg/ml | | 0,08 mg/ml | | 0,08 mg/ml | | 0,08 mg/ml | | 3,2 mcg/ml | 6,4 mcg/ml |
| E 32 mcg/ml | | 16 mcg/ml | | 16 mcg/ml | | 16 mcg/ml | | 0,64 mcg/ml | 1,28 mcg/ml |
| F 6,4mcg/ml | | 3,2 mcg/ml | | 3,2 mcg/ml | | 3,2 mcg/ml | | 0,128 mcg/ml | 0,256 mcg/ml |
| G 1,28 mcg/ml | | 0,64 mcg/ml | | 0,64 mcg/ml | | 0,64 mcg/ml | | 25,6 ng/ml | 51,2 ng/ml |
| H 0,256 мкг/мл | | 0,128 mcg/ml | | 0,128 mcg/ml | | 0,128 mcg/ml | | 5 ng/ml | 10 ng/ml |

FIG. 2

| № | Component | N-cadherin | | ICAM | |
|---|---|---|---|---|---|
| | | Number of cells with antigen, %, assessment from + to ++++ (expression level) | H-Score giving the range of 0 to 300 (record of number of cells and expression level) | Number of cells with antigen, %, assessment from + to ++++ (expression level) | H-Score giving the range of 0 to 300 (record of number of cells and expression level) |
| 1 | Control (no drug) | 20% ++<br>30% +<br>30% ±<br>20% - | 111 | 50% ++<br>50% + | 150 |
| 2 | $^{39}$K, 2 mg/ml | 25% +++<br>25% ++<br>50% + | 190 | 25% +<br>50% ±<br>25% - | 70 |
| 3 | $^{39}$K, 1 mg/ml | 10% ++<br>30% +<br>30% ±<br>30% - | 64 | 10% ++<br>20% +<br>35% ±<br>35% - | 62 |
| 4 | $^{64}$Zn, 10 mcg/ml | 20% ++<br>40% +<br>40% ± | 100 | 25% +<br>25% ±<br>50% - | 44 |
| 5 | $^{64}$Zn, 5 mcg/ml | 25% ++<br>35% +<br>40% ± | 105 | 50% +++<br>50% ++ | 210 |
| 6 | $^{24}$Mg, 2 mg/ml | 25% ++<br>50% +±<br>25% - | 128 | 20% +<br>50% ±<br>30% - | 53 |
| 7 | $^{24}$Mg, 0.5 mg/ml | 20% +<br>70% ±<br>10% - | 58 | 20% +<br>60% ±<br>20% - | 60 |

FIG. 6

Results of Immunocytochemical Analysis of Adhesion Proteins and Cytoskeleton of CD44 and IgM in Namalwa Cells after the Action of Components Containing $^{39}K$, $^{64}Zn$ and $^{24}Mg$

| № | Component | CD44 | | IgM | |
|---|---|---|---|---|---|
| | | Number of cells with antigen, %, assessment from + to ++++ (expression level) | H-Score giving the range of 0 to 300 (record of number of cells and expression level) | Number of cells with antigen, %, assessment from + to ++++ (expression level) | H-Score giving the range of 0 to 300 (record of number of cells and expression level) |
| 1 | Control (no drug) | 50% +++<br>50% ++ | 260 | 50% ++<br>20% +<br>20% ±<br>10% - | 145 |
| 2 | $^{39}K$, 2 mg/ml | 10% ++<br>50% ±<br>40% - | 61 | 50% ++<br>25% +<br>25% ± | 141 |
| 3 | $^{39}K$, 1 mg/ml | 30% +<br>50% ±<br>20% - | 70 | 30% ++<br>20% +<br>30% ±<br>20% - | 99 |
| 4 | $^{64}Zn$, 10 mcg/ml | 30% ++<br>30% +<br>40% ± | 118 | 30% ++<br>40% +<br>30% ± | 132 |
| 5 | $^{64}Zn$, 5 mcg/ml | 20% ++<br>30% +<br>50% ± | 106 | 10% +±<br>60% +<br>40% ± | 109 |
| 6 | $^{24}Mg$, 2 mg/ml | 55% +++<br>45% ++ | 234 | 10% ++<br>40% +<br>50% ± | 90 |
| 7 | $^{24}Mg$, 0.5 mg/ml | 50% +++<br>50% ++ | 257 | 10% ++<br>50% +<br>40% ± | 97 |

FIG. 7

Results of Immunocytochemical Analysis of Adhesion Proteins and Cytoskeleton of N-cadherin, ICAM and CD44 in HL-60 Cells after the Action of Components Containing $^{39}$K, $^{64}$Zn and $^{24}$Mg

| № | Component | N-cadherin | | ICAM | | CD44 | |
|---|---|---|---|---|---|---|---|
| | | Number of cells with antigen, %, assessment from + to ++++ (expression level) | H-Score giving the range of 0 to 300 (record of number of cells and expression level) | Number of cells with antigen, %, assessment from + to ++++ (expression level) | H-Score giving the range of 0 to 300 (record of number of cells and expression level) | Number of cells with antigen, %, assessment from + to ++++ (expression level) | H-Score giving the range of 0 to 300 (record of number of cells and expression level) |
| 1 | Control (no drug) | 20% + <br> 50% ± <br> 30% - | 50 | 30% + <br> 40% ± <br> 30% - | 57 | 40% +++ <br> 40% ++ <br> 10% + <br> 10% - | 230 |
| 2 | $^{39}$K, 2 mg/ml | 10% ++ <br> 50% +± <br> 20% + <br> 20% ± | 124 | 25% + <br> 50% ± <br> 25% - | 53 | 15% +++ <br> 15% ++ <br> 50% + <br> 20% ± | 156 |
| 3 | $^{39}$K, 0.5 mg/ml | 10% ++ <br> 30% + <br> 40% ± <br> 20% - | 75 | 50% ± <br> 50% - | 30 | 50% +++ <br> 20% + <br> 30% ± | 190 |
| 4 | $^{64}$Zn, 2 mg/ml | 25% +++ <br> 25% + <br> 30% ± <br> 20% - | 120 | 80% ± <br> 20% - | 40 | 20% +++ <br> 40% ++ <br> 20% + <br> 10% ± <br> 10% - | 198 |
| 5 | $^{24}$Mg, 2 mg/ml | 50% ++ <br> 30% +± <br> 20% ± | 161 | 25% ++ <br> 50% + <br> 25% ± | 58 | 50% ++ <br> 30% + <br> 20% ± | 140 |
| 6 | $^{24}$Mg, 0.1 mg/ml | 50% +± <br> 50% ± | 110 | 50% + <br> 50% ± | 57 | 25% ++++ <br> 25% +++ <br> 30% ++ <br> 20% ± | 220 |

FIG. 22

Effect of $^{39}$K, $^{64}$Zn and $^{24}$Mg on cells of strain of renal cell carcinoma in the in vitro experiment. Experiment with 30 000 cells.

| Component | $^{39}$K | | $^{64}$Zn | | $^{24}$Mg | |
|---|---|---|---|---|---|---|
| Component Dose | % and number of cells of types A and B | | | | | |
| | % and number of transformed cells of type A | % and number of transformed cells of type B | % and number of transformed cells of type A | % and number of transformed cells of type B | % and number of transformed cells of type A | % and number of transformed cells of type B |
| 10 mg/ml | 100% 30 000 | 0% | 0 | 100 % | 100% 30 000 | 0% |
| 2 mg/ml | 49.5±1.5 % 14 850 | 50.5% 15 150 | 0 | 100 % | 20% 6 000 | 80% 24 000 |
| 0.4 mg/ml | 33±1.5% 10 000 | 67±1.5% 20 100 | 0 | 100 % | 3.5±0.5 % 1 050 | 96.5±0.5 % 28 950 |
| 0.08 mg/ml | 7.5±1.5% 2 250 | 92.5±1.5 % 27 750 | 100% 30 000 | 0 % | 2.8±0.3 % 840 | 97.2±0.5 % 29 160 |
| 16 mcg/ml | 4.8±1.5% 1 440 | 95.2±1.5 % 28 560 | 61.4±3% 18 420 | 38.6% 11 580 | 2.5±0.5 % 750 | 97.5±0.5 % 29 250 |
| 3.2 mcg/ml | 4.1±1.5% 1 230 | 95.9±1.5 % 28 770 | 45.8±3% 13 740 | 54.2% 16 260 | 2.0±0.5 % 600 | 98±0.5% 29 400 |
| 0.64 mcg/ml | 2.5±1.5% 750 | 97.5±1.5 % 29 250 | 40±1.8% 12 000 | 60±1.8 % 18 000 | 1.5±0.5 % 450 | 98.5±0.5 % 29 550 |

FIG. 23

Effect of $^{39}$K, $^{64}$Zn and $^{24}$Mg on cells of strain of renal cell carcinoma in the in vitro experiment. Experiment with 300 000 cells

| Component | $^{39}$K | | $^{64}$Zn | | $^{24}$Mg | |
|---|---|---|---|---|---|---|
| | % and number of cells of types A and B | | | | | |
| Component Dose | % and number of transformed cells of type A | % and number of transformed cells of type B | % and number of transformed cells of type A | % and number of transformed cells of type B | % and number of transformed cells of type A | % and number of transformed cells of type B |
| 10 mg/ml | 100% - 300 000 | 0% | 0 | 100 % | 100% - 300 000 | 0% |
| 2 mg/ml | 53.4% 160 200 | 46.6% 139 800 | 0 | 100 % | 24% 72 000 | 76% 228 000 |
| 0.4 mg/ml | 35.5% 106 500 | 64.5% 193 500 | 0 | 100 % | 5% 15 000 | 95% 285 000 |
| 0.08 mg/ml | 5.5% 16 500 | 94.5% 283 500 | 100% - 300 000 | 0 | 2.5% 7 500 | 97.5% 292 500 |
| 16 mcg/ml | 4.5% 13 500 | 95.5% 286 500 | 65% 195 000 | 35% 105 000 | 2.5% 7 500 | 97.5% 292 500 |
| 3.2 mcg/ml | 4.0% 12 000 | 96% 288 000 | 51% 153 000 | 49% 147 000 | 2.5% 7 500 | 97.5% 292 500 |
| 0.64 mcg/ml | 2.0% 6 000 | 98% 294 000 | 45% 135 000 | 55% 165 000 | 2.5% 7 500 | 97.5% 292 500 |
| 0.128 mcg/ml | 2.0% 6 000 | 98% 294 000 | 30% 90 000 | 70% 210 000 | 2.5% 7 500 | 97.5% 292 500 |
| 0.025 mcg/ml | 2.0% 6 000 | 98% 294 000 | 5% 15 000 | 95% 285 000 | 2.5% 7 500 | 97.5% 292 500 |

FIG. 25

Effect of K, Zn and Mg elements with natural isotope distribution on the number of viable cells in the in vitro experiment. Experiment with 300 000 cells.

| Component | K | | Mg | | Zn | | Doxorubicin | |
|---|---|---|---|---|---|---|---|---|
| Component Dose | % and number of viable tumor cells | | | | | | | |
| | % of viable tumor cells | Number of live cells | % of viable tumor cells | Number of live cells | % of viable tumor cells | Number of live cells | % of viable tumor cells | Number of live cells |
| 10 mg/ml | 0 | 0 | 20±2.5 | 60 000 | 0 | 0 | 0 | 0 |
| 2 mg/ml | 45±3.85 | 135 000 | 80±10 | 240 000 | 0 | 0 | 0 | 0 |
| 0.4 mg/ml | 77±3 | 231 000 | 100 | 300 000 | 0 | 0 | 0 | 0 |
| 0.08 mg/ml | 100 | 300 000 | 100 | 300 000 | 75.8±6.8 | 227 400 | 0 | 0 |
| 16 mcg/ml | 100 | 300 000 | 100 | 300 000 | 93±2 | 279 000 | 5±1.5 | 15 000 |
| 3.2 mcg/ml | 100 | 300 000 | 100 | 300 000 | 100 | 300 000 | 51±2 | 153 000 |
| 0.64 mcg/ml | 100 | 300 000 | 100 | 300 000 | 100 | 300 000 | 61±2.5 | 183 000 |
| 0.128 mcg/ml | 100 | 300 000 | 100 | 300 000 | 100 | 300 000 | 100 | 300 000 |
| 0.025 mcg/ml | 100 | 300 000 | 100 | 300 000 | 100 | 300 000 | 100 | 300 000 |

FIG. 27

Concentration of $^{39}$K, $^{64}$Zn and $^{24}$Mg (as sulphates and chloride) which caused 50% and 100% changes in the appearance of cells from initial tumor cells into cells of type A based on Trypan blue staining

| № | Component | concentration at which 100% of A cells were detected (mcg/ml) | concentration at which 50% of A cells were detected (mcg/ml) | Minimal concentration at which A cells were detected (start of transformation process) (mcg/ml) |
|---|---|---|---|---|
| 1 | $^{39}$K | 10 000 | 2 000 | 80 |
| 2 | $^{64}$Zn | 80 | 3.2 | 0.025 |
| 3 | $^{24}$Mg | >10 000 | 3 000-4 000 | <400 - >80 |

FIG. 28

Comparative concentrations of K, Zn and Mg components with natural isotope distribution vs. Doxorubicin EBEWE, which caused death of 50 % and 100 % of tumor cells obtained using trypan blue and crystal violet staining methods

| № | Component | Dose at which 100% of dead cells were detected, mcg/ml | Dose at which 50% of dead cells were detected, mcg/ml | Minimal dose at which tumor cells start dying, mcg/ml |
|---|---|---|---|---|
| 1 | Doxorubicin | >16 | 3 | 0.1 |
| 5 | K | 10 000 | 2 000 | <400 - >80 |
| 6 | Mg | >10 000 | 4 000-5 000 | <2 000>400 |
| 7 | Zn | 400 | 300 | 76 |

FIG. 30

Ability of initial PA tumor cells to transform into A cells in the experiment with 30 000 tumor cells after treating them with $^{39}$K, $^{64}$Zn and $^{24}$Mg

| Mass / Isotope | Amount of preparation required for transformation of initial tumor cells into A cells, mcg/ml | | Amount of preparation required for transformation (mcg/200 mcl of medium, i.e. per one well) | | Ability of 1 microgram to transform initial tumor cells into A cells | |
|---|---|---|---|---|---|---|
| | 50 % of A cells | 100% of A cells | 30 000 initial tumor cells into 15 000 A cells, mcg | 30 000 initial tumor cells into 30 000 cells of A phenotype, mcg | with 50% transformation | with 100% transformation |
| $^{39}$K | 2 000 | 10 000 | 400 | 2 000 | 1 mcg ↓ 38 cells | 1 mcg ↓ 15 cells |
| $^{64}$Zn | 3.2 | 80 | 0.64 | 16 | 1 mcg ↓ 23 438 cells | 1 mcg ↓ 938 cells |
| $^{24}$Mg | 3 500 | 10 000 | 700 | 2 000 | 1 mcg ↓ 21 cells | 1 mcg ↓ 8 cells |

FIG. 45

Results of tests on renal cell carcinoma (PA) in a rat:

Table 1

Adhesion and cytoskeletal proteins in renal cell carcinoma (PA) cells after their exposure to the action of light isotopes $^{64}$Zn, $^{24}$Mg and $^{39}$K at doses D1 and D2

| Component | Dosage | Immunocytochemistry assay results (in scores, based on H-Score method) | | |
|---|---|---|---|---|
| | | E-cadherin | N-cadherin | CD44 |
| $^{64}$Zn | D 1<br>0,128 mcg/ml | 218 | 182 | 62 |
| | D 2<br>3,2 mcg/ml | 87 | 261 | 126 |
| $^{24}$Mg | D 1<br>2 mg/ml | 182 | 180 | 67 |
| | D 2<br>3,5 mg/ml | 194 | 187 | 225 / 144 |
| $^{64}$Zn – Z2<br>(14 days storage at<br>T = + 4°C) | D 1<br>0,128 mcg/ml | 300 | 150 | 175 |
| | D 2<br>3,2 mcg/ml | 180 | 172 | 118 |
| $^{39}$K | D 1<br>0,4 mg/ml | 132 / 251 | 170 | 81 / 129 / 172 |
| | D 2<br>2 mg/ml | 14 | 18 | 127 |
| Control (PA cells not exposed to the action of components) | - | 122 | 158 | 78 |

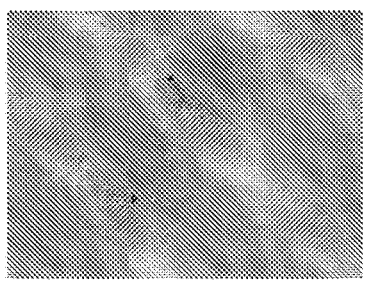 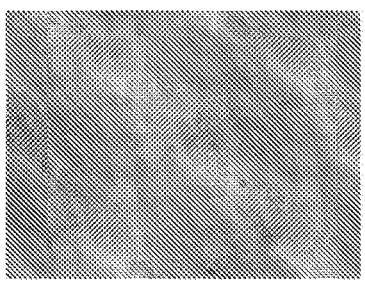 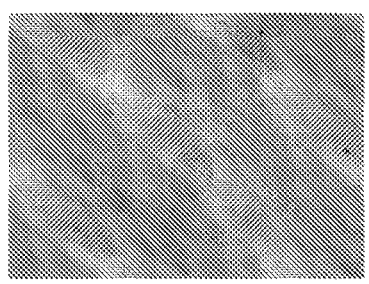
FIG. 66A          FIG. 66B          FIG. 66C
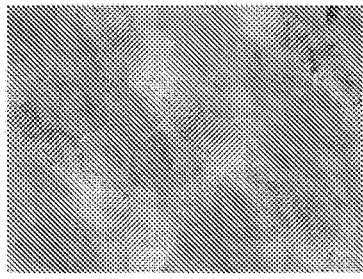 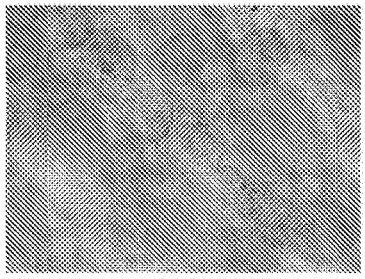 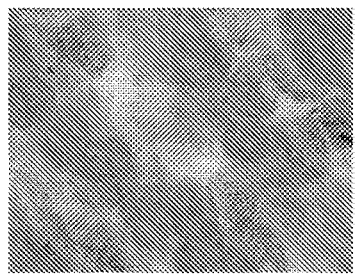
FIG. 66D          FIG. 66E          FIG. 66F

FIG. 67

Adhesion and cytoskeletal proteins in the cells of human non-small cell lung cancer (A-549 line) after their exposure to the action of $^{39}$K, $^{64}$Zn and $^{24}$Mg components at the dose of IC50

| Component | Immunocytochemistry assay results (in scores, based on H-Score method) | | |
|---|---|---|---|
| | E-cadherin | N-cadherin | CD44 |
| $^{39}$K | 47 ±4 | 129 ±2,5 | 209 ±16 |
| $^{64}$Zn | 161 ±3,2 | 130 ±17,4 | 271 ±11 |
| $^{24}$Mg | 141 ±11 | 141 ±17 | 264 ±23 |
| Control (no preparation) | 148 ±8 | 132 ±5 | 261 ±7 |

FIG. 68

Adhesion and cytoskeletal proteins in the cells of human breast cancer (MCF-7 line) after their exposure to the action of $^{64}$Zn and $^{24}$Mg components at the dose of IC50

| Component | Immunocytochemistry assay results (in scores, based on H-Score method) | | |
|---|---|---|---|
| | E-cadherin | N-cadherin | CD44 |
| $^{64}$Zn | 92 ±18,6 | 49 ±7 | 78 ±12 |
| $^{24}$Mg | 41 ±2 | 59 ±3,5 | 43 ±2 |
| Control (no preparation) | 91 ±6,4 | 51 ±4 | 72 ±5,5 |

FIG. 69

Adhesion and cytoskeletal proteins in the cells of human colon adenocarcinoma (COLO 205 line) after their exposure to the action of $^{39}$K, $^{64}$Zn and $^{24}$Mg components at the dose of IC50

| Component | Immunocytochemistry assay results (in scores, based on H-Score method) | | |
|---|---|---|---|
| | E-cadherin | N-cadherin | CD44 |
| $^{39}$K | 184 ± 4,8 | 69 ± 2,6 | 241 ± 16,4 |
| $^{64}$Zn | 141 ± 11,2 | 61 ± 8,4 | 230 ± 10,0 |
| $^{24}$Mg | 134 ± 13,4 | 68 ± 2,0 | 178 ± 8,6 |
| Control (no preparation) | 87 ± 1,4 | 51 ± 6,0 | 235 ± 15,0 |

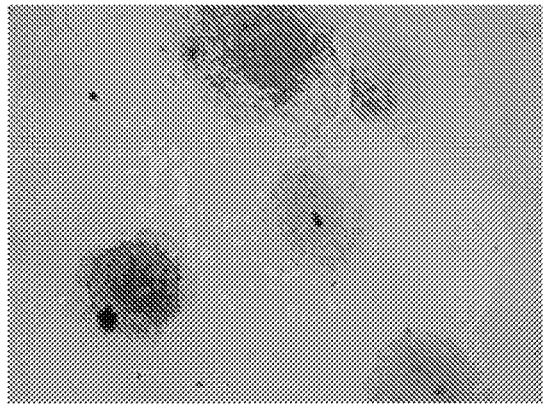
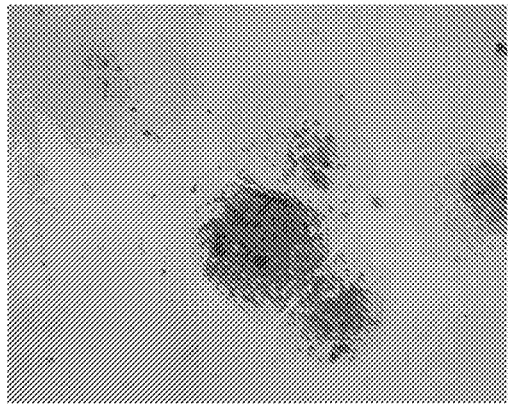
FIG. 71A          FIG. 71B
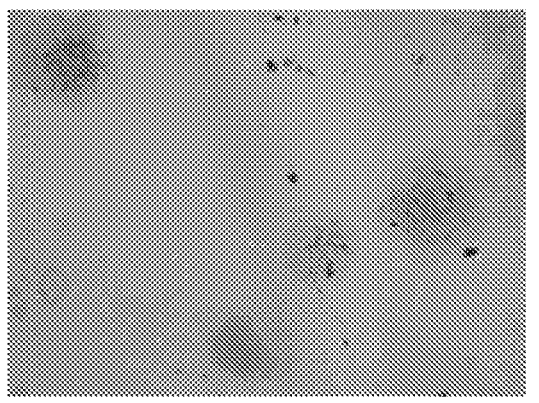
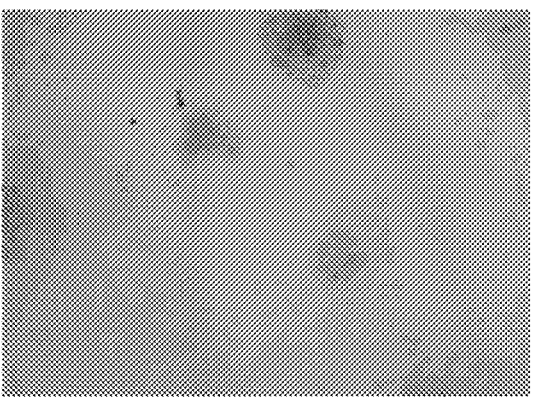
FIG. 71C          FIG. 71D
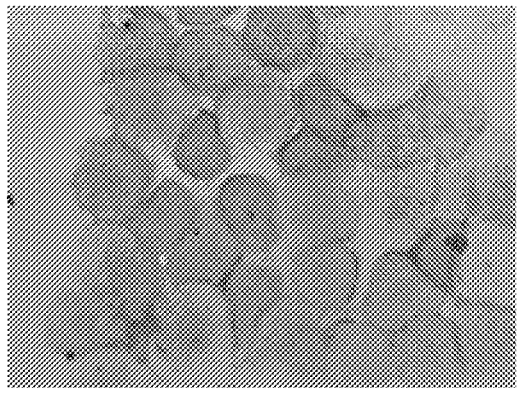
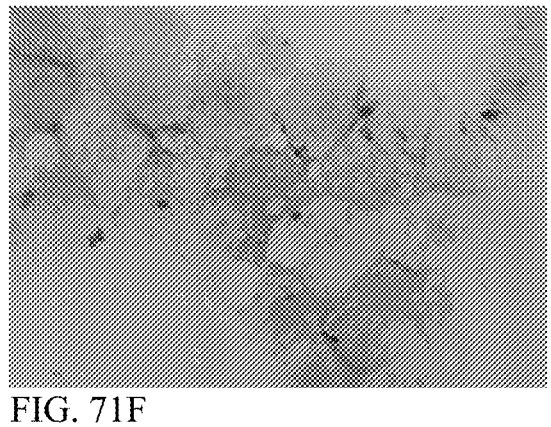
FIG. 71E          FIG. 71F

FIG. 72

Adhesion and cytoskeletal proteins in immortalized cells of a rat (NRK) after their exposure to the action of $^{64}$Zn and $^{64}$Zn- Z2 at a dose of IC50

| Component | Immunocytochemistry assay results (in scores, based on H-Score method) | | |
|---|---|---|---|
| | E-cadherin | N-cadherin | CD44 |
| $^{64}$Zn | 95 ± 2,4 | 213 ± 13,0 | 134 ± 8,4 |
| $^{64}$Zn- Z2 | 89 ± 7,0 | 190 ± 4,6 | 90 ± 2,6 |
| Control (no preparation) | 62 ± 4,2 | 163 ± 7,0 | 136 ± 4,0 |

($^{64}$Zn- Z2 component $^{64}$Zn after 14 days storage at T= +4°C)

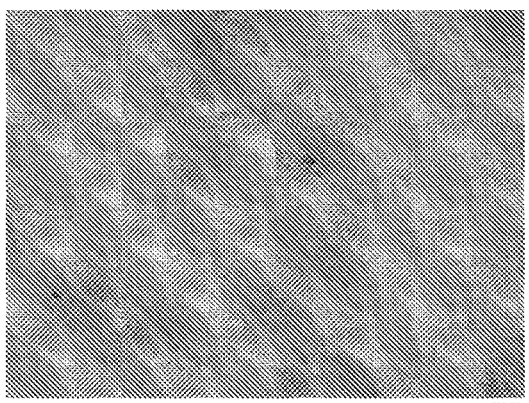
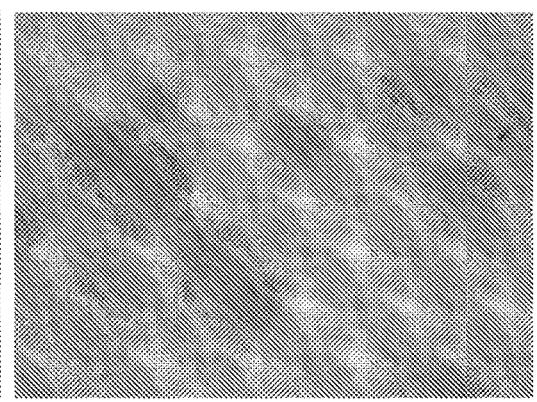
FIG. 73
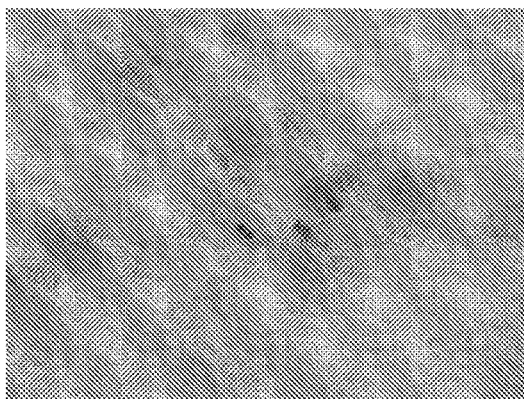
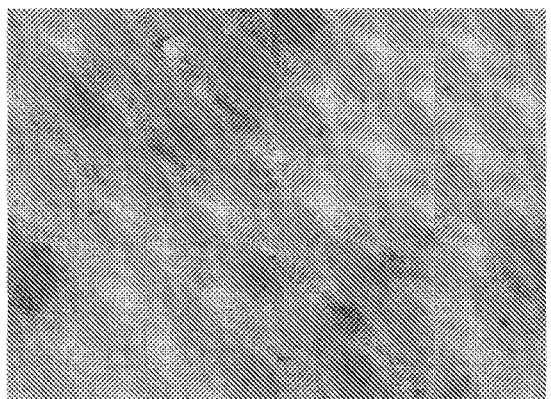
FIG. 74
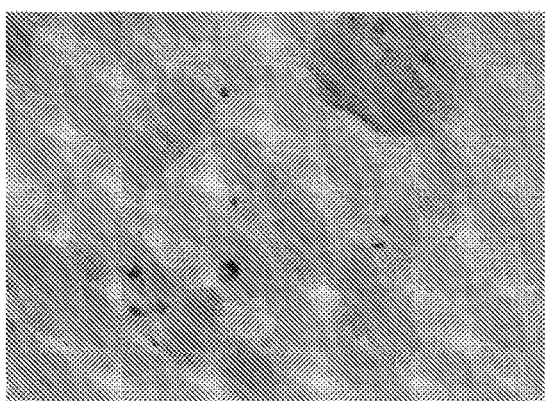
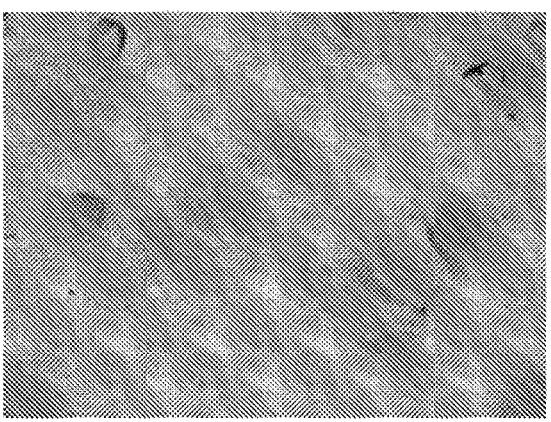
FIG. 75

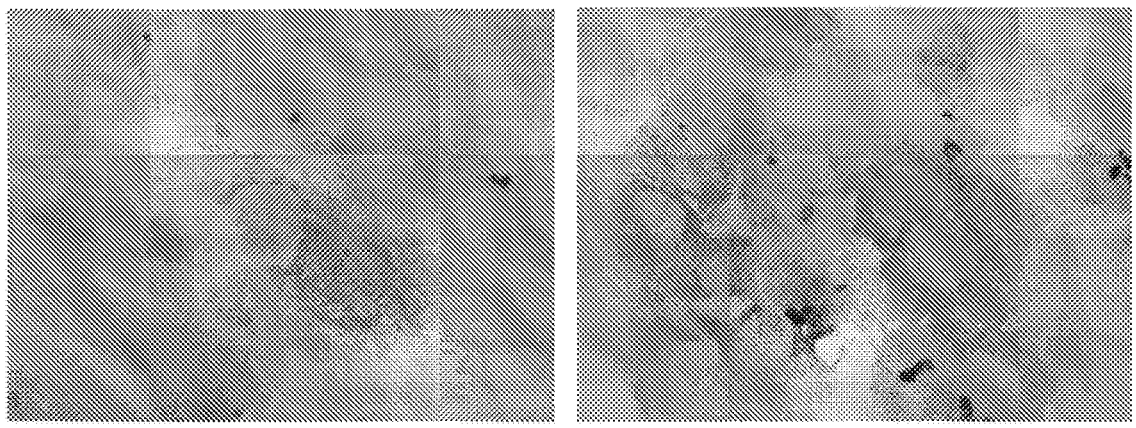
FIG. 89
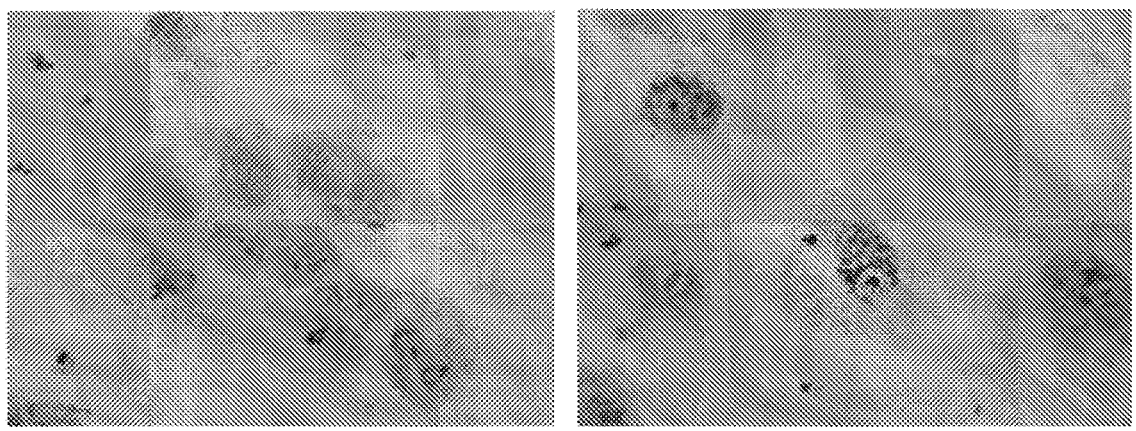
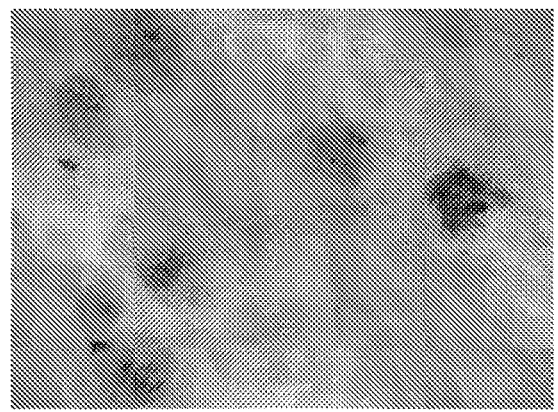
FIG. 90

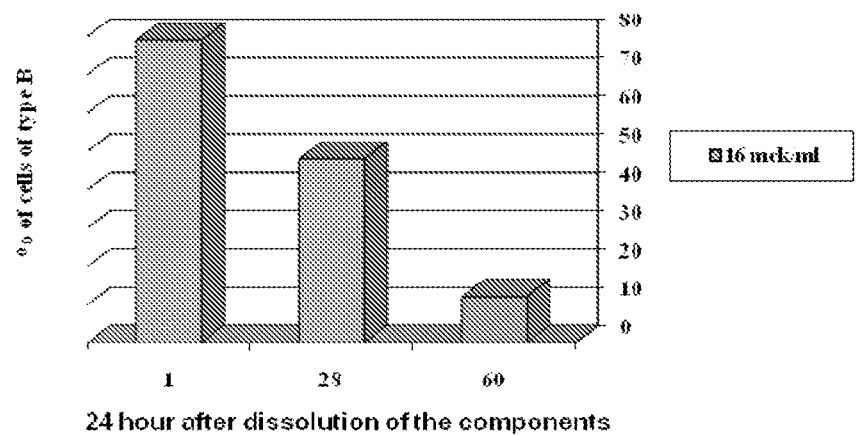
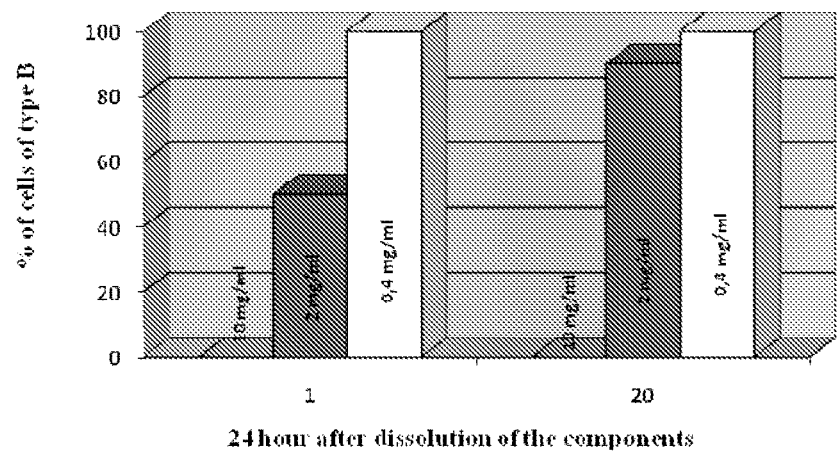
FIG. 91

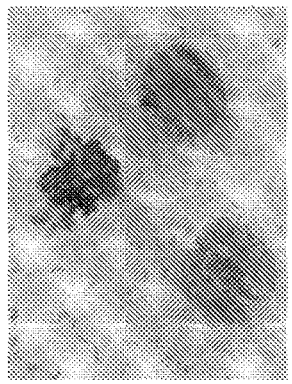 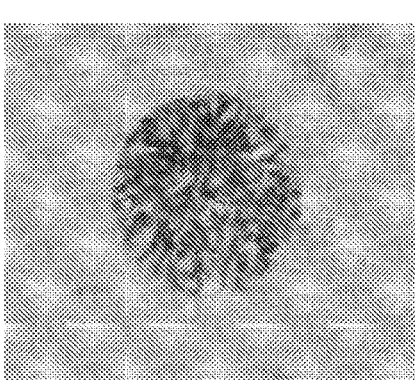 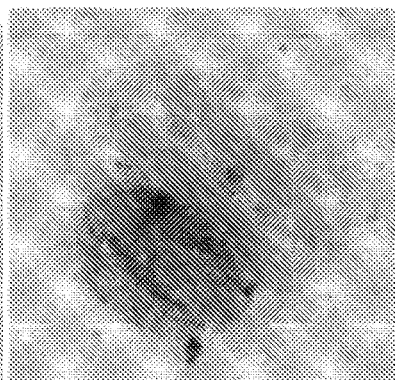
FIG. 98A            FIG. 98B            FIG. 98C
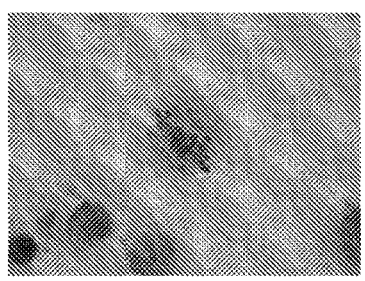 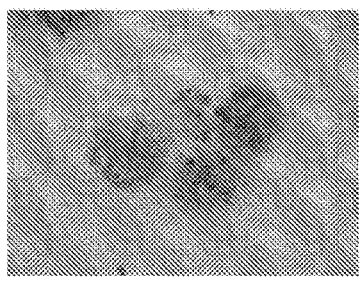 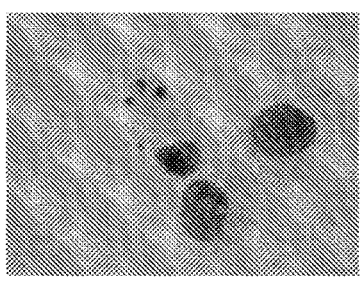
FIG. 98D            FIG. 98E            FIG. 98F
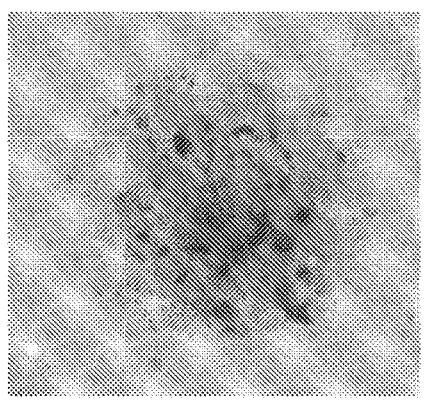 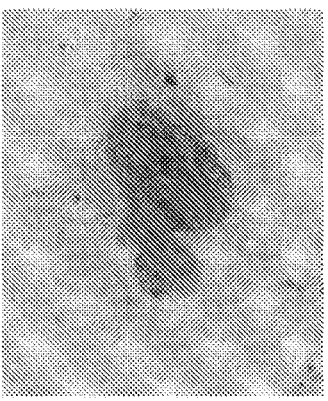 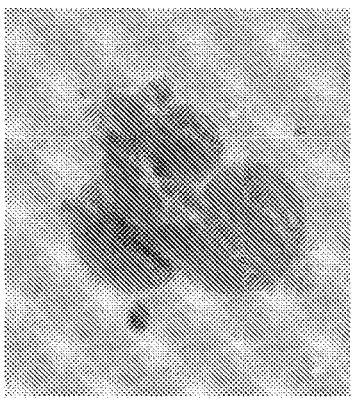
FIG. 98G            FIG. 98H            FIG. 98I

FIG. 99

Table 1. Level of cytogenetic characteristics in cells of COLO 205 line after their exposure to the action of the components

|  | PCC (PCC/Mitosis) | CNM | Mitosis | Apoptosis | Protrusions |
|---|---|---|---|---|---|
| COLO-205 Control | 1,3±0,6 (7,8%) | 3,3±2,5 | 15,3±2,5 | 0,6±0,6 | 2,0±1,0 |
| $^{39}$K 2 mg/ml | 6,6±2,5* (27,6%) | 4,3±0,6 | 17,3±3,7 | 9,1±1,1 | 47,2±4,1** |
| $^{64}$Zn 10mcg/ml | 2 (13%) | 1,6±0,6 | 13,3±4,0 | 16,4±1,0 | 34,5±3,5 |
| $^{64}$Zn 20mcg/ml | 7,0±2,6* (24%) | 6,3±1,5 | 22,0±6,2 | 13,8±0,6 | 44,3±6,6** |
| $^{24}$Mg 2 mg/ml | 0,6±0,6 (4,2%) | 3,3±1,1 | 13,6±1,5 | 10,3±0,6 | 19,8±4,5* |
| $^{24}$Mg 4 mg/ml | 5,0±2,0* (24,7%) | 7,3±1,5 | 15,3±2,0 | 12,4 | 39,8±8,3** |

Table 2. Cytogenetic characteristics in cells of A-549 line after their exposure to the action of the isotopes

|  | PCC | CNM | Mitosis | Apoptosis | Protrusions |
|---|---|---|---|---|---|
| A-549 Control | 1,3±0,6 (9%) | 4,3±0,6 | 13,0±0,6 | 0,5±0,6 | 3,0±0,6 |
| $^{39}$K 2 mg/ml | 1,3±0,6 (43%) | 11,7±2,5** | 1,7±0,6** | 18,3±1,5 | 199,5±6,6** |
| $^{64}$Zn 10mcg/ml | 0,6±0,6 (5,3%) | 9,6±2,5* | 10,6±3,5 | 15,8±2,5 | 51,5±5,5** |
| $^{64}$Zn 20mcg/ml | 0,7±0,6 (6,3%) | 6,7±1,5 | 10,3±1,5 | 19,3±1,8 | 153,9±12,5** |
| $^{24}$Mg 2 mg/ml | 0,6±0,6 (11,3%) | 4,7±1,5 | 4,7±1,5** | 14,4±1,2 | 26,6±2,5** |

*P<0,01, **P<0,05

FIG. 101
Table 3. Cytogenetic characteristics in cells of MCF-7 line after their exposure to the action of the components
|  | PCC | CNM | Mitosis | Apoptosis | Protrusions |
|---|---|---|---|---|---|
| MCF-7 Control | 2,3±1,5 (18,2%) | 2,3±1,1 | 10,3±1,5 | 0 | 3,3±1,1 |
| $^{64}$Zn 20mcg/ml | 1,0±1,0 (10%) | 5,7±1,1* | 9,0±1,7 | 10,4±0,6 | 27,0±3,0** |
| $^{24}$Mg 4 mg/ml | 0,3±0,6 (3,8%) | 4,7±2,0 | 10,6±2,3 | 11,2±0,6 | 28,0±3,6** |
*P<0,01, **P<0,05
FIG. 102A
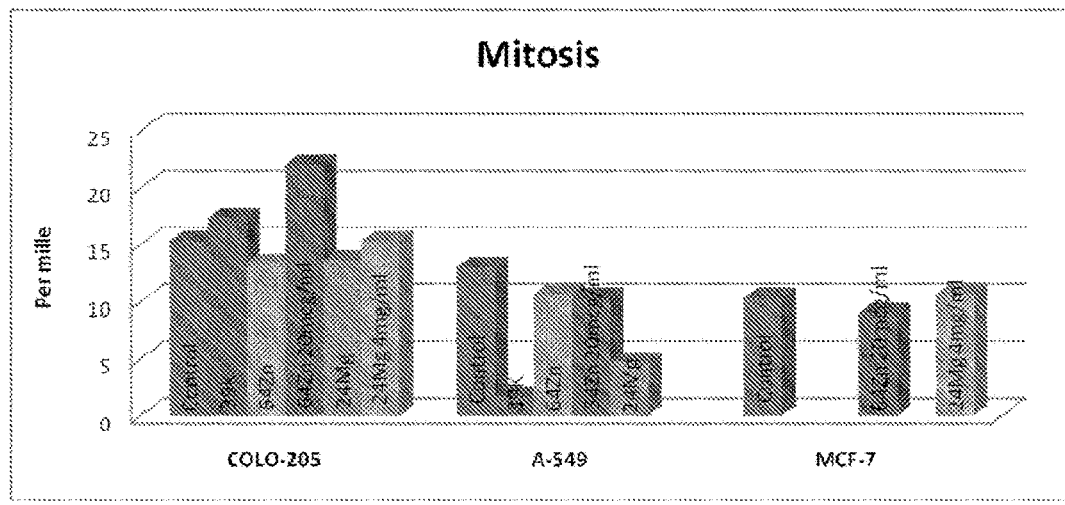
FIG. 102B
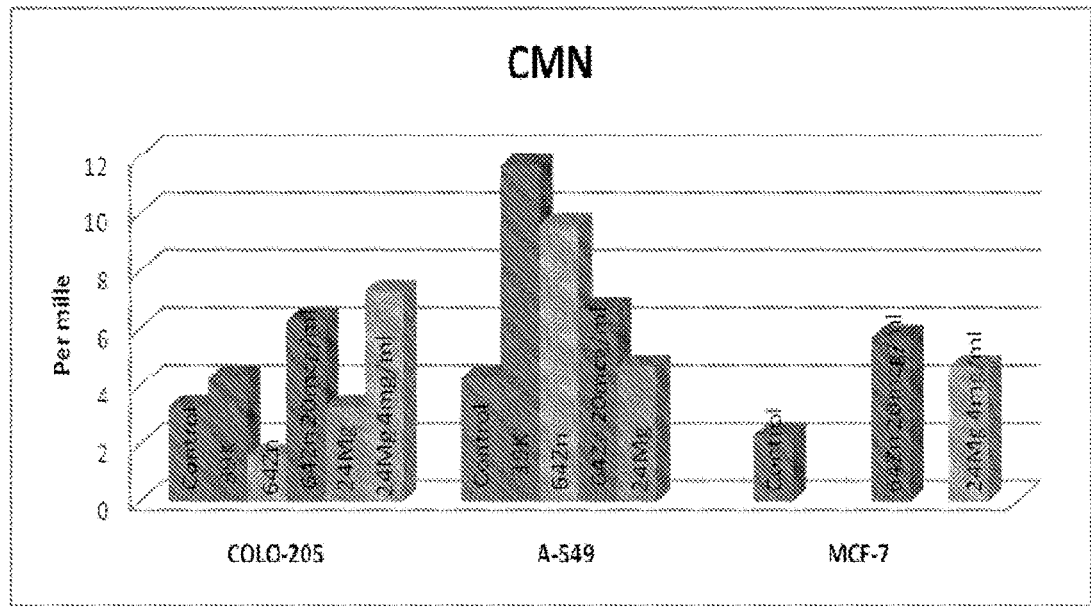

| Cell line | Type | Characteristics of effects of light isotope containing materials, control group of cells and Doxorubicin in the experiment using the scratch assay migrations. Character of the combined effects of Doxorubicin and light isotopes | | | |
|---|---|---|---|---|---|
| | | Light isotopes $^{39}K$ $^{64}Zn$ $^{24}Mg$ | Control group of cells | Doxorubicin | Doxorubicin + Components |
| A-549 | Tumor cells. Human non-small cell lung cancer | Increase the time of restoration of the monolayer from 24 to 72 hours $^{24}Mg$ – 3 mg/ml  4 mg/ml $^{39}K$ – 2 mg/ml  3 mg/ml $^{64}Zn$ – 20 mcg/ml  30 mcg/ml | Time of restoration of the monolayer is 24 hours. | Reduces the time of the monolayer healing increasing the malignant potential. | $^{64}Zn$ neutralizes the effects of Doxorubicin if used jointly at the following doses: 20 mcg/ml $^{64}Zn$ + 0.02 mcg/ml DOX. Time of restoration in this combination is 72 hour. |
| RF | Stem cells. Rat fibroplasts | Maintain the time of restoration of the monolayer that equals 72 hours. The speed restoration of control monolayer at the initial stages of the experiment is significantly higher when using a fresh solution. $^{24}Mg$ – 2 mg/ml  4 mg/ml $^{39}K$ – 1 mg/ml  2 mg/ml $^{64}Zn$ – 25 mcg/ml | Time of restoration of the monolayer is 72 hours. | Causes death of 95% of cells in 96 hours after the start of the experiment at a dose of 15 mg/ml. Causes reduction of the cell migration rate and loss of regeneration properties by cells. | The combined effect of Doxorubicin and $^{64}Zn$ equals to the effect of Doxorubicin. |
| NRK | Normal kidney cells | Maintain the time of restoration of the monolayer that equals 30 hours. The speed restoration of control monolayer at the initial stages of the experiment is significantly higher when using a fresh solution. | Time of restoration of the monolayer is 30 hours. | Causes significant reduction of the cell migration rate and loss of regeneration properties by cells after the use at a dose of 15 mg/ml. | |
| HaCaT | Human keratinocytes. Normal skin | Maintain the time of restoration of the monolayer within 36 hours from the start of the experiment. | Time of restoration of the monolayer is 36 | At a dose of 15 mg/ml significantly slows the rate of cell migration and causes loss | Light isotopic zinc neutralizes the negative effects of Doxorubicin completely. Time of restoration of |

FIG. 144A

| | cells | | hours. | of regeneration properties by cells | the monolayer in the DOX + $^{64}$Zn combination is the same as that of the control group and amounts to 36 hours. |
|---|---|---|---|---|---|
| A-431 | Human epidermoid carcinoma. Tumor cell line | Light isotopic component Zn increased the time of restoration of the monolayer to 72 hours. | Time of restoration of the control monolayer is 48 hours. | Slightly decreases the time of restoration of the monolayer to 45 hours. | Combination of $^{64}$Zn and Doxorubicin results in restoration of the control monolayer in 72 hours. Light isotopic zinc neutralizes the negative effects of Doxorubicin completely. |
| MM-4 | Melanoma. Tumor cell line | Light isotopic component Zn suppresses migration of melanoma tumor cells of the MM-4 cell line. The time of restoration of the monolayer after the use of 15 mcg/ml of $^{64}$Zn was 72 hours. | Time of restoration of the control monolayer of the MM-4 cell line is 48 hours. | If used at a dose of 0.01 mcg/ml, the cell monolayer is completely restored in 48 hours. | Combination of $^{64}$Zn and Doxorubicin results in restoration of the control monolayer in 70 hours. |

FIG. 144B

Fig. 163. Effects of Zn$^{64}_e$ Aspartate on survival of experimental animals (model L1210).

■ L1210 Control

▨ L1210+$^{64}$Zn$_e$ Aspartate, Intraperitoneally 25 mcg per mouse

▨ L1210+$^{64}$Zn$_e$ Aspartate, Intraperitoneally 50 mcg per mouse

▨ L1210+$^{64}$Zn$_e$ Aspartate, Intraperitoneally 75 mcg per mouse

▨ L1210+$^{64}$Zn$_e$ Aspartate, Intravenously 25 mcg per mouse

PHARMACEUTICAL COMPOSITION FOR IMPROVING HEALTH, CURE ABNORMALITIES AND DEGENERATIVE DISEASE, ACHIEVE ANTI-AGING EFFECT OF THERAPY AND THERAPEUTIC EFFECT ON MAMMALS AND METHOD THEREOF

RELATED APPLICATIONS

This application is a continuation-in-part of U.S. patent application Ser. No. 14/833,114, filed on Aug. 23, 2015, which claims the benefit of U.S. provisional application Ser. No. 62/123,900, filed on Dec. 1, 2014, and entitled "SYSTEM, APPARATUS. METHODS AND COMPOSITIONS FOR THE TREATMENT OF GROUP OF DISEASES INVOLVING ABNORMAL CELL GROWTH AND OTHER HEALTH ABNORMALITIES OF MAMMALS," all of which are incorporated herein by reference in their entirety.

FIELD OF THE INVENTION

The present invention relates to a pharmaceutical composition for improving health, cure abnormalities and degenerative disease, including suppression of the development of cancer, for example, suppressing the growth of tumors (solid and non-solid) and suppressing, partially or completely, the spread of cancer, i.e. metastasis; achieve anti-aging effect of therapy and therapeutic effect on mammals and method of administering the same.

BACKGROUND OF THE INVENTION

Cancer is one of the degenerative diseases. Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. There is an enormous variety of cancers which are described in detail in the medical literature. Examples include cancer of the lung, colon, rectum, prostate, breast, brain, and intestine.

At present, cancer is the second leading cause of death globally, after cardiovascular diseases. Statistics show that the incidence of oncological diseases is growing every year, and today this problem is one of the greatest challenges for medicine and the pharmaceutical industry.

The art is replete with various compositions and methods for treating cancer. One of such compositions is disclosed in US Patent Application Publication Number US 2014/0219961A1 to Jung et al. entitled "Pharmaceutical composition for treating cancer, comprising interferon alpha conjugate". The US Patent Application Publication Number US20140219961A1 to Jung et al., teaches a method for preventing or treating a cancer includes administering an anti-cancer pharmaceutical composition including an interferon alpha or a polymer conjugate thereof. The pharmaceutical composition can be co-administered with anti-cancer agents. The interferon alpha conjugate shows a longer in vivo half-life and a more excellent anti-cancer activity than the conventional interferon alpha, and in particular, its co-administration with an anti-cancer agent such as gemcitabine has synergistic inhibitory effects on cancer cell growth and proliferation so as to exhibit a remarkably excellent anti-cancer activity.

Another prior art reference, namely U.S. Pat. No. 8,846,630 to Won et al. entitled "Pharmaceutical composition for treating cancer". It discloses a pharmaceutical composition for treating cancer, comprising at least one selected from deoxyribonucleic acids (DNA) for encoding small interfering RNA (siRNA) which complementarily binds to the base sequence of the transcript (mRNA transcript) of the FLJ25416 gene, represented by sequence number 3, sequence number 5, and sequence number 7 to inhibit the intracellular expression of the FLJ25416 gene, antisense RNA which inhibits expression of the FLJ25416 gene, and short hairpin RNA (shRNA) which inhibits expression of the FLJ25416 gene. As the siRNA, which is complementary to the base sequence of the transcript (mRNA transcript) of the FLJ25416 gene, the antisense RNA, and the shRNA, according to the present invention, inhibit expression of the FLJ25416 gene which is known to be expressed in cancer cells, and thus kill cancer cells, the composition of the present invention can be used as a novel anti-cancer agent.

Today oncological diseases are mainly treated by chemotherapy that uses a number of chemotherapeutic drugs that are divided into several major groups (classes), such as alkylating agents, antimetabolites, antitumor antibiotics, alkaloids. Other biological active substances of plant origin, as well as enzyme and hormone preparations are also used in cancer treatment.

But these drugs are usually not very effective in treating the malignant ascites which is associated with the terminal stage of the disease and is very difficult to treat. Malignant ascites is a pathological accumulation of fluid in the peritoneal or pleural cavity that develops as a result of a malignant process in the peritoneum or lungs. Ascites leads to various functional disorders in patients with advanced stage cancer and is a complex clinical problem. Malignant ascites can be caused by a variety of primary tumors, such as, for example, breast cancer, ovarian cancer or gastrointestinal carcinoma. Despite the fact that in most patients ascites is found already at the first manifestation of tumor disease, its appearance indicates the progression of cancer.

In oncology, cancers that cause ascites pose a serious problem, as in most cases they result in the death of patients. The death of such patients occurs even in the absence of distant metastases and tumor progression. To treat such types of cancer, conventional types of cancer treatment are used, which to some extent improve the condition and prolong the life of a patient. The available options of therapy for ascites carcinomas include puncture, local chemotherapy or treatment with diuretics. All these options have significant drawbacks. Thus, puncture only results in short-term relief and should be repeated on average every 9.5 days (Mackey et al., J. Pain Symptom Manage, 19: 193, 2000). Chemotherapy can also be successful only in patients who have not yet developed tumor cells resistant to chemotherapy, which, unfortunately, occurs quite often. In particular, after the puncture is performed, intraperitoneal chemotherapy is used to remove exudates by administration of cytostatic agents such as adriamycin, thiotepa, cyclophosphamide, doxorubicin, paclitaxel, docetaxel, topotecan, etc., as well as their combinations (Brenner D E, Intraperitoneal chemotherapy: a review, J Clin Oncol, 1986, 4 (7): 1135-1147). At the same time, the peritoneum actively absorbs chemotherapeutic drugs, and they enter the bloodstream in significant concentrations. Thus metastases in the abdominal cavity directly contact the cytostatic agent, the tumor cells circulating in the blood are destroyed and the medicinal effect on all cancer sites in the body is produced. However, a disadvantage of such treatment is its relatively low efficiency with a short-term palliative effect.

In certain cases, platinum-based drugs, such as carboplatin and cisplatin (Meshcheryakova N. G. Platinum cytostatics in the treatment of tumor pleurisy. MD Dissertation, M., 1993), are used to treat ascites caused by the tumor process. These chemical compounds are complex inorganic compounds of transition metals (platinum), in contrast to the prevailing majority of antitumor drugs which according to their chemical structure are organic substances as a rule. The complex compounds of platinum include a central ion, or a complexing agent, which is divalent platinum surrounded by monodentate ligands, two of which are chlorine atoms and two are molecules of ammonia, in the cis-position, i.e. these ligands are located in square-built complexes on one side of the complexing agent. The geometric configuration of platinum complexes plays an important role in their biological activity. According to its physical and chemical properties, cisplatin is a neutral complex of platinum, which facilitates its transport through cell membranes. The chemical mobility of substitutable groups is quite high, and this creates good conditions for bonds of important biochemical substrates in the body with the nucleophilic centers. Among disadvantages of the methods using compositions comprising platinum compounds are increased nephrotoxicity and hepatotoxicity. In addition, methods that involve the use of cisplatin cause oppression of normal hematopoiesis, neuropathies, electrolyte disorders or reversible increase in the activity of aminotransferases. In addition, these methods do not completely stop the development of ascites, but only slow its growth to a certain extent.

It has been demonstrated by a large number of studies that the isotopic composition of tissues and organs can serve as a diagnostic marker. In particular, the study of the ratios of Cu and Zn isotopes in blood showed their promising interrelationships with age, sex and pathologies. For example, an estimate of the ratio of Cu isotopes in blood serum is a new approach to the diagnosis and prognosis of the development of cirrhosis (M. Costas-Rodriguez, Y. Anoshkina, S. Lauwens, H. Van Vlierberghe, J. Isotopic analysis of Cu in blood serum by multi-collector ICP-mass spectrometry: a new approach for the diagnosis and prognosis of liver cirrhosis, Metallomics 2015, 7. 491-498), and the isotopic composition of Zn in breast tissues enables diagnosis of cancer (F. Lamer, L. N. Woodley, S. Shousha, A. Moyes, E. Humphreys-Williams, S. Strekopytov, A. N. Halliday, M. Rehkamper, R. C. Coombes, Zinc isotopic compositions of breast cancer tissue, *Metallomics* 2015, 7. 107-112).

WO2001082871 discloses a method for therapy and diagnosis of colon cancer using a composition based on zinc isotopes having a short half-life, $^{62}$Zn in particular, selected from the group consisting of zinc acetate, zinc chloride, and zinc sulfate, to induce apoptosis in the tumor cells of the large intestine. As it is demonstrated therein, the composition containing $^{62}$Zn at a concentration of 60 to 80 μM, in the presence of phosphate binder, induces apoptosis in colon cancer cells. However, the data presented in the said publication relate only to the in vitro experiments on HT-29 cell lines (ATCC cell line number HTB 38) and T-84 (ATCC cell line number CCL 248) derived from a human colon tumor.

Another known method for inhibiting a malignant process is the employment of compositions comprising nanoparticles of porphyrinfulfullerenes (NP) containing such isotopes as $^{25}$Mg and $^{67}$Zn ($^{25}$Mg-NP and $^{67}$Zn-NP) (Orlova, M. A.; Osipova, E. Yu.; Rumyantsev, S. A.; Ashurko, S. P. Effect of the $^{67}$Zn isotope on leukemic cells and normal lymphocytes.—Russian Chemical Bulletin (2012), 61(2), 405-408). When using the described method and compositions, significant differences in the cytotoxic effect of magnetic and nonmagnetic zinc isotopes on tumor cells were observed, as well as the lack of effect of the complex of magnetic magnesium isotope and primary nanoparticles on such cells. $^{67}$Zn-NP showed potent cytotoxic activity against cells of acute B-lymphoblastic leukemia with LD50 almost three times lower than in healthy donors and four times lower than when using Zn-NP. However, as in the previous case, the experiments were performed in vitro on human leukemia cells, towards which a cytotoxic effect was observed. The efficacy of the described composition and method has not been evaluated in animal models or in a clinical trial.

However, the compositions and methods described in the prior art documents mentioned above, which involve the use of light isotopes $^{62}$Zn or $^{67}$Zn, differ from the claimed ones by the zinc isotope used, diseases that can be treated with it, and additional active ingredients that provide an inhibitory effect on tumors that cause ascites.

In addition to cancer, other chronic and degenerative diseases have become primary cause of mortality. Neoplasms, ischemic heart disease, and cerebrovascular disease cause three-quarters of all deaths at 35-69 years of age and two-thirds at older ages. Huge resources are committed to the reduction of mortality from leading killers. There is no doubt that eventually dramatic results will follow in this direction.

The problem is that most of the degenerative pathologies such as heart disease, cancer and Alzheimer disease are age related, and those at first glance are not considered being results of a specific tissue "local" aging. Therefore as best formulated by George Johnson/NY Times Jan. 4, 2014/" . . . barring an elixir for immortality, a body will come to a point where it has outwitted every peril life has thrown at it. And for each added year, more mutations will have accumulated. If the heart holds out, then waiting at the end will be cancer." As long as aging is not addressed properly, we can only hope for partially successful treatments that only pushing problem a little bit further in time, still failing to avoid final negative outcome.

When dealing with infectious diseases, the cause is clear. In case of degenerative diseases, there is much less clarity. Over the last hundred years, the focus of research was moving along the line "organ-tissue-cell-molecule/protein" providing precious data needed to crate new medicine. Yet in most cases, we have to evaluate success in terms of statistical outcome in treating not the cause but syndromes of disease. To change the current trend, we need a solution that provides a resistance to bacterial and virus attacks and should be able to repair damage from critical mutations on molecular level. Regenerate/renew "defective" tissue damaged by chronic degenerative disease. Prevent transformation of adult stem cells into cancer stem cells. Transform cancer cells into benign tissue cells or harmless stem-like cells. Prevent health deterioration in time on structural level and by increasing efficiency of immune system.

The current paradigm in cancer research is in the following statement: "cancer is a disease of cells, and the phenotypes of cancer cells can be understood by examining the genes and proteins within them". Correspondently one of the main problems scientists trying to address is how many intracellular regulatory circuits need to be perturbed in order to transform a normal human cell into a cancer cell?

Therefore, not only cancer research but any other pathology investigation will stop there. The question is whether it's good enough or not. It is perfectly fine if life exists due to a lucky coincident of random events. But what if life as we know it is a specific form of a universal algorithm expressed and evolving at given physical conditions here and now? We often speak in terms of mutations, genetic defects, DNA code. Well, behind every code must be an algorithm and behind any algorithm must be mathematics. If it is true, then the knowledge of it could be a precondition for successful control/correction of any life form.

There are 200 different types of cells in human body. Let us imagine that in each cell we select the same chromosome and purposely damage it. It may lead to the development of the disease in different cells, tissues, organs having different symptoms and even named differently, all due to one single type of damage given said damage is "essential". So, what defines the severity of the damage? There is a big variety of known pathogens including bacteria, viruses, chemicals, radiation etc. Irreversible damage may happen without a pathogen as well, such as mutation in the process of mitosis. At the same time, most of the mistakes during cell division are immediately repaired.

Infection diseases are sometimes defeated by immune system without irreversible changes in the organism. What may go wrong and where? Which change has a potential to become a fatale one? What is the first, elementary step of pathological change caused by any pathogen without exception? Life scientists would start answering with the reference to processes in the cells. However, it is the wrong level.

The fact is that we can completely ignore any pathogens as long as not a single chemical bond in the organism is damaged. It means that the interaction between pathogen and organism did not take place. When it does, a lot depends on the type of chemical bond that was destroyed and what have happened in the result. A lot of heavy smokers and alcohol consumers do not get cancer, but some of those with healthy life style are less lucky. Why? We need to understand that if damages caused by pathogens were limited to a certain level of chemical bond, then they would be repaired by internal mechanisms the same way as reparation of mistakes during mitosis happens.

The shocking truth is that damage sometime goes deeper than chemical bonds level—to the nucleus. Once it happens, there is no way back, and change becomes irreversible contributing to the unavoidable finale whether it is about illness or aging. Any efforts to change the situation on the level above the atom will be fruitless and in the best case capable to address just symptoms of diseases.

It is not enough to think in terms of homeostasis. It is essential to understand that homeostasis starts from elementary particles and goes up to the levels higher than individual mind or intellect and not limited by the currently agreed borders of life science. Inability of human (and all animals in general) as a stable system to control changes on atomic level allows to suggest that animals including humans were originated in the different and in a certain aspect artificial or selective environment. The one where damage of chemical bonds would never lead to the changes on atomic or subatomic levels and as a result the original hierarchical structure would never be jeopardized.

While not wishing to be bound by theory, the present inventors believe that certain elements, including each of potassium, magnesium, zinc, rubidium, silicon, calcium, copper, iron, chromium, nickel, molybdenum, selenium, bromine, and chlorine, play important roles in autocatalytic reactions in the body of an animal, such as a human or other mammal. The products of such autocatalytic reactions, such as proteins, play important chemical and structural roles in the body, including immune function. Fully functional products of such reactions require a specific, "correct" chirality at various chiral centers within the product. The inventors further understand that heavy isotopes accumulate in the body beginning at birth such that, over time, the relative abundance of each element's isotopes drifts further and further from the naturally occurring relative abundance, becoming increasingly over-weighted with respect to heavy isotopes. Heavy isotopes can affect autocatalytic reactions by reducing the proportion of products that have the "correct" chirality. See, e.g., Tsuneomi Kawasaki et al., *Asymmetric Autocatalysis Triggered by Carbon Isotope ($^{13}C/^{12}C$) Chirality*, Science 324: 492-95 (2009). This causes a reduction in the proportion of products of autocatalytic reactions that are fully functional. In sum, the cumulative divergence of the body's isotope relative abundances from the natural relative abundance causes a decrease in the functionality of various proteins and other molecules in the body, leading to a decline in health with age.

The present inventors believe such a decline can be countered by restoring the body's original isotope relative abundances, or by moving the isotope relative abundances in that direction. This can be achieved in accordance with the present invention by administering one or more of the above-listed elements enriched (relative to its natural abundance) with a corresponding "light isotope," specifically, enriched with $^{39}K$, $^{24}Mg$, $^{64}Zn$, $^{85}Rb$, $^{28}Si$, $^{40}Ca$, $^{63}Cu$, $^{54}Fe$, $^{52}Cr$, $^{58}Ni$, $^{92}Mo$, $^{74}Se$, $^{79}Br$, $^{35}Cl$, respectively, to a patient (human or non-human animal), which can alter the chirality of the autocatalytic products present in the patient, resulting in an improvement in the patient's health. Further, the quantity of light isotope that is effective may be proportional to the quantity of the corresponding element that is present in the body. Where the body contains a relatively large quantity of the element, a correspondingly relatively large amount of the element's light isotope will be required to provide an effective dosage amount. On the other hand, where the body contains a relatively small quantity of the element, a correspondingly relatively small amount of the element's light isotope will be required to provide an effective dosage amount.

The incidence of cancer continues to climb as the general population ages, as new cancers develop, and as susceptible populations (e.g., people infected with AIDS or excessively exposed to sunlight) grow. A tremendous demand therefore exists for new methods and compositions that can be used to treat patients with cancer.

SUMMARY OF THE INVENTION

A pharmaceutical composition of the present invention is used for improving health, cure abnormalities and degenerative disease; achieve anti-aging effect of therapy and therapeutic effect on mammals. The pharmaceutical composition includes a pharmaceutical carrier and an isotope selective ingredient including at least one of a chemical element and a chemical compound containing the chemical element whereby isotope distribution in the at least one of the chemical element and the chemical compound containing the chemical element is different from natural distribution of at least one of isotopes wherein the part of selected isotope of the chemical element ranges from 0 to 100%. The selected isotopes include at least one of K-39; Mg-24;

Zn-64; Rb-85; Si-28 and combination thereof. The selected isotopes also include at least one of Ca-40; Cu-63; Fe-54; Cr-52; Ni-58; Mo-92; Se-74; Br-79; Cl-35 and combination thereof. The pharmaceutical of the carrier pharmaceutical composition is used in the form of a solution, a gel, a cream, a spray, an aerosol, a patch, nanoparticles, inorganic molecules, organic molecules, a plant, a fruit and a vegetable.

One specific technical problem to be solved by the present invention is to provide a composition comprising an active ingredient and a method for suppression of the development of cancer, including suppressing the growth of tumors (solid and non-solid) and suppressing, partially or completely, the spread of cancer, i.e. metastasis, wherein the method entails administering the composition, which possesses anticancer activity and also does not produce side effects as toxic as those associated with the use of known cytostatic agents. The composition of the invention generally is a pharmaceutical composition that contains as an active ingredient one or more light-isotope enriched elements selected from $^{64}$Zn-enriched zinc, $^{39}$K-enriched potassium, $^{85}$Rb-enriched rubidium, $^{24}$Mg-enriched magnesium, $^{54}$Fe-enriched iron, $^{74}$Se-enriched selenium, $^{28}$Si-enriched silicon, $^{40}$Ca-enriched calcium, and $^{63}$Cu-enriched copper, either in elemental form or, preferably, in the form of a chelate, salt, complex, or other pharmaceutically acceptable compound. The composition preferably contains at least one excipient.

The pharmaceutical composition includes combination of at least two of the isotopes wherein one of the isotopes is lighter in weight than the other of the isotopes to achieve therapeutic effect. The light isotopes of the pharmaceutical composition are K-39; Mg-24; Zn-64; Rb-85; Si-28; Ca-40; Cu-63; Fe-54; Cr-52; Ni-58; Mo-92; Se-74; Br-79; Cl-35. The chemical compounds of the pharmaceutical composition include the isotopes such as at least one of oxides, sulfates, citrates, gluconate, and a chelate containing a ligand bonded to a central metal atom at least two points. The chemical elements and chemical compounds are food supplements. (Throughout this application, isotopes are designated interchangeably two different ways: for example, $^{35}$Cl and Cl-35 refer to the same chlorine isotope.)

In another embodiment, the composition comprises an effective therapeutic amount of at least one light isotope selected from the group consisting of K-39, Mg-24, Zn-64, Rb-85, Si-28, Ca-40, Cu-63, Fe-54, Cr-52, Ni-58, Mo-92, Se-74, Br-79, and Cl-35 either in elemental form or in the form of a pharmaceutically acceptable salt, compound, chelate, or complex, wherein the composition is enriched for the at least one light isotope relative to the natural abundance of the isotope. In preferred embodiments, the composition is suitable for various routes of administration, such as topical or oral administration or administration by injection. In certain embodiments, the composition further comprises at least one additional ingredient suitable to the form of the composition, including carriers and excipients such as diluents, solvents (such as water), binders, lubricants, coloring agents, and preservatives, which are conventional and known to the person of ordinary skill in the art. The composition preferably is formulated for a specific route of administration such as, but not limited to, injection (e.g. intravenous, intraperitoneal, or subcutaenous injection), topical administration and oral administration, and other parenteral routes not mentioned above (e.g. via suppository). Other conventional routes of administration may also be used as appropriate to the condition being treated. Specific exemplary forms of the composition include a topical solution, spray, lotion, salve, ointment, gel, cream, soap, shampoo, patch, powder and foam, and an oral tablet, capsule, syrup, suspension, lozenge, gum, spray, and solution, and a solution or other composition suitable for intravenous, intraperitoneal, subcutaneous, or other route of administration by injection. In one embodiment, the light isotope is packaged in liposomes, which in turn are dissolved or suspended in an appropriate liquid and packaged in capsules that are administered orally. In other embodiments, oral compositions of the invention may be formulated for immediate, delayed, or sustained release and may also be formulated for enteric release. Topical compositions of the invention may include at least one absorption-enhancing agent such as DMSO.

Compositions in the form of a solution (for any appropriate route of administration, including by injection) may be prepared in which the solvent is water; in a preferred embodiment, the water is enriched with $^{16}$O and/or depleted of $^{2}$H, both with respect to the isotopes' natural abundance. For example, the hydrogen of the deuterium-depleted water may be at least 99.99% $^{1}$H on a mole fraction basis. Further, the oxygen of the deuterium-depleted water may be at least 99.9% $^{16}$O on a mole fraction basis. In an embodiment, the composition also contains compounds that promote better penetration of the agent into body cells. In a preferred embodiment, the at least one light isotope that the composition is enriched for is one or more of $^{64}$Zn, $^{24}$Mg, $^{39}$K, $^{54}$Fe, $^{85}$Rb, and $^{28}$Si. In preferred embodiments, in a solution as described above, $^{64}$Zn$_e$ is present at a concentration of from 10 µg/ml to 10 mg/ml, most preferably from 100 µg/ml to 2 mg/ml; in these embodiments, $^{64}$Zn$_e$ is present in the form of a chelate of an amino acid, preferably a chelate of aspartate or asparaginate.

When the enriched-for light isotope is $^{64}$Zn, the $^{64}$Zn preferably constitutes at least about 80% $^{64}$Zn of the zinc on a mole fraction basis (that is, 80% of the zinc atoms are $^{64}$Zn atoms), more preferably at least about 90% $^{64}$Zn, such as at least 90%, at least 95%, or at least 99% $^{64}$Zn, or between about 90% and about 99.9% $^{64}$Zn (all on a mole fraction basis). When the enriched-for light isotope is $^{64}$Zn, the $^{64}$Zn-enriched zinc ("$^{64}$Zn$_e$") preferably is present as a chelate of an amino acid, such as of asparaginate, aspartate or glutamate. $^{64}$Zn-enriched zinc may also be provided, for example, in the form of a salt or chelate with sulfate, citrate, or ethylene diamine disuccinic acid (referred to herein both as "EDDA" and as "EDDS").

In alternative embodiments, any of the above compositions can comprise as a therapeutic agent at least one light isotope selected from any subgroup selected from the group consisting of K-39, Mg-24, Zn-64, Rb-85, Si-28, Ca-40, Cu-63, Fe-54, Cr-52, Ni-58, Mo-92, Se-74, Br-79, and Cl-35, each independently either in elemental form or in the form of a pharmaceutically acceptable salt, compound, chelate, or complex, wherein the composition is enriched for the at least one light isotope relative to the natural abundance of the isotope.

In various embodiments, the light isotope in the composition of the invention is present in elemental form or in the form of one or more of an oxide, sulfate, citrate, gluconate, chelate, or other compound, or in any other pharmaceutically acceptable form. The at least one light isotope may be present in the composition in the form of a salt or chelate with a pharmaceutically acceptable inorganic or organic acid. Exemplary salts and chelates of the light isotope include the sulfate, glutamate, asparaginate, aspartate, citrate, and ethylene diamine disuccinate of the light isotope. Preferred chelates and salts of the light isotope are formed in combination with an amino acid generally, preferably an amino acid that occurs naturally, such as one of the twenty amino acids that occur in the vast majority of proteins.

In an embodiment, the composition of the invention further comprises an active ingredient in addition to the light isotope active ingredient. In an embodiment, the composition of the invention comprises an agent that enhances the stability of the composition.

The light isotope may constitute between about 0.1% and about 99% of the composition by weight. When the light isotope is present in the form of a salt, the anionic portion of the salt acts as a carrier. When water is part of the said composition, it may function as a carrier and diluent.

The composition of the invention can be used in medicine to treat humans and non-human animals, including veterinary mammals. The compositions described above can be used in the methods detailed below.

A method of using the pharmaceutical composition to improve health, cure abnormalities and degenerative disease and achieve therapeutic effect on mammals is provided. The method begins with preparing the pharmaceutical carrier and the isotope selective ingredient including at least one of the chemical element and the chemical compound containing the chemical element whereby isotope distribution in the at least one of the chemical element and the chemical compound containing the chemical element is different from natural distribution of at least one of isotopes wherein the part of selected isotope of the chemical element ranges from 0 to 100%.

The next step of the method includes administering the first of the isotopes at least prior to and after surgical removal of a solid tumor to prevent possible metastases and occurrence of secondary effects and to prevent metastasizing followed by administering a second of the isotopes to transform a cancer cell phenotype into a normal cell. The first of the isotopes administered prior to and after surgical removal of the solid tumor to prevent possible metastases include at least one of K-39; Mg-24; Zn-64; Rb-85; Si-28; Ca-40; Cu-63; Fe-54; Cr-52; Ni-58; Mo-92; Se-74; Br-79; Cl-35 and combination thereof. The second of the isotopes used to transform the cancer cell phenotype into the normal cell includes at least one of K-39, Mg-24, Zn-64, Rb-85, Si-28 and combination thereof. The step of administering the pharmaceutical carrier can be carried out orally, intravenously and locally without limiting the scope of the present invention. The isotope selective ingredient may be administered prior to and after surgical removal of a solid tumor to prevent further spreading of cancer cells and metastasizing of a primary tumor. The chemotherapeutic agent includes at least one of Actinomycin, All-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, and Vinorelbine. The method of the present invention allows administering the isotope selective ingredient to cause fast and significant reduction in degree of malignancy and to induce changes of cells phenotype form malignant phenotype to a benign or normal phenotype.

The isotope selective ingredient administered at least prior to, after and simultaneously with chemotherapeutic agent are used to amplify therapeutic effect on cancer tissue and to protect healthy tissue from chemotherapy side effects and from immunotherapy side effect. The method of the present invention allows administering the isotope selective ingredient to cause fast and significant reduction in degree of malignancy and to induce changes of cells phenotype form malignant phenotype to a benign or normal phenotype. The person skilled in the art can provide shifting the balance in favor of youth and health with right combination of light isotopes in optimal doses. In general, isotope compositions and doses are always case specific. For the purpose of diseases and aging prevention, daily intake doses are sufficient. For therapeutic treatment much higher doses like triple daily intake are more suitable.

In another embodiment, the invention provides a method for suppressing the development of malignant ascites in a human or animal patient (e.g. a veterinary animal) and also provides a method for the treatment of cancers causing ascites and/or the suppression of cancer metastasis both in humans and in animals. Alternatively viewed, the invention provides a method of treating cancer, such as solid and non-solid tumors, and of preventing, suppressing, or reducing the extent of metastasis. The method comprises the step of administering the composition of the invention, described above, to a patient in need of such treatment by a route suitable to the form of the composition and the form of cancer being treated, e.g. orally, topically, or by injection (such as intravenous injection, intraperitoneal injection, or injection into the tumor itself). In a preferred aspect, the composition is a liquid composition, e.g. an aqueous solution as described above, and the method comprises administering the liquid composition via intraperitoneal injection, intravenous injection or injection into the tumor. It is preferred that the administration of the liquid composition be intraperitoneal. The dose of the light isotope-enriched compound may vary depending on the severity of the disease, the condition of the patient and other factors that will be considered by a practitioner skilled in the art when determining the dosage and administration route for the particular patient. In preferred embodiments of the method, the composition comprises an effective amount of one or more of $^{64}$Zn-enriched zinc, $^{24}$Mg-enriched magnesium, $^{85}$Rb-enriched rubidium, $^{39}$K-enriched potassium, and $^{54}$Fe-enriched iron. In preferred embodiments, the cancer treated is breast cancer or leukemia.

Both oral and intravenous administration of pharmaceutical compositions are considered as efficient. Ideally, the supply/intake of any heavy isotopes (especially K, Zn and Mg) should be excluded for as long as possible, but at least several hours prior and after administration of medicine. Food with natural distribution of isotopes to be avoided. To get better and staying healthy requires constant isotope-selective treatment or diet. Taking into consideration current situation with price and availability of light isotopes—for as long as practical. In vivo experiments results demonstrate that isotope-selective treatment allows for transformation of pathology affected cells into ones with normal or close to normal phenotype in the matter of days.

An advantage of the present invention is to provide a pharmaceutical composition and a method of using the pharmaceutical composition to improve health, cure abnormalities and degenerative disease and achieve therapeutic effect on mammals.

Another advantage of the present invention is to provide the pharmaceutical composition and the method of using the pharmaceutical composition to amplify therapeutic effect on cancer tissue and to protect healthy tissue from chemotherapy side effects and from immunotherapy side effect.

Still another advantage of the present invention is to provide the pharmaceutical composition and the method of using the pharmaceutical composition to allow administering the isotope selective ingredient to cause fast and significant reduction in degree of malignancy and to induce changes of cells phenotype form malignant phenotype to a benign or normal phenotype.

Still another advantage of the present invention is to provide the pharmaceutical composition and the method of using the pharmaceutical composition to allow administering the first of the isotopes at least prior to and after surgical removal of a solid tumor to prevent possible metastases and occurrence of secondary effects and to prevent metastasizing followed by administering a second of the isotopes to transform a cancer cell phenotype into a normal cell. The first of the isotopes administered prior to and after surgical removal of the solid tumor to prevent possible metastases.

These and other objects of the present invention will become readily apparent upon further review of the following specification and drawings.

Other objects, features, and advantages of the present invention will become apparent upon consideration of the following detailed description of a preferred embodiment thereof, when taken in conjunction with the appended drawing.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1B illustrates a Table of Concentration Characteristics of Components;

FIG. 2 illustrates results of Immunocytochemical Analysis of Adhesion Proteins and Cytoskeleton of N-cadherin and ICAM in Namalwa Cells after the Action of Components Containing $^{39}$K, $^{64}$Zn and $^{24}$Mg;

FIG. 6 illustrates results of Immunocytochemical Analysis of Adhesion Proteins and Cytoskeleton of CD44 and IgM in Namalwa Cells after the Action of Components Containing $^{39}$K, $^{64}$Zn and $^{24}$Mg;

FIG. 7 illustrates results of Immunocytochemical Analysis of Adhesion Proteins and Cytoskeleton of N-cadherin, ICAM and CD44 in HL-60 Cells after the Action of Components Containing $^{39}$K, $^{64}$Zn and $^{24}$Mg;

FIG. 22 illustrates an effect of $^{39}$K, $^{64}$Zn and $^{24}$Mg on cells of strain of renal cell carcinoma in the in vitro experiment, experiment with 30 000 cells;

FIG. 23 illustrates an effect of $^{39}$K, $^{64}$Zn and $^{24}$Mg on cells of strain of renal cell carcinoma in the in vitro experiment Experiment with 300 000 cells;

FIG. 25 illustrates an effect of K, Zn and Mg elements with natural isotope distribution on the number of viable cells in the in vitro experiment, experiment with 300 000 cells;

FIG. 27 illustrates a concentration of $^{39}$K, $^{64}$Zn and $^{24}$Mg (as sulphates and chloride) which caused 50% and 100% changes in the appearance of cells from initial tumor cells into cells of type A based on Trypan blue staining;

FIG. 28 illustrates a comparative concentrations of K, Zn and Mg components with natural isotope distribution vs. Doxorubicin EBEWE, which caused death of 50% and 100% of tumor cells obtained using trypan blue and crystal violet staining methods;

FIG. 30 illustrates an ability of initial PA tumor cells to transform into A cells in the experiment with 30 000 tumor cells after treating them with $^{39}$K, $^{64}$Zn and $^{24}$Mg;

FIG. 45 illustrates results of tests on renal cell carcinoma (PA) in a rat: Adhesion and cytoskeletal proteins in renal cell carcinoma (PA) cells after their exposure to the action of light isotopes $^{64}$Zn, $^{24}$Mg and $^{39}$K at doses D1 and D2;

FIGS. 66A-66F illustrate E-cadherin expression in cells after the action of $^{39}$K component: A-549 (A, B, C), COLO 205 (D, E, F), (magnification ×100);

FIG. 67 illustrates Adhesion and cytoskeletal proteins in the cells of human non-small cell lung cancer (A-549 line) after their exposure to the action of $^{39}$K, $^{64}$Zn and $^{24}$Mg components at the dose of IC50;

FIG. 68 illustrates an adhesion and cytoskeletal proteins in the cells of human breast cancer (MCF-7 line) after their exposure to the action of $^{64}$Zn and $^{24}$Mg components at the dose of IC50;

FIG. 69 illustrates an adhesion and cytoskeletal proteins in the cells of human colon adenocarcinoma (COLO 205 line) after their exposure to the action of $^{39}$K, $^{64}$Zn and $^{24}$Mg components at the dose of IC50

FIGS. 71A-71F illustrate E-cadherin expression in cells after their exposure to the action of $^{24}$Mg: A-549 (A, B), MCF-7 (C, D), COLO 205 (E, F) (magnification ×100);

FIG. 72 illustrates an adhesion and cytoskeletal proteins in immortalized cells of a rat (NRK) after their exposure to the action of $^{64}$Zn and $^{64}$Zn-Z2 at a dose of IC50 ($^{64}$Zn-Z2 component $^{64}$Zn after 14 days storage at T=+4° C.);

FIG. 73 illustrates E-cadherin expression in control cells NRK (not exposed to the action of preparations) (magnification ×100);

FIG. 74 illustrates N-cadherin expression in control cells NRK (not exposed to the action of preparations) (magnification ×100);

FIG. 75 illustrates CD44 expression in control cells NRK (not exposed to the action of preparations) (magnification ×100);

FIG. 89 illustrates slug marker expression in cells of MCF-7 line after their exposure to the action of $^{64}$Zn at a dose of IC50 (magnification ×100

FIG. 90 illustrates slug marker expression in cells of MCF-7 line after their exposure to the action of $^{24}$Mg at a dose of IC50 (magnification ×100);

FIG. 91 illustrates quantitative characteristics of cells of type A in A-549 cell line (%) after their exposure to the action of $^{39}$K stored at T+4° C. for 20 days in a dissolved state in comparison with the efficiency of a fresh solution;

FIGS. 98A-98I illustrate cytogenetic characteristics: a) mitosis; b) premature chromosome condensation; d, e, f) cells with micronuclei and apoptotic cells; g) nucleus with a protrusion; h, i) nuclear protrusions;

FIG. 99 illustrates a level of cytogenetic characteristics in cells of COLO 205 line after their exposure to the action of the components;

FIG. 100 illustrates a cytogenetic characteristics in cells of A-549 line after their exposure to the action of the isotopes FIG. 101 illustrates a cytogenetic characteristics in cells of MCF-7 line after their exposure to the action of the components;

FIGS. 102A-102D illustrate the number of cellular abnormalities in various cell lines as compared to control depending on the concentration of the components used;

Figure 1A:
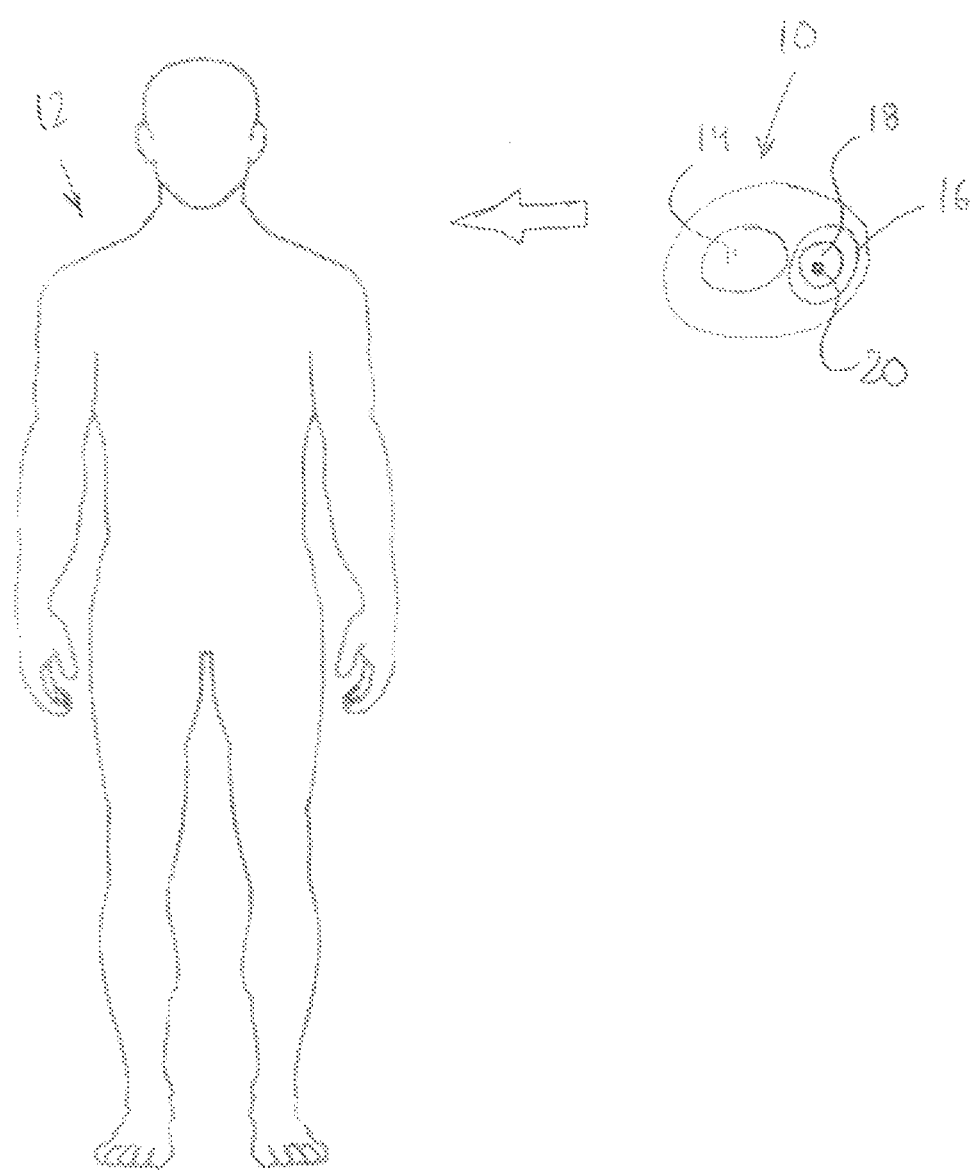
FIG. 1A is a schematic view of a pharmaceutical composition of the present invention used for improving health, cure abnormalities and degenerative disease, achieve anti-aging effect of therapy and therapeutic effect on a mammal.
Figure 3A:
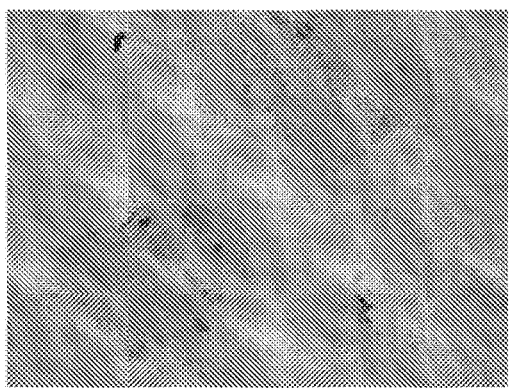
FIGS. 3A-3D illustrate an expression of N-cadherin in Namalwa cells.
Figure 3B:
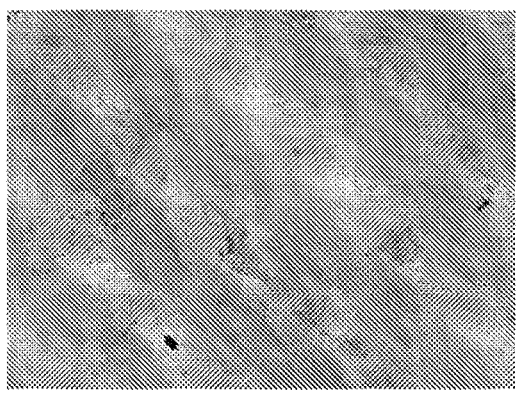
Figure 3C:
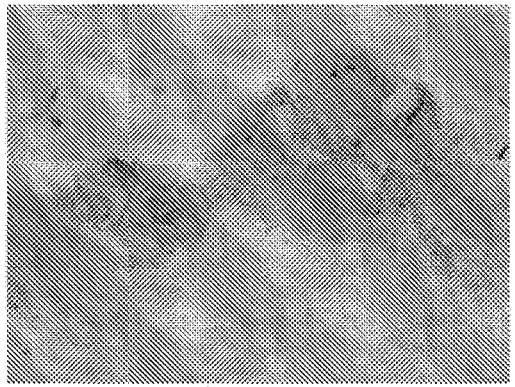
Figure 3D:
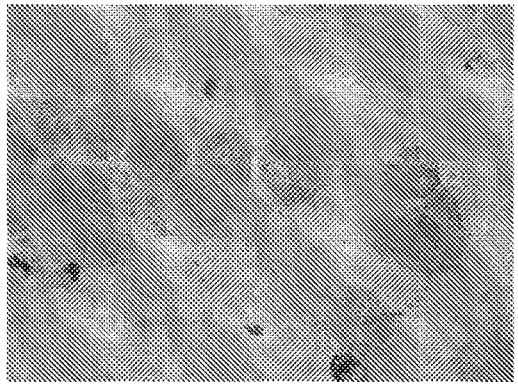
Figure 4A:
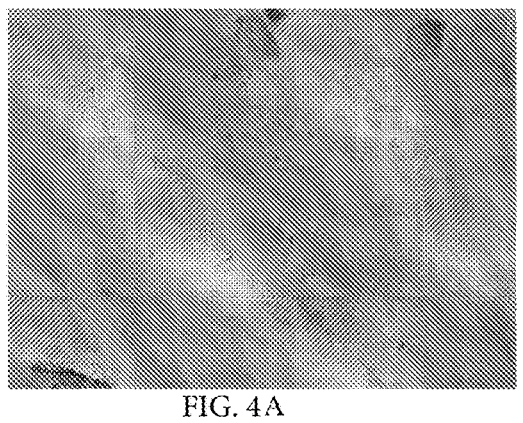
FIGS. 4A-4D illustrate an expression of CD44 marker in Namalwa cells A: control cells (no influence of the components), B: cells after the action of component containing $^{39}$K at a dose of 2 mg/ml, C: cells after the action of component containing $^{64}$Zn at a dose of 10 mcg/ml, D: cells after the action of component containing $^{24}$Mg at a dose of 2 mg/ml (lens ×100)
Figure 4B:

Figure 4C:
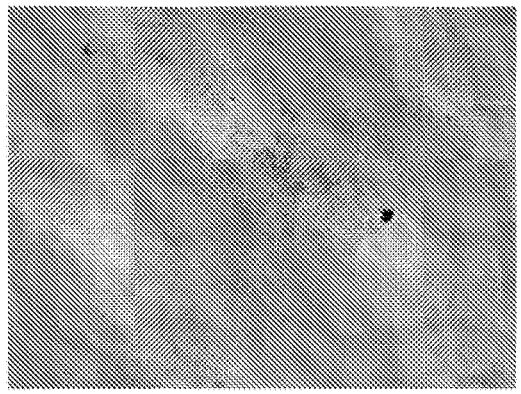
Figure 4D:
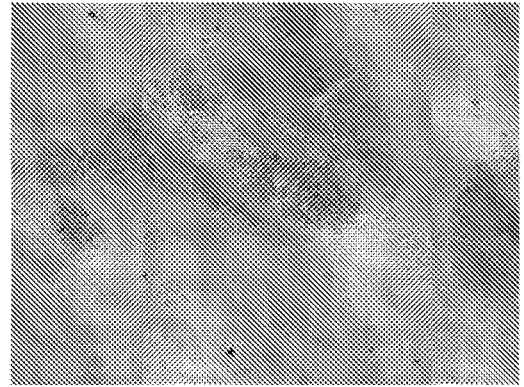
Figure 5A:
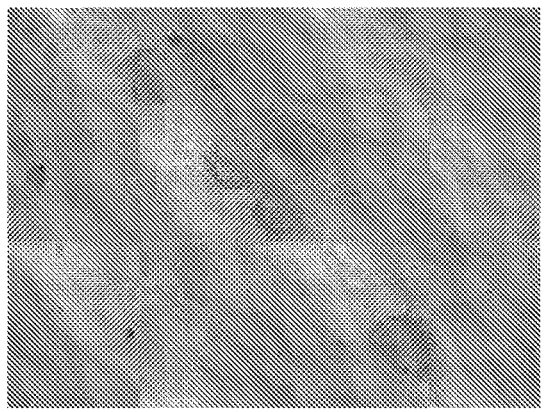
FIGS. 5A-5F illustrate an expression of ICAM in Namalwa cells A: control cells (no influence of the components), B: cells after the action of component containing $^{39}$K at a dose of 2 mg/ml, C and D: cells after the action of component containing $^{64}$Zn at a dose of 10 mcg/ml, E and F: cells after the action of component containing $^{24}$Mg at a dose of 2 mg/ml (lens ×100)
Figure 5B:
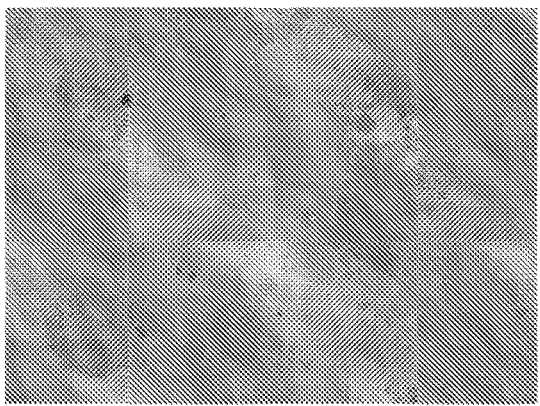
Figure 5C:
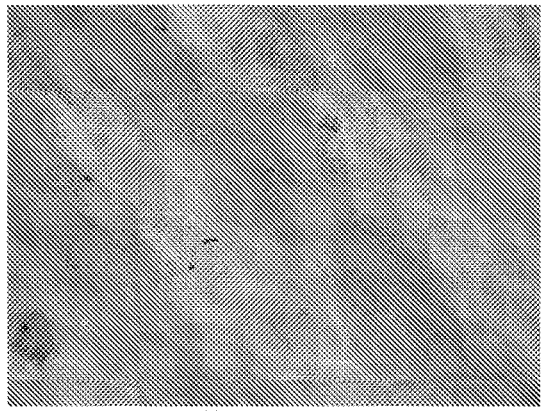
Figure 5D:
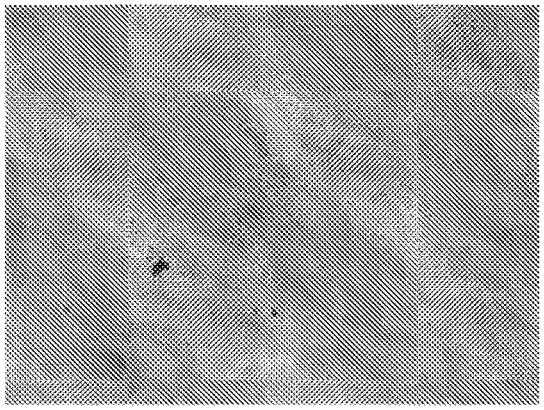
Figure 5E:
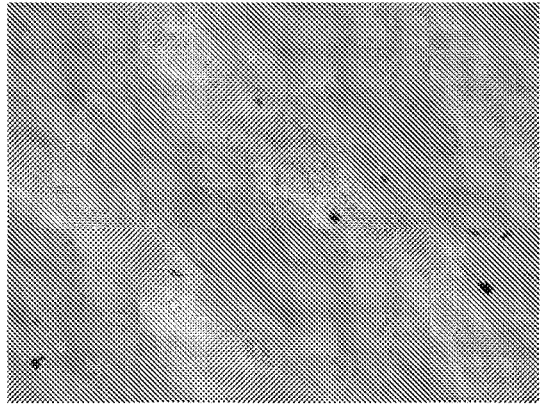
Figure 5F:
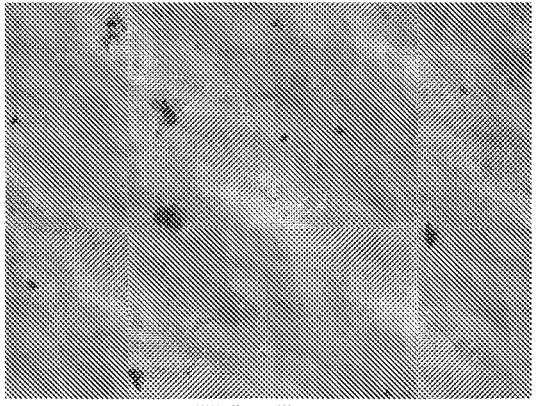
Figure 8A:
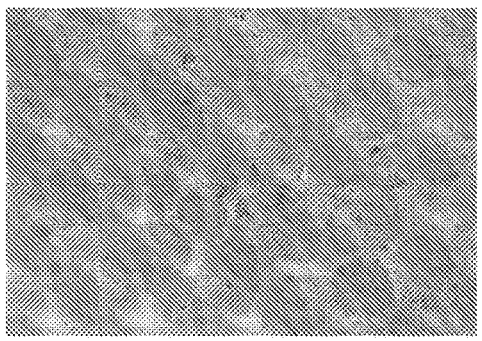
FIGS. 8A-8H illustrate an expression of CD44 in HL-60 cells A and B: control cells (no influence of the components), C and D: cells after the action of component containing $^{39}$K at a dose of 2 mg/ml, E and F: cells after the action of component containing $^{64}$Zn at a dose of 10 mcg/ml, G and H: cells after the action of component containing $^{24}$Mg at a dose of 2 mg/ml (lens ×100)
Figure 8B:
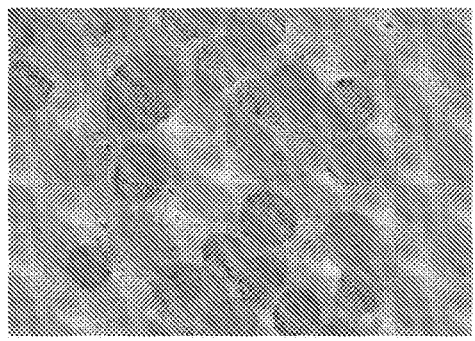
Figure 8C:
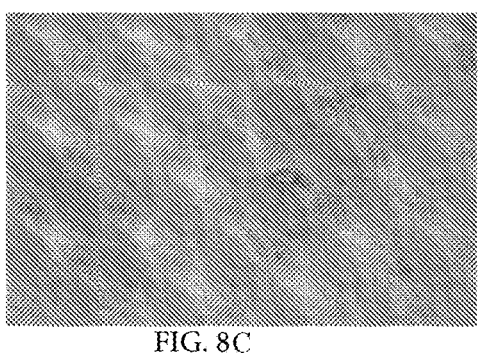
Figure 8D:
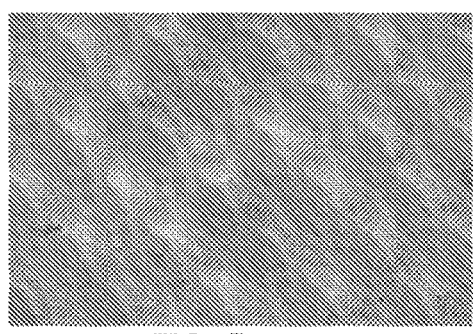
Figure 8E:
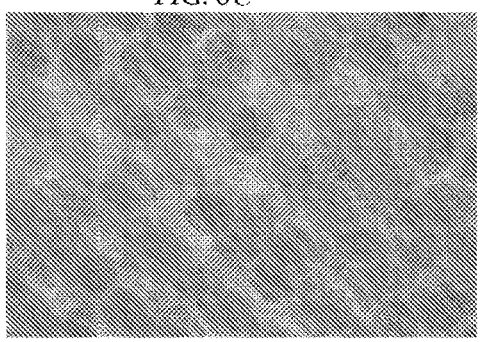
Figure 8F:
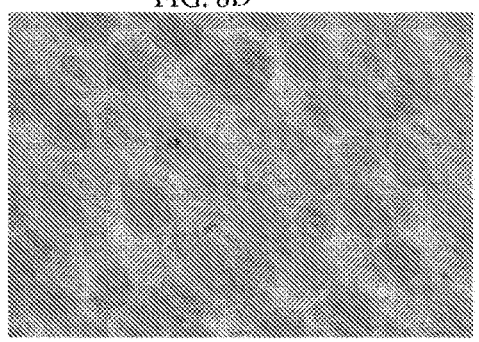
Figure 8G:
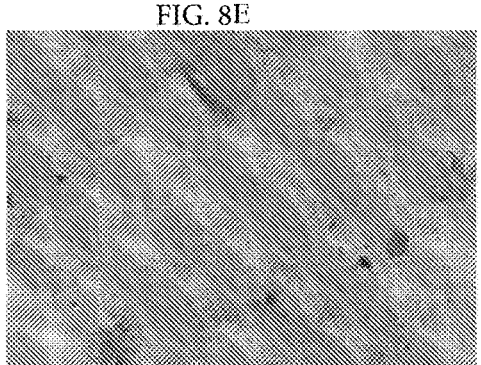
Figure 8H:
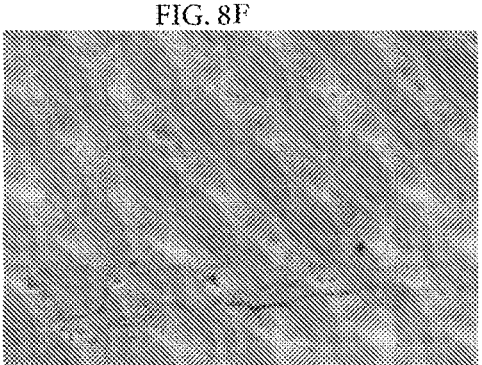
Figure 9A:
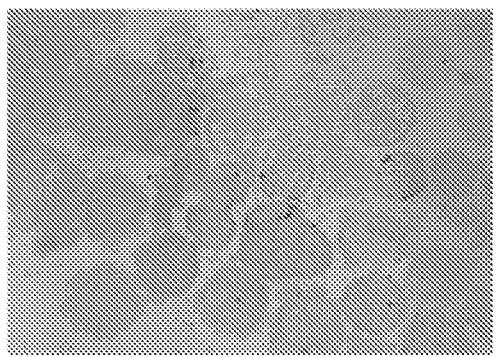
FIGS. 9A-9H illustrate an expression of ICAM in HL-60 cells A and B: control cells (no influence of the components), C and D: cells after the action of component containing $^{39}$K at a dose of 2 mg/ml, E and F: cells after the action of component containing $^{64}$Zn at a dose of 10 mcg/ml, G and H: cells after the action of component containing $^{24}$Mg at a dose of 2 mg/ml (lens ×100)
Figure 9B:
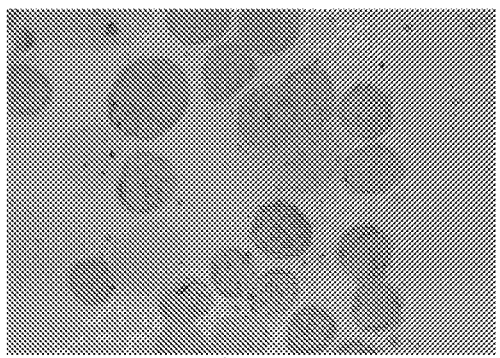
Figure 9C:
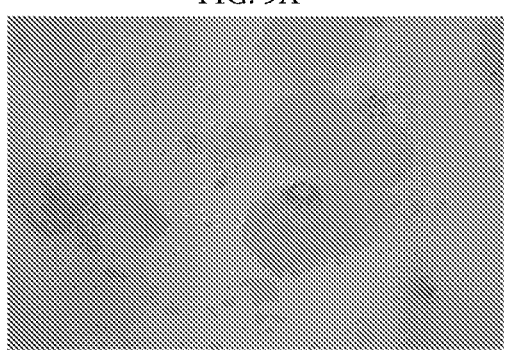
Figure 9D:
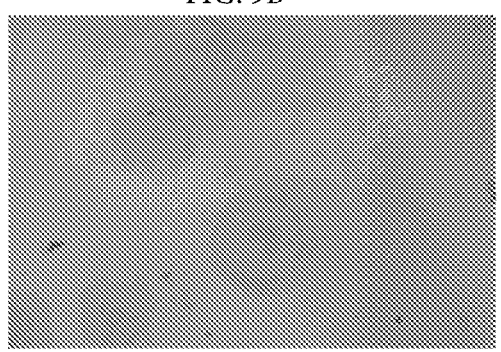
Figure 9E:
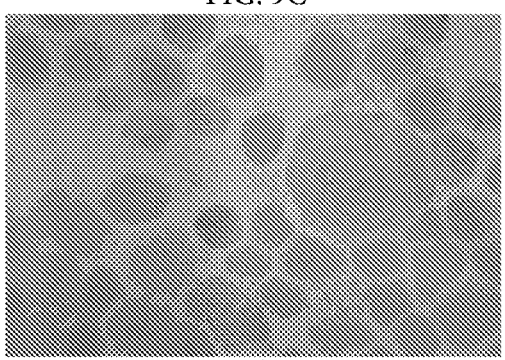
Figure 9F:
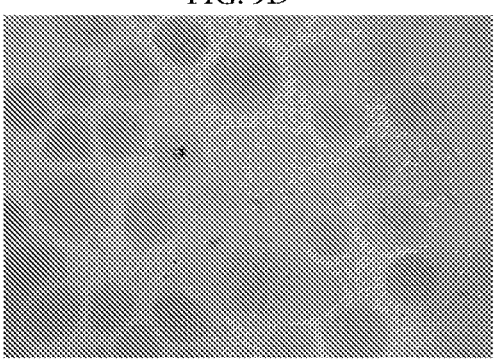
Figure 9G:
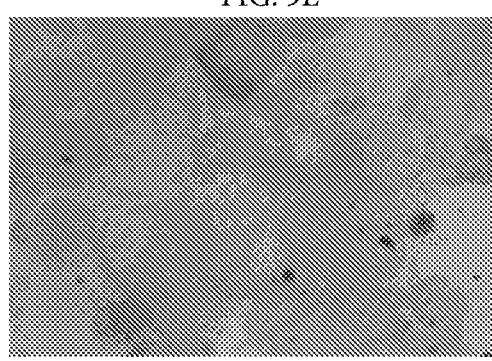
Figure 9H:
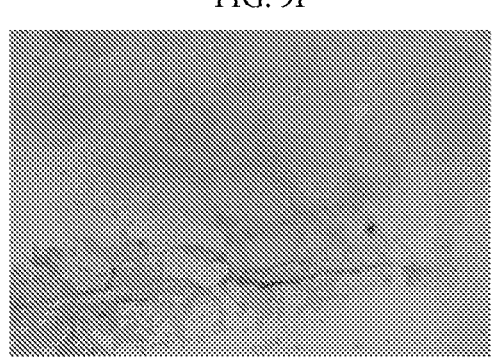
Figure 10A:
FIGS. 10A-10L illustrate Morphological and growth characteristics of cells of HL-60 cell line after their treatment with components containing $^{39}$K, $^{64}$Zn and $^{24}$Mg.
Figure 10B:
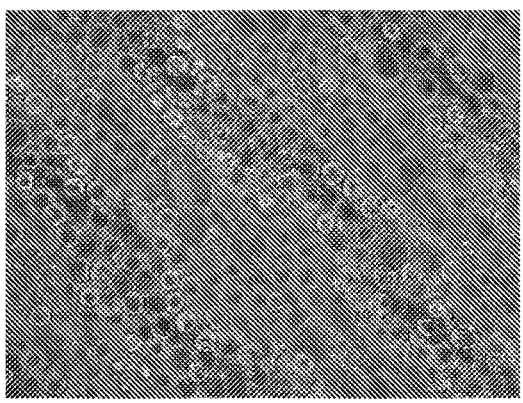
Figure 10C:
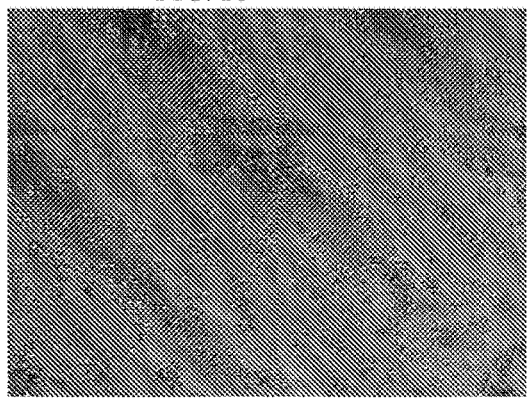
Figure 10D:
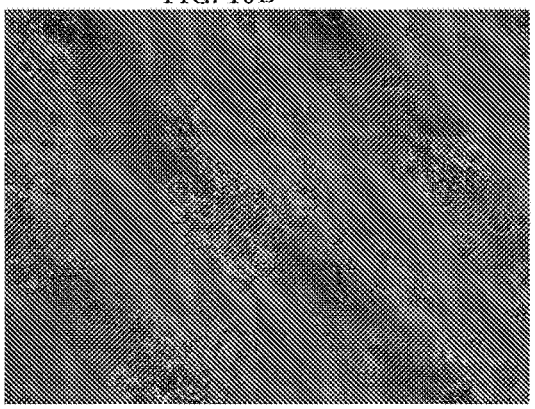
Figure 10E:
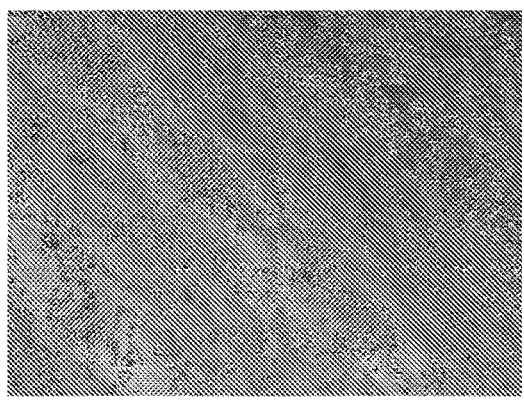
Figure 10F:
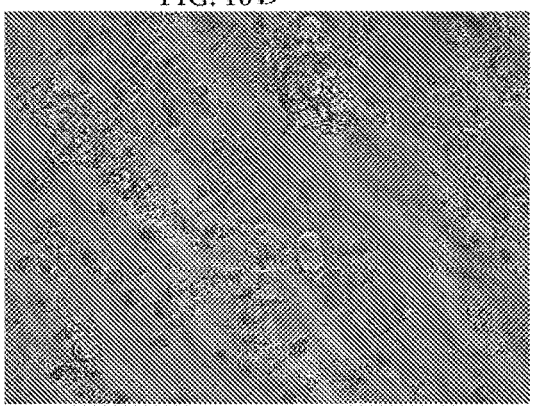
Figure 10G:
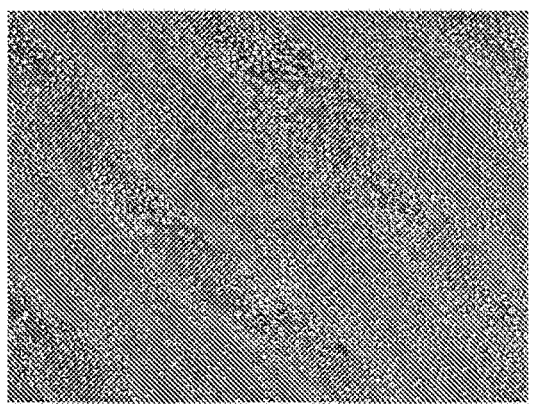
Figure 10H:
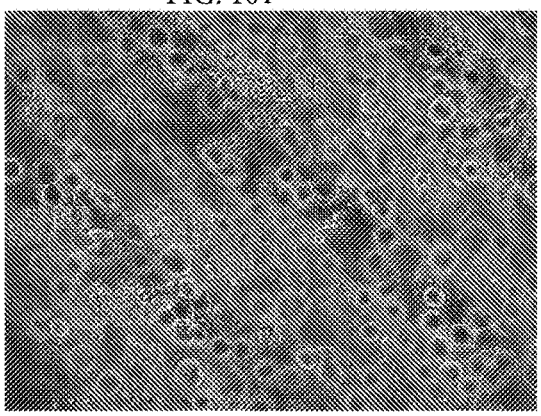
Figure 10I:
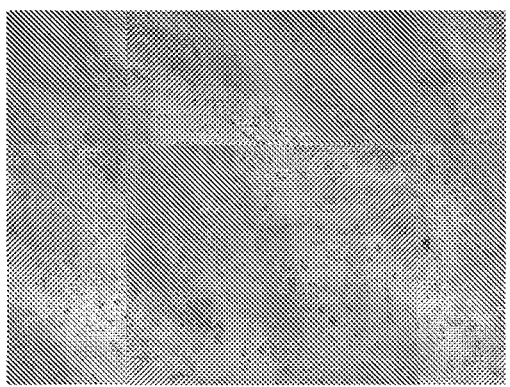
Figure 10J:
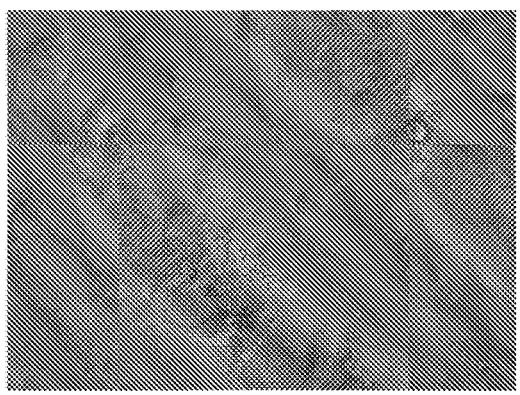
Figure 10K:
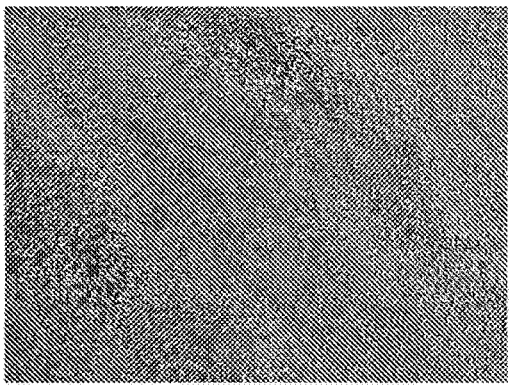
Figure 10L:
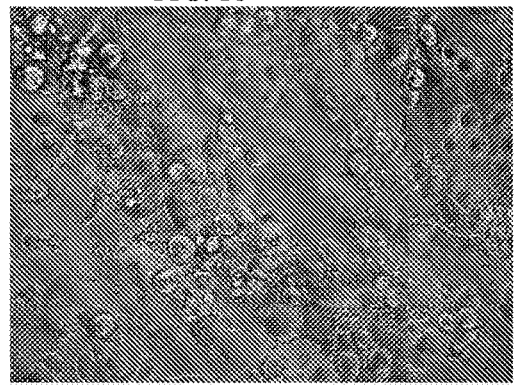
Figure 124A:
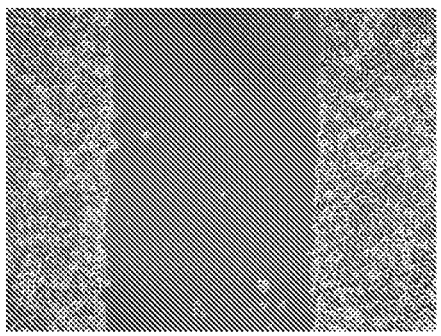
Figure 124B:
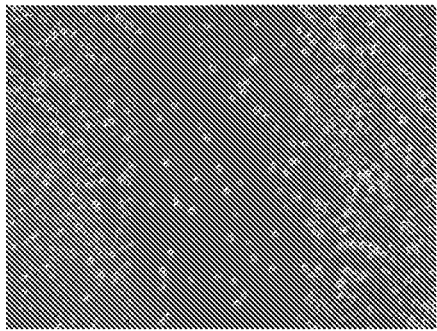
Figure 124C:
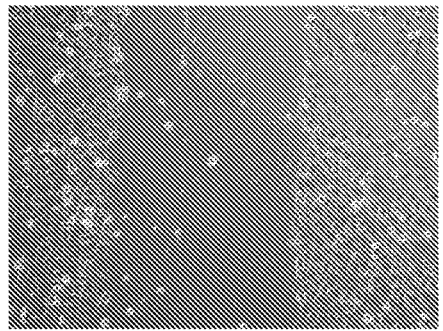
Figure 124D:
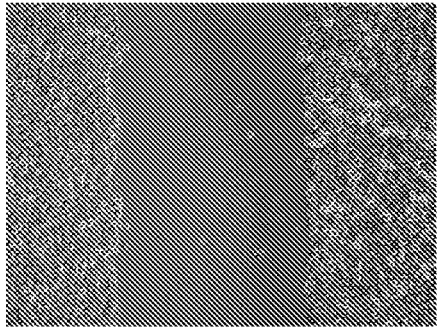
Figure 124E:
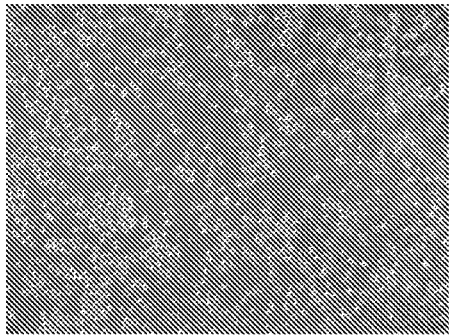
Figure 124F:
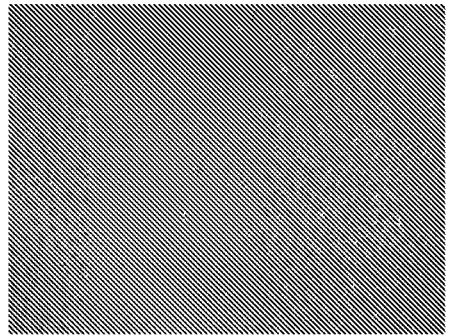
Figure 125A:
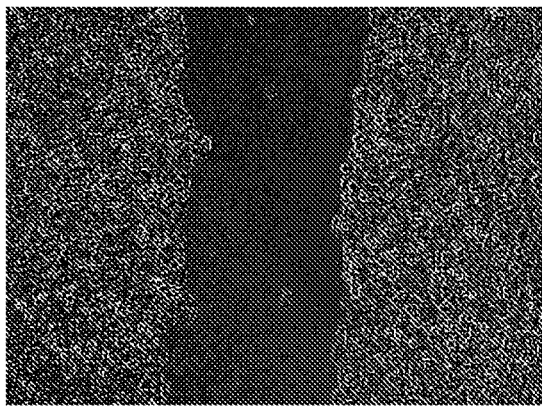
Figure 125B:
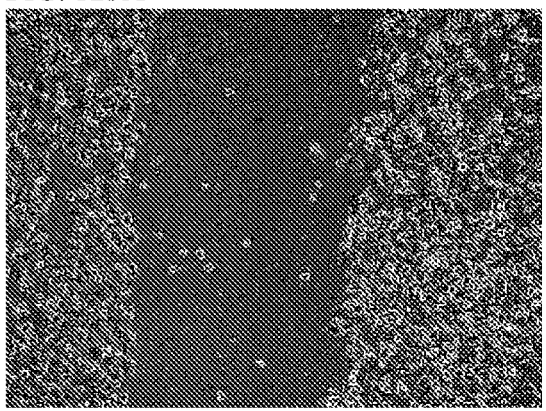
Figure 125C:
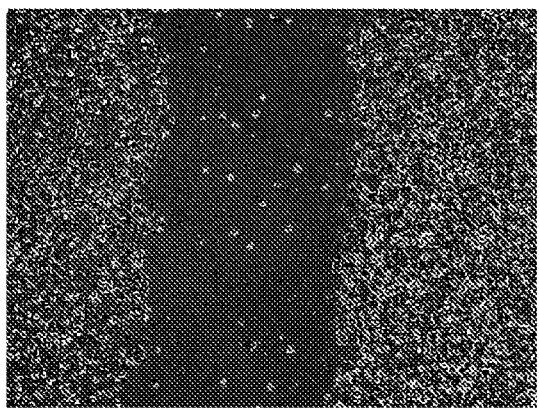
Figure 125D:
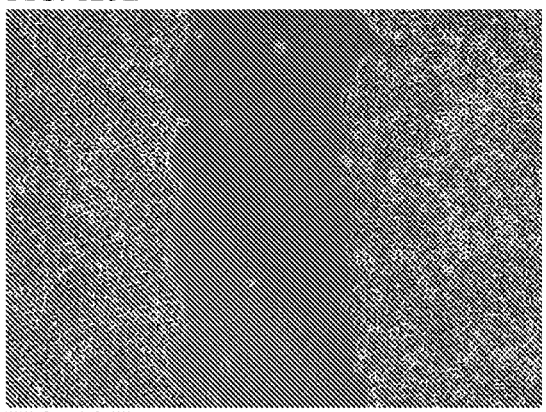
Figure 125E:
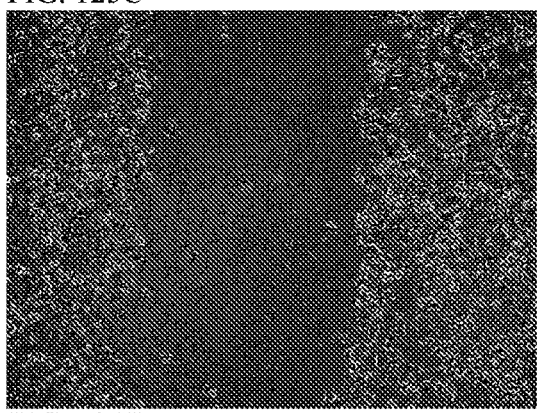
Figure 126A:
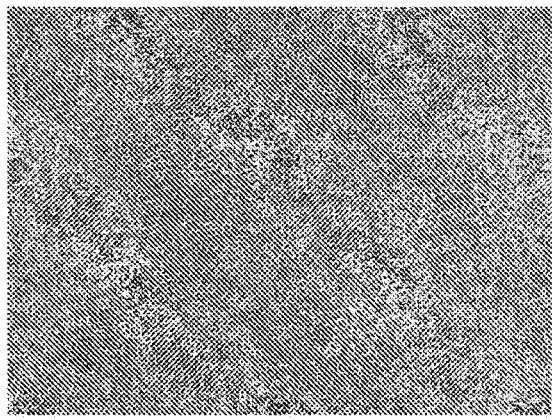
Figure 126B:
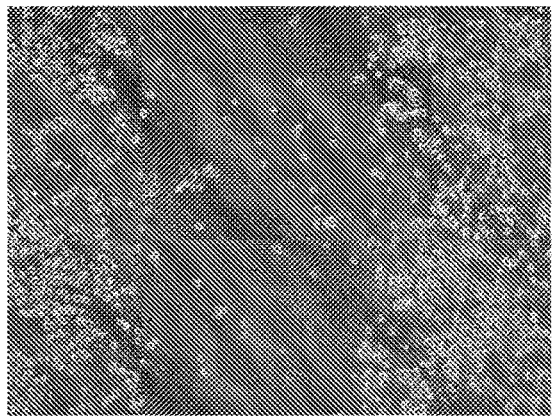
Figure 126C:
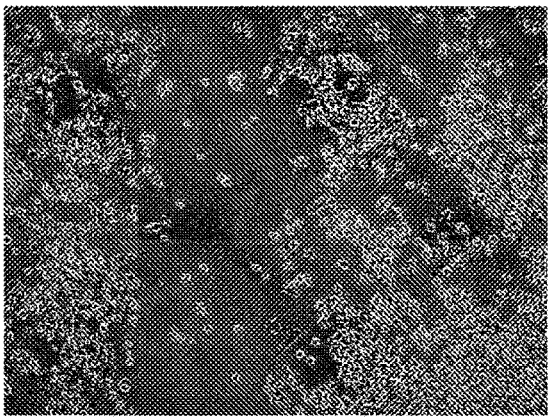
Figure 126D:
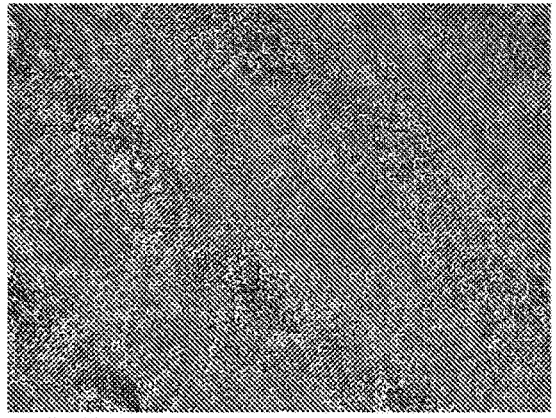
Figure 126E:
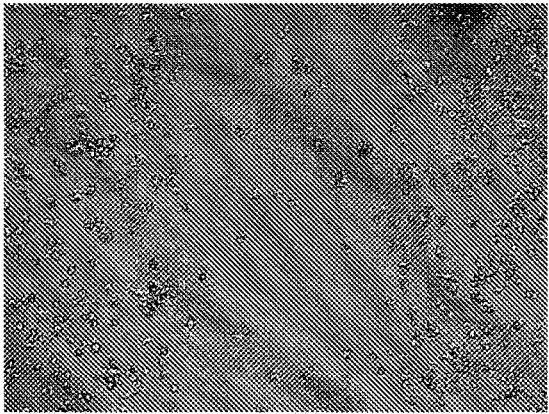
Figure 127:
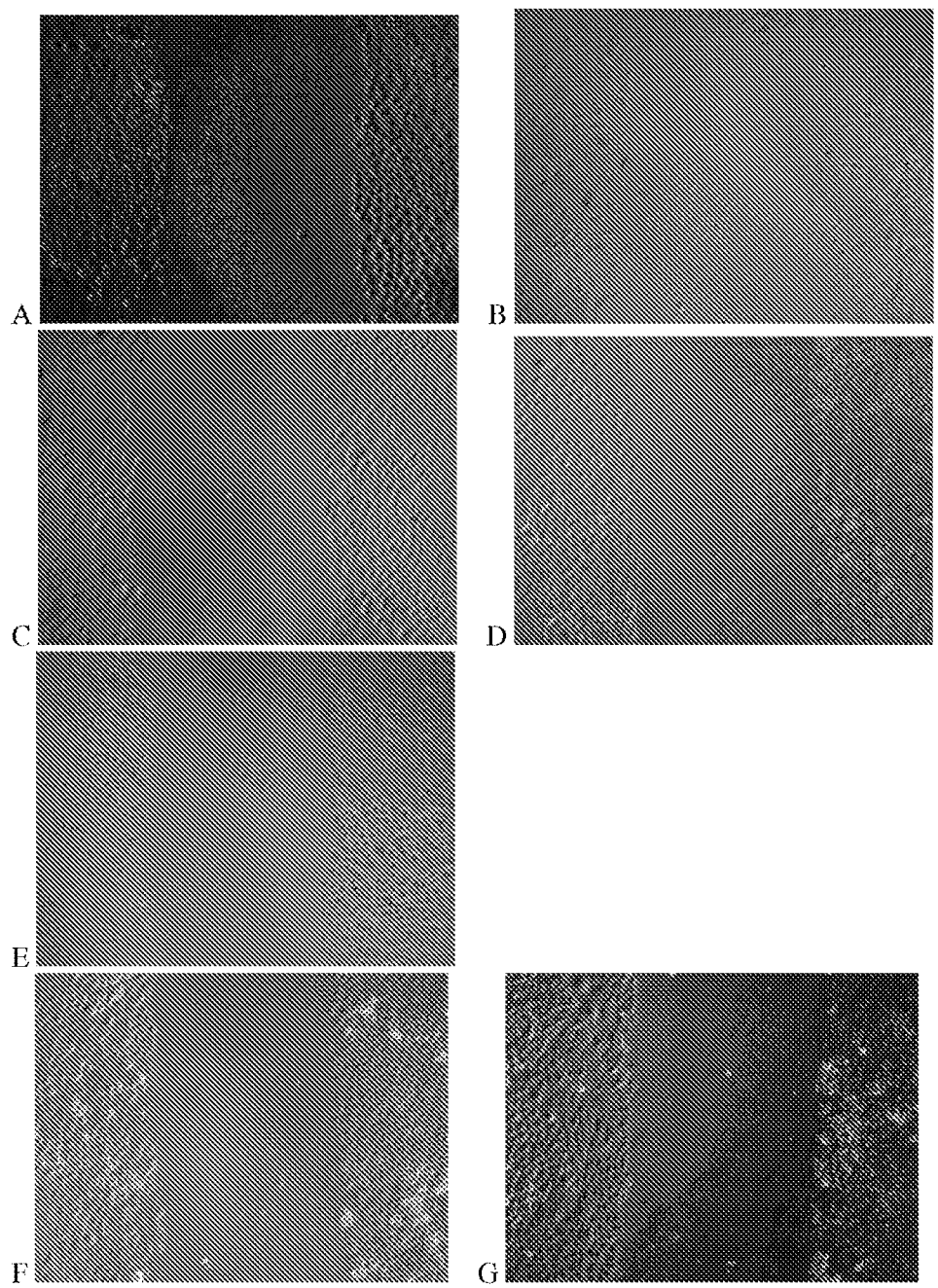
Figure 128:
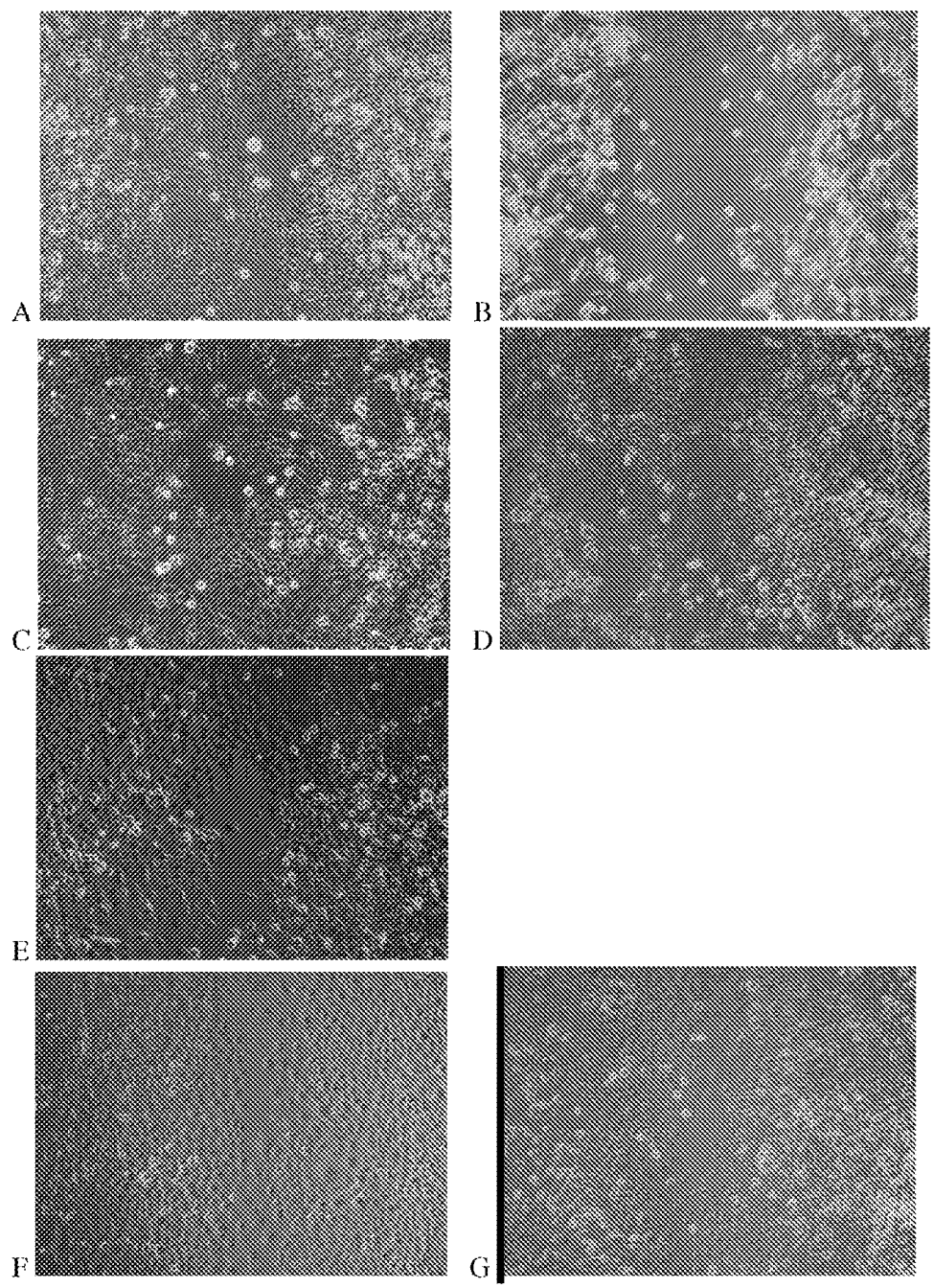
Figure 129:
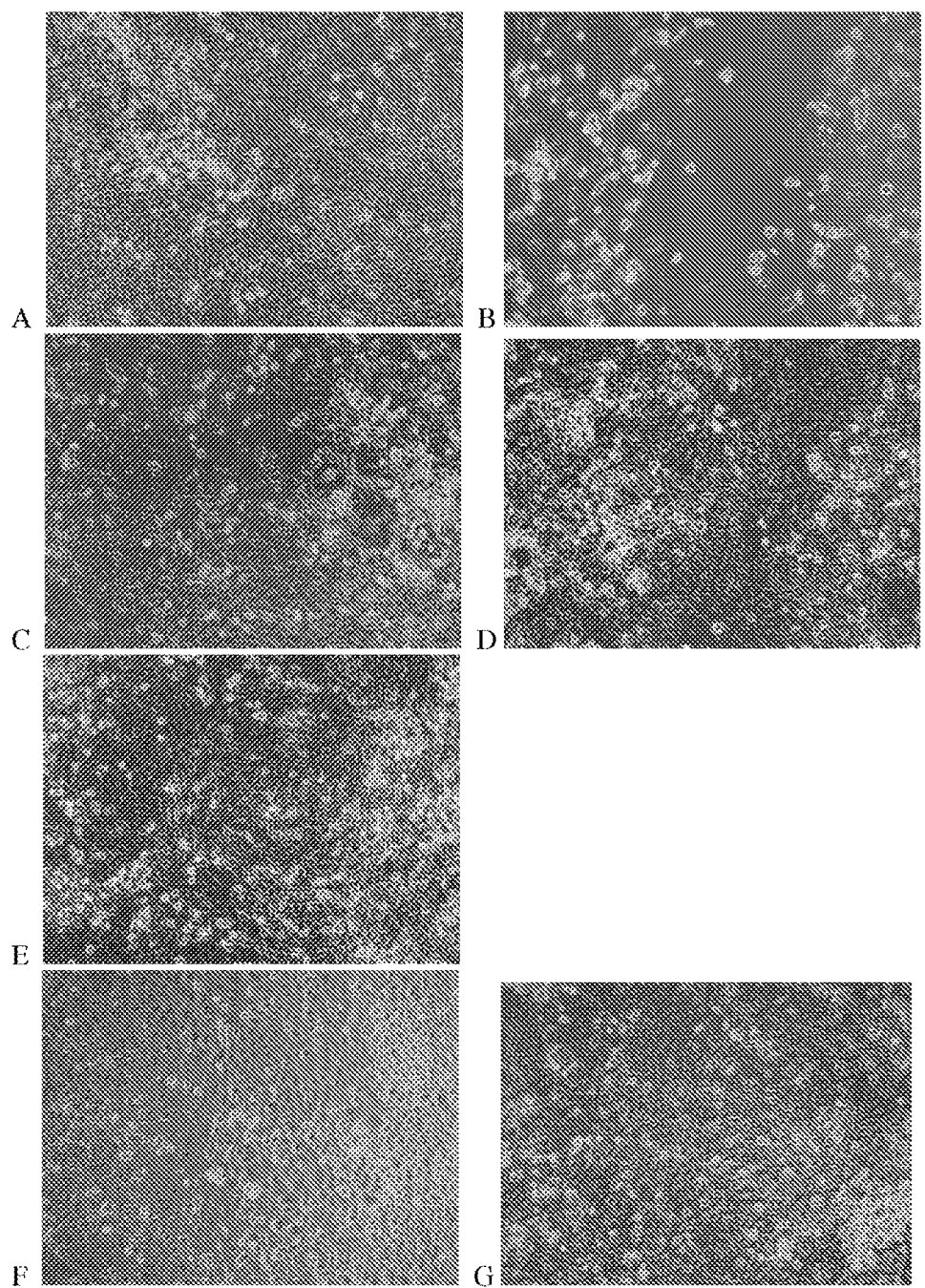

FIGS. 116A-116H illustrate a character of migration of tumor cells of A-549 cell line in the in vitro experiment with $^{39}$K, $^{64}$Zn and $^{24}$Mg components 72 hours following the cell monolayer damage: A. Control, B. A-549+Doxorubicin (2 meg/nil), C. A-549+$^{39}$K preparation (2 mg/ml), D. A-549+$^{39}$K preparation (3 mg/ml), E. A-549+$^{64}$Zn preparation (20 meg/nil), F. A-549+$^{64}$Zn preparation (30 meg/nil), G. A-549+$^{24}$Mg preparation (3 mg/ml), H. A-549+$^{24}$Mg preparation (4 mg/ml);

FIGS. 117A-117G illustrate a migration activity of cells of A-549 cell line after their processing with the experimental preparation (1 hour following the violation of the monolayer integrity): A. Control, B. A-549+Doxorubicin (0.2 meg/nil), C. A-549+$^{64}$Zn preparation (20 meg/nil), D. A-549+$^{64}$Zn preparation (10 meg/nil), E. A-549+$^{64}$Zn preparation (20 mcg/ml)+Doxorubicin (0.02 meg/nil), F. A-549+$^{64}$Zn preparation (10 mcg/ml)+Doxorubicin (0.2 meg/nil), G. A-549+$^{64}$Zn preparation (10 mcg/ml)+Doxorubicin (0.02 mcg/ml);

FIGS. 118A-118G illustrate a migration activity of cells of A-549 cell line after their processing with the experimental preparation (24 hours following the violation of the monolayer integrity): A. Control, B. A-549+Doxorubicin (0.2 meg/nil), C. A-549+$^{64}$Zn preparation (20 meg/nil), D. A-549+$^{64}$Zn preparation (10 meg/nil), E. A-549+$^{64}$Zn preparation (20 mcg/ml)+Doxorubicin (0.02 meg/nil), F. A-549+$^{64}$Zn preparation (10 mcg/ml)+Doxorubicin (0.2 meg/nil), G. A-549+$^{64}$Zn preparation (10 mcg/ml)+Doxorubicin (0.02 mcg/ml);

FIGS. 119A-119G illustrate a migration activity of cells of A-549 cell line after their processing with the experimental preparation (60 hours following the violation of the monolayer integrity): A. Control, B. A-549+Doxorubicin (0.2 meg/nil), C. A-549+$^{64}$Zn preparation (20 meg/nil), D. A-549+$^{64}$Zn preparation (10 meg/nil), E. A-549+$^{64}$Zn preparation (20 mcg/ml)+Doxorubicin (0.02 meg/nil), F. A-549+$^{64}$Zn preparation (10 mcg/ml)+Doxorubicin (0.2 meg/nil), G. A-549+$^{64}$Zn preparation (10 mcg/ml)+Doxorubicin (0.02 mcg/ml);

FIGS. 120A-120G illustrate a character of the migration activity of cells of RF cell line in the in vitro experiment with $^{39}$K, $^{64}$Zn and $^{24}$Mg components after the first hour of observation of the cell monolayer: A. Control, B. RF+Doxorubicin C. RF+$^{39}$K preparation (2 mg/ml), D. RF+$^{39}$K preparation (1 mg/ml), E. RF+$^{64}$Zn preparation (25 meg/nil) F. RF+$^{24}$Mg preparation (4 mg/ml) G. RF+$^{24}$Mg preparation (2 mg/ml);

FIGS. 121A-121G illustrate a character of the migration activity of cells of RF cell line in the in vitro experiment with $^{39}$K, $^{64}$Zn and $^{24}$Mg components after the 24-hour observation of the cell monolayer: A. Control, B. RF+Doxorubicin C. RF+$^{39}$K preparation (2 mg/ml), D. RF+$^{39}$K preparation (1 mg/ml), E. RF+$^{64}$Zn preparation (25 meg/nil) F. RF+$^{24}$Mg preparation (4 mg/ml) G. RF+$^{24}$Mg preparation (2 mg/ml);

FIGS. 122A-122G illustrate a character of the migration activity of cells of RF cell line in the in vitro experiment with $^{39}$K, $^{64}$Zn and $^{24}$Mg components after the 48-hour observation of the cell monolayer: A. Control, B. Effect of Doxorubicin C. Fibroblasts+$^{39}$K preparation (2 mg/ml), D. RF+$^{39}$K preparation (1 mg/ml), E. RF+$^{64}$Zn preparation (25 meg/nil) F. RF+$^{24}$Mg preparation (4 mg/ml) G. RF+$^{24}$Mg preparation (2 mg/ml);

FIGS. 123A-123G illustrate a character of the migration activity of cells of RF cell line in the in vitro experiment with $^{39}$K, $^{64}$Zn and $^{24}$Mg components after the 72-hour observation of the cell monolayer: A. Control, B. Effect of Doxorubicin C. Fibroblasts+$^{39}$K preparation (2 mg/ml), D. RF+$^{39}$K preparation (1 mg/ml), E. RF+$^{64}$Zn preparation (25 meg/nil) F. RF+$^{24}$Mg preparation (4 mg/ml) G. RF+$^{24}$Mg preparation (2 mg/ml);

FIGS. 124-124F illustrate a migration activity of cells of the RF cell line after their processing with the experimental preparation (1 hour following the violation of the monolayer integrity): A. Control, B. RF+Doxorubicin (15 ng/ml), C. RF+Doxorubicin (5 ng/ml), D. RF+$^{64}$Zn preparation (25 meg/nil), E. RF+$^{64}$Zn preparation (25 mcg/ml)+Doxorubicin (15 ng/ml), F. RF+$^{64}$Zn preparation (25 mcg/ml)+Doxorubicin (5 ng/ml);

FIGS. 125A-125E illustrate a migration activity of cells of the RF cell line after their processing with the experimental preparation (24 hours following the violation of the monolayer integrity): A. Control, B. RF+Doxorubicin (15 ng/ml), C. RF+Doxorubicin (5 ng/ml), D. RF+$^{64}$Zn preparation (25 mcg/ml), E. RF+$^{64}$Zn preparation (25 mcg/ml)+Doxorubicin (5 ng/ml);

FIGS. 126A-126E illustrate a migration activity of cells of the RF cell line after their processing with the experimental preparation (72 hours following the violation of the monolayer integrity): A. Control, B. RF+Doxorubicin (15 ng/ml), C. RF+Doxorubicin (5 ng/ml), D. RF+$^{64}$Zn preparation (25 meg/nil), E. RF+$^{64}$Zn preparation (25 mcg/ml)+Doxorubicin (5 ng/ml);

FIGS. 127A-127G illustrate a cell migration of the NRK cell line in vitro after their processing with the experimental preparations (1 hour following the violation of the monolayer integrity): A. Control, B. NRK+Doxorubicin, C. NRK+$^{39}$K component (2 mg/ml), D. NRK+$^{39}$K component (1 mg/ml), E. NRK+$^{64}$Zn component (25 meg/nil), F. NRK+$^{24}$Mg component (4 mg/ml), G. NRK+$^{24}$Mg component (2 mg/ml).

Figure 14:
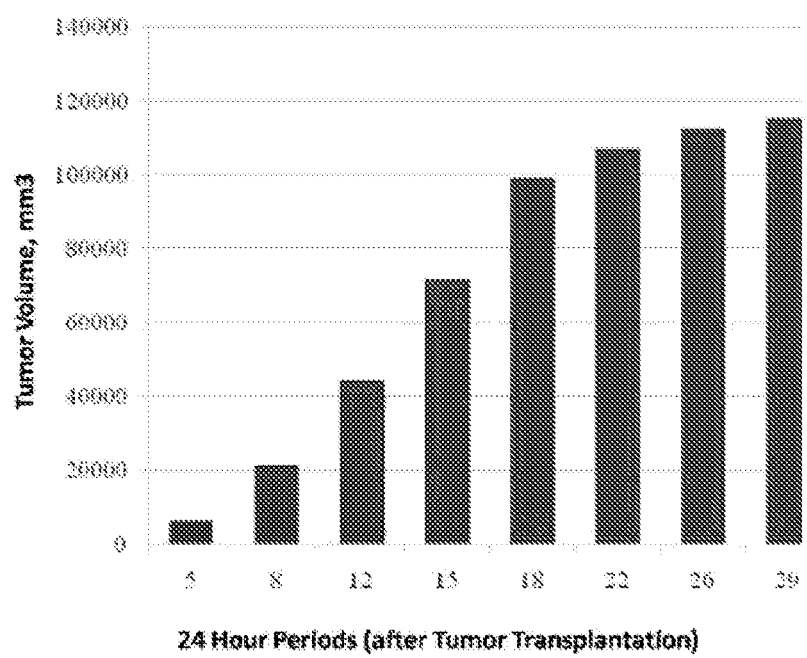
FIG. 14 illustrates a tumor growth chart built on the results of observations of an animal with the transplanted tumor for 29 days, which chart clearly describes the kinetics of the tumor growth (FIG. 3, 4)
Figure 15:
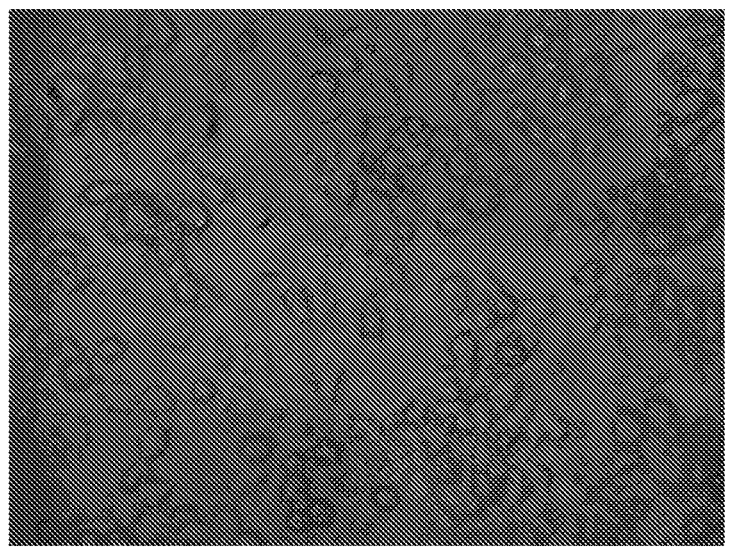
FIG. 15 illustrates kinetics of PA tumor growth in the laboratory animal.
Figure 130A:
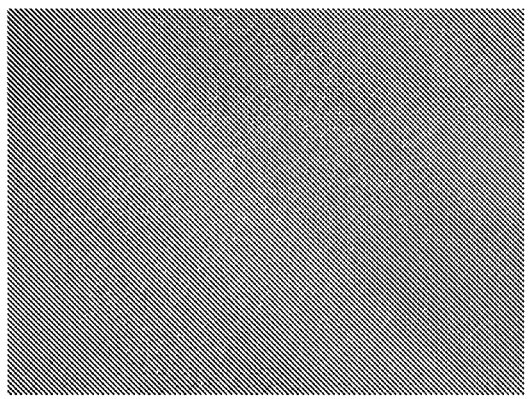
Figure 130B:
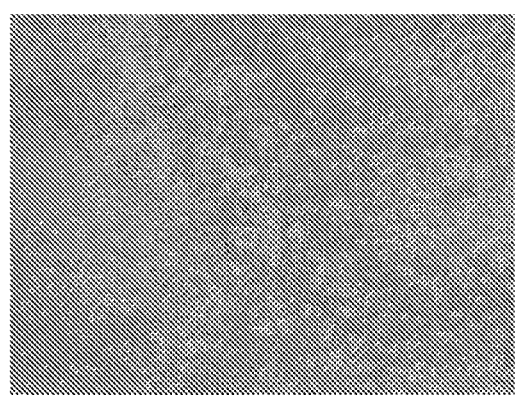
Figure 131A:
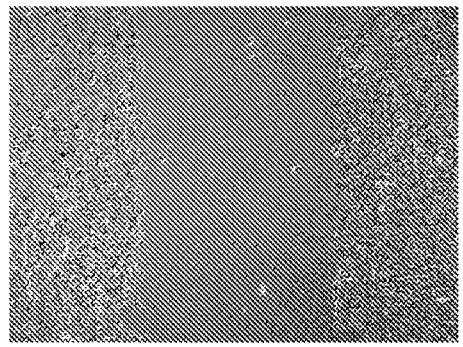
Figure 131B:
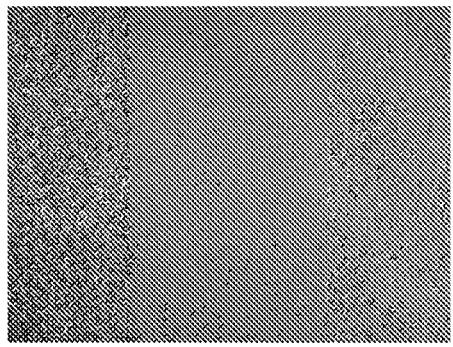
Figure 131C:
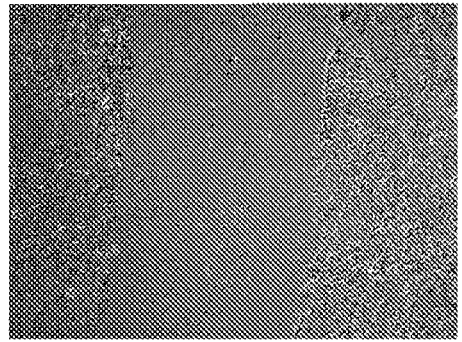
Figure 131D:
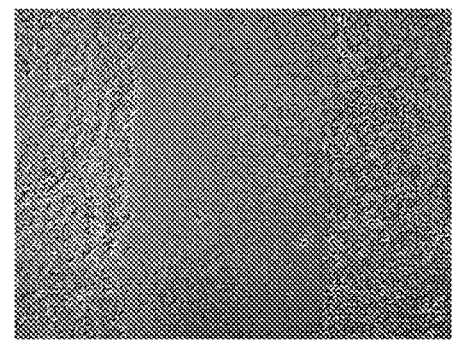
Figure 131E:
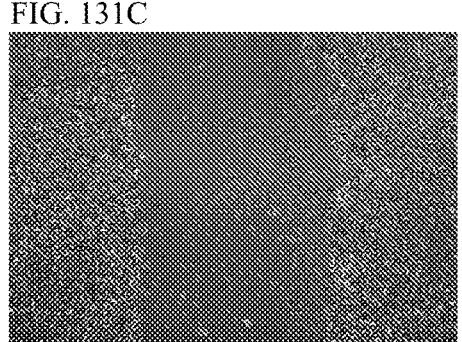
Figure 131F:
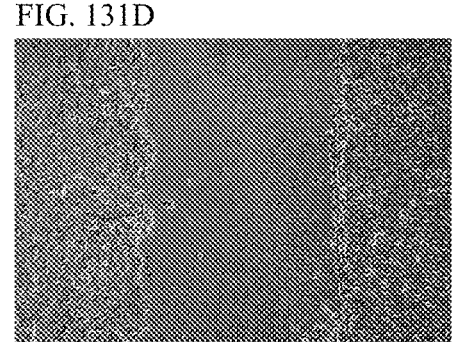
Figure 132A:
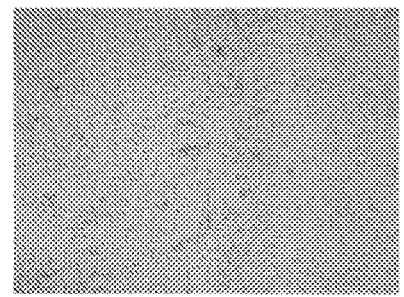
Figure 132B:
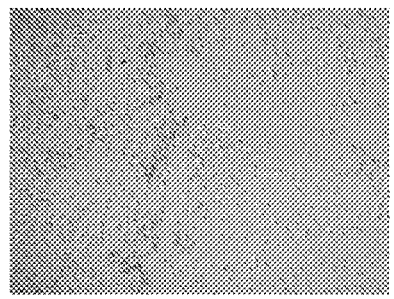
Figure 132C:
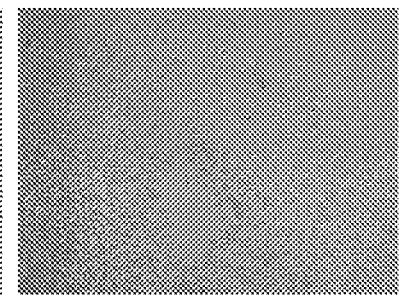
Figure 132D:
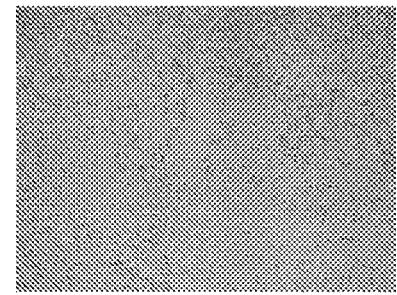
Figure 132E:
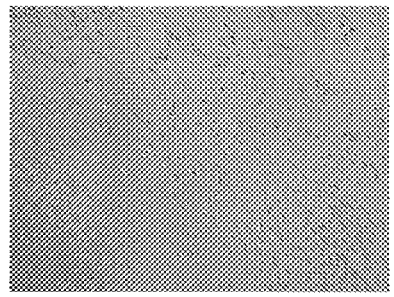
Figure 132F:
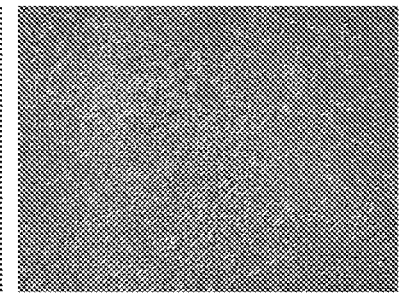
Figure 133A:
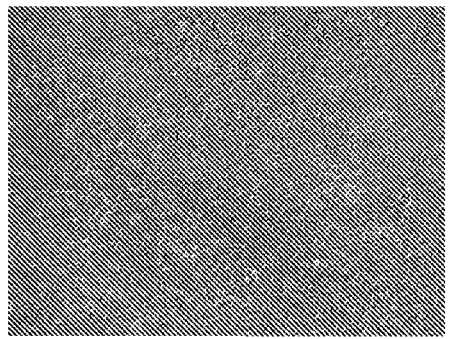
Figure 133B:
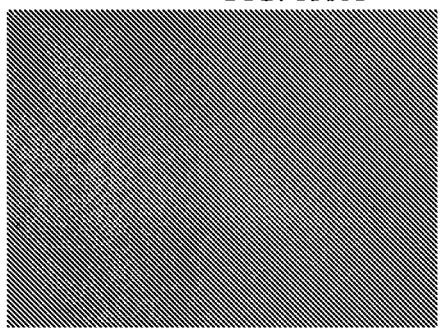
Figure 133C:
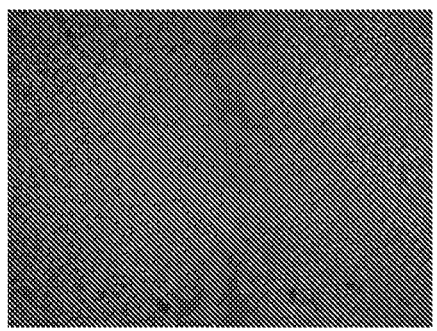
Figure 133D:
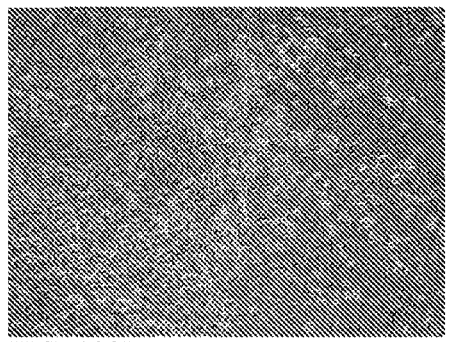
Figure 133E:
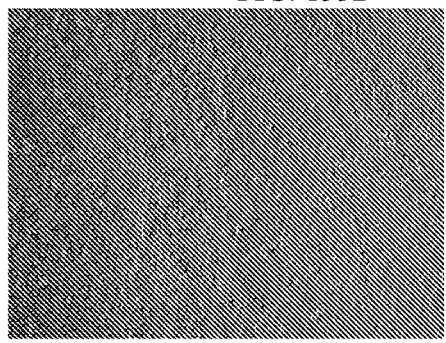
Figure 133F:
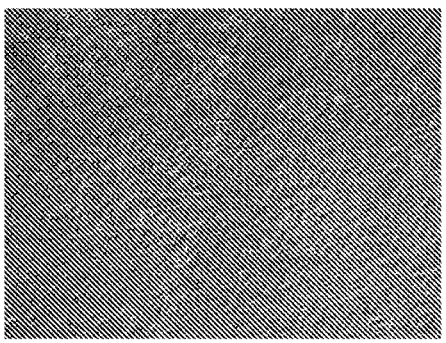
Figure 134A:
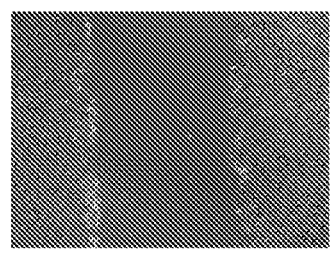
Figure 134B:
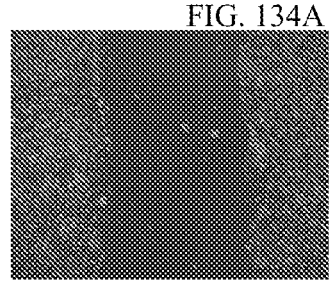
Figure 134C:
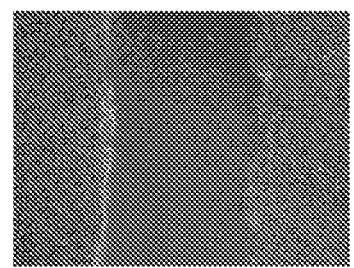
Figure 134D:
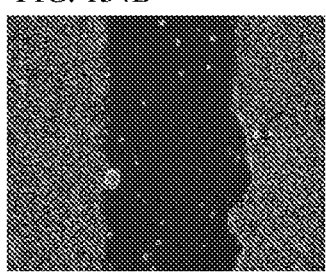
Figure 134E:
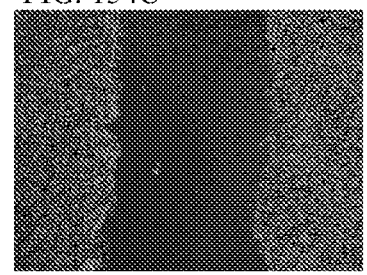
Figure 134F:
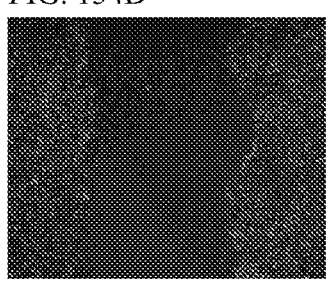
Figure 134G:
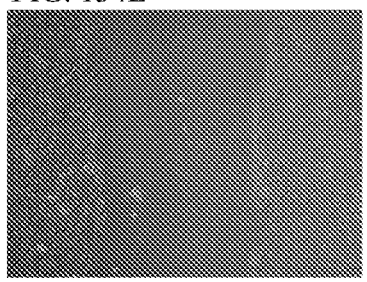
Figure 134H:
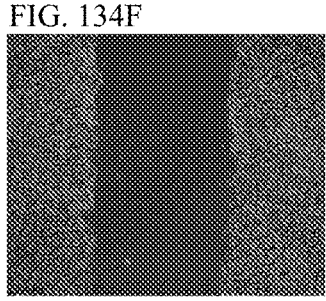
Figure 134I:
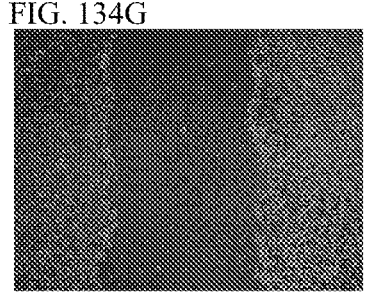
Figure 135A:
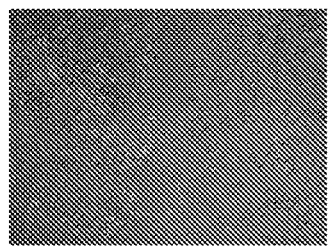
Figure 135B:
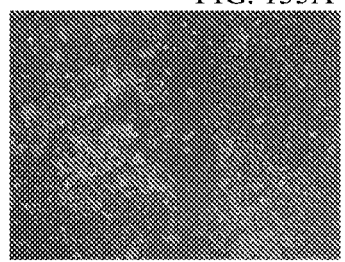
Figure 135C:
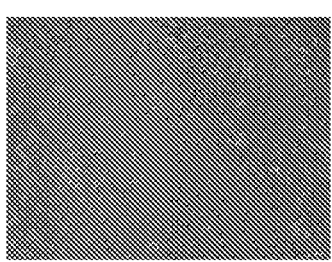
Figure 135D:
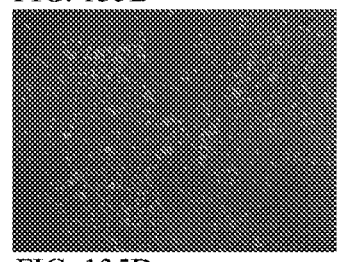
Figure 135E:
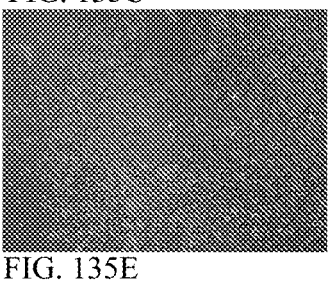
Figure 135F:
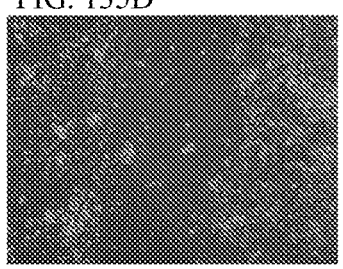
Figure 135G:
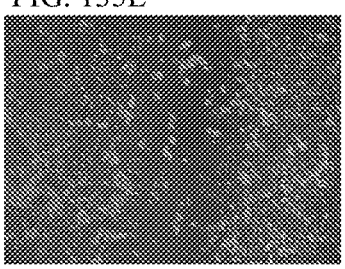
Figure 135H:
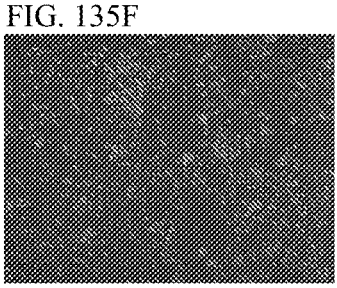
Figure 135I:
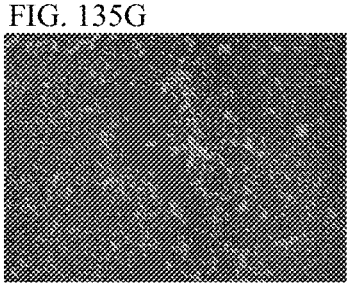
Figure 136A:
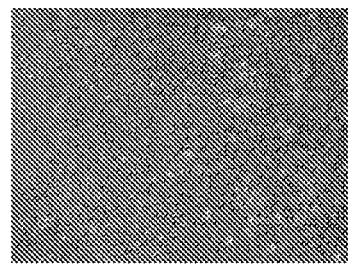
Figure 136B:
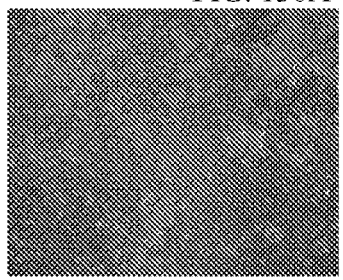
Figure 136C:
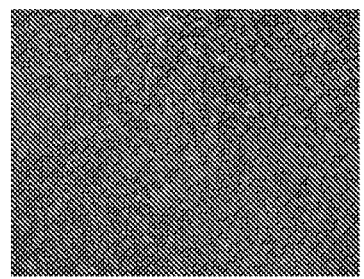
Figure 136D:
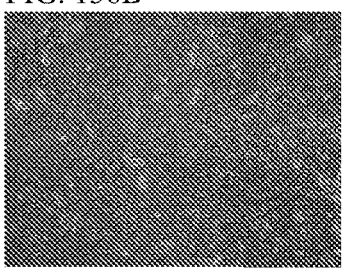
Figure 136E:
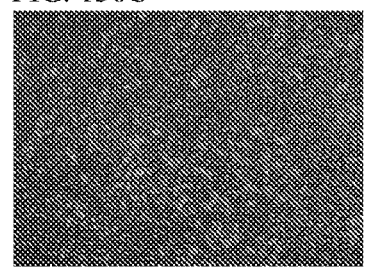
Figure 136F:
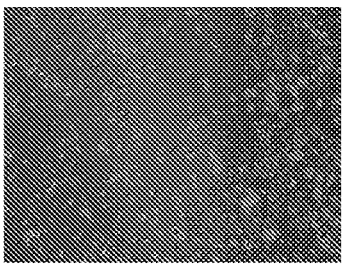
Figure 136G:
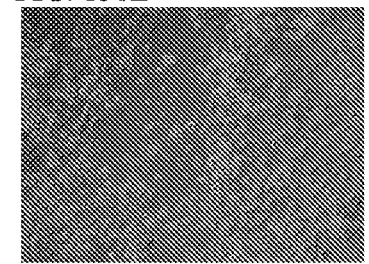
Figure 136H:
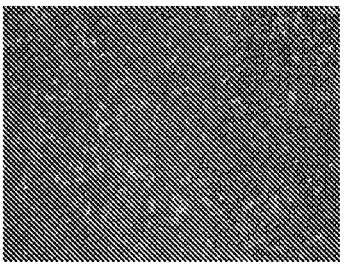
Figure 136I:
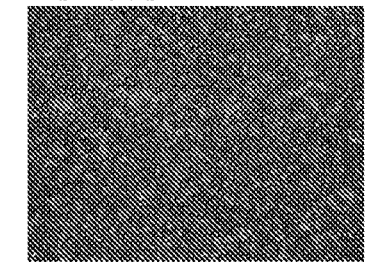
Figure 137A:
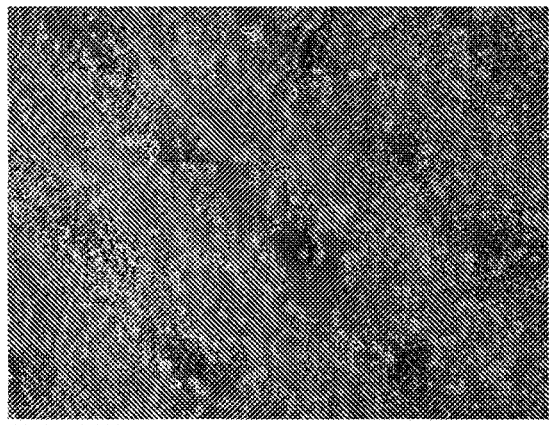
Figure 137B:
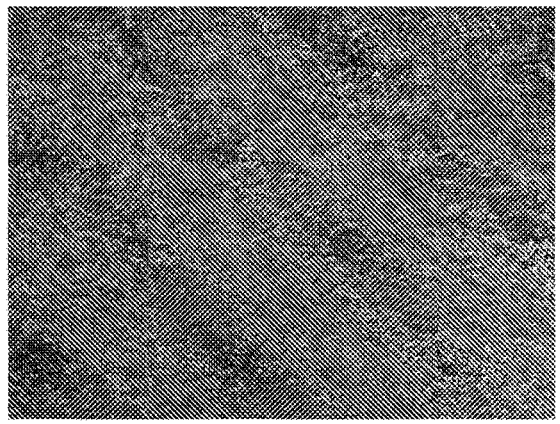
Figure 138A:
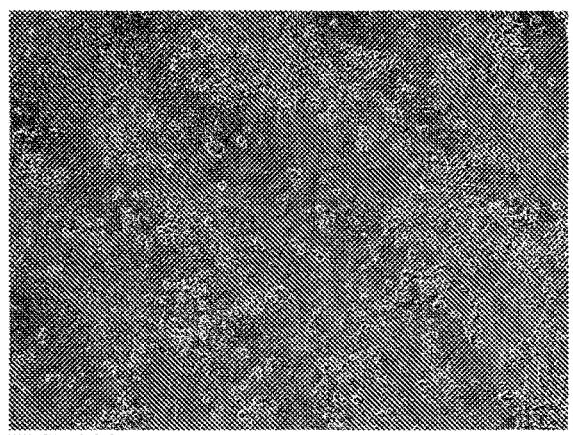
Figure 138B:
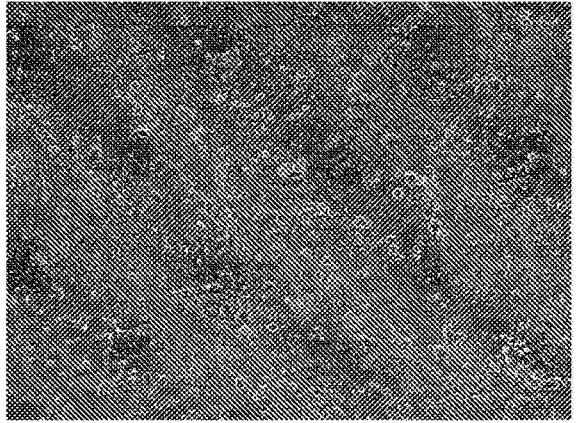
Figure 142A:
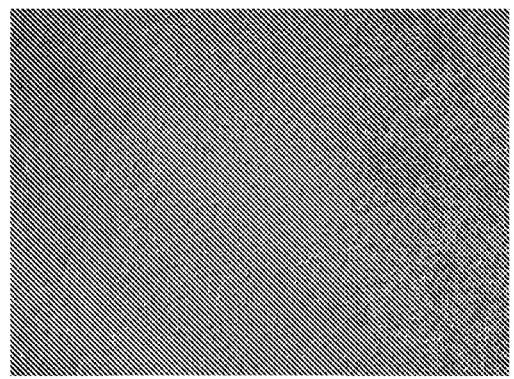
Figure 142B:
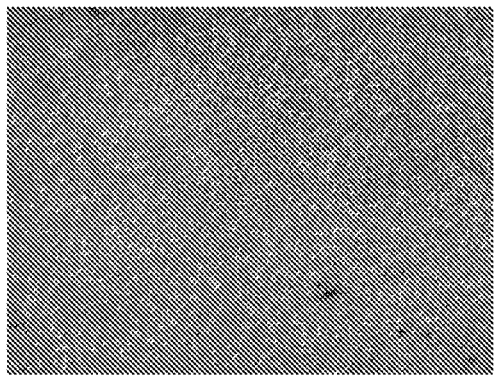
Figure 142C:
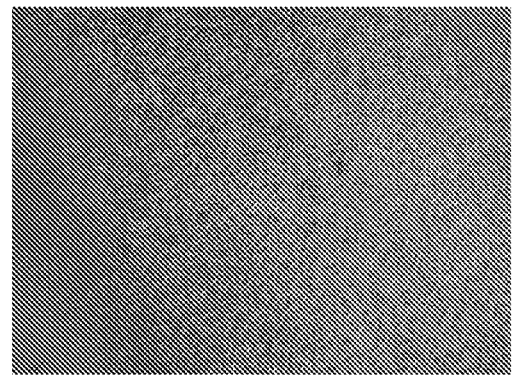
Figure 143A:
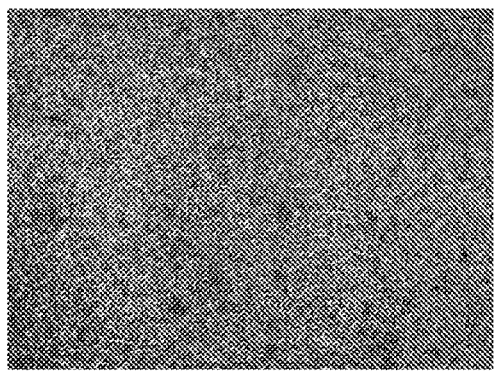
Figure 143B:
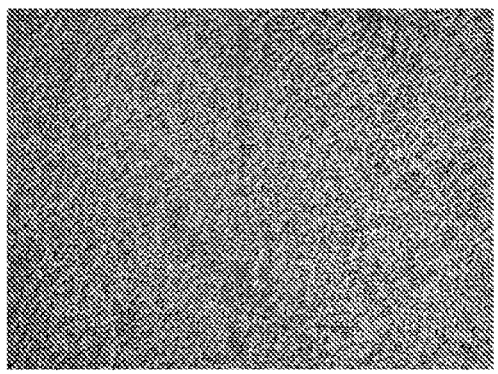
Figure 145:
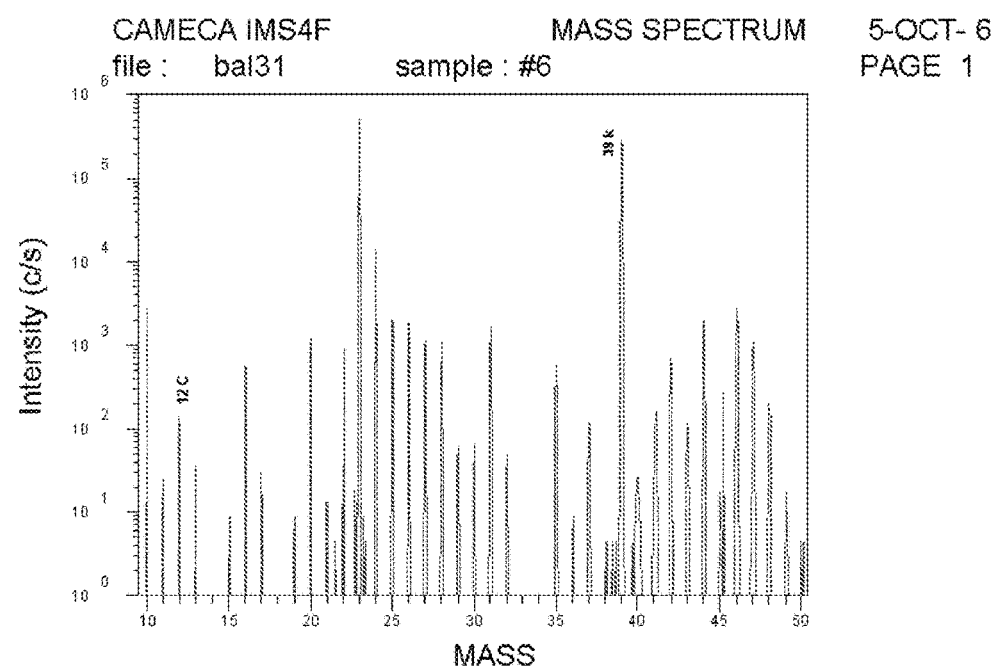
Figure 146:
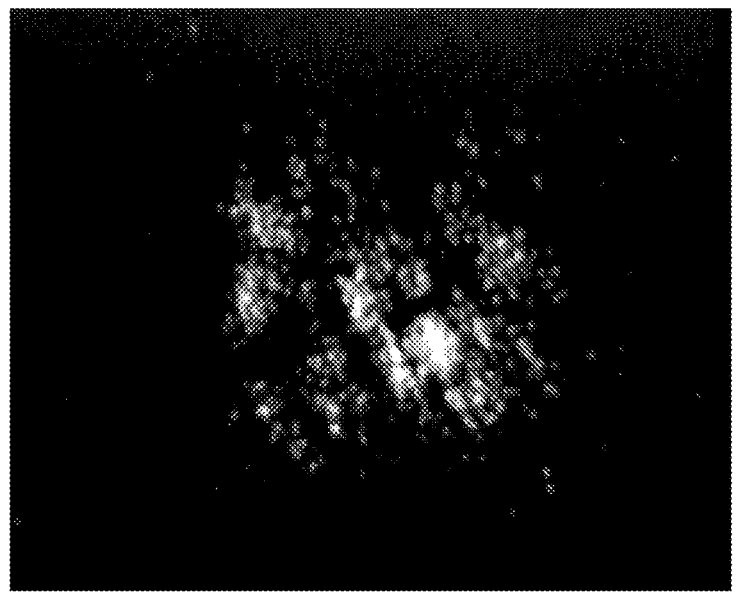
Figure 147:
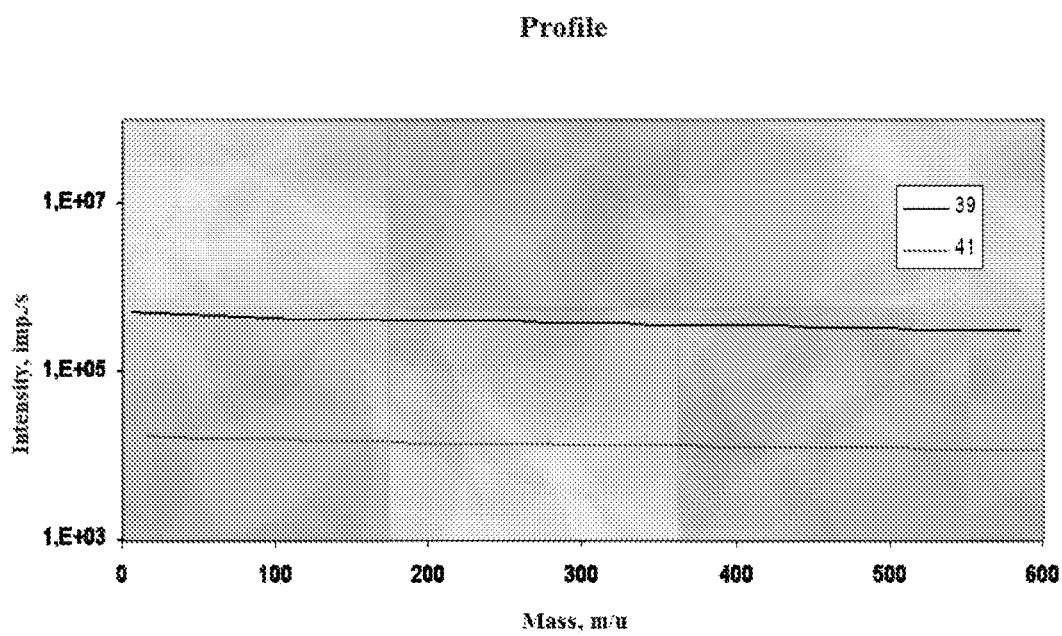
Figure 148A:
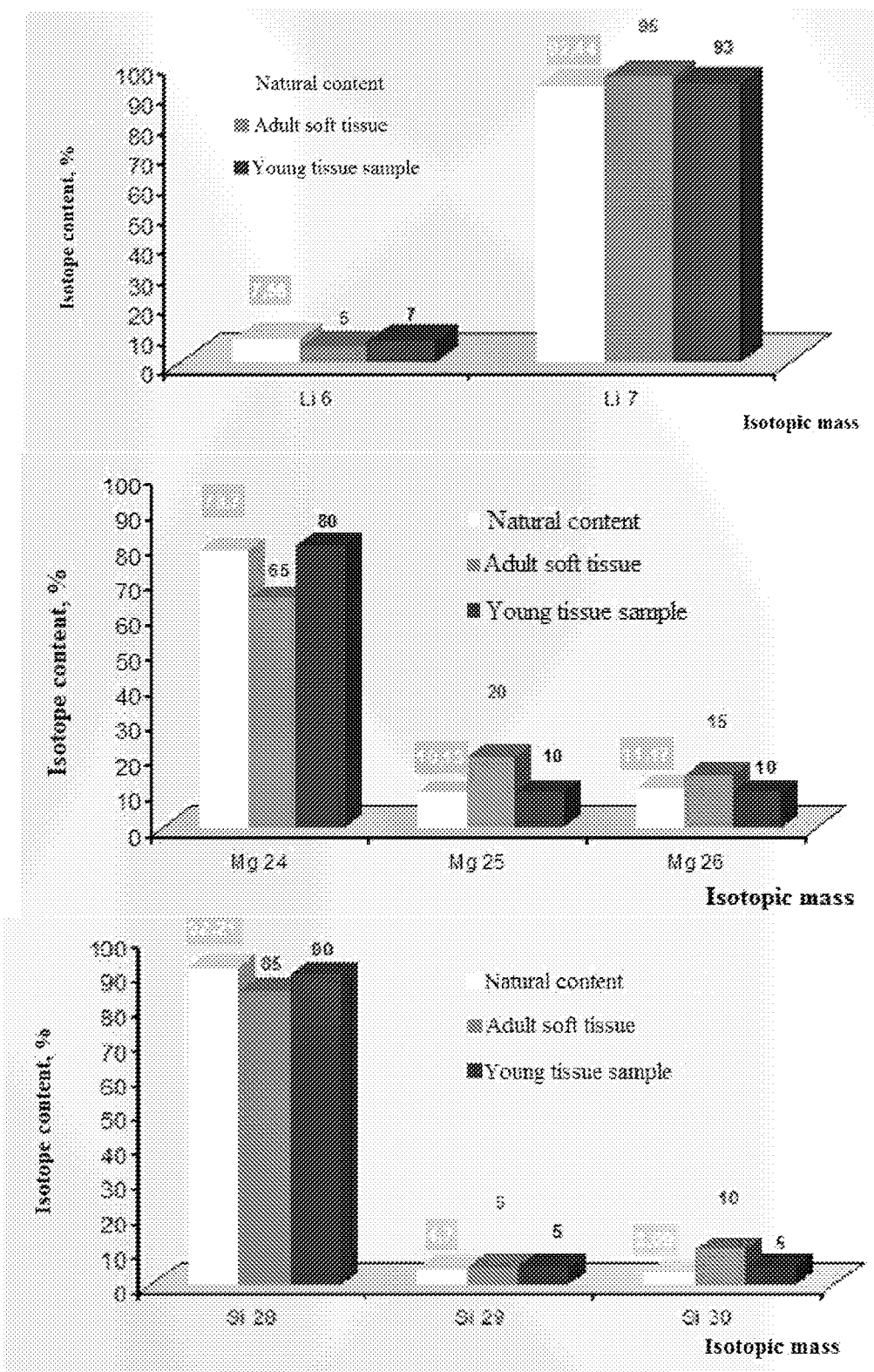
Figure 148B:
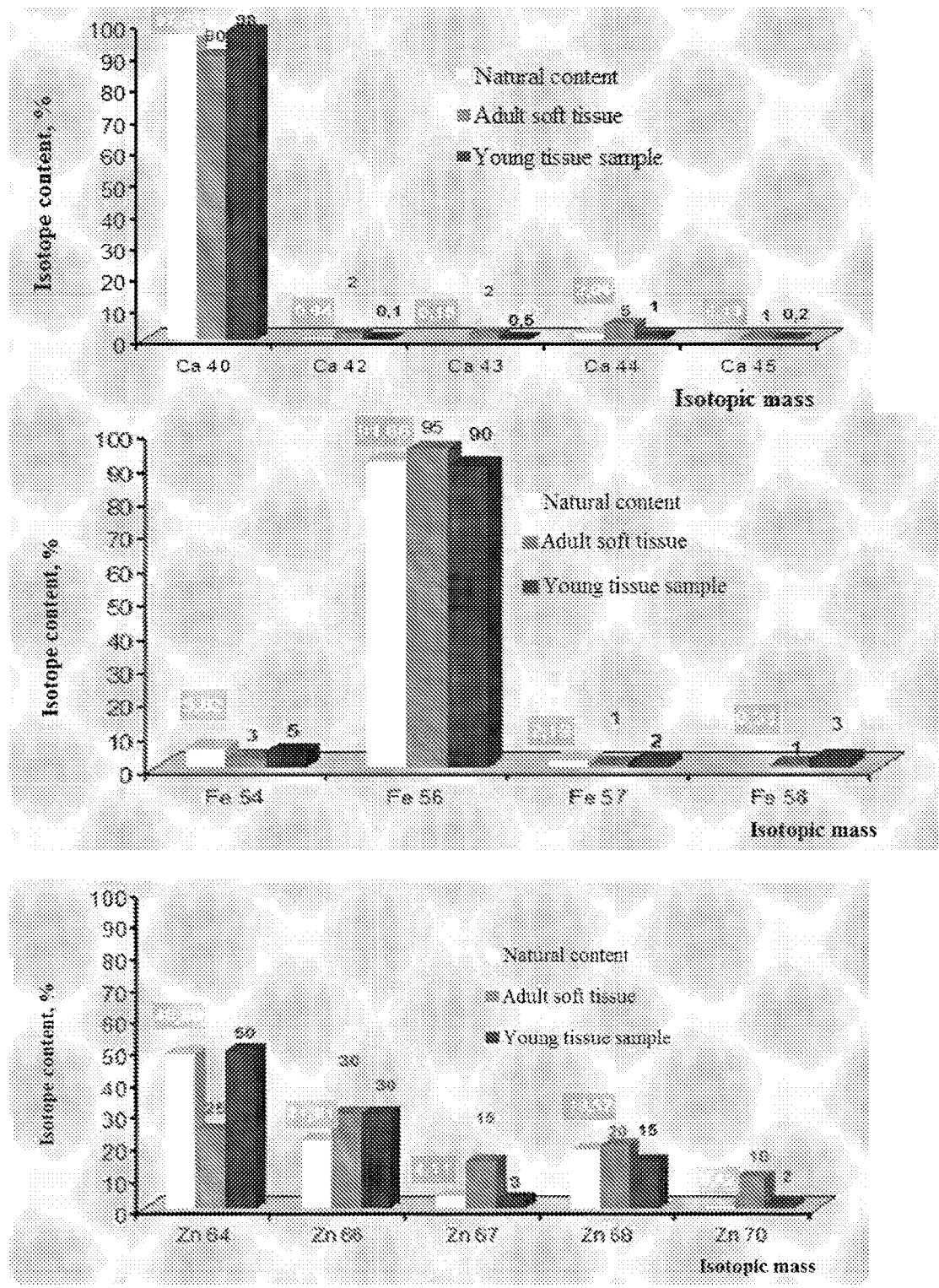
Figure 148C:
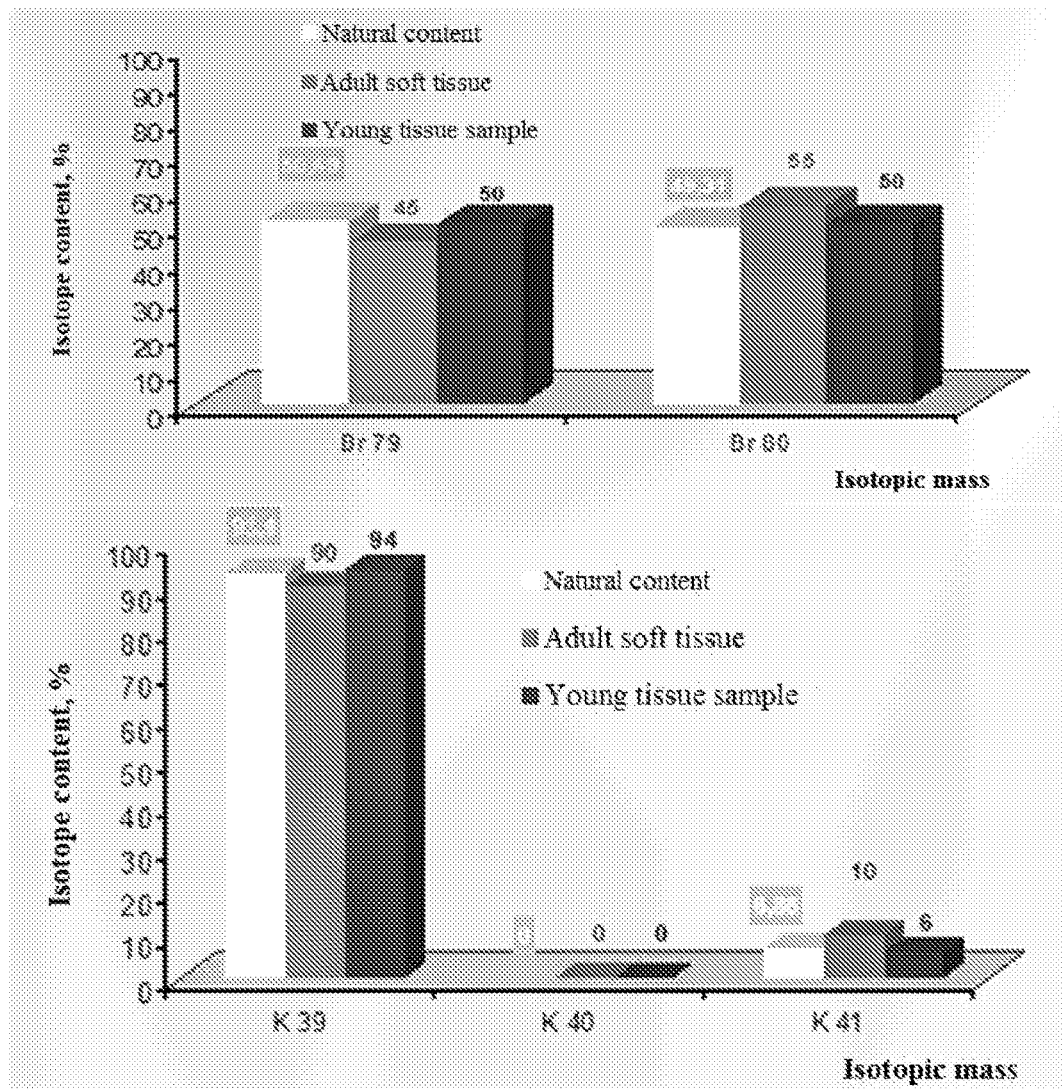
Figure 149:
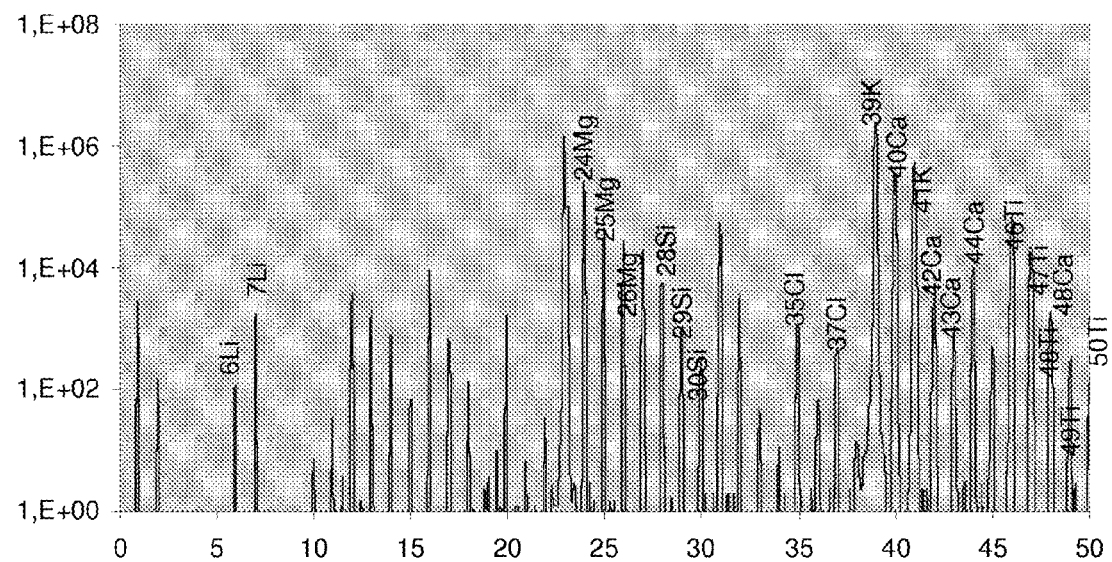
Figure 150:
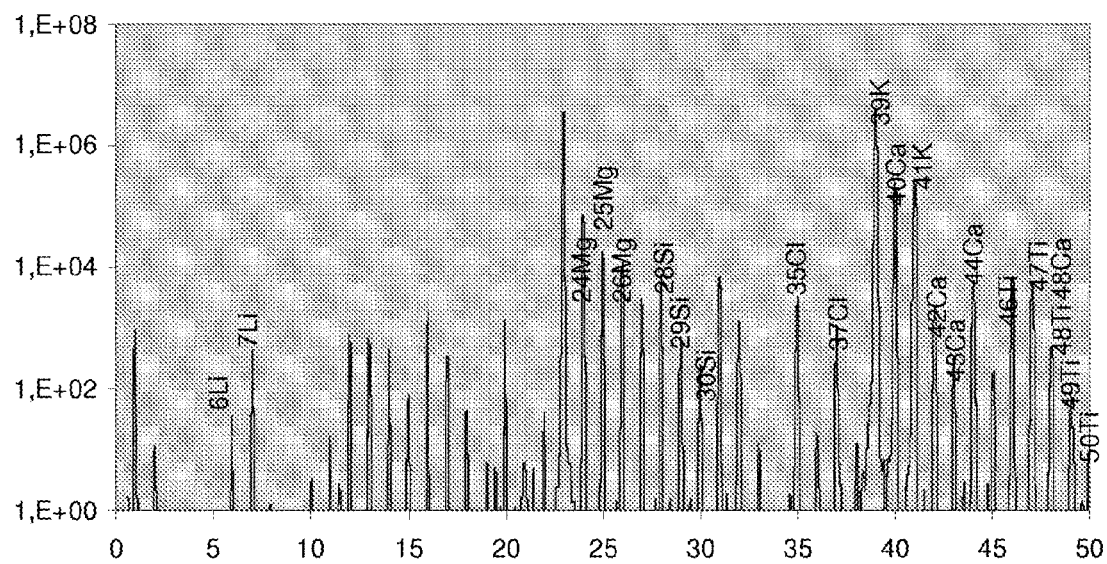
Figure 151:
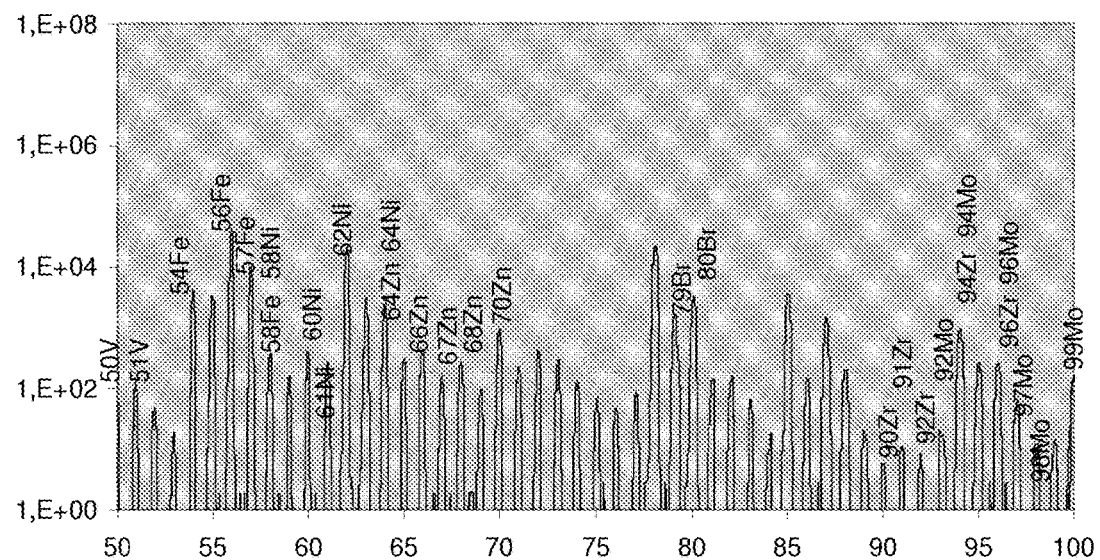
Figure 152:
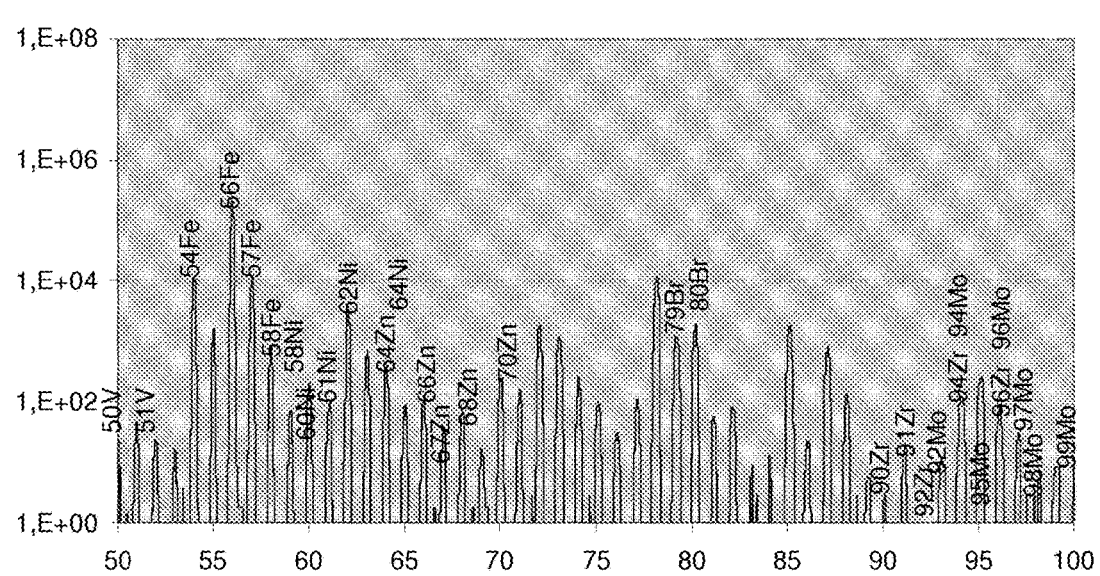
Figure 153:
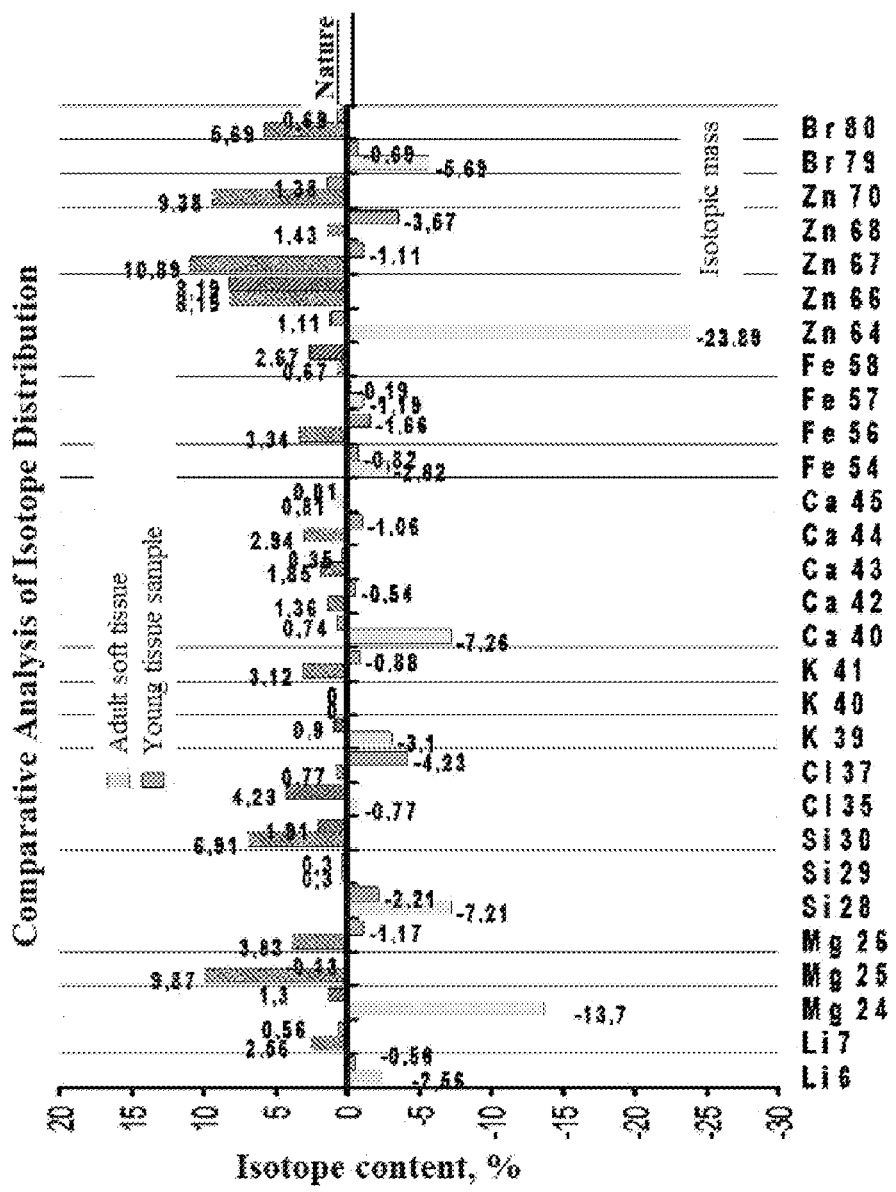
Figure 154:
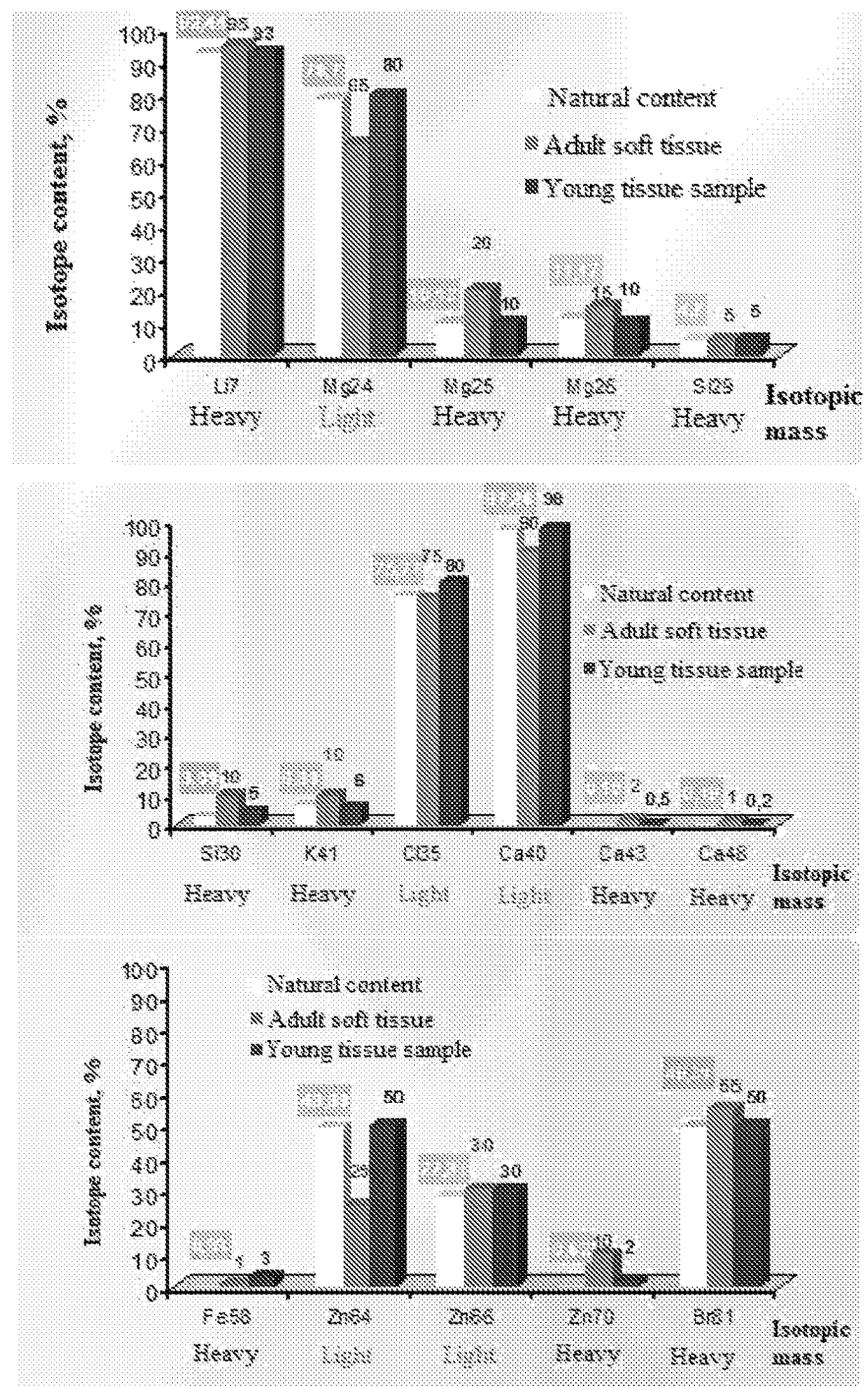
Figure 155A:
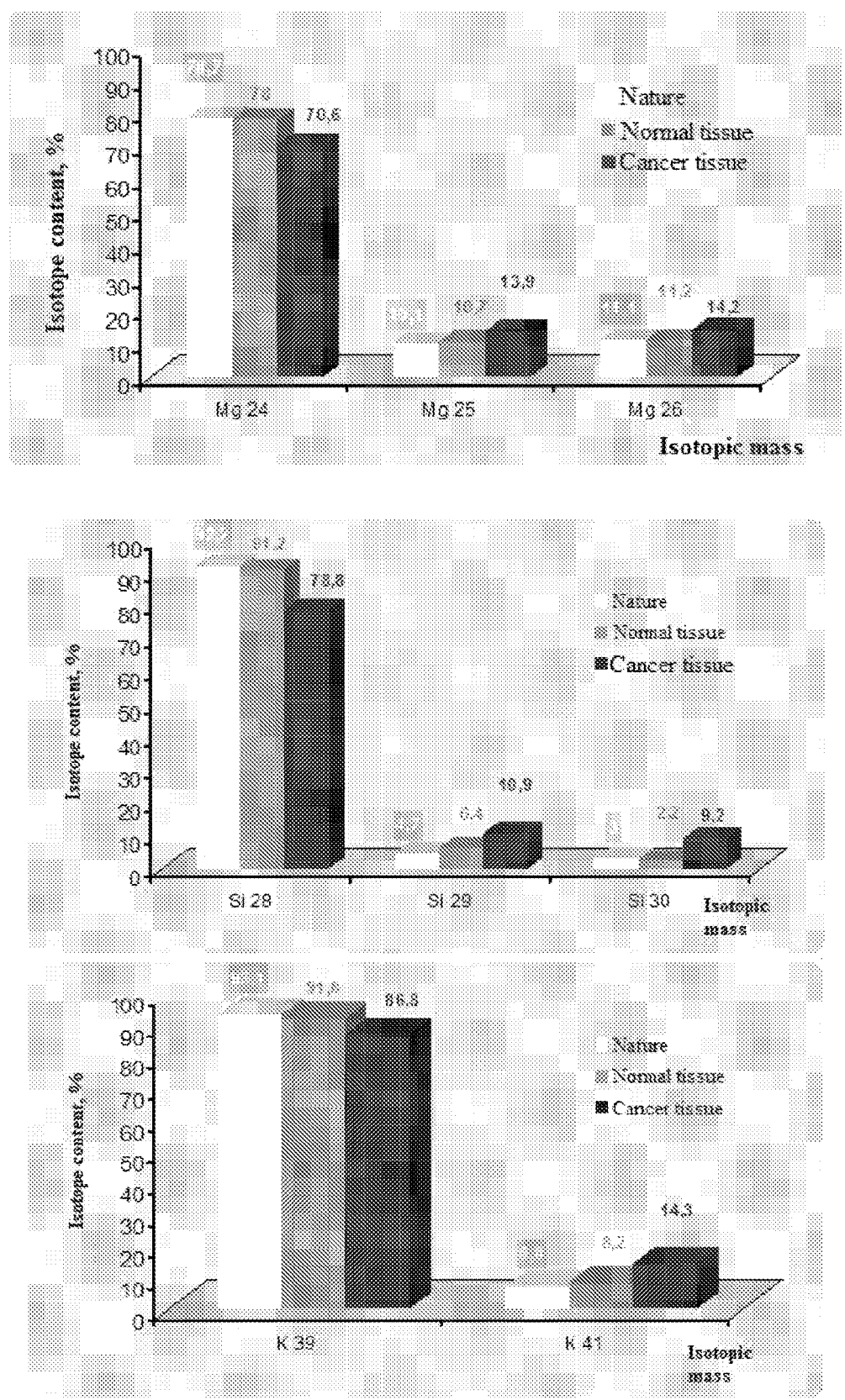
Figure 155B:
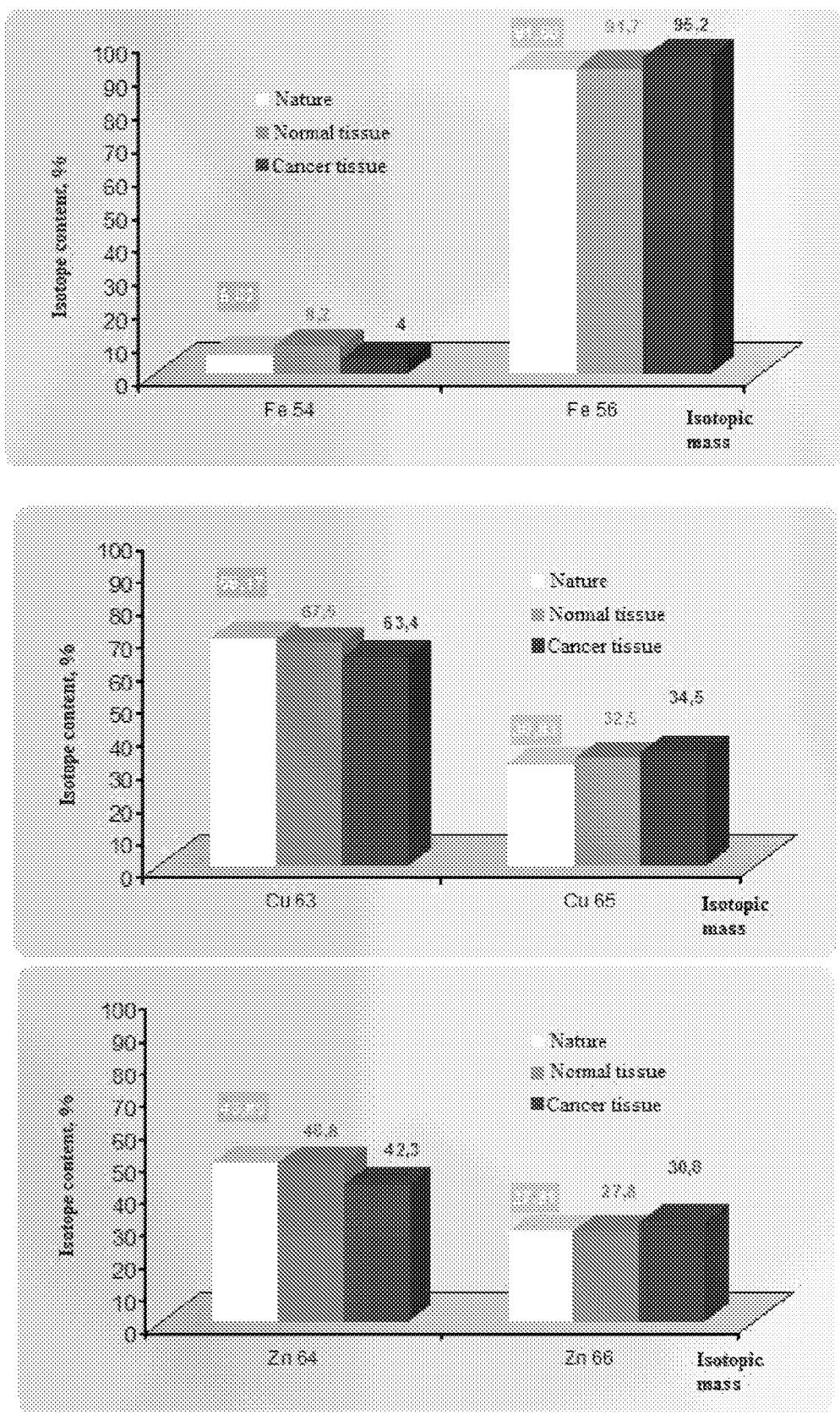
Figure 155C:
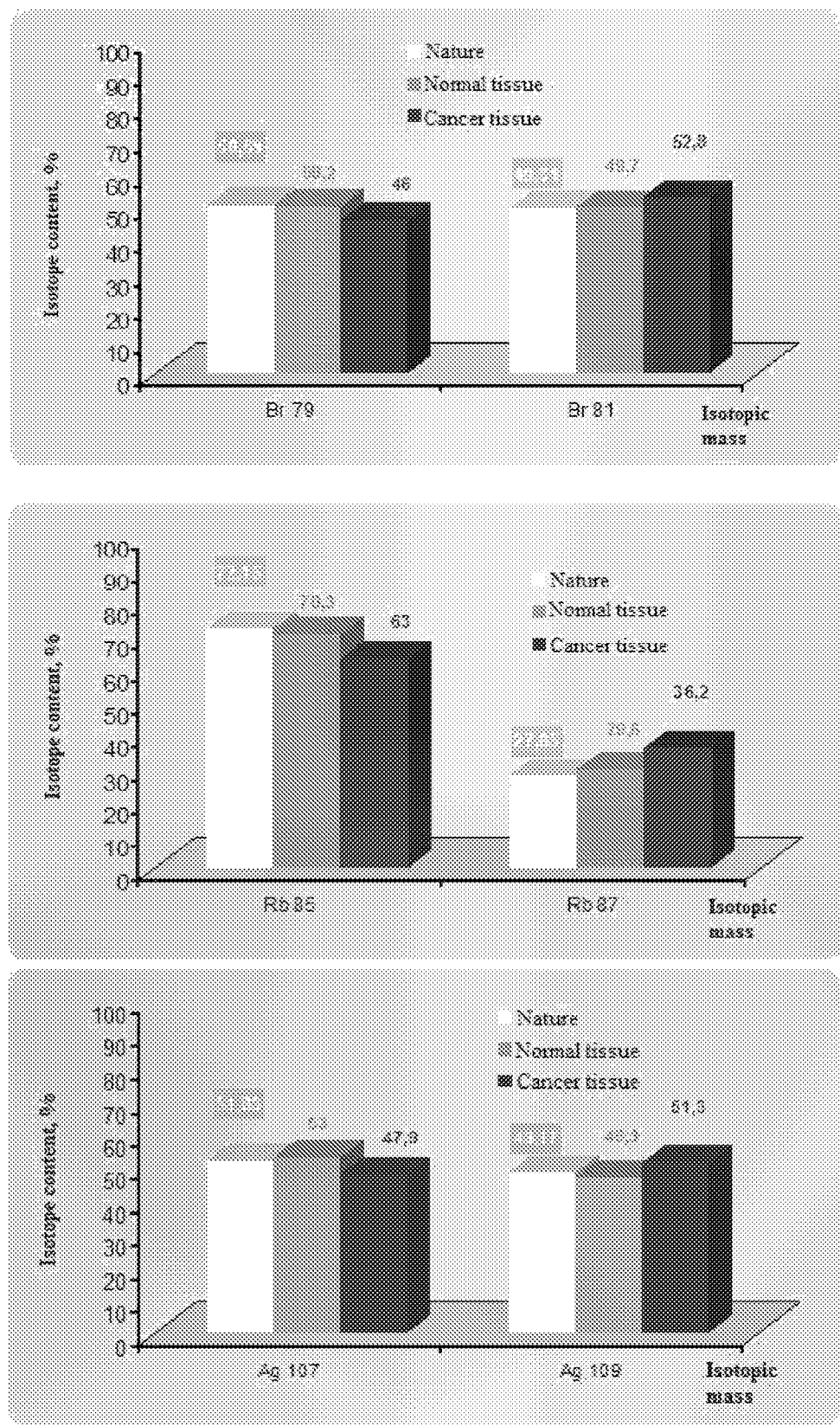
Figure 156A:
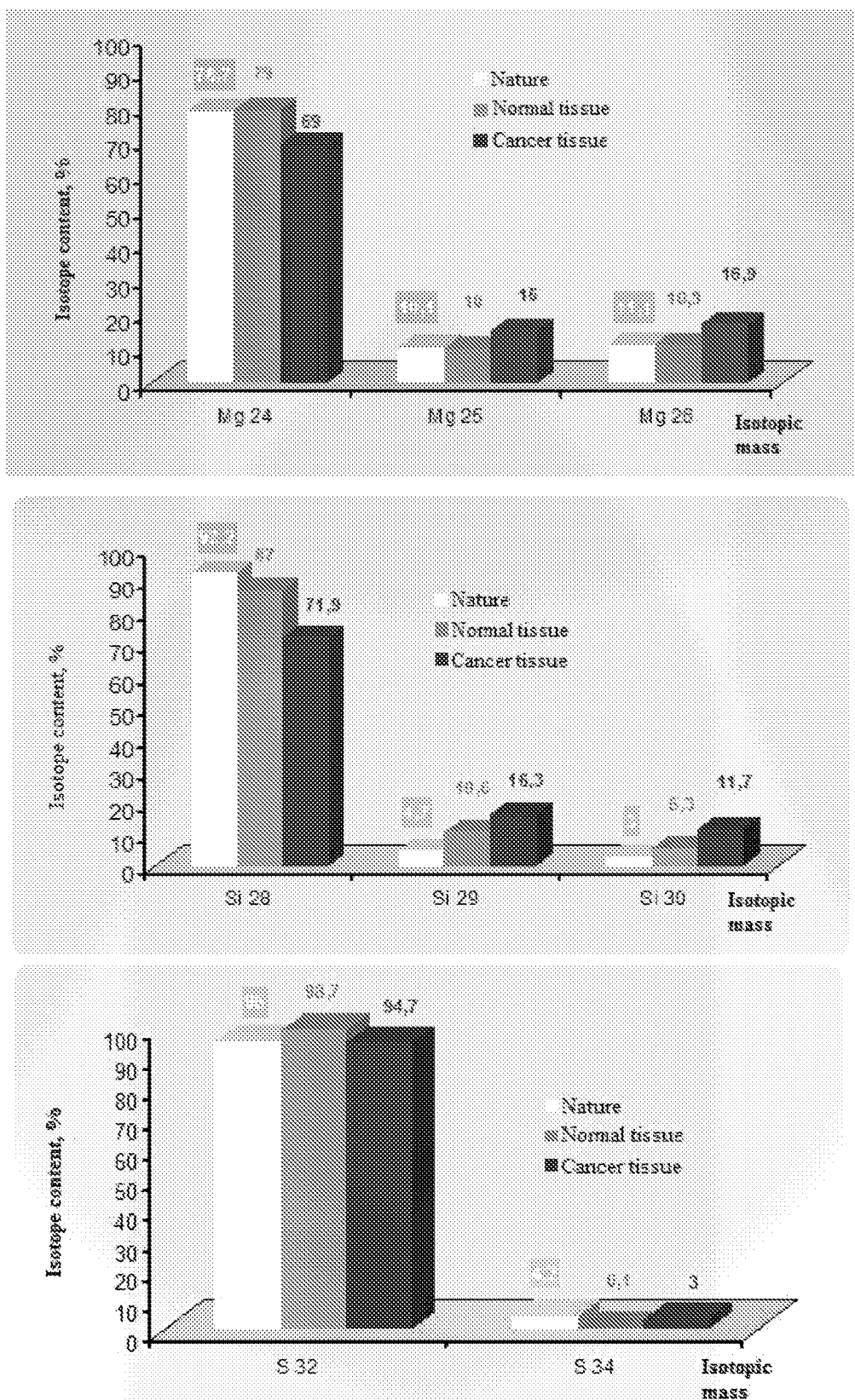
Figure 156B:
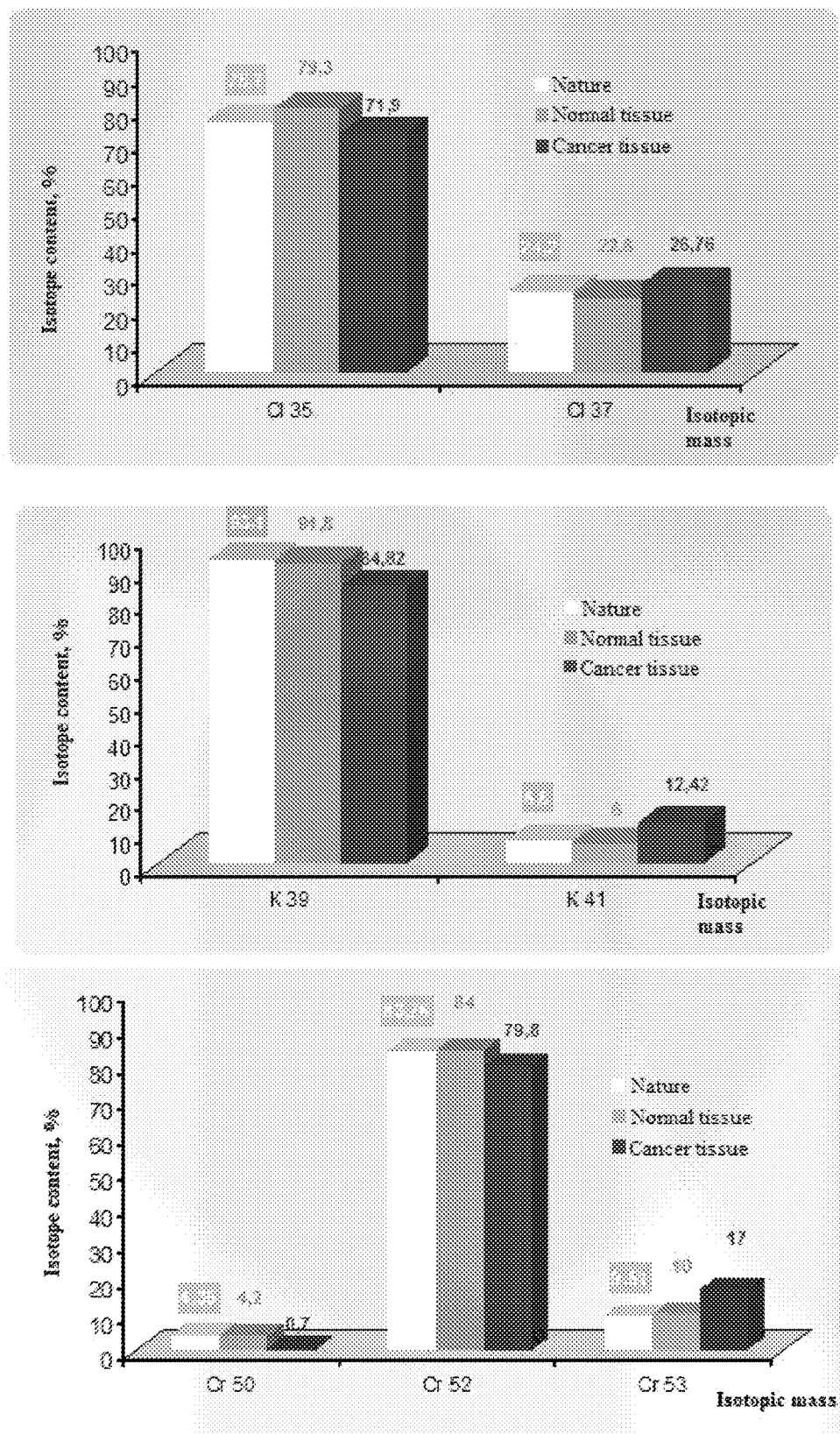
Figure 156C:
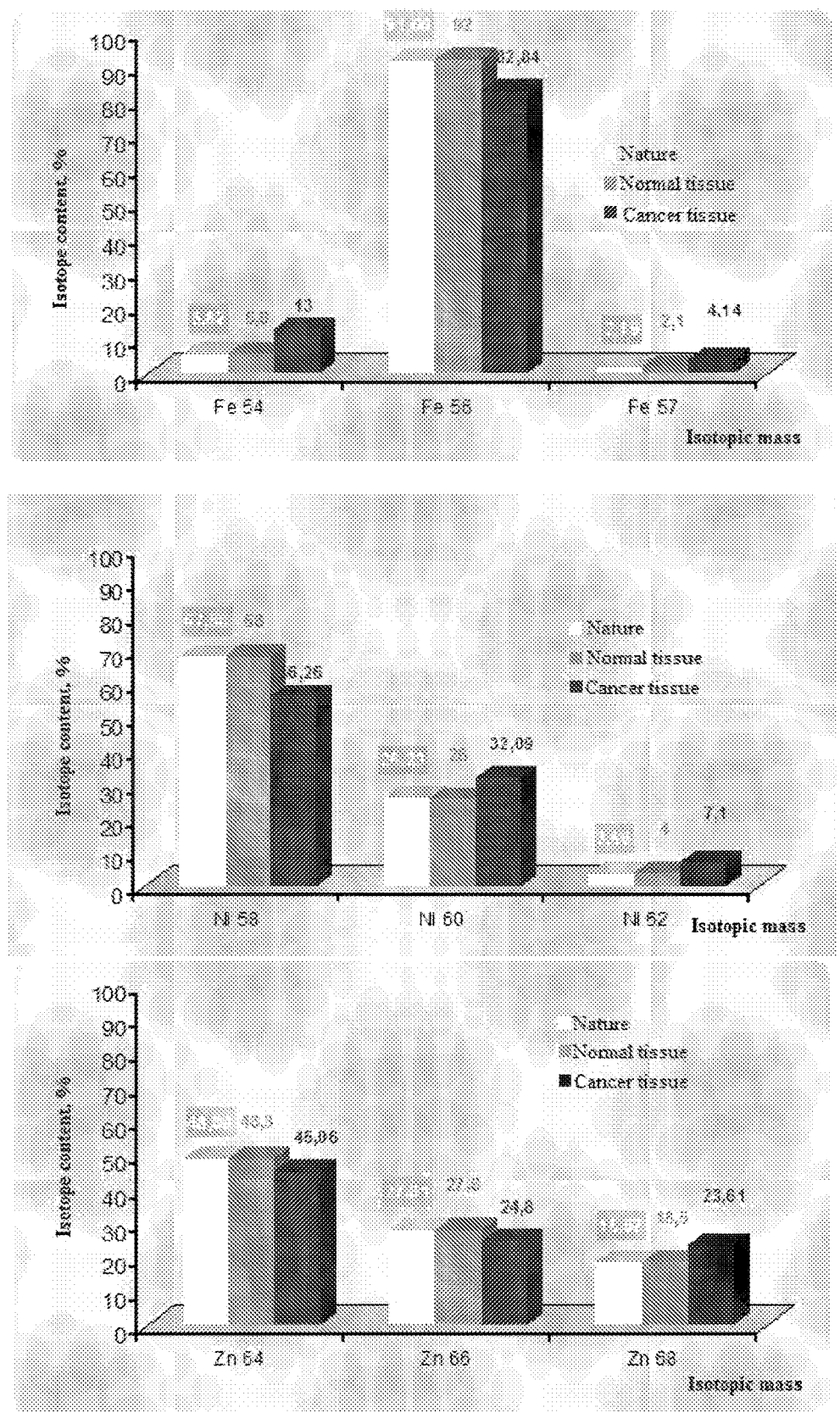
Figure 156D:
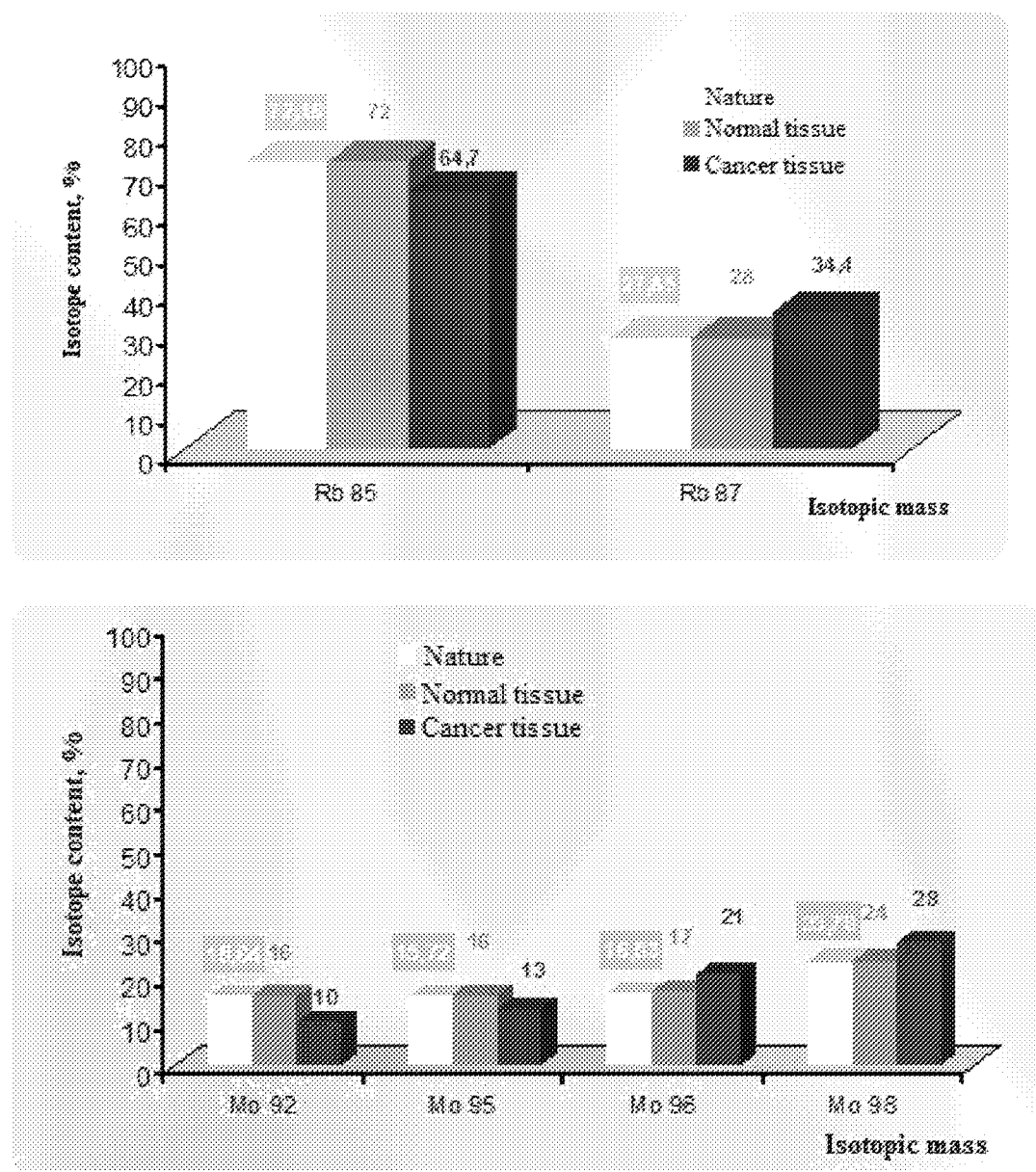
Figure 157:
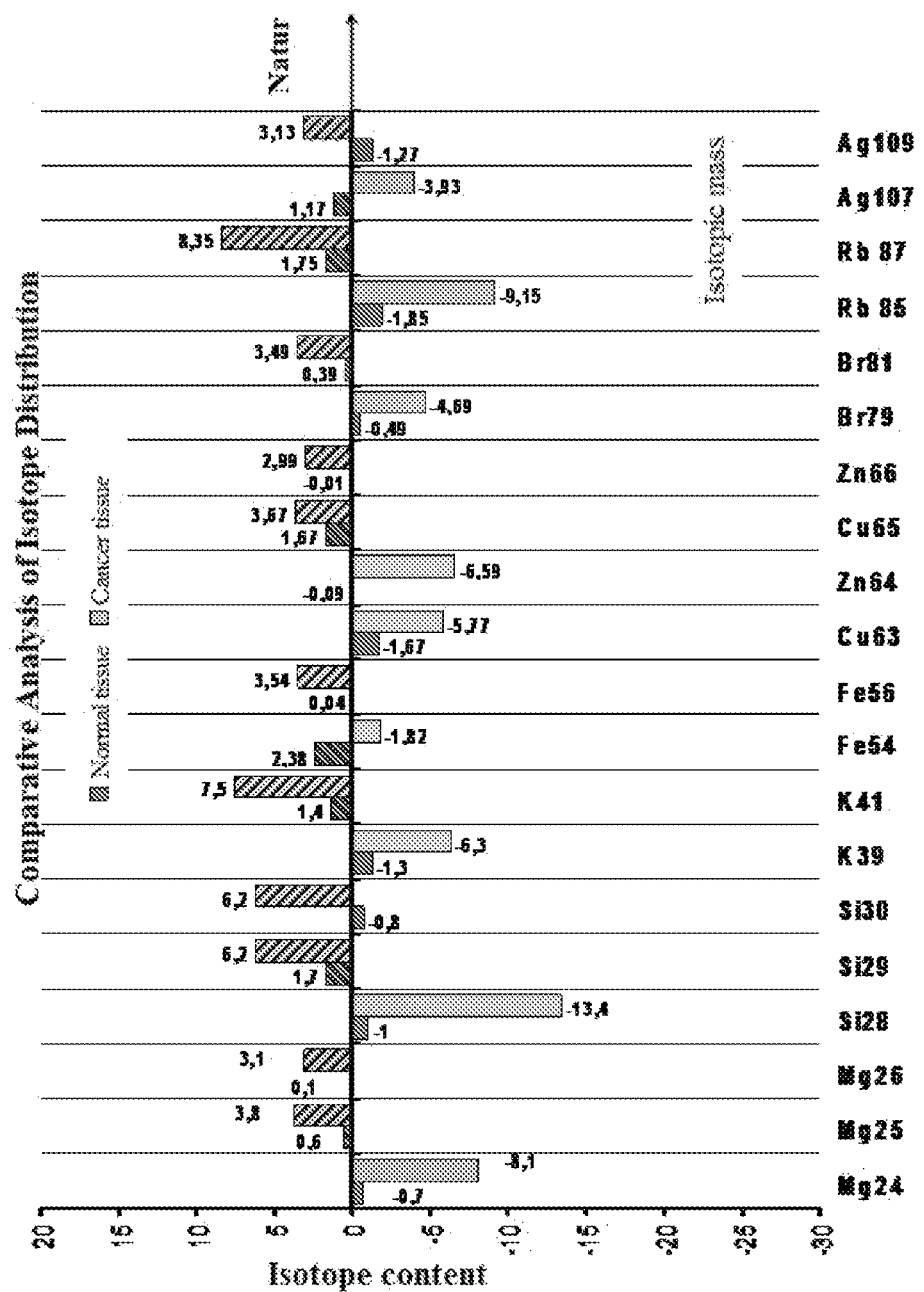
Figure 158:
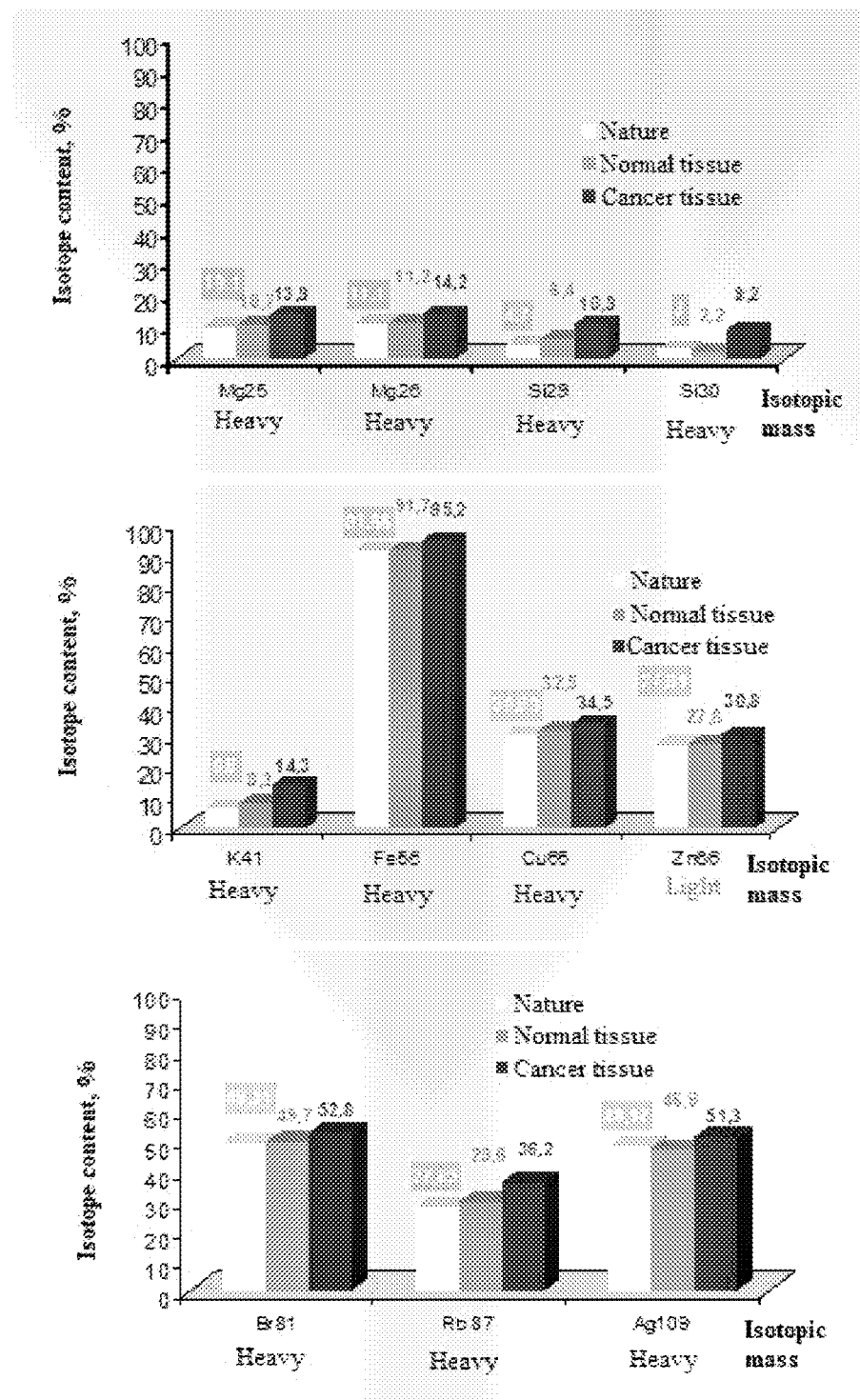
Figure 159:
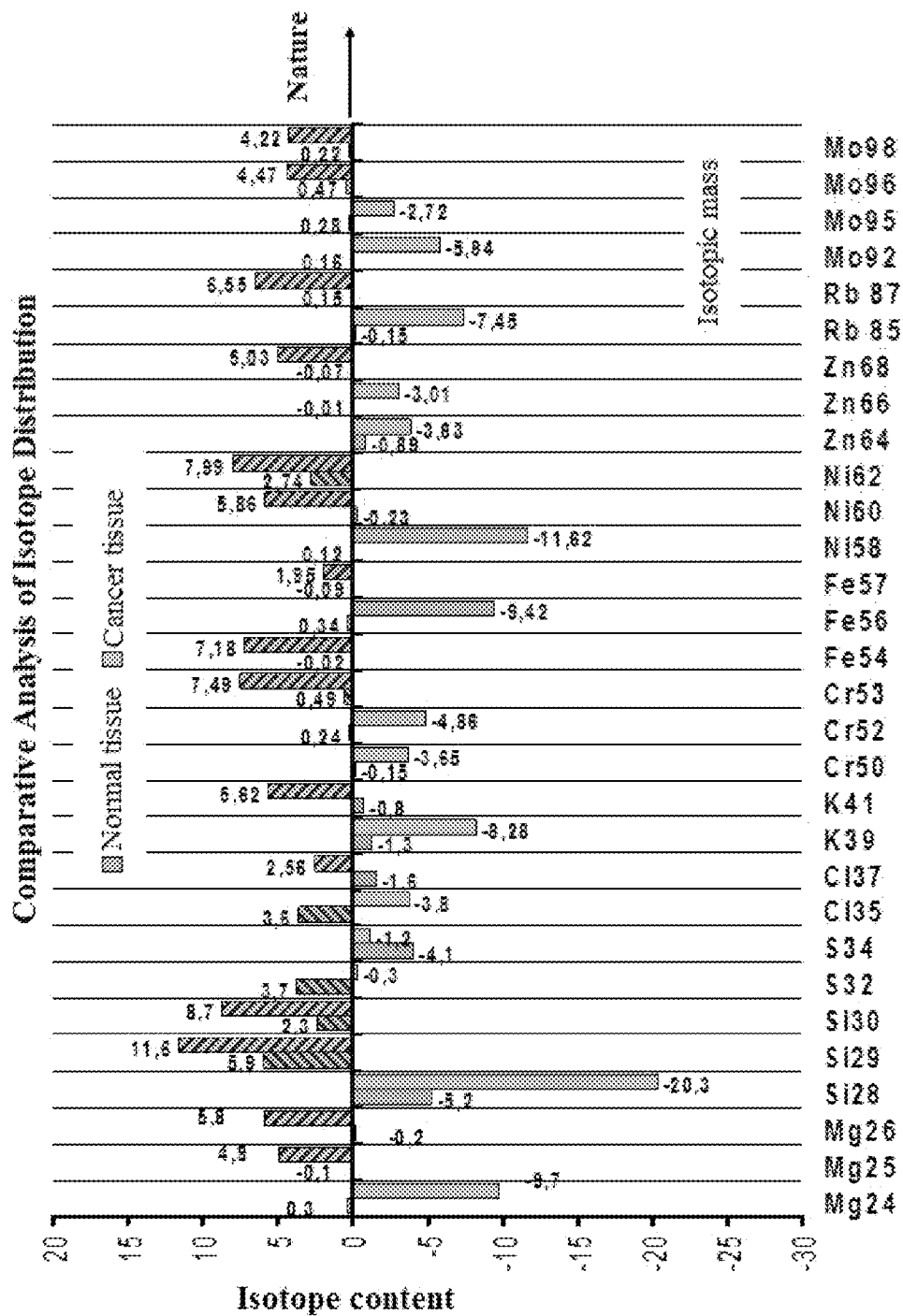
Figure 160:
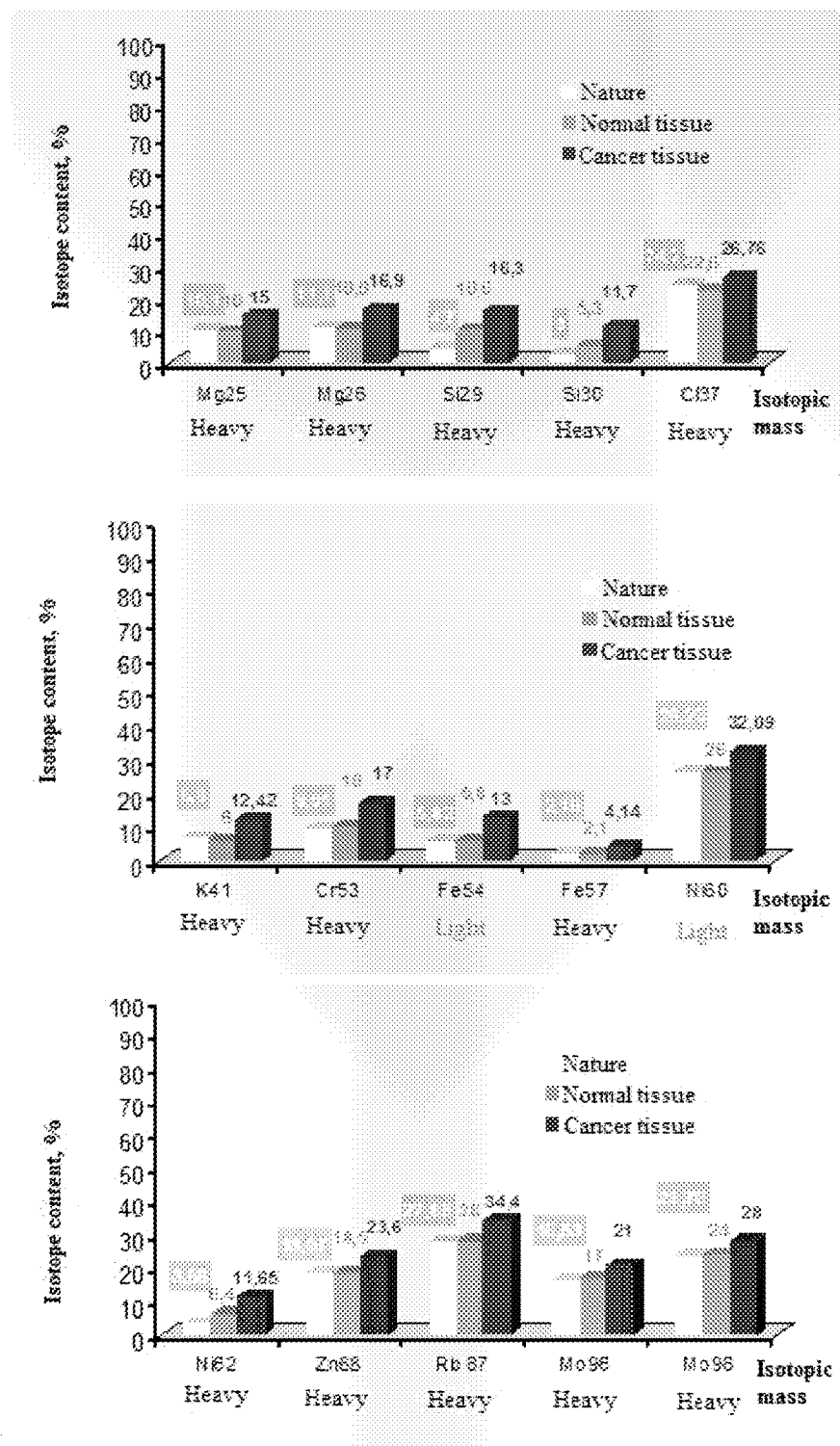
Figure 161A:
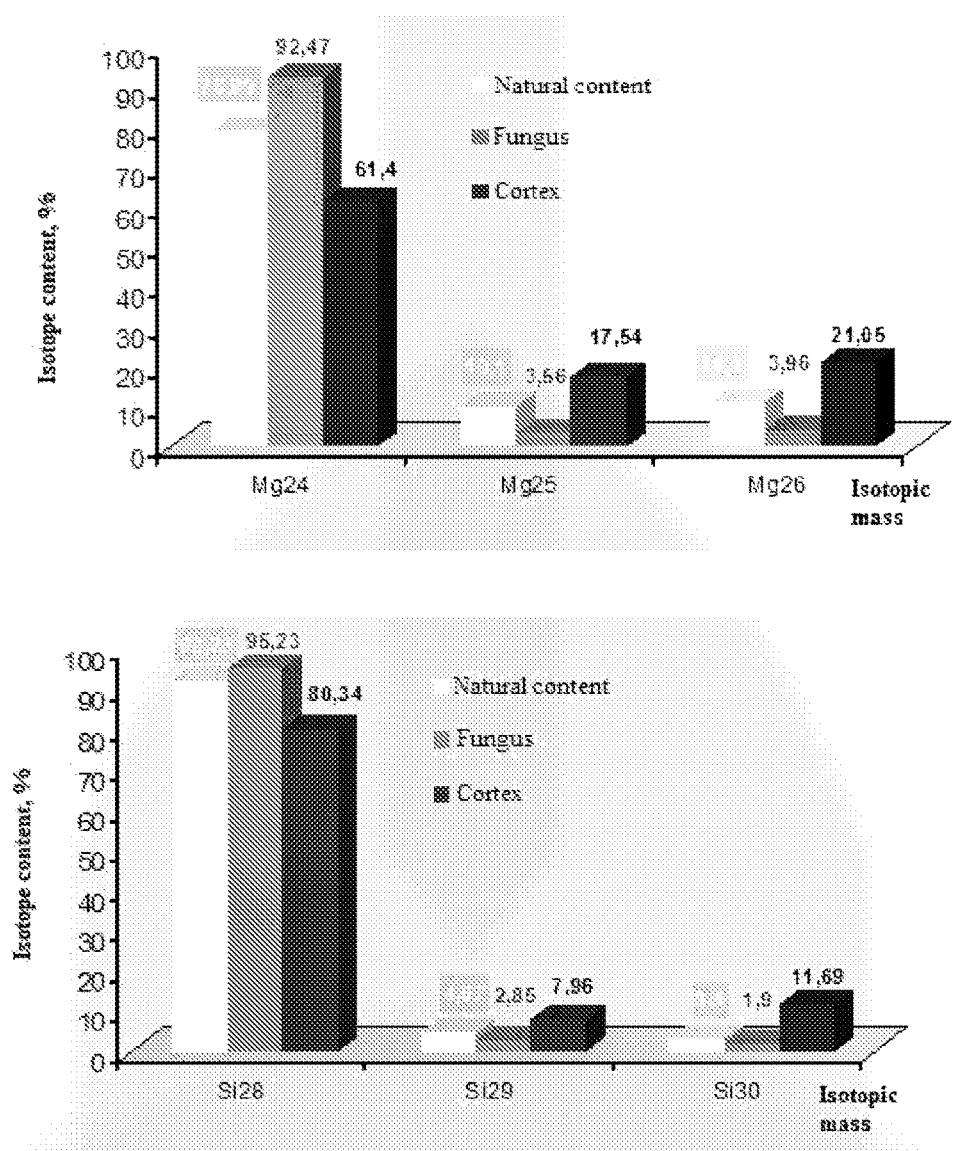
Figure 161B:
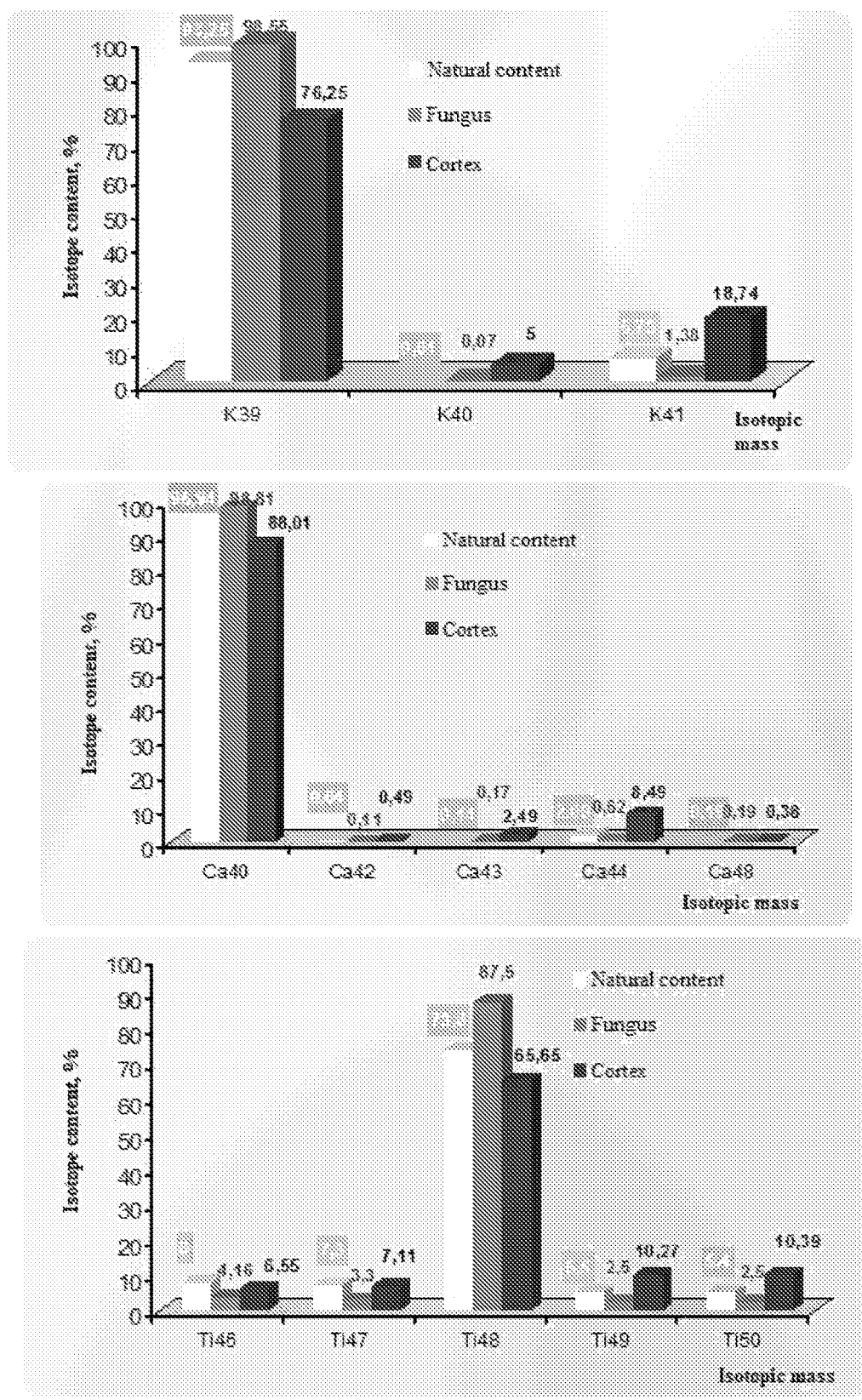
Figure 161C:
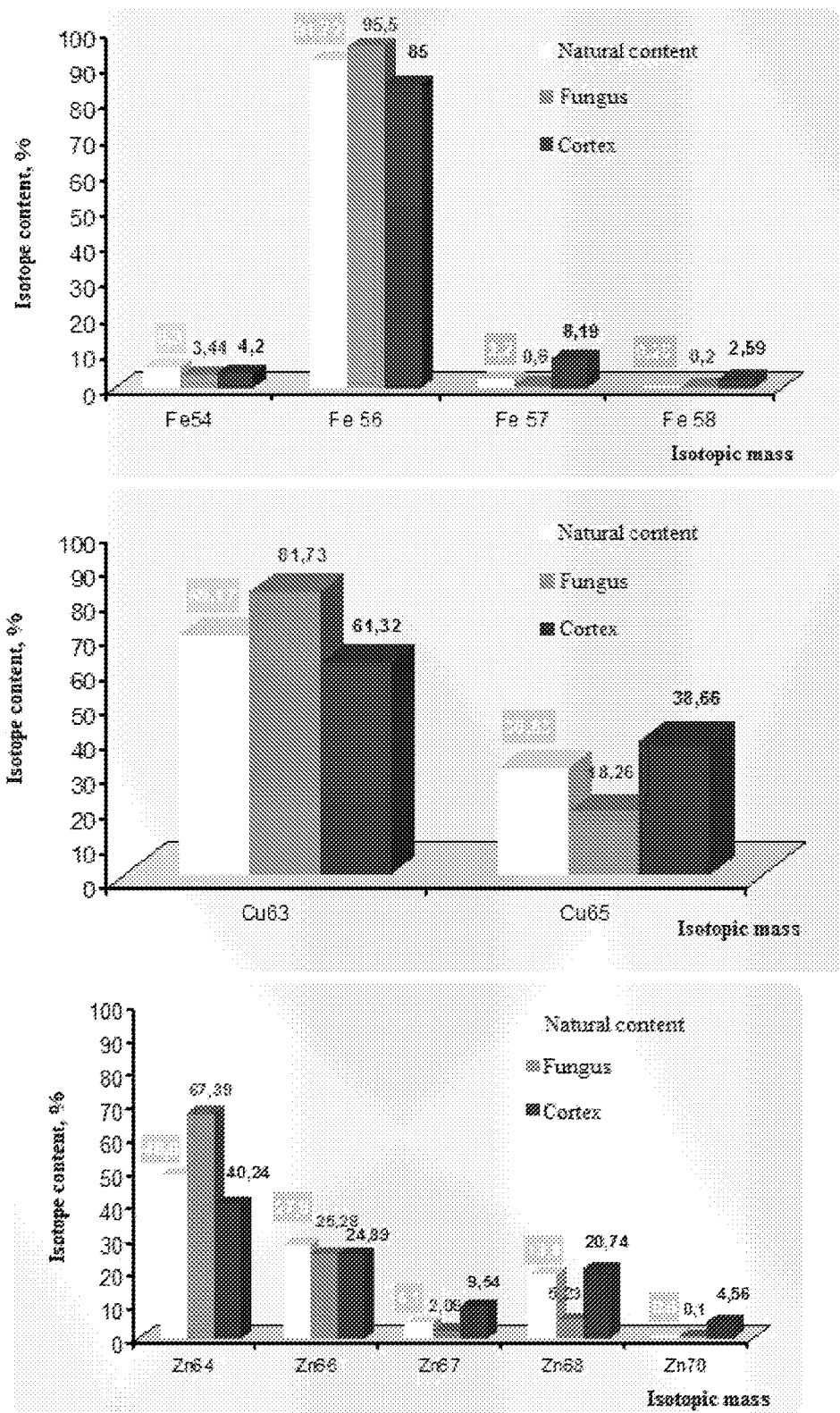
Figure 161D:
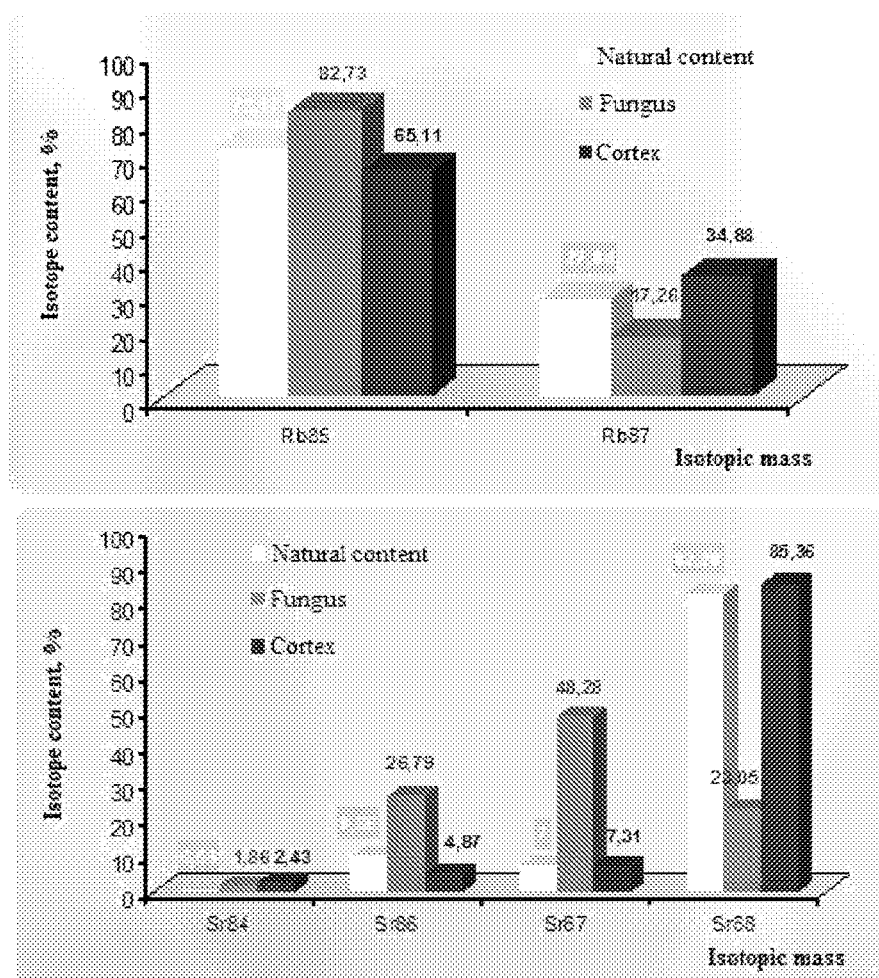
Figure 162:
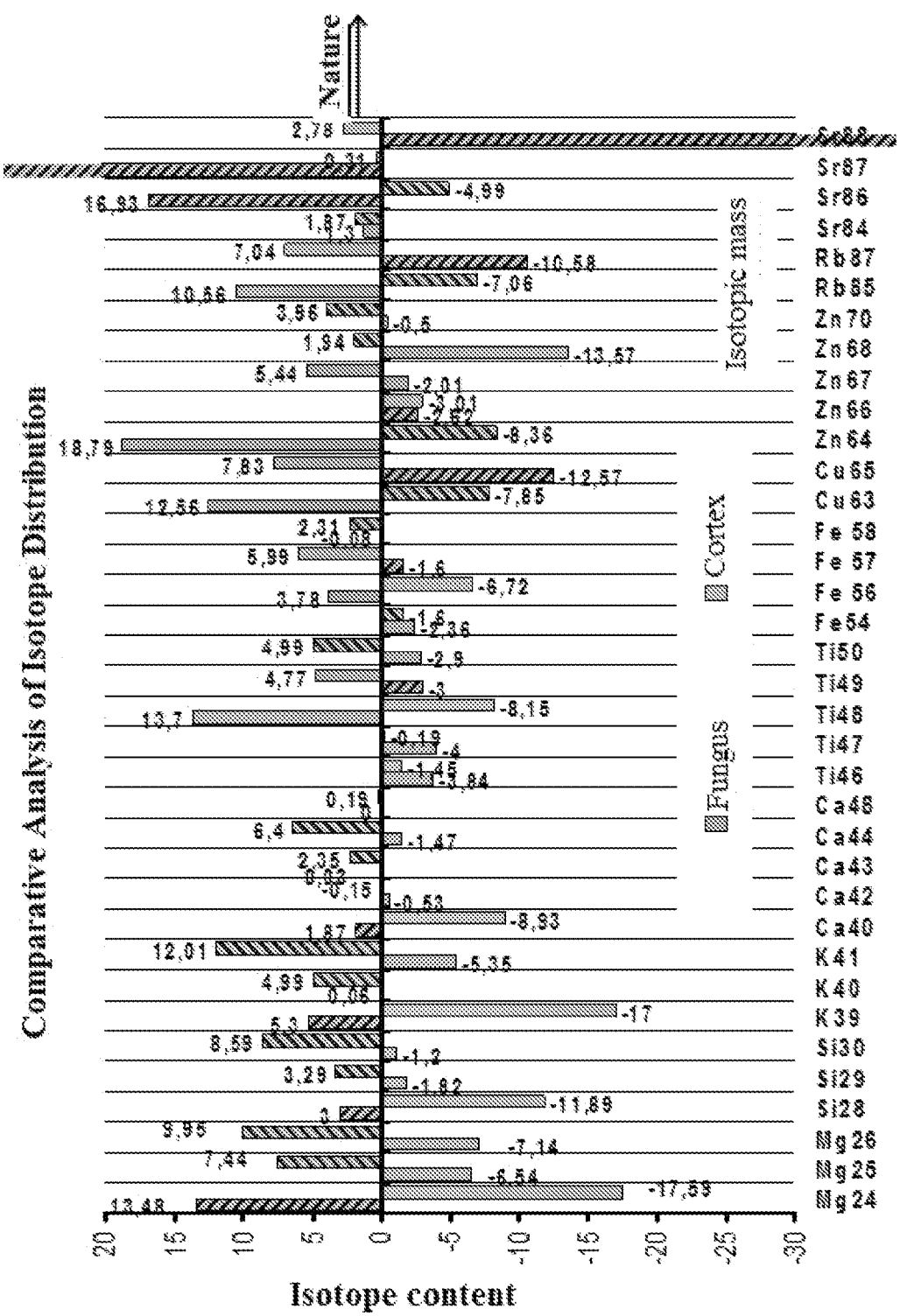
Figure 163:
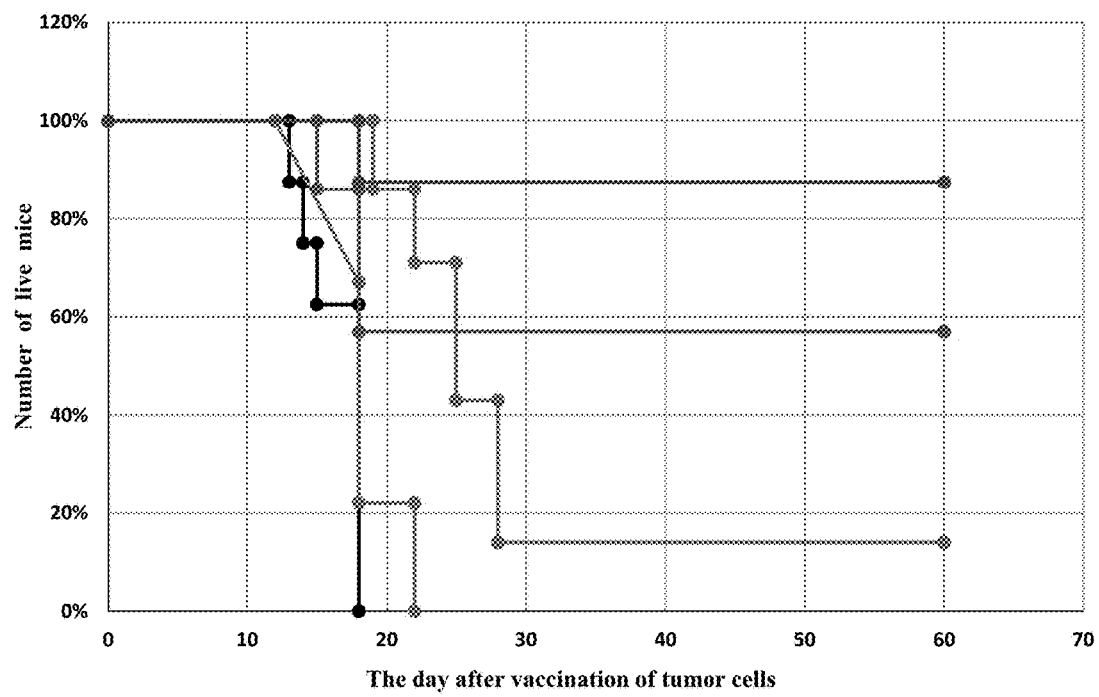
Figure 164:
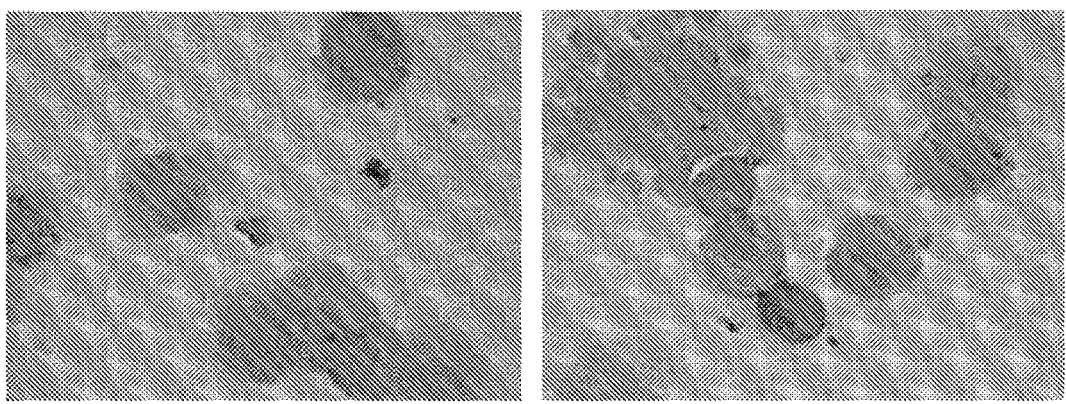
Figure 165:
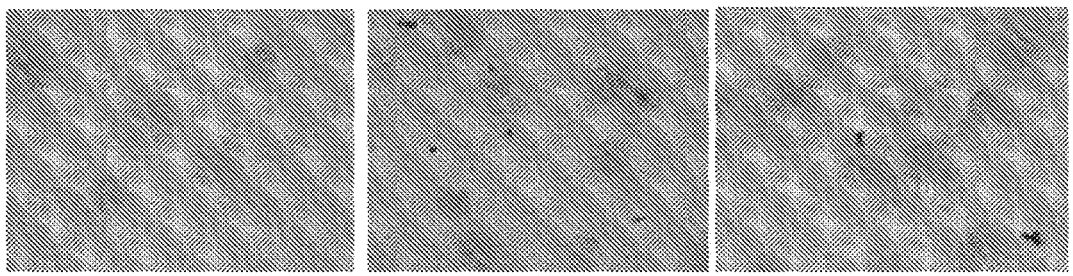

FIGS. 128A-128G illustrate a cell migration of the NRK cell line in vitro after their processing with the experimental preparations (24 hours following the violation of the monolayer integrity): A. Control, B. NRK+Doxorubicin, C. NRK+$^{39}$K component (2 mg/ml), D. NRK+$^{39}$K component (1 mg/ml), E. NRK+$^{64}$Zn component (25 meg/nil), F. NRK+$^{24}$Mg component (4 mg/ml), G. NRK+$^{24}$Mg component (2 mg/ml);

FIGS. 129A-129G illustrate a cell migration of the NRK cell line in vitro after their processing with the experimental preparations (36 hours following the violation of the monolayer integrity): A. Control, B. NRK+Doxorubicin, C. NRK+$^{39}$K component (2 mg/ml), D. NRK+$^{39}$K component (1 mg/ml), E. NRK+$^{64}$Zn component (25 meg/nil), F. NRK+$^{24}$Mg component (4 mg/ml), G. NRK+$^{24}$Mg component (2 mg/ml);

FIGS. 130A-130B illustrate a cell migration of the NRK cell line in vitro after their processing with the experimental preparations (72 hours following the scratch of the monolayer integrity): A. Control, B. NRK+Doxorubicin;

FIGS. 131A-131F illustrate a migration activity of cells of the HaCaT cell line after their processing with the experimental preparations (1 hour following the violation of the monolayer integrity): A. Control, B. HaCaT+Doxorubicin (15 ng/ml), C. HaCaT+Doxorubicin (5 ng/ml), D. HaCaT+$^{64}$Zn component (25 meg/nil), E. HaCaT+$^{64}$Zn component (25 mcg/ml)+Doxorumbicin (15 ng/ml), E. HaCaT+$^{64}$Zn component (25 mcg/ml)+Doxorubicin (5 ng/ml);

FIGS. 132A-132F illustrate a migration activity of cells of the HaCaT cell line after their processing with the experimental preparations (24 hours following the violation of the monolayer integrity): A. Control, B. HaCaT+Doxorubicin (15 ng/ml), C. HaCaT+Doxorubicin (5 ng/ml), D. HaCaT+$^{64}$Zn component (25 mcg/ml), E. HaCaT+$^{64}$Zn component (25 mcg/ml)+Doxorubicin (15 ng/ml), E. HaCaT+$^{64}$Zn component (25 mcg/ml)+Doxorubicin (5 ng/ml);

FIGS. 133A-133F illustrate a migration rate of cells of the HaCaT cell line after their processing with the experimental preparation (36 hours following the violation of the monolayer integrity): A. Control, B. HaCaT+Doxorubicin (15 ng/ml), C. HaCaT+Doxorubicin (5 ng/ml), D. HaCaT+$^{64}$Zn component (25 meg/nil), E. HaCaT+$^{64}$Zn component (25 mcg/ml)+Doxorumbicin (15 ng/ml), E. HaCaT+$^{64}$Zn component (25 mcg/ml)+Doxorubicin (5 ng/ml);

FIGS. 134A-134I illustrate a migration activity of cells of the A-431 cell line after their processing with the experimental preparation (1 hour following the violation of the monolayer integrity): A. Control, B. A-431+Doxorubicin (0.1 meg/nil), C. A-431+Doxorubicin (0.02 meg/nil), D. A-431+$^{64}$Zn component (20 meg/nil), E. A-431+$^{64}$Zn component (10 meg/nil), F. A-431+$^{64}$Zn component (20 mcg/ml)+Doxorubicin (0.1 meg/nil), G. A-431+$^{64}$Zn component (10 mcg/ml)+Doxorubicin (0.1 meg/nil), H. A-431+$^{64}$Zn component (20 mcg/ml)+Doxorubicin (0.02 meg/nil), I. A-431+$^{64}$Zn component (10 mcg/ml)+Doxorubicin (0.02 mcg/ml);

FIGS. 135A-135I illustrate a migration activity of cells of the A-431 cell line after their processing with the experimental preparation (24 hours following the violation of the monolayer integrity): A. Control, B. A-431+Doxorubicin (0.1 meg/nil), C. A-431+Doxorubicin (0.02 meg/nil), D. A-431+$^{64}$Zn component (20 meg/nil), E. A-431+$^{64}$Zn component (10 meg/nil), F. A-431+$^{64}$Zn component (20 mcg/ml)+Doxorubicin (0.1 meg/nil), G. A-431+$^{64}$Zn component (10 mcg/ml)+Doxorubicin (0.1 meg/nil), H. A-431+$^{64}$Zn component (20 mcg/ml)+Doxorubicin (0.02 meg/nil), I. A-431+$^{64}$Zn component (10 mcg/ml)+Doxorubicin (0.02 mcg/ml);

FIGS. 136A-136I illustrate a migration activity of cells of the A-431 cell line after their processing with the experimental preparation (48 hours following the violation of the monolayer integrity): A. Control, B. A-431+Doxorubicin (0.1 meg/nil), C. A-431+Doxorubicin (0.02 meg/nil), D. A-431+$^{64}$Zn component (20 meg/nil), E. A-431+$^{64}$Zn component (10 meg/nil), F. A-431+$^{64}$Zn component (20 mcg/ml)+Doxorubicin (0.1 meg/nil), G. A-431+$^{64}$Zn component (10 mcg/ml)+Doxorubicin (0.1 meg/nil), H. A-431+$^{64}$Zn component (20 mcg/ml)+Doxorubicin (0.02 meg/nil), I. A-431+$^{64}$Zn component (10 mcg/ml)+Doxorubicin (0.02 mcg/ml);

FIGS. 137A-137B illustrate a migration of cells of the A-431 cell line after their processing with Doxorubicin at a dose of 0.1 mcg/ml: A. in 40 hours after the start of the experiment, B. in 45 hours after the start of the experiment;

FIGS. 138A-138B illustrate a migration of cells of the A-431 cell line after their processing with the experimental preparation (72 hours following the violation of the monolayer integrity): A. A-431+$^{64}$Zn component (20 mcg/ml)+Doxorubicin (0.1 mcg/ml), B. A-431+$^{64}$Zn component (10 mcg/ml)+Doxorubicin (0.1 mcg/ml);

FIGS. 139A-139F illustrate a migration activity of cells of the MM-4 cell line in vitro after their processing with the experimental preparation (3 hours following the violation of the monolayer integrity): A. Control, B. MM-4+Doxorubicin (0.1 meg/nil), C. MM-4+Doxorubicin (0.01 meg/nil), D. MM-4+$^{64}$Zn component (15 meg/nil), E. MM-4+$^{64}$Zn component (15 mcg/ml)+Doxorubicin (0.1 meg/nil), F. MM-4+$^{64}$Zn component (15 mcg/ml)+Doxorubicin (0.01 meg/nil);

FIGS. 140A-140F illustrate a migration activity of cells of the MM-4 cell line in vitro after their processing with the experimental preparation (24 hours following the violation of the monolayer integrity): A. Control, B. MM-4+Doxorubicin (0.1 meg/nil), C. MM-4+Doxorubicin (0.01 meg/nil), D. MM-4+$^{64}$Zn component (15 meg/nil), E. MM-4+$^{64}$Zn component (15 mcg/ml)+Doxorubicin (0.1 meg/nil), F. MM-4+$^{64}$Zn component (15 mcg/ml)+Doxorubicin (0.01 meg/nil);

FIGS. 141A-141F illustrate a migration activity of cells of the MM-4 cell line in vitro after their processing with the experimental preparation (48 hours following the violation of the monolayer integrity): A. Control, B. MM-4+Doxorubicin (0.1 meg/nil), C. MM-4+Doxorubicin (0.01 meg/nil), D. MM-4+$^{64}$Zn component (15 meg/nil), E. MM-4+$^{64}$Zn component (15 mcg/ml)+Doxorubicin (0.1 meg/nil), F. MM-4+$^{64}$Zn component (15 mcg/ml)+Doxorubicin (0.01 meg/nil);

FIGS. 142A-142C illustrate a restoration of cell monolayer of the MM-4 cell line in the in vitro experiment in 70 hours after they were processed with the experimental components A. Control, B. MM-4+$^{64}$Zn component (15 mcg/ml)+Doxorubicin (0.1 meg/nil), C. MM-4+$^{64}$Zn component (15 mcg/ml)+Doxorubicin (0.01 mcg/ml);

FIGS. 143A-143B illustrate a restoration of cell monolayer of the MM-4 cell line in the in vitro experiment in 72 hours after they were processed with the experimental components A. Control, B. MM-4+$^{64}$Zn component (15 mcg/ml);

FIGS. 144A-14.4B present a table setting forth the characteristics of effects of light isotope containing materials, control group of cells and Doxorubicin in the experiment using the scratch assay migrations and the character of the combined effects of doxorubicin and light isotopes;

FIG. 145 illustrates a mass spectrum representing recorded m/z relationship graphically;

FIG. 146 illustrates a method of direct imaging of isotope K-39 on the sample surface;

FIG. 147 illustrates a view of homogeneity of potassium isotope distribution obtained by producing a profilogram;

FIGS. 148A-148C illustrate an isotope distribution in young and old biological tissue;

FIG. 149 illustrates a mass spectrum of the young tissue sample in a range of 1 to 50 amu;

FIG. 150 illustrates a mass spectrum of the old tissue sample in a range of 1 to 50 amu;

FIG. 151 illustrates a mass spectrum of the young tissue sample in a range of 50 to 100 amu;

FIG. 152 illustrates a mass spectrum of the old tissue sample in a range of 50 to 100 amu;

FIG. 153 illustrates a diagram of deviation of the isotopic composition of young and old tissues from the natural isotope distribution;

FIG. 154 illustrates a comparative assessment of changes in the concentration of heavy and light isotopes in biological tissues of different ages;

FIGS. 155A-155C illustrate an isotope distribution in samples 12 and 14;

FIGS. 156A-156D illustrate an isotope distribution in samples 18 and 20;

FIG. 157 illustrates a diagram of deviations of the isotopic composition in normal and pathological tissues of an adult from the natural isotope distribution obtained as a result of analysis of samples 12 and 14;

FIG. 158 illustrates a comparative assessment of changes in the concentration of heavy isotopes in samples 12 and 14;

FIG. 159 illustrates a diagram of deviations of the isotopic composition in normal and pathological tissues of an adult from the natural isotope distribution obtained as a result of analysis of samples 18 and 20;

FIG. 160 illustrates a comparative assessment of changes in the concentration of heavy isotopes in samples 18 and 20;

FIGS. 161A-161D illustrate a quantification of isotope content in the samples of fungus and cortex and comparison of the obtained results with natural distribution of isotopes;

FIG. 162 illustrates a diagram of deviation of the isotopic composition in the samples of fungus and cortex from the natural isotope distribution;

FIG. 163 presents data on the effect of the deuterium-depleted solution comprising $^{64}Zn_e$ aspartate on survival of experimental animals (model L1210);

FIG. 164 illustrates N-cadherin expression in NRK cells after their exposure to the action of $^{64}Zn$ (magnification ×100);

FIG. 165 illustrates CD44 expression in NRK cells after their exposure to the action of $^{64}Zn$ (magnification ×100).

DETAILED DESCRIPTION OF THE INVENTION

Unless otherwise specifically stated, all scientific and technical terms used herein have the same meaning as commonly understood by a person of ordinary skill in the art.

The term "isotope", as used herein, refers to a variant of a particular chemical element which are rather similar in their physical and chemical properties but have a different atomic mass. According to the proton-neutron model developed by D. I. Ivanenko and W. Heisenberg (1932), atoms of all chemical elements consist of three types of elementary particles: positively charged protons, negatively charged electrons, and neutrons that have no charge. The number of protons p in the nucleus determines the atomic number Z of the chemical element in Mendeleev's periodic table. The proton and the neutron, which have a common name—nucleons—have almost identical weight. The mass of the neutron (1.00866 amu) is somewhat greater than the proton mass (1.00727 amu). The electron mass is much smaller than that of the nucleons (for example, the proton-to-electron mass ratio is 1836.13). Therefore, the mass of the atom is concentrated in its nucleus. Hence, the mass number of the atom A is connected with the atomic number by a simple relation A=p+n=Z+n, where n is the number of neutrons in the nucleus of an atom. The number of protons in the nucleus of an atom uniquely determines the position of an element in the periodic table of the elements. Furthermore, the number of protons determines the number of electrons present in a neutral atom thus determining the chemical properties of this atom. However, atoms with the same atomic number Z (and hence the number of protons p) may have different neutron numbers n. Thus atoms with different atomic mass numbers may occupy the same position on the periodic table. Chemical elements having the same atomic number but a different atomic mass are known as isotopes.

The "light isotopes" of interest for the present invention include K-39, Mg-24, Zn-64, Rb-85, Si-28, Ca-40, Cu-63, Fe-54, Cr-52, Ni-58, Mo-92, Se-74, Br-79, and Cl-35.

The "natural abundance" of an isotope refers to the fraction of the total amount of the corresponding element that the isotope represents, on a mole-fraction basis (that is, not, for example, on a mass basis). For example, if $^{64}Zn$ had an earth natural abundance of 48.63%, that would mean that 48.63% of Zn atoms on earth are the isotope $^{64}Zn$. When a composition is "enriched" for a certain isotope, the abundance of the isotope in the composition is greater than the isotope's natural abundance. For the preceding $^{64}Zn$ example, a composition in which $^{64}Zn$ constitutes more than 48.63% of the total Zn in the composition, on a mole-fraction basis, would be "enriched" for $^{64}Zn$. Throughout this application, a subscript "e" following a light isotope chemical symbol or element name indicates that the designated element is enriched for that isotope. For example, $^{64}Zn$ refers to the light isotope zinc-64, whereas $^{64}Zn_e$ refers to zinc that is enriched for zinc-64. Thus, "$^{64}Zn_e$ aspartate," for example, refers to zinc aspartate in which the zinc is enriched for zinc-64.

The proportion of an element that is present as a particular isotope of the element is often expressed relative to a ratio called the standard isotope ratio or SIR. The abundance of the isotope of interest is the numerator of the SIR and the abundance of the most abundant isotope is the denominator. For example, $^{12}C$ is the most abundant carbon isotope and $^{13}C$ is a second carbon isotope. Assuming a standard abundance value for C-12 of 98.89% and a standard abundance value for $^{13}C$ of 1.11%, the SIR for $^{13}C$ would be 1.11/98.89=0.01122. Each SIR is obtained from a reference material. Deviations from the SIR may be observed in non-reference materials.

For ease and convenience, the abundance of a heavy isotope in a material of interest may be expressed relative to the heavy isotope's "standard" abundance in the reference material by reference to the difference in isotope ratios, expressed in parts per thousand or "‰" and referred to as delta-[isotope] or δ-[X], where "[X]" represents the isotope of interest. The δ value is calculated as $((R_{sample}-SIR)/SIR)\times 1000‰$, equivalent to $((R_{sample}/SIR)-1)\times 1000‰$, where $R_{sample}$ is the isotope ratio of the sample under evaluation. For example, if the carbon standard contains 99% $^{12}C$ and 1% $^{13}C$, and the sample has 98.95% $^{12}C$ and 1.05% $^{13}C$, then the corresponding SIR, or $^{13}C/^{12}C$ of the standard, is 1/99, or 0.0101, and the $^{13}C/^{12}C$ of the sample is 1.05/98.95, or 0.0106, so $\delta^{13}C_{sample}=((0.0106/0.0101)-1)\times 1000\%0=49.5‰$ (also known as 49.5 permil) or 0.0495.

Relative abundance of an isotope can also be expressed with respect to different isotopes' absolute abundances expressed in terms of "atom percent" and "fractional abundance." Atom percent is calculated as ($^AX$/(sum of all X isotopes))×100, whereas fractional abundance is simply $^AX$/(sum of all X isotopes), where "$^AX$" is a measure of the quantity of isotope A of element X in a sample, and "sum of all X isotopes" is a measure of the total quantity of element X in a sample. Enrichment for a specific isotope in a sample of interest may be expressed as a percentage of the fractional abundance or atom percent of a reference standard. For example, if a reference standard contained potassium, of which 93.3% was $^{39}K$, then the atom percent of $^{39}K$ would be 93.3% and its fractional abundance would be 0.933. If a sample were to contain potassium, of which 95.0% was $^{39}K$, then the sample would be enriched with respect to $^{39}K$ by (95.0−93.3)/93.3=1.82%. If a sample were said to be enriched with respect to $^{39}K$ by 5% relative to the standard, then the percentage of the potassium in the sample that is $^{39}K$ would be 1.05×93.3=97.97%.

The degree of enrichment of a certain isotope also may be expressed with respect to the difference D(I) (where "I" represents the identity of the isotope) between 100% and the isotope's natural abundance, expressed as a mole percentage of the total amount of the corresponding element. For example, if $^{64}Zn$ had a natural abundance of 48.63%, then $D(^{64}Zn)=100\%-48.63\%=51.37\%$. A sample's enrichment may then be expressed as the amount by which D is reduced. For the $^{64}$Zn example, for a sample in which D($^{64}$Zn) is reduced by 10%, D($^{64}$Zn) would equal 51.37% minus (10%×51.37), which equals 46.233%, and the $^{64}$Zn atom percent in the sample would be (100%−46.233%), which equals 53.767%. The sample would thus be characterized as enriched for $^{64}$Zn by 10% of D.

The authors of the present invention have discovered that a composition that comprises at least one light isotope selected from the group consisting of K-39, Mg-24, Zn-64, Rb-85, Si-28, Ca-40, Cu-63, Fe-54, Cr-52, Ni-58, Mo-92, Se-74, Br-79, and Cl-35, wherein the composition is enriched for the at least one light isotope relative to the natural abundance of the isotope, has pronounced therapeutic effects, as further described below. In addition to being enriched for a light isotope as described above, the composition may comprise one or more additional active ingredients, as well as water and inert auxiliary ingredients such as carriers, diluents and the like which are used to formulate the said composition and may be pharmaceutically acceptable or pharmaceutically unacceptable (which are used as intermediates in the preparation of pharmaceutically acceptable agents).

As used herein, the terms "treat," "treating," "treatment of" a condition encompass performing an act (such as administering the composition of the invention) in order to cure, eradicate, or diminish the severity of, the condition treated. These terms thus encompass accomplishing any one or more of curing, eradicating, and diminishing the severity of the condition treated. As used herein, the terms "prevent," "preventing," "prevention of" a condition encompass performing an act (such as administering the composition of the invention) in order to prevent the occurrence of the condition and diminish the severity of the condition if it occurs subsequent to the act. These terms thus encompass accomplishing any one or more of wholly preventing the condition from occurring and diminishing the severity of the condition if it occurs subsequent to the act.

For reference with respect to the invention, the above-listed isotopes are considered to have the natural abundances, on a mole-fraction basis, shown in the following table. The table also shows the corresponding percentages preferred for use in the compositions of the invention, on a mole-fraction basis (lower limits are provided; in every case, the maximum theoretical upper limit is 100%). For example, in a composition of the invention that uses a therapeutic amount of $^{64}$Zn, the zinc in the composition preferably would contain at least about 90% $^{64}$Zn. Compositions that contain isotopes with lower levels of enrichment may also be effective and are within the scope of the invention.

| Isotope | Natural abundance (%) | % for therapeutic use |
|---|---|---|
| $^{39}$K | 93.2581 | at least about 98% |
| $^{24}$Mg | 78.99 | at least about 95%* |
| $^{64}$Zn | 48.63 | at least about 90%* |
| $^{85}$Rb | 72.17 | at least about 90%* |
| $^{28}$Si | 92.2297 | at least about 95% |
| $^{40}$Ca | 96.94 | at least about 98% |
| $^{63}$Cu | 69.17 | at least about 90%* |
| $^{54}$Fe | 5.845 | at least about 80%* |
| $^{52}$Cr | 83.789 | at least about 90% |
| $^{58}$Ni | 68.0769 | at least about 90%* |
| $^{92}$Mo | 14.84 | at least about 80%* |
| 74Se | 0.89 | at least about 50%* |
| $^{79}$Br | 50.69 | at least about 90%* |
| $^{35}$Cl | 75.78 | at least about 90%* |

*In some embodiments, an enrichment level about 10 percentage points lower may be used for this isotope for therapeutic application and preferably for prophylactic use. For example, for $^{64}$Zn, a composition in which the zinc contains at least about 80% $^{64}$Zn may be administered for therapeutic purposes.

In a therapeutic composition of the invention, the composition is enriched for at least one light isotope selected from the group that includes $^{39}$K, $^{24}$Mg, $^{64}$Zn, $^{85}$Rb, $^{28}$Si, $^{40}$Ca, $^{63}$Cu, $^{54}$Fe, $^{52}$Cr, $^{58}$Ni, $^{92}$Mo, 74Se, $^{79}$Br, and $^{35}$Cl, or any combination thereof. At least one light isotope may be present as a component of a chemical compound, such as the salt of an organic or inorganic acid, which is pharmaceutically acceptable and can be administered to humans and veterinary animals (such as veterinary mammals). Exemplary salts include the chloride, citrate, sulfate, aspartate, glutamate, asparaginate and ethylene diamine disuccinic acid (referred to herein interchangeably as "EDDS" and "EDDA") salts of the light isotope, and hydrates of such salts. For example, zinc enriched for $^{64}$Zn may be present in the form of the salt zinc aspartate or the salt zinc asparaginate.

The therapeutic composition of the invention may be prepared by making a compound that is enriched for a light isotope, such as the salt of an organic or inorganic acid and the light isotope, purifying the obtained compound by standard methods, and subsequent preparation of the composition of the invention in any appropriate form, such as an aqueous solution. Such methods are well known and the person of ordinary skill in the art can prepare a compound containing a light isotope of a particular chemical element, its salt in particular. The preparation process of the complex of aspartic acid and zinc which is enriched for the isotope $^{64}$Zn is described in an Example below. The light isotope-enriched compound may be administered as a component or ingredient of any convenient dosage form. Such dosage forms include topical dosage forms such as solutions, sprays, lotions, salves, ointments, gels, creams, soaps, shampoos, and foams, oral dosage forms such as tablets, capsules, syrups, suspensions, lozenges, gums, sprays, patches, and solutions, injection dosage forms such as solutions, e.g. aqueous solutions, and conventional dosage forms suitable for other conventional routes of administration. Conventional dosage forms are well-known to the person of ordinary skill in the art. Examples of such dosage forms and their preparation are described in, for example, Loyd V. Allen, Jr. et al., *Ansel's Pharmaceutical Dosage Forms and Drug Delivery Systems* (8th ed. 2005) (Lippincott Williams & Wilkins), and publications cited therein.

The therapeutic composition of the invention may contain water as solvent. The composition of the invention may be in the form of an aqueous solution to be administered by any suitable route, such as orally and topically, or in the form of a gel, salve, ointment, paste, cream, foam, lotion, drops, or other topical composition. In a preferred aqueous solution, the water used is enriched for $^{16}$O and enriched for $^{1}$H by being depleted for $^{2}$H. The composition may further include any suitable excipient known to the person of ordinary skill in the art, including solvents, binders, lubricants, emulsifiers, detergents, surfactants, buffers, stabilizers, and preservatives. These are described in commonly used references, such as the Handbook of Pharmaceutical Excipients.

The concentration of the light isotope-enriched element in a composition of the invention, relative to the total weight of the composition, varies according to conventional composition weights and the dosage of the light isotope-enriched element. Appropriate dosages of the light isotope-enriched element are set forth below. Preferably the composition of the invention comprises an effective amount of at least one light isotope, wherein "effective amount" refers to that amount that provides a therapeutic effect such as an anti-cancer effect. As stated above, the quantity of light isotope that is effective is proportional to the quantity of the corresponding element that is present in the body. Where the body contains a relatively large quantity of the element, a correspondingly relatively large amount of the element's light isotope will be required to provide an effective dosage amount. On the other hand, where the body contains a relatively small quantity of the element, a correspondingly relatively small amount of the element's light isotope will be required to provide an effective dosage amount. These quantities are reflected in the "guidance amounts" for each element, the recommended amount for daily human consumption, as detailed below.

In certain embodiments, the preferred dosage of any of the light isotopes is proportional to various authoritative daily ingestion guidances (e.g. recommended dietary allowance (USRDA), adequate intake (AI), recommended dietary intake (RDI)) of the corresponding element. The light isotope dosage is preferably between about ½ and about 30 times the guidance amount of the corresponding element, more preferably between about 1 and about 10 times the guidance amount, even more preferably between about 1 and about 3 times the guidance amount. Generally, the low end of the dose range to be administered daily is about ½ the guidance daily amount, whereas the high end is as follows: total daily oral doses can be as high as about 30 times the guidance daily amount, total daily doses administered by intraperitoneal injection can be as high as about 20 times the guidance daily amount, and total daily doses administered intravenously can be as high as about 7 times the guidance daily amount.

Thus, in preferred embodiments, a single dose of a composition of the invention for daily administration would be formulated to comprise a quantity within these ranges, such as about ½, about 1, about 3, about 5, about 10, and about 20 times the guidance amount. These amounts generally are for oral intake or topical application. In some embodiments, the preferred intravenous dosage is lower, such as from about 1/10 to about ½ the guidance amount. Doses at the low end of these ranges are appropriate for anyone with a heightened sensitivity to a specific element or class of elements (e.g., those with kidney problems). For zinc, the guidance amount ranges from 2 mg in infants to 8-11 mg (depending on sex) for ages 9 and up. Guidance amounts for some of the elements used in the compositions of the invention are presented below based on information obtained from https://ods.od.nih.gov/factsheets/list-all/ and https://health.gov/dietaryguidelines/2015/guidelines/appendix-7/, summarized below. Daily dosages discussed throughout this application may be subdivided into fractional dosages and the fractional dosages administered the appropriate number of times per day to provide the total daily dosage amount (e.g. ½ the daily dose administered twice daily, ⅓ the daily dose administered three times daily, etc.).

| Element/Isotope | guidance amount, daily |
|---|---|
| magnesium/ $^{24}$Mg | 30-420 mg (400-420 mg in males 14+; 310-360 mg in females 14+) |
| potassium/ $^{39}$K | 1 to 3 years: 3 g/day<br>4 to 8 years: 3.8 g/day<br>9 to 13 years: 4.5 g/day<br>14 to 18 years: 4.7 g/day<br>Age 19 and older: 4.7 g/day |
| chromium/ $^{52}$Cr | Hexavalent chromium should be avoided. Chromium complexes are preferred for oral administration (e.g. picolinate, dinicocysteinate, as nicotinic acid complex). For parenteral administration, chromic chloride at 4 mcg/ml may be used.<br>0-6 mos. 0.2 mcg<br>7-12 mos. 5.5 mcg<br>1-3 yrs 11 mcg<br>4-8 yrs 15 mcg<br>9-13 yrs females: 21 mcg, males: 25 mcg<br>14-18 yrs females: 24 mcg, males: 35 mcg<br>19-50 yrs females: 25 mcg, males: 35 mcg<br>>50 yrs females: 20 mcg, males: 30 mcg |
| Iron/ $^{54}$Fe | Birth to 6 months 0.27 mg<br>7-12 months 11 mg<br>1-3 years 7 mg<br>4-8 years 10 mg<br>9-13 years 8 mg<br>14-18 years males: 11 mg, females: 15 mg<br>19-50 years males: 8 mg, females: 18 mg<br>Adults 51 years and older 8 mg |
| Copper/ $^{63}$Cu | adequate:<br>0 to 6 months: 200 mcg<br>7 to 12 months: 220 mcg<br>recommended:<br>1 to 3 years: 340 mcg<br>4 to 8 years: 440 mcg<br>9 to 13 years: 700 mcg<br>14 to 18 years: 890 mcg<br>19 and older: 900 mcg |
| Zinc/ $^{64}$Zn | Birth to 6 months 2 mg<br>7 months-3 years 3 mg<br>Children 4-8 years 5 mg<br>Children 9-13 years 8 mg<br>14-18 years (boys) 11 mg<br>14-18 years (girls) 9 mg<br>Adults (men) 11 mg<br>Adults (women) 8 mg |
| Calcium/ $^{40}$Ca | 1-3 years 700 mg<br>4-8 years 1000 mg<br>9 years-adult 1300 mg |
| Chlorine/ $^{35}$Cl | 0-6 mos. 180 mg<br>6-12 mos. 570 mg<br>1-10 yrs. 1.75 g<br>11-18 yrs. 2.2 g<br>19-50 yrs. 2.3 g<br>over 50 yrs. 1.9 g |
| Selenium/ $^{74}$Se | Birth to 6 months 15 mcg<br>7 months-3 years 20 mcg<br>Children 4-8 years 30 mcg<br>Children 9-13 years 40 mcg<br>14 years and older 55 mcg |

For purposes of the invention, for the following substances, the following amounts are considered to be benchmark daily intakes (guidance amounts): rubidium: between about 1 and 2 mg per day; silicon: about 10 mg; molybdenum: about 1.5 mg; nickel: about 100 mcg; bromine: 1 mg/kg body mass. Thus, a composition of the invention that contains light rubidium, for example, preferably contains $^{85}Rb_e$ in an amount between about 1 times and about 20 times these amounts (between about 1 mg and about 40 mg), more preferably between about 1 and about 10 times these amounts, and even more preferably between about 1 and about 3 times these amounts. (Throughout the application, the term "mcg" has its conventional meaning of "microgram(s)".)

Based on the above, in certain embodiments, a composition of the invention containing $^{64}Zn_e$ as the active ingredient, prepared for administration to a male 19 years of age or older, preferably contains, in a single dose, between about 11 mg and about 220 mg $^{64}Zn_e$ (zinc enriched for $^{64}Zn$), more preferably between about 11 mg and about 110 mg $^{64}Zn_e$, even more preferably between about 11 mg and about 33 mg $^{64}Zn_e$. Such a composition may be, for example, for oral administration, such as a tablet or capsule, or for topical administration, such as a cream, gel, ointment, or lotion (optionally containing DMSO or other absorption-enhancing agent and other appropriate excipients).

In certain preferred embodiments, the daily dosages of $^{64}Zn_e$ in a composition of the invention, such as a tablet, capsule, salve, cream, lotion, or ointment, comprise between about 10 and about 50 mg of $^{64}Zn_e$, such as about 15 mg, about 30 mg, or about 45 mg of $^{64}Zn_e$, which may be elemental or in the form of $^{64}Zn_e$ asparaginate, $^{64}Zn_e$ aspartate, or another pharmaceutically acceptable $^{64}Zn_e$ salt or complex. Such compositions preferably contain, in addition to the $^{64}Zn_e$ compound, excipients suitable to the formulation type. In analogous preferred embodiments, the daily dosages of another light isotope may be determined relative to these dosages and the relative guidance amounts of $^{64}Zn_e$ and the other light isotope. For example, if the guidance amount of another light isotope were one-half (½) that of zinc, then preferred daily doses of the other light isotope in a composition of the invention would be between about 5 mg and about 25 mg, such as about 7.5 mg, about 15 mg, or about 22.5 mg, in elemental form or as a pharmaceutically acceptable salt or complex.

In some embodiments, a composition of the invention may contain two or more compounds that are each enriched for a light isotope. The percentages and masses above may represent each of the light isotope-enriched compounds and may alternatively represent their total percentage or mass.

The composition of the invention may include an additional active agent, as well as auxiliary agents which improve the stability and therapeutic properties of the composition and are generally present in many finished pharmaceutical products.

Compositions that contain zinc are known and include topical formulations that contain 20% or 40% w/w zinc oxide and oral formulations such as tablets and capsules that contain 30 mg or 50 mg zinc in various forms. In an embodiment, the present invention provides comparable compositions in which the zinc is enriched for $^{64}Zn$. For example, the zinc in such compositions may contain at least about 90% $^{64}Zn$, such as between about 90% and about 99.9% $^{64}Zn$, such as about 90%, about 95%, about 99%, or about 99.9% $^{64}Zn$, on a mole fraction basis. Examples of such compositions include: a paste that contains between about 20% w/w and about 40% w/w $^{64}Zn_e$ oxide, such as about 20%, about 30%, or about 40% w/w $^{64}Zn_e$ oxide; an ointment that contains about 20% w/w $^{64}Zn_e$ oxide; tablets and capsules that contain between about 30 mg and about 50 mg of $^{64}Zn_e$, such as about 30, about 40, or about 50 mg $^{64}Zn_e$, present in the form of zinc gluconate, zinc bisglycinate chelate, or any pharmaceutically acceptable zinc salt such as those enumerated above (aspartate, asparaginate, glutamate, EDDA, etc.). Such compositions preferably also contain excipients suitable to each formulation type. Examples of such excipients and representative paste, ointment, tablet and capsule compositions, and their preparation, are disclosed, for example, in *Ansel's Pharmaceutical Dosage Forms and Drug Delivery Systems* (8th ed. 2005) (Lippincott Williams & Wilkins) (capsules and tablets are discussed, for example, at pages 204-75, and ointments and pastes are discussed, for example, at pages 276-97; both sections are incorporated by reference herein in their entirety), and publications cited therein. Dosage amounts of any topical compositions of the invention preferably vary with skin thickness at the site of administration, with higher dosage amounts being used on thicker skin and lower dosages on thinner skin.

The pH of the said composition, when aqueous (including emulsions such as oil-in-water and water-in-oil emulsions), may be between about 2 and about 10, such as between about 2 and about 4, between about 4 and about 6, between about 6 and about 8, and between about 8 and about 10. For example, the composition may have a pH of about 2, about 3, about 4, about 5, about 6, about 7, or about 8, as appropriate for the route of administration and site of administration.

Referring to FIG. 1, a pharmaceutical composition of the present invention is generally shown at 10. The pharmaceutical composition 10 is used for improving health, cure abnormalities and degenerative disease; achieve anti-aging effect of therapy and therapeutic effect on mammals, such as, for example, a human 12. The pharmaceutical composition 10 includes a pharmaceutical carrier 14 and an isotope selective ingredient 16 including at least one of a chemical element 18 and a chemical compound 20 containing the chemical element whereby isotope distribution in the at least one of the chemical element 18 and the chemical compound 20 containing the chemical element 18 is different from natural distribution of at least one of isotopes wherein the part of selected isotope of the chemical element 18 ranges from 0 to 100%.

As discussed above, the selected isotopes include at least one of K-39; Mg-24; Zn-64; Rb-85; Si-28; Ca-40; Cu-63; Fe-54; Cr-52; Ni-58; Mo-92; Se-74; Br-79; Cl-35 and combinations thereof. The pharmaceutical of the carrier pharmaceutical composition is used in the form of a solution, a gel, a cream, a spray, an aerosol, a patch, nanoparticles, inorganic molecules, organic molecules, a plant, a fruit and a vegetable. The pharmaceutical composition 10 includes combination of at least two of the isotopes wherein one of the isotopes is lighter in weight than the other of the isotopes to achieve therapeutic effect. The light isotopes of the pharmaceutical composition are K-39; Mg-24; Zn-64; Rb-85; Si-28; Ca-40; Cu-63; Fe-54; Cr-52 Ni-58; Mo-92; Se-74; Br-79; (1-35. The chemical compounds 20 of the pharmaceutical composition 10 include the isotopes such as at least one of oxides, sulfates, citrates gluconate, and a chelate containing a ligand bonded to a central metal atom at least two points. The chemical elements 18 and the chemical compounds 20 are food supplements.

A method of using the pharmaceutical composition to improve health, cure abnormalities and degenerative disease and achieve therapeutic effect on mammals is provided. The method begins with preparing the pharmaceutical carrier and the isotope selective ingredient including at least one of the chemical element and the chemical compound containing the chemical element whereby isotope distribution in the at least one of the chemical element and the chemical compound containing the chemical element is different from natural distribution of at least one of isotopes wherein the part of selected isotope of the chemical element ranges from 0 to 100%.

The next step of the method includes administering the first of the isotopes at least prior to and after surgical removal of a solid tumor to prevent possible metastases and occurrence of secondary effects and to prevent metastasizing followed by administering a second of the isotopes to transform a cancer cell phenotype into a normal cell. The first of the isotopes administered prior to and after surgical removal of the solid tumor to prevent possible metastases include at least one of K-39, Mg-24, Zn-64, Rb-85, Si-28 and combination thereof. The second of the isotopes used to transform the cancer cell phenotype into the normal cell includes at least one of K-39, Mg-24, Zn-64, Rb-85, Si-28 and combination thereof. The step of administering the pharmaceutical carrier can be carried orally, intravenously and locally without limiting the scope of the present invention. The isotope selective ingredient may be administered prior to and after surgical removal of a solid tumor to prevent further spreading of cancer cells and metastasizing of a primary tumor.

The isotope selective ingredient is administered at least prior to, after and simultaneously with chemotherapeutic agent are used to amplify therapeutic effect on cancer tissue and to protect healthy tissue from chemotherapy side effects and from immunotherapy side effect. The chemotherapeutic agent includes at least one of Actinomycin, All-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, and Vinorelbine. The method of the present invention allows administering the isotope selective ingredient to cause fast and significant reduction in degree of malignancy and to induce changes of cells phenotype form malignant phenotype to a benign or normal phenotype.

Numerous comprehensive Assessment of Antitumor Activity of $^{39}$K, $^{64}$Zn and $^{24}$Mg in In Vitro and In Vivo Experiments were conducted pertaining to preparation and administration of the inventive the pharmaceutical composition. Such experiments and tests will be presented and described herebelow as Example 1, Leukemia Cell Lines, Burkitt lymphoma (Namalwa line) and acute promyelocyte leukemia (HL-60 line) cells under the action of components containing $^{39}$K, $^{64}$Zn and $^{24}$Mg and Phenotypic features of acute promyelocyte leukemia cells (HL-60 line) under the action of components containing $^{39}$K, $^{64}$Zn and $^{24}$Mg, Example 2, Cells of Renal Carcinoma in a Rat (PA), Antitumor and biological activity of components containing $^{64}$Zn and $^{24}$Mg and Zn, Mg, K elements on a model of renal carcinoma (PA) in a rat in the in vitro experiment, Immunocytochemical study of adhesion proteins, cytoskeleton (cadherins) and CD 44 stem cell marker after their exposure to the action of components containing $^{39}$K, $^{64}$Zn and $^{24}$Mg on a model of renal cell carcinoma (PA) in a rat, Detection of cumulative properties of $^{64}$Zn, Example 3, Phenotype and cytogenetic characteristics of A-549, MCF-7 and COLO 205 human tumor cell lines. Cumulative effect of anti-tumor properties of light isotopes, Epithelial-mesenchymal transition and a transcription factor as criteria for assessing phenotype in A-549, MCF-7 and COLO 205 human tumor cells and normal rat cells after their exposure to the action of components containing $^{39}$K, $^{64}$Zn and $^{24}$Mg. Detection of the effect of cumulation of antitumor properties in the group of substances under study on the A-549 cell line, Cytogenetic characteristics of A-549, MCF-7 and COLO-205 cell lines after their exposure to the action of components containing $^{39}$K, $^{64}$Zn and $^{24}$Mg, Example 4, Comparative characteristics of the action of Doxorubicin and the action of components containing $^{39}$K, $^{64}$Zn and $^{24}$Mg on normal rat kidney cells (NRK), Comparative assessment of the effects of $^{39}$K, $^{64}$Zn and $^{24}$Mg vs Doxorubicin, an anti-cancer agent, on normal rat kidney cells (NRK cell line), Example 5, Assessment of migration characteristics of A-549, FC, NRK, HaCaT, A-431 and MM-4 cell lines after their exposure to the action of components containing $^{39}$K, $^{64}$Zn and $^{24}$Mg. Analysis of the combined effect of each of the components of $^{39}$K, $^{64}$Zn and $^{24}$Mg and Doxorubicin, Assessment of the combined effect of the component containing $^{64}$Zn and Doxorubicin, Assessment of the effect of $^{39}$K, $^{64}$Zn and $^{24}$Mg on migration characteristics of stem cells derived from rat fibroblasts, Combined effect of the component containing $^{64}$Zn and Doxorubicin on stem cells from rat fibroblasts, Migration activity of normal rat kidney cells (NRK cell line) after their exposure to the action of components containing $^{39}$K, $^{64}$Zn and $^{24}$Mg compared to the effect of Doxorubicin, Combined effect of the component containing $^{64}$Zn and Doxorubicin on the migration activity of healthy human skin cells (HaCaT cell line), Combined effect of the component containing $^{64}$Zn and Doxorubicin on the migration activity of human epidermoid carcinoma cells (A-431 cell line), Combined effect of the component containing $^{64}$Zn and Doxorubicin on the migration activity of human melanoma tumor cells (MM4 cell line).

Referring now to Example 1, Burkitt lymphoma (Namalwa line) and acute promyelocyte leukemia (HL-60 line) cells under the action of components containing $^{39}$K, $^{64}$Zn and $^{24}$Mg, the main objective was to assess the phenotypic differences between cells of Burkitt lymphoma and acute promyelocyte leukemia under the action of components containing $^{39}$K, $^{64}$Zn and $^{24}$Mg. The assessment of changes in the cell phenotype was carried out in relation to the cytoskeleton and adhesion proteins in the human tumor cells of Burkitt lymphoma (Namalwa line) and acute promyelocyte leukemia (HL-60 line) after their exposure to the effect of components containing $^{39}$K, $^{64}$Zn and $^{24}$Mg.

The chemical form of the active ingredients is KCL for $^{39}$K and sulfates for $^{64}$Zn and $^{24}$Mg. The following antigens/markers that distinguish a differentiation status of the cells and their malignancy were used in the research: ICAM-1 or CD54 marker is a single chain glycoprotein with a molecular mass of 55 kDa. It is an integral membrane protein that contains five extracellular Ig-like domains. ICAM-1 has a myeloid and B-cell origin on the tumor cells. In lymph proliferative diseases ICAM-1 expression is associated with the degree of malignant transformation. ICAM-1 is expressed on various types of endothelial cells, epithelial cells, tissue macrophages, mitogen-stimulated T-cells, in the germinal center cells, dendritic cells and in lymph nodes. ICAM-1 fibroblasts and endothelial cells are induced by such inflammatory mediators as IL-1, TNF α and IFN γ: ICAM-1 expression increases during 6 to 8 hours after stimulation and persists for at least 48 hours.

E- and N-cadherin family mediates cell-cell adhesion in the presence of calcium ions. The cadherin family consists of structurally similar molecules composed of 723 to 748 amino-acid residues. The degree of homology between cadherins from a variety of tissues and samples reaches 50 to 60%. The cadherin family includes three subclasses: E-cadherins found in epithelial cells and known as uvomorulin, a cell adhesion molecule (CAM 120/80 or L-CAM), N-cadherins found in the mature nervous and muscular tissue and known as A-CAM and P-cadherins originally found in the placenta and epithelium but expressed transiently by other tissues as well during their development. Cadherins play an important role in the formation of adhesive contacts responsible for the organization of the cytoskeleton of cells. CD44 marker is a glycoprotein with a molecular mass of 80 to 95 kDa and is a cell-surface marker for T-lymphocytes and B-lymphocytes, monocytes, macrophages, granulocytes, fibroblasts, epithelial cells and cells of the brain, red blood cells.

Alluding to the above, CD44 is involved in cell-matrix interaction, activation of lymphocytes and in lymph node homing. In addition to participating in the formation of physical contact between stromal cells and early B-cell precursors, it is involved in other forms of cell-cell interactions as well as in cell migration and metastasis processes. In addition, examination of these antigens from the perspective of research into the epithelial-mesenchymal transformation (EMT) process is of immediate interest since the above named proteins are also EMT associated markers. It is important to note that EMT, a highly conserved cellular program that leads to the transformation of adherent polarized epithelial cells into mobile morphologically altered mesenchymal stem cells, is mostly studied only in relation to solid tumors.

However, articles about an important role of EMT in the study of lymphomas and leukemias as well have started coming out recently, which is an interesting stage in the research into the tumor process as a whole, since these tumors radically differ from "usual solid neoplasias" in their histogenesis and, accordingly, in their phenotypic characteristics. Thus, such comprehensive research into adhesion proteins and cell cytoskeleton in the tumor cells of Burkitt lymphoma and acute promyelocyte leukemia after the action of the group of components under study is a relevant and contemporary attempt of a deeper analysis of the modification of a cell phenotype of tumor cells in order to assess changes in the degree of their malignancy. Materials and methods for leukemia cell lines HL-60 and Namalva and cell culture conditions will now be described. Initial HL-60 and Namalva cells were cultured in complete RPMI 1640 medium (PAA) (PAA, Austria) supplemented with 10% fetal calf serum (PAA) and incubated in 5% $CO_2$ humidified atmosphere at 37° C. The culture medium was replaced in 2 to 3 days and the cells were passaged in 4 to 5 days. The effect of $^{39}K$, $^{64}Zn$ and $^{24}Mg$ components and doxorubicin (chosen as a reference drug) on viability of cell lines HL-60 and Namalva was assessed using 2 plates (Type of cell plate—TPP, Italy). The first plate was for coloring cells with trypan blue and the second one was for the MTT assay.

To carry out this experiment, the components under study, namely chloride (for $^{39}K$) and sulphates (for $^{64}Zn$ and $^{24}Mg$), were introduced in the respective wells of the 96-well plates for cell culture (evenly for the 2 plates) according to the scheme shown below. Initial concentrations of the components. Initial solutions of chloride (for $^{39}K$) and sulphates (for $^{64}Zn$ and $^{24}Mg$) were administered at the doses of 20 mg/ml, 4 mg/ml, 0.8 mg/ml, 0.16 mg/ml, 32 mcg/ml, 6.4 mcg/ml, 1.28 mcg/ml, 0.256 mcg/ml to 100 mcl of complete medium (RPMI 1640 (PAA, Austria)+10% fetal calf serum (PAA, Austria)+40 mcg/ml of gentamicin (Pharmak, Ukraine).

These initial concentrations of the components were prepared separately in sterile microtubes before the start of the experiment. Initial concentrations of doxorubicin. Initial (prior to the experiment) concentrations of doxorubicin prepared in a similar manner in sterile microtubes were as follows: 0.8 mg/ml, 0.16 mg/ml, 32 mcg/ml, 6.4 mcg/ml, 1.28 mcg/ml, 0.256 mcg/ml, 51.2 ng/ml, 10 ng/ml and were also added to 100 mcl of complete medium. Differences in initial concentrations of the components under study and doxorubicin are due to the various degree of their activity:

we compared those concentrations which produced a statistically significant effect. The main purpose of the research was to assess the phenotypic changes in the cells after they were exposed to the action of the group of components under study containing $^{39}K$, $^{64}Zn$ and $^{24}Mg$. As is known (Nekludov A. D., 1990; Belokrylov G. A. et al., 1996; Kolganov A. S., 2001; Horwitz L. D., 1994; Zhou S. et al., 2001), doxorubicine has pronounced cytostatic effect (starts the process of dying of both affected and healthy cells as evidenced by the picture of their death in FIG. 10C, 10D, 10E, 10F) starting from the minimal doses of action of this component.

The cytotoxic properties of doxorubicin (especially its selective cardiotoxicity and expressed depression of bone marrow function) were studied in detail in several papers (Stukov A. V. et al., 1998; Vatutin N. V. et al., 2001; Kolygin B. A., 2002; Lushnikova E. L. et al., 2004; Singal P. K., Iliskovic N., 1998; Lebrecht D. et al., 2004; Giri S. N. et al., 2004) and pose a major problem in its widespread use in cancer patients due to reduction in the length and quality of life of the patients and sometimes resulting in lethal outcome. Thus doxorubicin as a reference drug is characterized by a negative effect both on healthy cells, as it triggers the mechanism of cell death, and on the whole body.

After preparation of the corresponding concentrations of the components, they were introduced into appropriate wells of the plate in which HL-60 or Namalva cell were in complete medium. The volume of the culture medium with cells was 100 mcl per well and the concentration of cells in the suspension was 3×105 cells/ml (3×106/plate). After the components were placed into the wells, the final concentration (component+cells in the suspension) became smaller and corresponded to the values given in the Table of Concentration Characteristics. For components containing $^{39}K$, $^{64}Zn$ and $^{24}Mg$ the values of final concentrations (chloride and sulfates) are shown in FIG. 1, in 1st, 2nd and 3rd column of the table and for doxorubicin its concentrations in the wells.

After the components were placed into the wells, the plate was placed in an incubator in 5% $CO_2$ humidified atmosphere at 37° C. Quantitative characteristics of live cells and dead cells (coloring of the cell suspension with trypan blue) or their viability (MTT assay) The quantitative assessment of live and dead cells after the action of doxorubicin was performed by their coloring with trypan blue (HyClon, USA), 20 mcl of the suspension of the test cells were mixed with 20 mcl of the trypan blue solution and then resuspended. The obtained solution was placed into the Goryaev chamber and the number of live and dead cells was calculated using the following formula: A/80×2=X*106 cells per 1 ml of medium, where A is a number of cells calculated in the Goryaev chamber (in 5 squares) and x 2 is trypan blue dilution (1:1). The cell viability after the action of the group of components under study containing $^{39}K$, $^{64}Zn$ and $^{24}Mg$ was determined using MTT (Methylthiazoletetrazolium). To do this, 10 mcl of MTT solution (Sigma, USA) (5 mg/ml of dye in PBS) were added in each well of the plate. Then the plate was incubated in a $CO_2$ incubator at t 37° C. for 3 hours.

After the incubation the medium was removed from the wells and the formed tetraformazan crystals were dissolved in 50 mcl of dimethylsulphoxide (Applichem, Germany). The results were fixed using a multi-well spectrophotometer with an excitation wave length of 540 nm. The percent of inhibition of cell viability was calculated using the following formula: IR=(1−A 540 (experiment)/A540 (control))×100%. In carrying out the immunocytochemical (ICC) assay, cells on microscope glasses (cytospin preparations) were fixed in the solution (methanol+acetone (1:1)) for 2 hours at t−20° C. and then incubated with a 1% solution of bovine serum albumin (BSA) for 20 minutes.

Then such monoclonal antibodies as CD44, N-cadherin, ICAM and IgM were applied for the period of time specified in the manufacturer's instructions (30 to 60 minute time intervals), after which Poly Vue imaging system conjugated with peroxidase was used and the enzyme activity was detected using diaminobenzidine (ThermoScientific) as a substrate. After the immunocytochemical reaction, the preparations were rinsed with water and counterstained with hematoxylin and eosin for 15 to 30 seconds. The results were analyzed by a quantitative estimation of cells with the marker expression (increased brown color of cells corresponded to a higher degree of expression of the marker) using a light microscope and assessed using the classical H-Score method: $S=1 \times A + 2 \times B + 3 \times C$, where S is the H-Score index the values of which are within the scope of 0 (protein is not detectable) to 300 (high-level expression in 100% of the cells), A is a percentage of weakly stained cells, B is the percentage of moderately stained cells, and C the percentage of strongly stained cells.

The result of comprehensive assessment of the effect of components containing $^{39}K$, $^{64}Zn$ and $^{24}Mg$ and doxorubicin, as a reference element, on the HL-60 and Namalwa tumor cells showed that the components containing $^{39}K$, $^{64}Zn$ and $^{24}Mg$ in most cases increased the amount of N-cadherin-positive cells both in the Namalwa and in HL-60 cell lines. An exception was $^{39}K$ at a dose of 2 mg/ml and $^{24}Mg$ at the same dose of 2 mg/ml in the Namalwa cell line. Increase in the number of cells expressing N-cadherin is first of all indicative of an effect of these components not only on the adhesion of cells and their cytoskeleton, but also on the cell cycle programs, as N-cadherin has an inhibitory effect on cell proliferation in mesenchymal (malignant) cells, i.e., its overexpression suppresses cell proliferation by extension of G2/M phase through activation of catenin-dependent expression of p21 (an inhibitor of cyclin-dependent kinase).

Thus N-cadherin-dependent signaling pathways inhibit tumor cell proliferation due to deceleration of G2/M phase and prevent tumor growth by stopping cells in their specific points of the cell cycle. As for ICAM (another adhesion marker), an interesting data was obtained on the reduction in the number of cells that express this marker after they are exposed to the action of components containing $^{39}K$ (at the two doses-2 mg/ml and 0.5 mg/ml) and $^{64}Zn$ (at a dose of 10 mcg/ml) which is indicative of a dose-related effect in suppression of the malignant phenotype of HL-60 cells.

Values of expression at the control level are shown in the HL-60 cell line by the component containing $^{24}Mg$. All the tested components in the Burkitt lymphoma tumor line (Namalwa) showed decrease in the expression level compared to the control group of cells. Reduced compared with the control values, parameters of expression of the ICAM adhesion marker are characterized as a positive point in terms of a prognostic factor of development of atherosclerotic vascular changes in cardiac and vascular pathologies (coronary heart disease, thrombosis, venous varices, coronary syndromes) and reflect the decline in metastasis processes and malignant potential of cells. Increase in the number of ICAM-positive cells with the action of component containing $^{64}Zn$ as sulfate at a dose of 5 mcg/ml on the Namalwa cell line (up to 210 according to the H-Score method) may be indicative of an enhancement of reactivity of the immune system and the targets for the anticancer targeted therapy. The result of effect of ICAM marker on HL-60 was a decrease in the number of cells expressing it for the entire test group. The result of effect of components containing $^{24}Mg$ and $^{64}Zn$ as sulfates was a significant change in the morphological and growth characteristics of the cells: there was a significant enhancement of adhesion of cells to the substrate and their spreading all over the culture plastic surface, as shown in FIGS. 10I, 10J, 10K, 10L, which was observed on the living cell culture.

The adhesive characteristics of tumor cells directly correlate with their invasion, migration and, as a consequence, with metastasis and recurrence in the development of neoplastic process. The process of epithelial-mesenchymal transition (EMF) of tumor cells, which also involves cell adhesion proteins and cytoskeleton, plays a key role in the metastatic cascade. During changes in the cell morphology, (both: when adhering to a substrate and when spreading on the surface) the membrane properties and the cell cytoskeleton also change, which in its turn results in changes in the receptor profile of cells, and variability of various signaling pathways of cells including those pathways that are associated with an increase in the sensitivity of cells to antitumor agents.

Strengthening of the adhesive properties of cells both among themselves and to the culture plastic, characterizes the decrease in their tumor and metastatic potential, and is also indicative of an increase in the degree of differentiation of cells and thus of a decrease in their malignant phenotype, and the fact of change in the cell sensitivity to anticancer preparations when their morphology changes is still of great interest. Morphological and phenotypic changes in the cells after the action of components containing $^{24}Mg$ and $^{64}Zn$ provide opportunities for combined use of the components under study and officially registered chemotherapeutic agents as a complex therapy which consists in sequential administration of the component under study ($^{24}Mg$ or $^{64}Zn$) followed by a well-known anticancer agent. The proposed complex approach is based on the increased sensitivity of tumor cells to an antitumor toxic agent at the first stage due to the use of $^{24}Mg$ or $^{64}Zn$ and an effect of the official antitumor agent at the second stage. Considering fact of negative effects of any official antitumor preparation on the human body, by increasing the sensitivity of cells, e.g., to doxorubicin, via $^{24}Mg$ and $^{64}Zn$ at the first stage we reduce the amount of chemotherapeutic agent injected into the patient's body at the second stage of the treatment.

Thus, the result of the proposed complex approach will be a decrease in the toxic effects of known anticancer agents on the human body. The combined (alternate) use of components containing $^{24}Mg$ and $^{64}Zn$ looks quite promising in terms of the synergistic effect. By significantly changing the cell morphology via component $^{24}Mg$ at the first stage (in the absence of its toxic properties) and using a combination with the highly effective $^{64}Zn$ in the second stage (so far as $^{64}Zn$ is close to doxorubicin in an effective dose of exposure but without a negative effect on healthy cells of the body) one can obtain a highly effective complex of $^{24}Mg+^{64}Zn$ with a potential modifying effect on the process of epithelial-mesenchymal transition with antitumor and antimetastatic properties.

Also interesting was the fact of significant inhibition of expression of CD44 marker in Namalwa cells after they were exposed to the action of components containing $^{39}K$ and $^{64}Zn$ and a tendency to decrease in the level of expression of the protein in the cells of HL-60 line (especially in high doses). Since this antigen in the tumor cells is often associated with an aggressive, malignant phenotype, thus its decrease is a favorable factor in predicting the flow of a tumor process as a whole. Characteristics of IgM marker in the Namalwa cell line showed a decrease in its expression compared to the control group of cells. Inhibition of IgM is associated with induction of cell differentiation as well as activation of the signaling pathways of apoptosis.

Thus through the example of all the components under study we showed the activation of apoptotic pathways that brings a tumor cell closer to the state of its natural programmed death by reducing its malignant and metastatic potential. Phenotypic Features of Human Burkitt Lymphoma Cells (Namalwa Line) under the Action of Components Containing $^{39}$K, $^{64}$Zn and $^{24}$Mg Results of Immunocytochemical Analysis of Adhesion Proteins and Cytoskeleton of N-cadherin and ICAM in Namalwa Cells after the Action of Components Containing $^{39}$K, $^{64}$Zn and $^{24}$Mg.

FIG. 10 illustrates a morphological and growth characteristics of cells of HL-60 cell line after their treatment with components containing $^{39}$K, $^{64}$Zn and $^{24}$Mg A: Control cells of original HL-60 cell line (×10), B: control—cells of original HL-60 cell line (×40), C: HL-60 cells+doxorubicin at a dose of 0.08 mg/ml (×10), D: HL-60 cells+doxorubicin at a dose of 0.08 mg/ml (×40), E: HL-60 cells+doxorubicin at a dose of 32 mg/ml (×10), F: HL-60 cells+doxorubicin at a dose of 3.2 mg/ml (×40), G: HL-60 cells+component containing $^{39}$K as chloride at a dose of 2 mg/ml (×10), H: HL-60 cells+component containing $^{39}$K as chloride at a dose of 2 mg/ml (×40), I: HL-60 cells+component containing $^{64}$Zn as sulphate at a dose of 16 mcg/ml (×10), J: HL-60 cells+component containing $^{64}$Zn as sulphate at a dose of 16 mcg/ml (×40), K: HL-60 cells+components containing $^{24}$Mg as sulphate at a dose of 2 mg/ml (×10), L: HL-60 cells+ components containing $^{24}$Mg as sulphate at a dose of 2 mg/ml (×40).

Following the results of immunocytochemical analysis of adhesion proteins and cytoskeleton obtained experimentally as a result of action of the group of components under study containing $^{39}$K, $^{64}$Zn and $^{24}$Mg on the cell lines of human Burkitt lymphoma (Namalwa line) and acute promyelocyte leukemia (HL-60 line) we can state the main findings: Via example of N-cadherin marker, we demonstrated an increase in the adhesion properties of Namalwa and HL-60 tumor cells both among themselves and to the culture plastic, which directly correlates with the reduction of invasive and metastatic properties of tumor cells.

A decrease in ICAM marker expression (compared to the control cells) after the use of components containing $^{39}$K, $^{64}$Zn and $^{24}$Mg is a positive result in terms of the following forecast: the risk of atherosclerotic changes in the cardiovascular system in the form of thrombosis, varicose veins and coronary syndromes sufficiently reduced; an increase in the marker expression on most cell lines is associated with an increase in their malignant potential, therefore, the result of reduction of such parameters after the action of the group of components under study is indicative of the attenuation of malignant properties of tumor cells.

Due to changes in the sensitivity of cells to antitumor agents under the effect of $^{64}$Zn and $^{24}$Mg (for example, changes in the cell morphology) there is a possibility of the combined therapy that involves the integrated use of the group of components under study in combination with the official antitumor drugs, which will result in reducing the negative impact of antitumor components by down-titrating the latter. There are changes in the cell morphology (in the form of enhancement of their adhesiveness both among themselves and to the culture plastic) after the action of $^{64}$Zn and $^{24}$Mg which is indicative of a decrease in the metastatic potential of tumor cells.

A decrease in the level of expression of CD 44 marker after the action of components containing $^{39}$K, $^{64}$Zn and $^{24}$Mg, which in the tumor cells is associated with a more aggressive and malignant phenotype, characterizes said light isotopes as inhibitors of malignant and invasive properties. Via example of IgM marker, we showed an activation of signaling pathways of apoptosis after the use of components containing $^{39}$K, $^{64}$Zn and $^{24}$Mg in the Namalwa tumor cell line which is confirmed by a decrease in the expression level of the marker. Activation of the apoptotic pathway contributes to the return of the cell to a state of its natural programmed death thus reducing its tumor and metastatic potential.

Assessment of antitumor and biological activity of components, containing $^{64}$Zn, $^{24}$Mg and $^{39}$K and Zn, Mg, and K elements on a model of renal cell carcinoma (PA) in a rat in an in vitro experiment will be discussed. The data represented in this section allows to o assess the degree of antitumor and biological activity of $^{39}$K, $^{64}$Zn and $^{24}$Mg components from the standpoint of their changing the morphology and phenotype of tumor cells of PA renal cell carcinoma in the in vitro experiment and compare the obtained result with the effect of K, Zn and Mg elements which have a natural distribution of isotopes. It also allows making a quantitative assessment of changes in the cells phenotype in terms of correlation between the number of the acting components and the number of transformed cells.

By using different methods of staining cells after their exposure to the action of the components, to make a comparative assessment of cells after treatment. To compare the obtained result with the effects of the official antitumor agent doxorubicin EBEWE. In this example, we had potassium, magnesium and zinc in 2 groups: Group No 1 contained light isotope components $^{39}$K, $^{64}$Zn and $^{24}$Mg, and Group No 2 contained the same elements—K, Zn and Mg but with a natural distribution of isotopes. Doxorubicin Ebewe (Austria), an official anticancer chemotherapeutic drug, was used for reference. Light isotope components as well as zinc and magnesium, components with the natural distribution of isotopes, were used in the form of sulphates, and potassium as a chloride. 0.9% NaCl solution supplemented with 5% glucose was used as a solvent.

Staining of Cell Suspension with Trypan Blue and Visual Control of Changes in the Shape, Color and Size of the Cells will now be discussed. The visual control method was based on the observation of state of the plasma membrane permeability after the action of materials under study, and reflects the degree of membrane's damage, making it possible to estimate an ability of nuclear proteins to absorb the dye.

To make the analysis, the cell suspension, after it was exposed to the action of materials, in a volume of 20 mcl was mixed with 20 mcl of trypan blue solution and resuspended. The obtained solution was placed in a hemocytometer chamber for visual analysis and quantitative estimation of the cells. To make the quantitative estimation of the cells, they were separated from the substrate using Versene solution and counted by staining cells with trypan. A change in the color of a cell was indicative of the violation of intactness of the cell membrane, and the more pronounced was the coloration, the less viable the cell was. Undamaged parenchymatous cells had a convex, well-defined surface line that reflected light and colored ranging from yellow to nearly transparent color. They are easily distinguishable from dark damaged cells and easily identified with ordinary light microscope. This method does not characterize any changes in the cell phenotype.

Alluding to the above, staining the Cells with Crystal Violet and their Quantitative Analysis will be discussed. Utilization of this method of assessment in the experiment makes it possible to quantify cells classified according to the living-dead criterion. The method is based on statistical evaluation of cells able to adhere to the substrate (to the plastic plate), cells capable of further proliferation. The criterion of the evaluation is the degree of optical permeability of a well with the cell sediment for a luminous flux of a certain wavelength. Removal of the culture medium from the wells is also accompanied by removal of non-adhering and unstained cells from the substrate, and adhesion and staining of the residue left on the substrate provides a quantitative characteristic of the number of cells which are capable of further division and multiplication.

Alluding to the above, viable tumor cells capable of further proliferation were fixed to the plastic surface and stained blue (after they were exposed to the action of components with natural distribution of isotopes) using the dye powder dissolved in 70% methanol solution. After 10 minutes the dye was removed from the wells with a micropipette and the cells were thoroughly rinsed three times with clean running water. The cell sediment fixed by the dye was dissolved with ethanol followed by determination of its concentration (which is indicative of the number of viable cells) and fixed via multi-well spectrophotometer with an excitation wave 540 nm in length.

Figure 11:
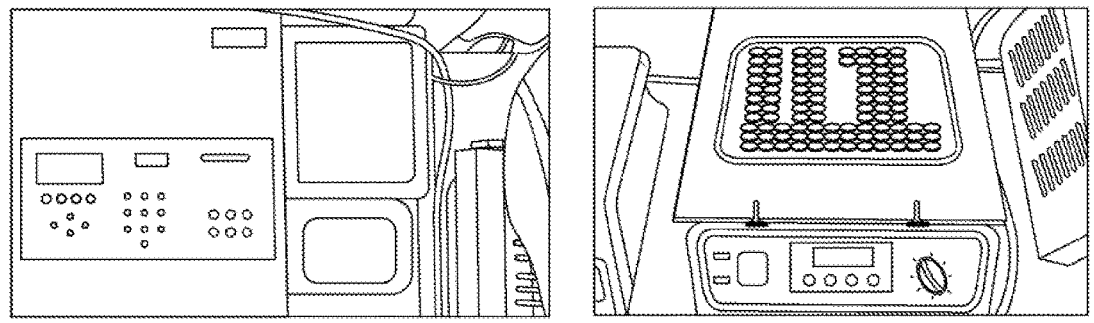
FIG. 11 illustrates views of Spectophotometer (left) and samples (right) prepared for the analysis after they were treated with components with the natural isotope distribution.

Since the method does not characterize an appearance and shape of the cells after their treatment with the medication under study, as shown in FIG. 11, the assessment was carried out only for the components with the natural distribution of isotopes without consideration of light isotope components.

Primary cell culture for our in vitro experiments was obtained by enzymatic treatment of tumor material (using trypsin solution) from a strain of renal cell carcinoma (PA) in a rat Visually (after its removal from the animal), the tumor looked as a nodular fleshy growth of a whitish-pink color of rather dense consistency, marginated from other tissues by a joint capsule. The main morphological signs of PA tumor in the animal can be described as follows. Small (1.5 to 2 grams) fragments without vessels and blastic lesions were excised aseptically from the surgically removed tumor and then cut them with scissors to smaller pieces of 0.2 to 0.3 mm in size and cultured in a solution of trypsin. The culture medium contained the following components: RPMI-1640 (Sigma, USA) as the base plus 10% newborn calf serum and 40 mcg/ml of gentamicin. Trypsinization was performed in a humidified atmosphere of 5% $CO_2$ at 37° C. with constant mixing of the contents in a magnetic stirrer. The isolated cells were washed three times in a culture medium by centrifuging and before starting the experiment a quantitative assessment of cells was carried out in the Goryaev chamber with supravital staining of the cells with trypan blue.

Complex clusters of polymorphic cells dispersed in the form of separate islands separated from each other by layers of edematous connective tissue were detected in the main part of the tumor. Most of the tumor featured pronounced polymorphism which was expressed as significant differences both in cell shapes and sizes. We detected polygonal, oval and round cells, as well as their components which can be attributed to atypical fibroblasts. The cell nuclei had a considerable variation depending on the size of the cell itself, and most of them were large enough and occupied the main volume of the cell. Chromatin of the cells had a grid structure, the cytoplasm was characterized by a pronounced basophile.

Figure 12:
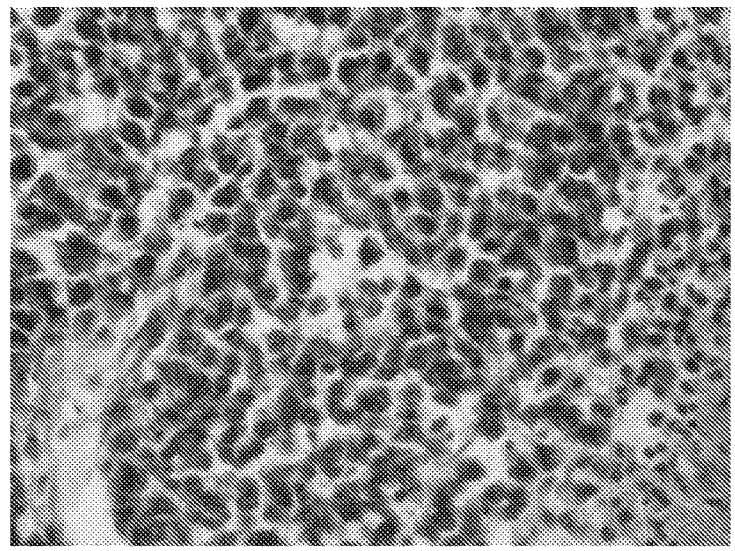
FIG. 12 illustrates renal cell carcinoma (PA) and tumor fragment with extensire polymorphism, lymphoid cells and blood capillaries.
Figure 13:
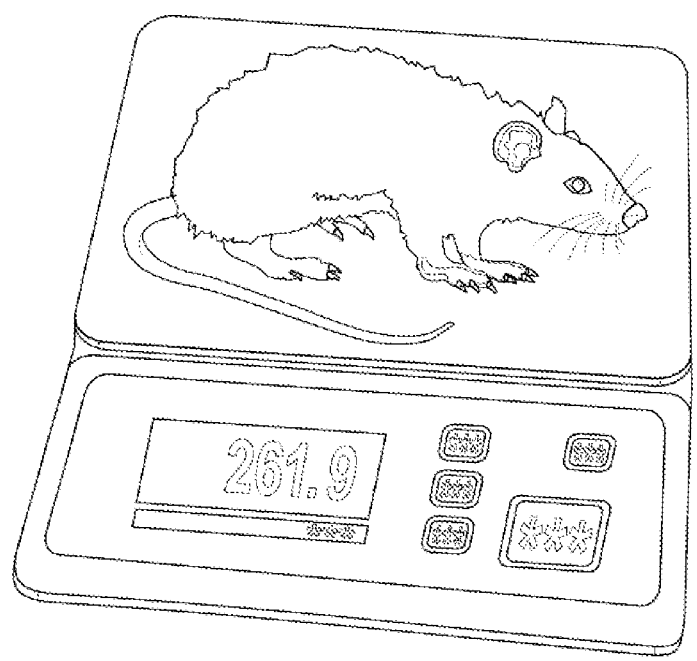
FIG. 13 illustrates an animal weight on the 29th day after inoculation with the renal cell carcinoma (PA)

Stroma and tumor borders had quite an extensive network of blood vessels like capillaries through which the tumor tissue was fed. The edematous connective tissue contained a lymphoid net. A granulation connective tissue containing lymphoid cells was detected along the perimeter. There were some figures of cell division as shown in FIG. 12. A tumor growth chart built on the results of observations of an animal with the transplanted tumor for 29 days clearly describes the kinetics of the tumor growth as shown in FIGS. 13, 14.

The suspension of tumor cells was transplanted into the animal weighing 120 g, and according to the data obtained during the 29 day it increased in volume to almost 120,000 mm3 which corresponds to the tumor weight of 120 g. The obtained result characterizes a fairly high degree of its malignancy with its growth under in vivo conditions as such dynamics of growth is not peculiar to most transplanted strains. We also made a quantitative estimation of the ability of tumor cells to further proliferation. Transplantation of a tumor strain into the animal was carried out using the cells frozen at −196° C. After thawing of the ampoule it was noted that the cell suspension had a sufficiently low number of tumor cells capable of further division which was confirmed by calculation of their number in the Goryaev chamber.

Analysis of the thawed suspension was conducted by staining the cells with trypan blue and it showed that after thawing a number of viable cells in the suspension did not exceed 150 thousand, which is approximately 10% of the total number of cells. Development of the tumor process, the beginning of which was observed as early as on the 5th day after 150 thousand unfrozen cells were transplanted into the animal, also characterizes a fairly high degree of malignancy of the tumor. The cell material used in further in vitro experiments was obtained after the third passage of the strain in vivo.

Analysis of the effect of all components on the renal cell carcinoma (PA) was conducted to determine the relationship between the amount of the preparation (concentration characteristics of the component) and the quantitative characteristics of the cells. Assessment of the effect of the components was carried out on 2 concentration models with 30 and 300 thousand original tumor cells. After the cells were cultured, cell suspensions were prepared in the plates with the culture medium and an effect of the preparations (in various concentrations) on the tumor cells was assessed. The experiment was started with the concentration of 10 mg of the active substance per 1 ml of the solvent (saline with 5% glucose).

The amount of culture medium in each well was 200 mcl for 30 thousand cells and 2 ml for 300 thousand cells, respectively. The amounts of drugs (active substances) for 2 concentration models differed according to the amount of cells and culture medium, i.e., the amount of drug in the experiment with 300 thousand cells was ten times as large as compared with the same in the experiment with 30 thousand cells. The result of effects of the components is shown in FIGS. 22, 23 for light isotope components and in FIG. 25 for the elements with natural distribution of isotopes. Assessment of the effect of the components was performed by comparing the external factors of cells (color, size, shape) prior to the experiment and after staining.

Figure 16:
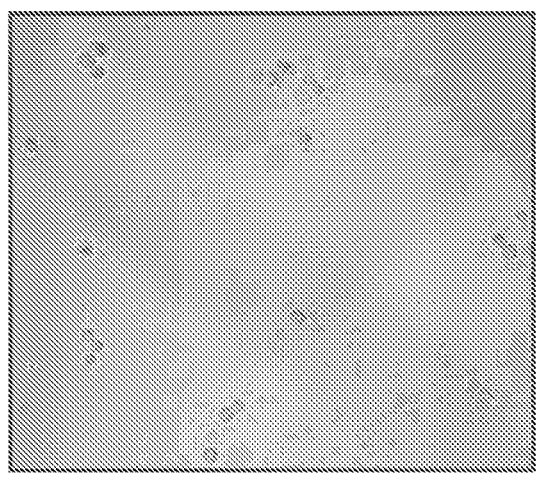
FIG. 16 illustrates an initial cells of the tumor strain of renal cell carcinoma (PA) in a rat.
Figure 17:
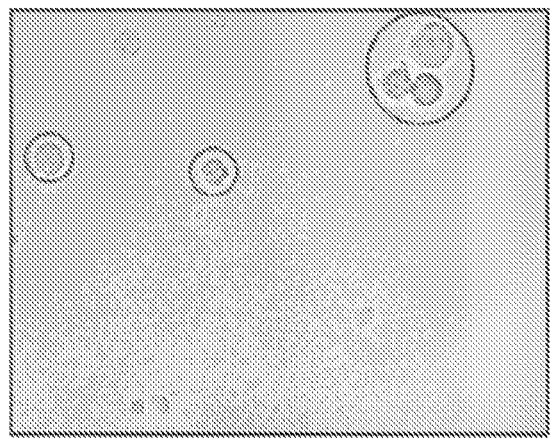
FIG. 17 illustrates two cell types after treating them with $^{64}$Zn, $^{24}$Mg and $^{39}$K. Staining method—Trypan blue.
Figure 18:
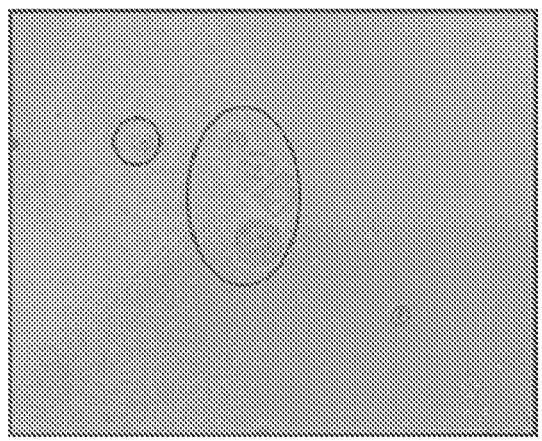
FIG. 18 illustrates a cell membrane is not damaged, cells of type B.
Figure 19:
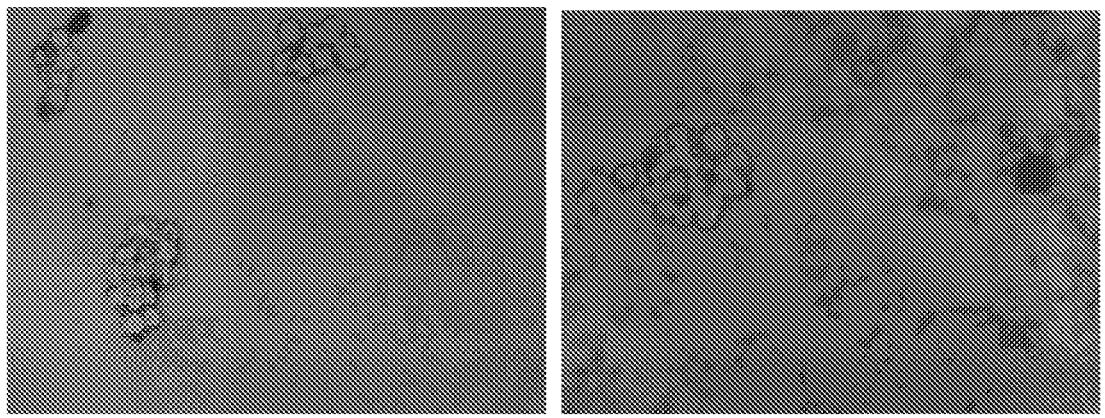
FIG. 19 illustrates cells of type A.
Figure 20:
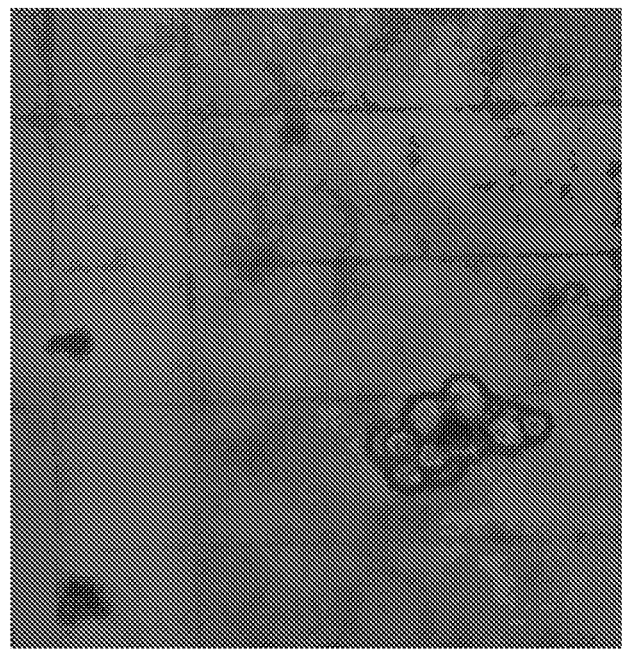
FIG. 20 illustrates PA tumor cells after treating them with the elements with natural isotope distribution. Dark (dead) and white (living) cells.
Figure 21:
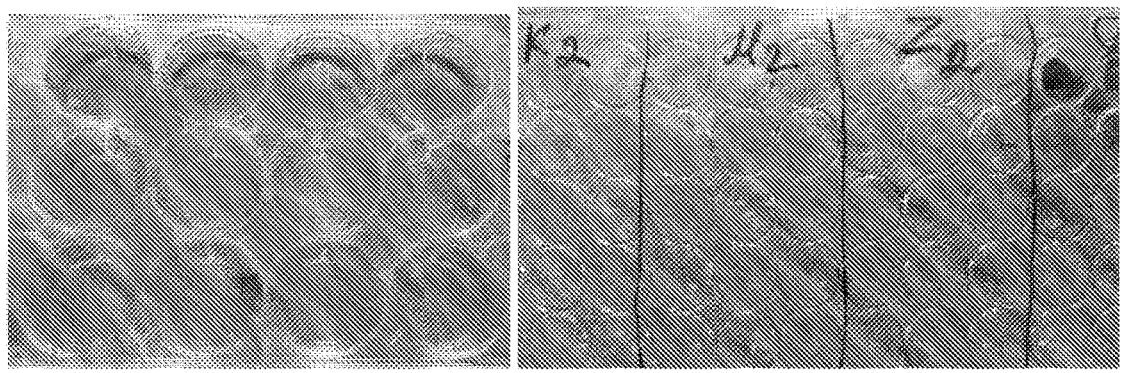
FIG. 21 illustrates an initial cell suspension in the plates in two concentration models.

As a result of the action of $^{64}Zn$, $^{24}Mg$ and $^{39}K$ on the PA tumor cells, after their staining with trypan blue, the presence of cells of 2 types referenced by letters "A" and "B" as shown in FIGS. 16, 17, 18, was detected. Classification of the cells after their exposure to Zn, Mg and K elements with the natural distribution of isotopes and Doxorubicin Ebewe was carried out by the living-dead criterion. These differences are shown in FIGS. 19, 20. The initial concentration of the components in the experiment was 10 mg of the active substance (sulphate or chloride) per 1 ml of saline and it was changed towards decrease in accordance with the "component dose" column in FIGS. 22, 23, 25. Changes in the appearance of cells from the initial tumor cells to the cells with morphology of types A and B were noted with regard to all light isotope components but with the following differences.

To obtain an accurate statistics, the experiment was conducted in 2 concentration models: for 30 thousand and 300 thousand cells. $^{24}$Mg and $^{39}$K components in both concentration models, after their adding into the wells with the cell suspension and first calculation conducted 10 hours after the start of the experiment, showed 100% concentration of the cells of type A. Effect of $^{64}$Zn (also shown in both concentration models) consisted in its ability to transform cells from the initial tumor cells into cells of type A. Cells of type B were detected within the concentration range of 10 mg/ml to 0.4 mg/ml. The concentration range of type A cells was from 0.08 mg/ml to 0.025 mcg/ml. Registration and calculation of the quantitative characteristics of were carried out every 10 hours, and the total time of the experiment was 140 hours with a total of 14 plates. All nine concentrations were used within one 96-well plate which is reflected in tables and graphs. A quantitative assessment of cells of each type which was conducted with 10-hour intervals. The concentrations of the substances were tested in the following order: 10 mg/ml, 2 mg/ml, 0.4 mg/ml, 0.08 mg/ml, 16 mcg/ml, 3.2 mcg/ml, 0.64 mcg/ml, 0.128 mcg/ml, 0.025 mcg/ml.

Figure 24:
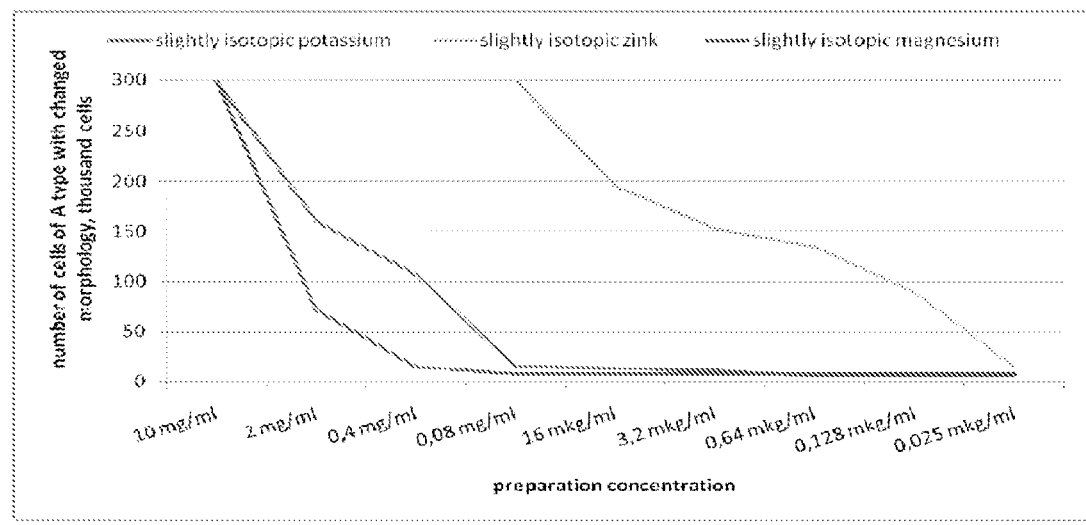
FIG. 24 illustrates an interrelation between quantitative characteristics of $^{64}$Zn, $^{24}$Mg and $^{39}$K and a number of cells of type A.

Referring now to FIGS. 22, 23, 24 the presentations shown there on made to show the concentration effect of $^{64}$Zn, $^{24}$Mg and $^{39}$K components on the 2 models (for 30 000 and 300 000 cells in the culture medium). Analysis of the malignancy of cells of type B was planned to be made in a test for tumorigenicity in the agar medium. Since the PA cell line showed the initial development of colonies in the agar medium starting with a concentration of 500 thousand cells and their weak growth even in this concentration, it was decided to make an assessment of malignancy based on the level of expression of markers in 3 human cell lines.

Figure 26:
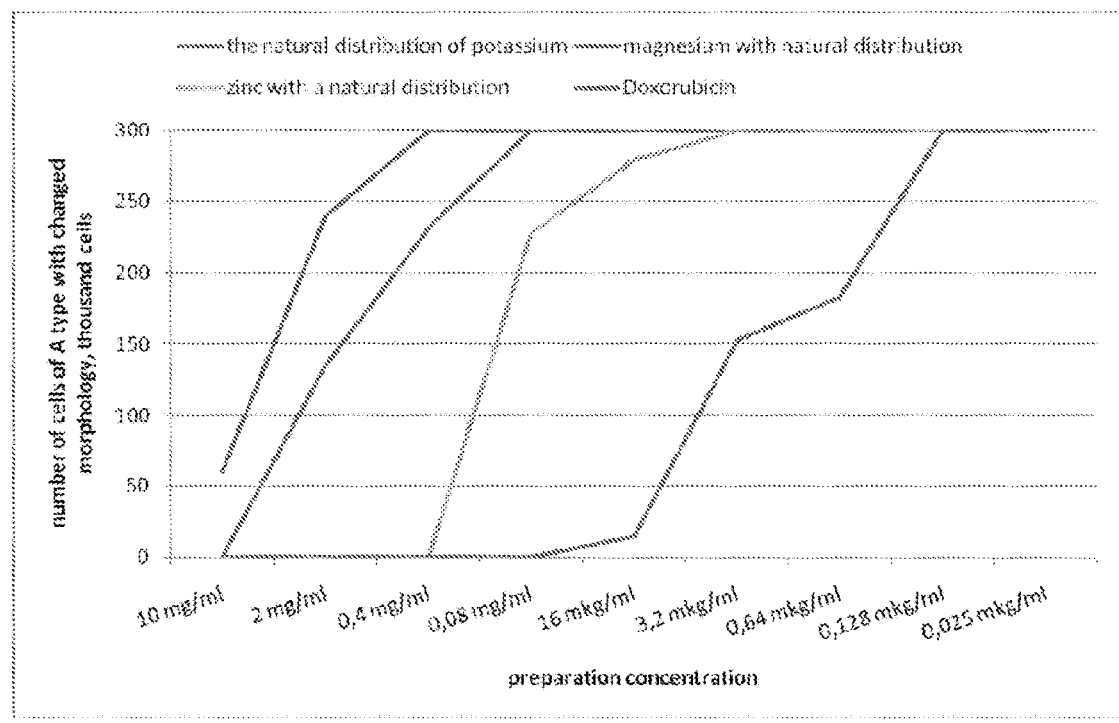
FIG. 26 illustrates a number of viable tumor cells depending on concentrations of K, Zn and Mg with natural isotope distribution.

After the action of components with natural isotope distribution on PA tumor cells (in all 9 concentration dilutions of the preparations), they were stained with trypan blue. Staining cells (after the effect of the components) in blue is indicative of the respiratory impairment of the cells, which allows of classifying them as non-viable tumor units. The part of the cells remained uncolored is characterized as viable with the ability for further proliferation. The results presented in FIG. 25 and in FIG. 26 show interrelation between the active dose of the components with natural isotope distribution and a number of viable tumor cells. The assessment was performed on 14 plates with 300 thousand cells in each well by counting the number of viable cells in the Goryaev chamber. Quantitative analysis of the cells was performed visually every 10 hours of the experiment. Statistical quantification of both viable and unable to reproduction tumor cells was performed using 2 methods: staining the cells with trypan blue and crystal violet. The photomicrographs of cells in the Goryaev chamber made after staining clearly characterize a classical picture of violations of the integrity of the membrane, which gives reason to characterize cells colored in blue as non-viable, as shown in FIG. 19, 20.

In order to make a comparative (concentration and visual) assessment of cells, the action of antitumor drug Doxorubicin Ebewe was tested. The concentrations of Zn, Mg and K elements (with natural distribution of isotopes) and Doxorubicin Ebewe showed the following. The initial concentration of substances was 10 mg per 1 ml of solvent. According to the data in FIGS. 25, 28, which generalize the statistical estimation of the number of live tumor cells performed by staining cells with crystal violet and trypan blue, Doxorubicin Ebewe kills 50% of the tumor cells (leaving unaffected the remaining 50% viable tumor cells) at the concentration of 3.2 mcg/ml. Elements Zn, Mg and K with the natural distribution of isotopes demonstrated much lower ability to kill tumor cells, which was exhibited in their significantly higher concentrations as shown in FIG. 28. The main differences of the effects of $^{64}$Zn, $^{24}$Mg and $^{39}$K on the PA tumor cells consisted in the following. The ability of the initial tumor cells to transform into the cells with the changed color was noted. It was also found that the cell adhesion to the culture plastic had a different character as well.

Figure 36:
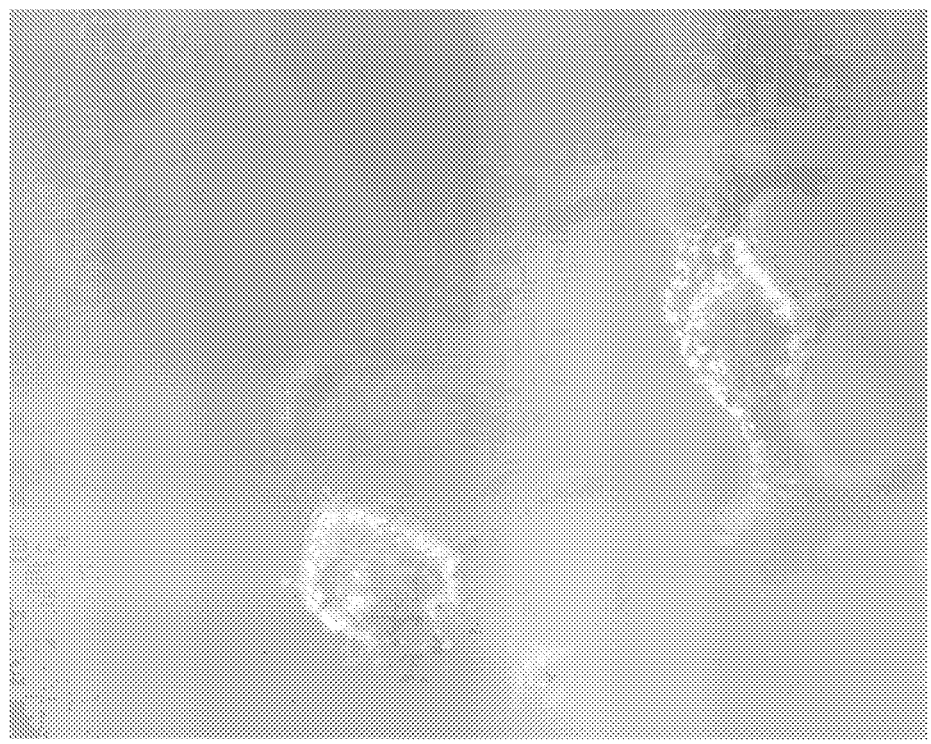
FIG. 36 illustrates cells of type A at the magnification of 1500 9K Concentration is 10 mg/ml.
Figure 37:
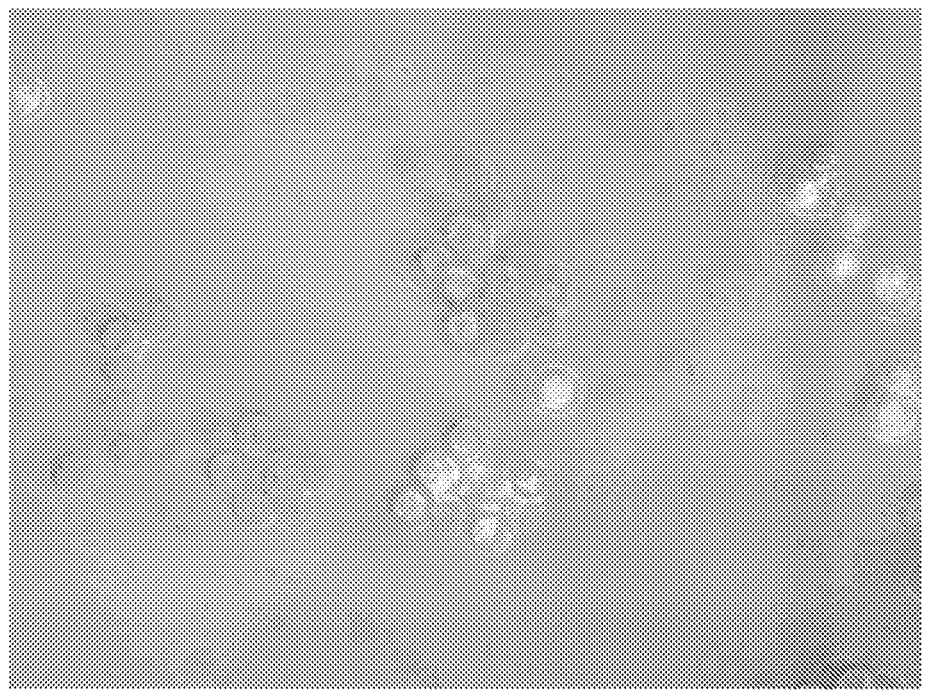
FIG. 37 illustrates $^{39}$K Effect. About 50% A Cells at $^{39}$K concentration of 2 mg/ml.
Figure 38:
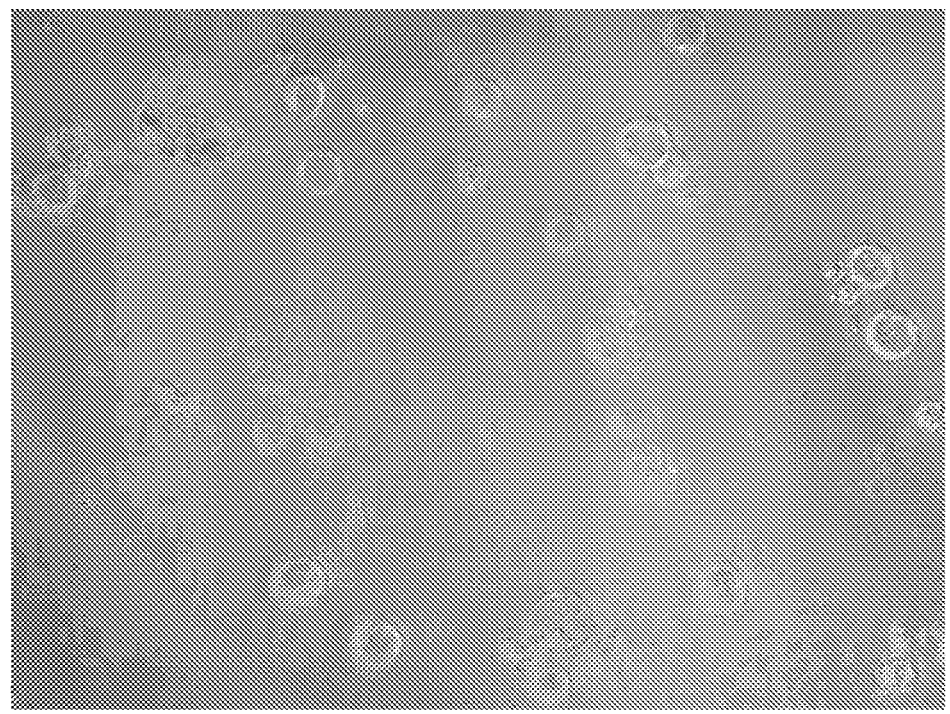
FIG. 38 illustrates a cell to B cell transformation. About 50% A Cells at $^{39}$K concentration of 2 mg/ml.
Figure 39:
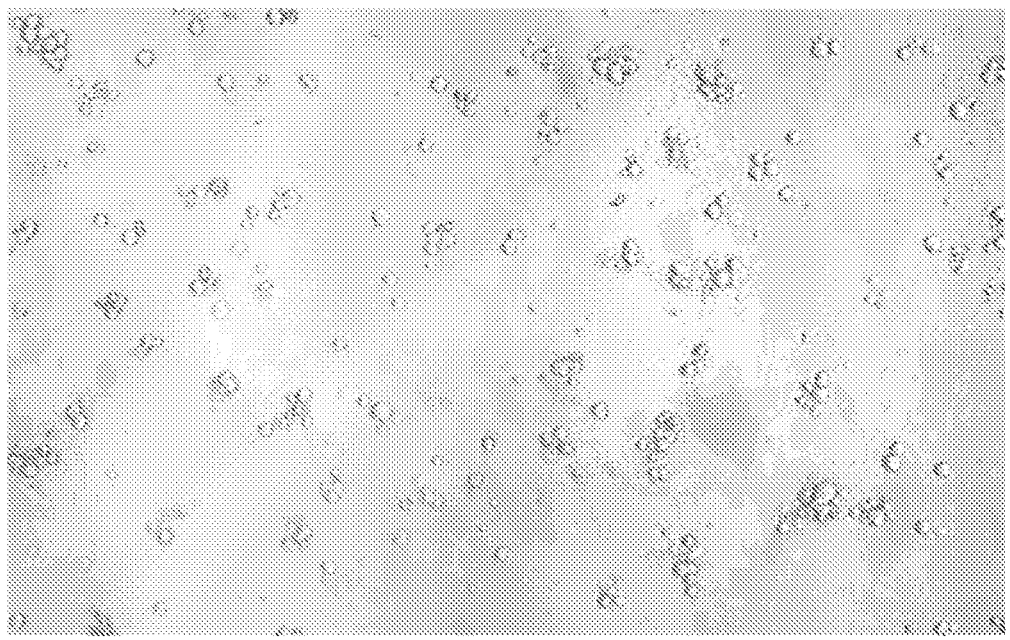
FIG. 39 illustrates 100% cells of type A at $^{24}$Mg dose of 10 mg/ml.
Figure 40:
FIG. 40 illustrates 100% cells of type A at $^{24}$Mg dose of 10 mg/ml 1000 Magnification.
Figure 41:
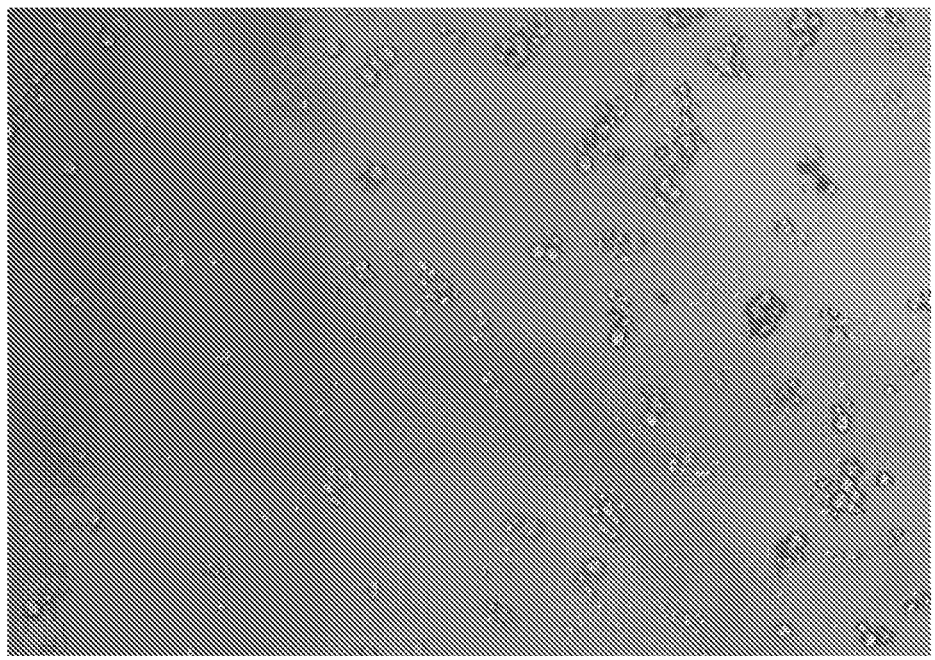
FIG. 41 illustrates 25% cells of type A at $^{24}$Mg concentration of 2 mg/ml.
Figure 42:
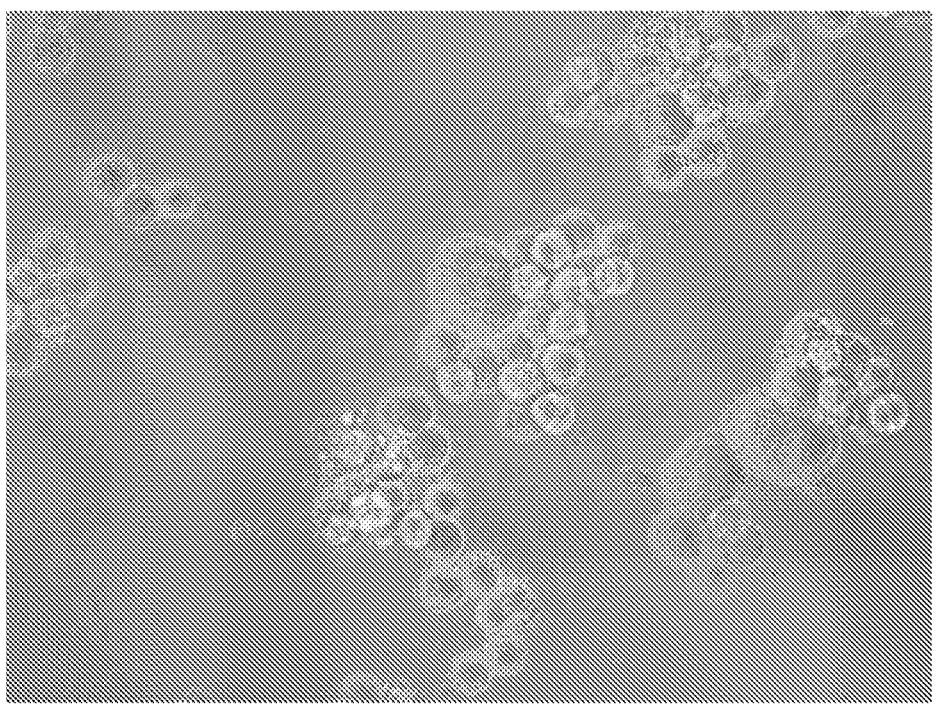
FIG. 42 illustrates 50% to 50% ratio of A and B types at the transition stage $^{24}$Mg dose is 10 mg/ml.
Figure 43:
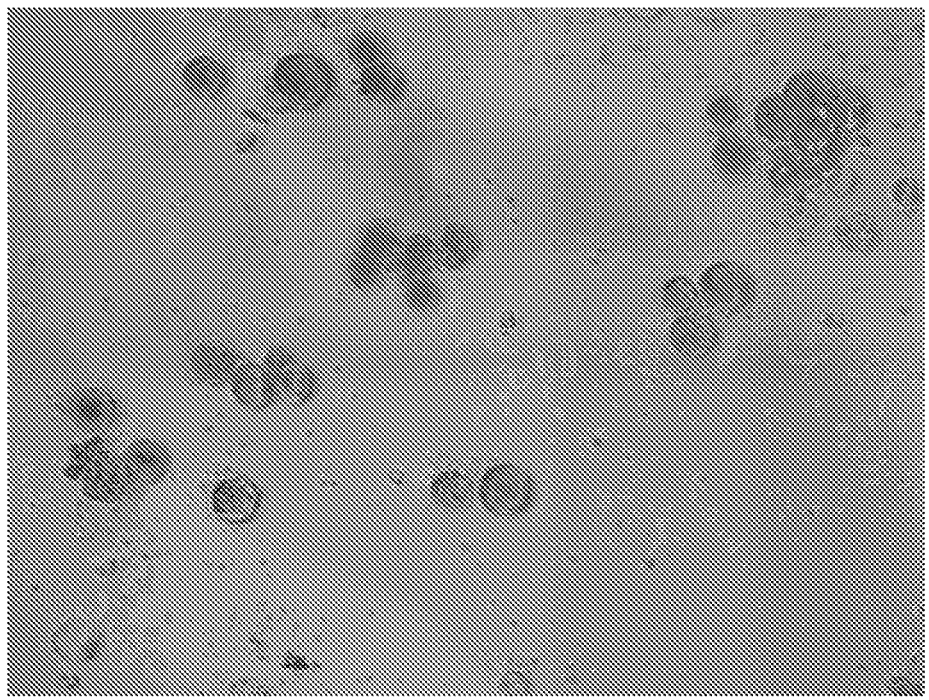
FIG. 43 illustrates 75% cells of type B at $^{24}$Mg dose of 2 mg/ml.
Figure 44:
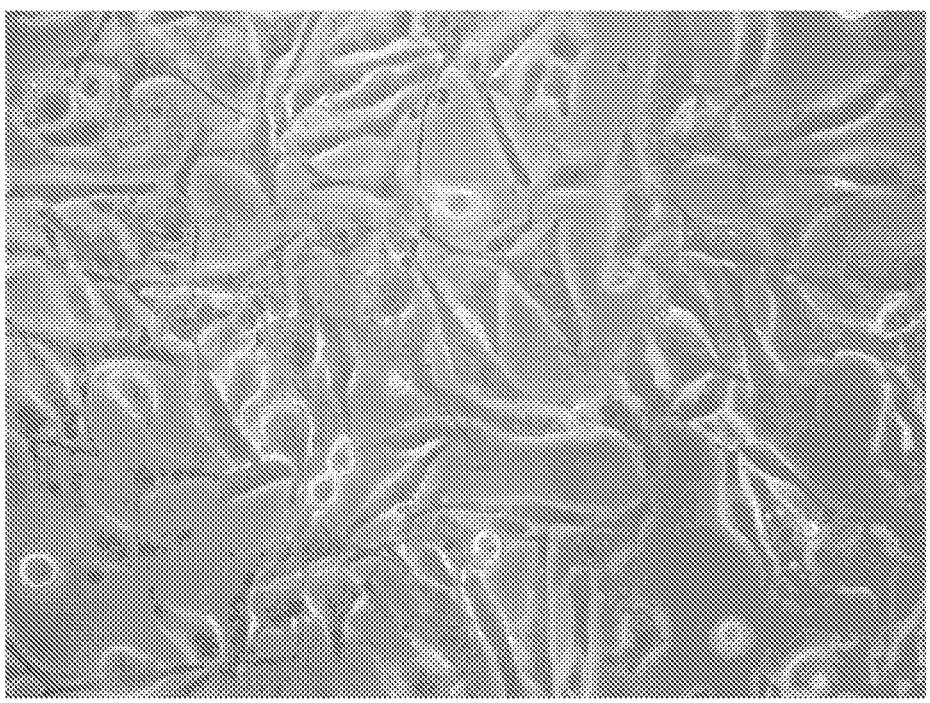
FIG. 44 illustrates about 5% cells of type A at $^{24}$Mg concentration of 0.4 mg/ml.
Figure 46A:
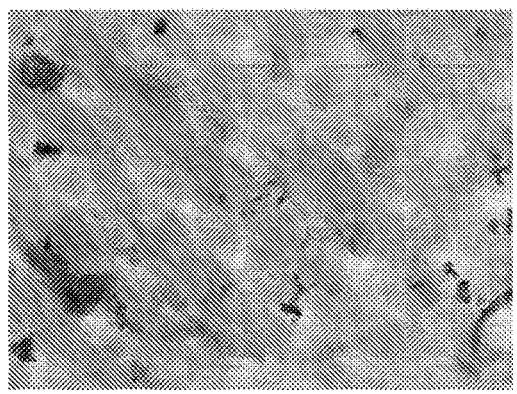
FIGS. 46A-46B illustrate E-cadherin expression in PA cells after the action of $^{64}$Zn at doses D2 (A) and D1 (B) (magnification ×100)
Figure 46B:
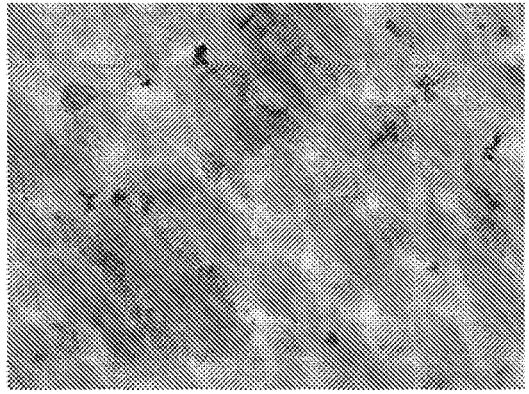
Figure 47A:
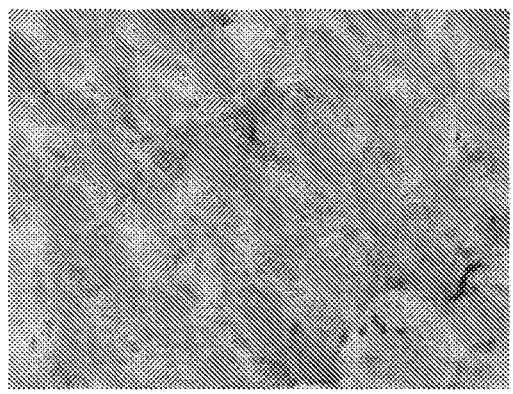
FIGS. 47A-47B illustrate N-cadherin expression in PA cells after the action of $^{64}$Zn at doses D2 (A) and D1 (B) (magnification ×100)
Figure 47B:
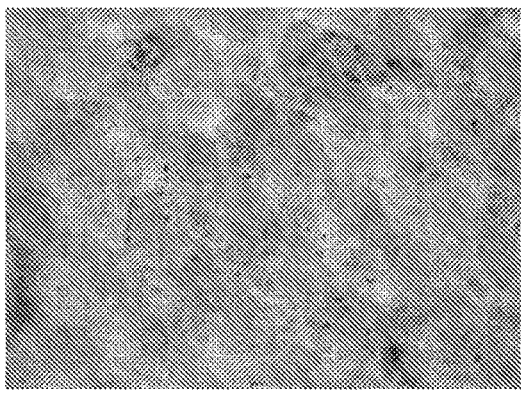
Figure 48A:
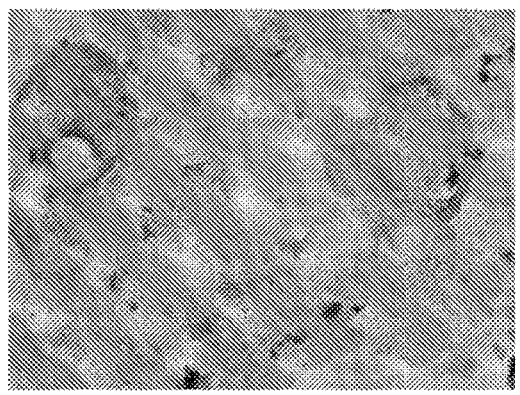
FIGS. 48A-48B illustrate CD44 marker expression in PA cells after the action of $^{64}$Zn at doses D2 (A) and D1 (B) (magnification ×100)
Figure 48B:
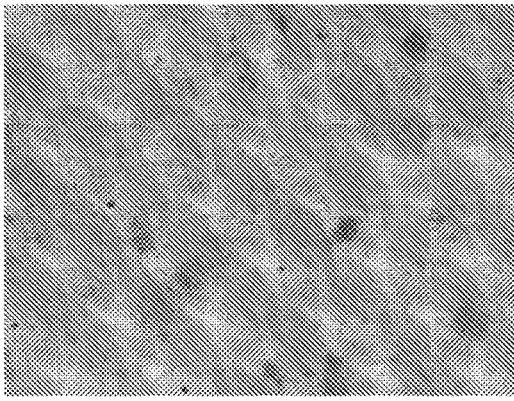

The effects of $^{64}$Zn, $^{24}$Mg and $^{39}$K in two concentration models are shown in FIGS. 22, 23 that shows the results of the experiment. The changed character of the cell adhesion after treating the cells with all the light isotope elements is shown in FIG. 36 of the presentation and is characterized by the presence of the cells spread on the culture plastic. In order to better display the whole picture of concentration in the experiment, the main results of effects of the components are shown in 2 tables: see FIG. 27, 28 on $^{64}$Zn, $^{24}$Mg and $^{39}$K and Table 3.2 on K, Zn and Mg (with the natural distribution of isotopes).

The number of cells after the action of the preparations was calculated at each control point (covering all 96 wells of the plate and all 9 concentrations of each component). The number of type A cells was determined after the action of $^{39}$K, $^{64}$Zn and $^{24}$Mg and the number of viable cells—after the action of K, Zn and Mg with a natural isotope distribution. Characteristics of changes of the cell phenotype through time after they were exposed to the action of $^{39}$K, $^{64}$Zn and $^{24}$Mg are as follows. The main result, which consists in the transformation of 100% initial tumor cells in the type A cells was detected with the light isotope group of components within the first 80 hours of the experiment with the following differences for each of the light isotopes as shown in FIG. 30.

Cells exposed to the action of $^{64}$Zn showed 100% change in their phenotype during the first 50 hours of the experiment with 80% of said changes during first 10 hours. Transformation time of the initial tumor cells into cells of phenotype A after the action of $^{39}$K was 80 hours, and after the action of $^{24}$Mg-70 hours. Beside the time interval during which transformation from the initial tumor cells into cells of phenotype A was observed, the stability of the obtained results was checked. Thus out of the total number of control points which was equal to 14, the number of additional monitoring points for zinc was 9 for potassium-6 and for magnesium-7.

According to monitoring of the results during the first 80 hours there were cell changes from the original tumor cells to cells of type A and no further changes were observed. Quantitative analysis of the cells at the last 14th point of the experiment confirmed that the cells maintained the acquired phenotype. No quantitative changes in the opposite direction were detected.

Figure 29:
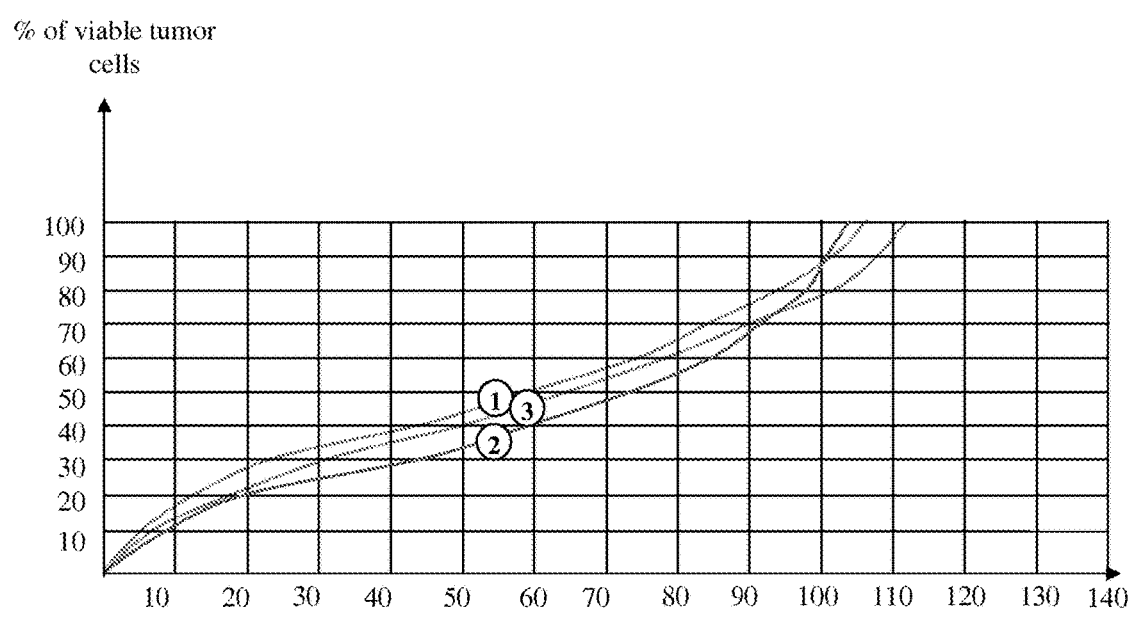
FIG. 29 illustrates characteristics of the number of non-viable tumor cells depending on the time of action of K (1), Zn (2) and Mg (3) components with natural distribution of isotopes.
Figure 31:
FIG. 31 illustrates $^{64}$Zn concentration of 0.128 mg/ml at which about 30% cells of type A were found.
Figure 32:
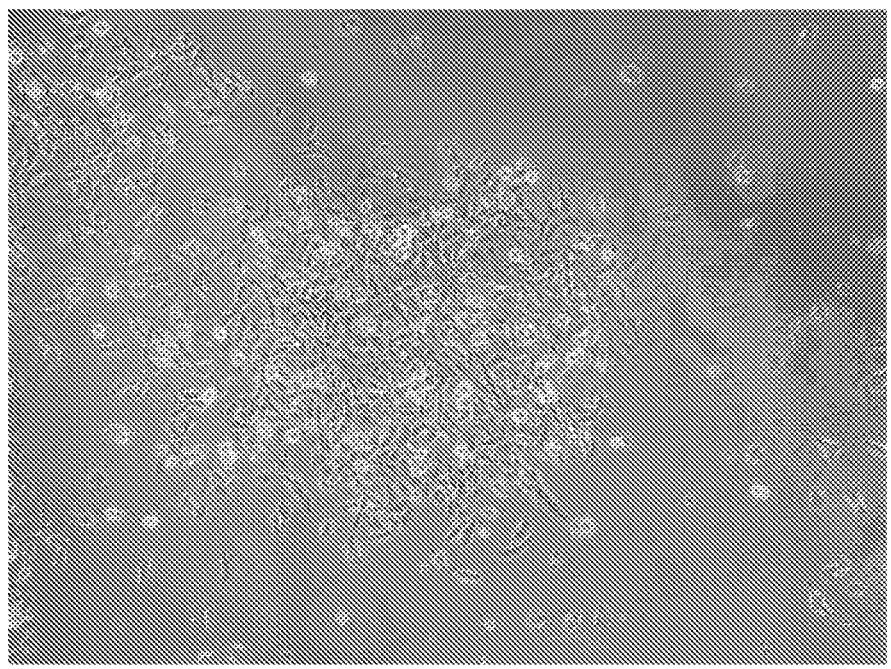
FIG. 32 illustrates 50/50% ratio of cells of types A and B at $^{64}$Zn concentration of 3.2 mcg/ml.
Figure 33:
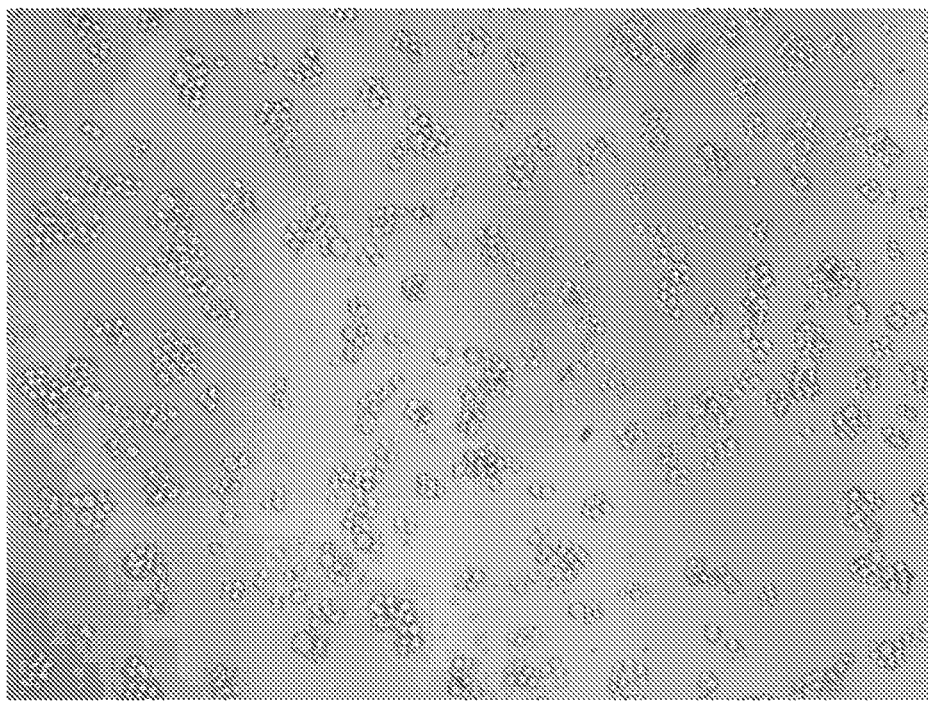
FIG. 33 illustrates 100% A cells at $^{64}$Zn concentration of 0.08 mg/ml.
Figure 34:
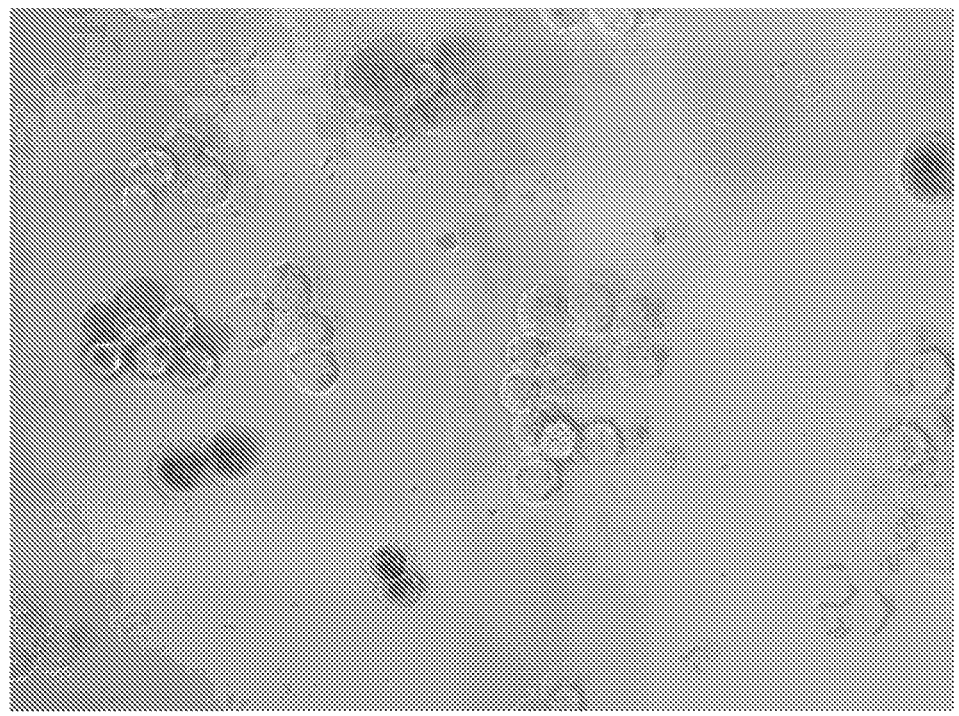
FIG. 34 illustrates about 30 to 35% B Cells at $^{64}$Zn concentration of 16 mcg/ml.
Figure 35:
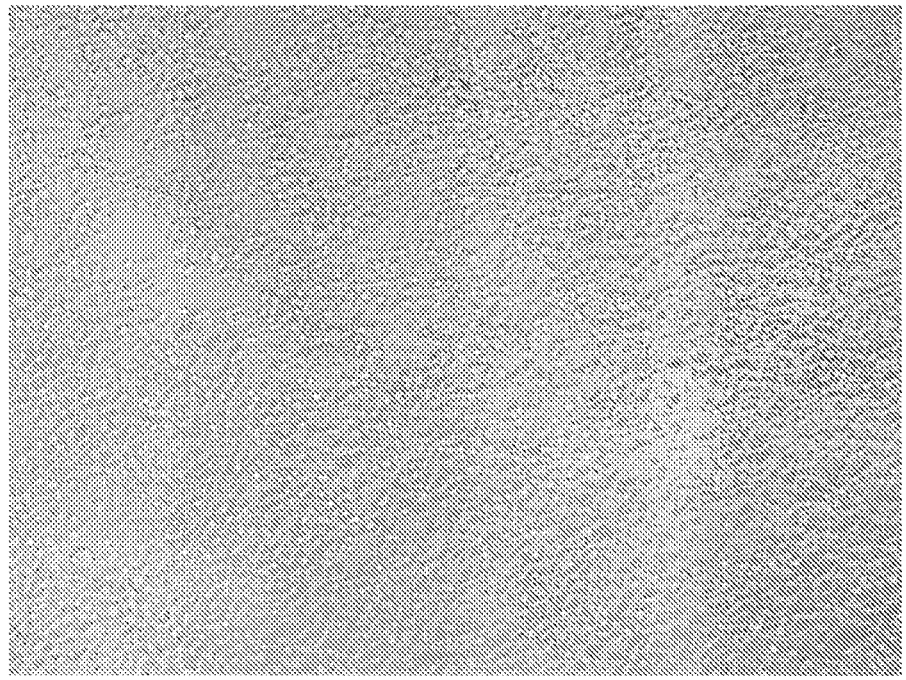
FIG. 35 illustrates 100% cells of type A at $^{39}$K concentration of 10 mg/ml.

The data about kinetics of the cell transformation process caused by $^{39}$K, $^{64}$Zn and $^{24}$Mg components are illustrated in FIG. 30. The experiment on assessment of the effects of K, Zn and Mg elements (with the natural distribution of isotopes) on renal carcinoma cells (PA) was conducted in a similar manner but with a quantitative assessment of viable tumor cells. The assessment criterion in this case was the integrity of the cell membrane which did not allow the dye to penetrate deep into cells and stain them. Dependence of the number of viable tumor cells versus the time of action of the components is shown in FIG. 29.

The results of effects of K, Zn and Mg with a natural distribution of isotopes and the reference drug Doxorubicin Ebewe on a strain of renal cell carcinoma (PA) manifested themselves as follows. Dynamics of the rate of activity of K, Zn and Mg elements with a natural distribution of isotopes did not differ significantly within the group of 3 elements. All components showed their ability to kill 100% of tumor cells within a time range of 105 to 112 hours.

According to FIG. 25 and summarized data in FIG. 28 the reference drug, Doxorubicin EBEWE, showed the highest activity, which at a dose of 3.2 mg/ml killed 50% of tumor cells. The doses of other elements were significantly higher to achieve the same effect. Zn showed the same ability (50% live, 50% dead) at a dose 100 times as high (300 microgram), the dose for Mg will be 1600 times as high (about 5 mg), and for K-650 times as high (about 2 mg). Doses required for complete 100% elimination of tumor cells are roughly the same.

A comparative assessment of the ability of light isotope components to change the phenotype of initial PA tumor cells to cells of type A was made based on data of concentrations of active substances and quantitative characteristics of the cells after their exposure to the action of the materials. The result is shown in FIG. 30.

DNA Analysis of Stem and Experimental Cells using Fluorescent Dye Hoechst 33258 will now be discussed. The main objectives was to study the quality (visual) picture of the structure of DNA (genome) in a variety of cellular structures due to the formation of a stable complex between DNA and the fluorescent nucleotide-specific dye. The dye, entering the cell through the membrane, is selectively embedded along the minor groove of the double helix of DNA and thus makes it possible to use the method for staining both nucleus and the surrounding cell areas. The molecules of the dye tied with DNA thus exhibit sufficiently strong fluorescence when exposed to UV light. Characteristics of the intensity of the fluorescent staining allow for qualitative comparative assessment of the genomes belonging to different types of cells. The advantages of the method are its rapidity and sensitivity to small amounts of DNA in the test items. Comparative assessment of the genome was determined on the following cell types: human stem cells, cells of renal carcinoma (PA) cell line after their exposure to the action of $^{39}$K, $^{64}$Zn and $^{24}$Mg, cells of renal carcinoma (PA) cell line after their exposure to the action of K, Zn and Mg with a natural distribution of isotopes, and cells of renal carcinoma (PA) cell line after their exposure to the action of anticancer drug Doxorubicin EbEWE.

The sequence of actions when staining the preparations consisted of the following steps. Cells, after their incubation with the components under study, were washed from the culture medium in PBS by centrifugation at 1000 rev/min within for 7 minutes. Then a working solution of Hoechst 33258 in a volume of 200 mcl was added to the cell sediment and incubated in $CO_2$ incubator for 30 minutes at 37° C. After incubation, the cells were washed with PBS. Prior to photographing of the cells, their sediment was diluted in 30 mcl of glycerol and applied onto a specimen slide. The preparation was covered with a cover glass with glycerin to prevent air bubbles. The microscopic examination of the preparations was carried out using fluorescence microscope Axiostar plus with a UV lamp. The comparative analysis made using Hoechst 33258 dye revealed the following.

Assessment of the color intensity of human stem cells and tumor cells of renal carcinoma (PA) after their exposure to the action of $^{39}$K, $^{64}$Zn and $^{24}$Mg shows similarity in the intensity of fluorescence. Utilization of the reference drug Doxorubicin Ebewe, as shown in FIGS. 15, 20, 31, 32 show induction of apoptosis and the presence of apoptotic bodies. Assessment of action of the dye was conducted on the preparations with the active substance concentration that caused 50% cell transformation to phenotype A for the light isotope components and at a dose of 50 IC for the elements with a natural distribution of components.

Comparative analysis of the appearance, color and shape of cells under the action of $^{64}$Zn, $^{24}$Mg and $^{39}$K, after cells were stained with crystal violet demonstrated that the effect of said components consist in the formation of cells of 2 types which in their appearance differ from the cells exposed to the action of Zn, Mg and K elements with a natural isotope distribution.

The action of $^{64}$Zn produced largest morphological differences between cells prior and after the exposure. By visual observation of the cells after the action of $^{64}$Zn, $^{24}$Mg and $^{39}$K they were divided into groups A and B. The effect of Zn, Mg and K elements with a natural isotope distribution on PA tumor cells (stained with trypan blue) consisted in the damage of the cells membrane. The cell classification was performed according to the live-dead criterion. Action of materials containing $^{64}$Zn, $^{24}$Mg and $^{39}$K on the cells of a tumor strain of renal cell cancenoma (PA) produced an increase in the degree of their adhesion as compared with the action of Zn, Mg and K elements with a natural distribution of isotopes.

Morphological differences after the exposure of cells to the action of $^{64}$Zn, $^{24}$Mg and $^{39}$K, as compared with Zn, Mg and K elements with a natural distribution of isotopes, were expressed by the increased degree of adhesion of cells to the culture plastic surface. In most cases a tumor growth in a biological organism is associated with the transport of cells via the blood circulatory and lymphatic systems and formation of secondary lesions (metastases). Materials containing light isotopes are effective in strengthening structural integrity of the tissue and in suppression of tumor cells migration through the bloodstream, i.e. in the prevention of metastasis. $^{64}$Zn containing material is capable of modifying the phenotype of original tumor cells. In vitro experiment demonstrated ability of this component to transform initial tumor cells of renal cell carcinoma (PA) in a rat into cells of 2 phenotypes. It is efficient within the same concentration range as Doxorubicin EBEWE.

Comparable concentration ranges in which the antitumor effect of Doxorubicin EBEWE and the components of the test group were detected were as follows: the concentration range in which the effect of Doxorubicin EBEWE was detected was from 16 mcg/ml (5% live and 95% dead cells were detected) to 0.64 mcg/ml (61% live and 39% dead cells were detected), which is shown in FIG. 28. Using Doxorubicin in concentrations below 0.64 mcg/ml showed that all tumor cells remained viable. All tumor cells beyond the upper limit of the range of action of Doxorubicin (concentration above 16 mcg/ml) were dead.

Zn with a natural distribution of isotopes (in sulfate form) showed an effect similar to that of Doxorubicin which consisted in the presence of live and dead cells after the action of sulfate, and the differences were recorded within the range. The upper point at which the start of the action of zinc was detected had the concentration of 80 mcg/ml and was characterized by 25% of live tumor cells and 75% of dead tumor cells (based on trypan blue staining). The lower limit of the concentration range was expressed by the value of 16 mcg/ml with which 7% of dead tumor cells and 93% live tumor cells were detected. Beyond the lower limit of the range (less than 16 mcg/ml) all tumor cells were viable and beyond the upper limit (80 mcg/ml) all cells were dead. Doxorubicin Ebewe produces a similar effect outside the upper and lower limits.

Action of $^{64}$Zn in the concentration of 3.2 mcg/ml resulted in a change in the cell morphology and phenotype. The cells transformed into 2 types of cells the first of which (type A), based on the results of comparative analysis of the color and shape, has signs of similarity to the stem cells. $^{24}$Mg and $^{39}$K components possess similar properties but when taken in much higher concentrations. Thus, the action of $^{64}$Zn is most effective in terms of specific characteristics of a mass unit of the substance able to transform the initial tumor cells into A cells.

The kinetic curves of the rate of transformation of initial tumor cells into cells with an altered phenotype (after the action of 64Zn, $^{24}$Mg and $^{39}$K) showed that for $^{64}$Zn 80% of changes occurred in the first 10 hours of the experiment. The rate indicators of cell transformation for $^{24}$Mg and $^{39}$K were 62% and 40% respectively over the same time. Analysis based on staining cells with Hoechst 33258 dye revealed a similarity in the intensity of fluorescence of human stem cells and cancer cells exposed to the action of $^{64}$Zn, $^{24}$Mg and $^{39}$K.

The fluorescent ability of cells after their treatment with the components with a natural distribution of isotopes was significantly lower. Dynamics of the activity of $^{64}$Zn, $^{24}$Mg and $^{39}$K components with regard to their ability to transform initial PA tumor cells into cells of phenotype A showed 80% of the transformation in the first 10 hours for $^{64}$Zn, in the first 20 hours for $^{39}$K and in the first 45 hours for $^{24}$Mg out of the total time of the experiment which equalled 140 hours.

The highest efficiency among $^{64}$Zn, $^{24}$Mg and $^{39}$K (with regard to the ability of the components to transform initial tumor cells into those of an altered phenotype) was observed for $^{64}$Zn. Assuming 50% of the cells transformed from tumor cells to A cells, 1 microgram of $^{64}$Zn sulfate demonstrated a possibility of obtaining 23438 cells of type A, and assuming 100% transformation with the same amount of $^{64}$Zn sulfate, only 938 cells of type A can be obtained or 25 times less. It means there is non-linear dependence between dosage of isotope containing material and efficiency of treatment.

Comparative assessment of the genome, carried out based on the intensity of fluorescence using Hoechst 33258 dye demonstrates similarity of the phenotype of stem cells and cells of phenotype A produced in result of the action of $^{64}$Zn, $^{24}$Mg and $^{39}$K on cancer cells. The dynamics of growth of the PA tumor strain in the in vivo experiment showed the following: development of the tumor process in an animal with a transplanted unfrozen strain was initiated with 10% of viable cells; biochemical kinetics of the PA tumor growth for 29 days showed an increase in its weight to 120 grams, and initial signs of the tumor growth after the transplantation (start of increase in weight) were observed already on the 5th day. All these parameters in combination confirm an extremely high degree of malignancy of the strain of renal cell carcinoma (PA).

Example 2, Section 2 will now be discussed. Immunocytochemistry of adhesion proteins, cytoskeleton (cadherins) and CD 44 stem cell marker after their exposure to the action of $^{39}$K, $^{64}$Zn and $^{24}$Mg on a model of renal cell carcinoma (PA) in a rat. Detection of cumulative properties of $^{64}$Zn.

Cadherins are a group of glycosylated proteins and they are mainly responsible for the formation of cell-cell interactions providing adhesion between two identical molecules that are expressed on the surfaces of two cells of one and the same type. Besides the physical contact that cadherins provide between the two cells, they facilitate the transfer of a number of signals through cytoskeletal structures thus controlling cell growth and differentiation. Cadherins appear mainly in intercellular adhesion at the stages of morpho- and organogenesis. They provide structural integrity of tissues (especially the epithelial monolayer).

When making the immunocytochemistry (ICC) assay, cells on microscope glasses (cytospin preparations) were fixed in the solution (methanol+acetone 1:1) for 2 hours at t 20° C. and incubated with 1% solution of bovine serum albumin (BSA) for 20 minutes. Then the monoclonal antibodies—CD44 (Diagnostic BioSystems), E-cadherin (ThermoScientific), N-cadherin (NeoMarker, BioLegend)—were applied for 60 minutes, after which the Poly Vue imaging system conjugated with peroxidase was used and the enzyme activity was detected using diaminobenzidine (ThermoScientific) as a substrate.

After the immunocytochemical reaction the preparations were washed with water and counterstained with hematoxylin-eosin (for 15-30 seconds). The results were analyzed by counting cells with expression (brown colored cells), using a light microscope and were assessed using the classical H-Score method: $S=1\times A+2\times B+3\times C$, where S is the H-Score index giving a range of 0 (protein is not detected) to 300 (high-level expression in 100% of the cells); A is the percentage of weakly stained cells, B is the percentage of moderately stained cells and C is the percentage of strongly stained cells.

Three components—$^{64}$Zn, $^{24}$Mg and $^{39}$K at doses D1 and D2 were used, and the action of $^{64}$Zn was tested on 2 models: on freshly prepared solution (which was tested immediately after it was prepared) and on a solution which was stored for 14 days at temperature+4° C. $^{64}$Zn solution after 14 days of storage at T=+4° C. is designated as $^{64}$Zn-Z2 in charts and tables.

As a result of immunocytochemistry assay of cell antigens-cadherins and CD44 marker, significant changes in the studied proteins after their exposure to the action of the components were detected. The effects observed in the course of the experiment differed depending on the doses of the preparations, and $^{64}$Zn-Z2 component showed increased activity after its storage for 14 days at temperature+4° C.

The action of $^{64}$Zn at a dose of 0.128 mcg/ml resulted in increased number of E-cadherin-positive cells (cells with E-cadherin expression) and a slight increase in N-cadherin positive cells. At a dose of 3.2 mcg/ml, this material caused a decrease in the number of E-cadherin-positive cells and a substantial increase in N-cadherin-positive cells and CD44 marker, as shown in FIGS. 45, 46, 47, 48. This fact evidences blocking one of the pathogenic ways of the tumor growth—metastasis of tumor cells. An increase in the number of E-cadherin-positive cells causes an increase in their adhesive properties and, as a consequence, reduction of their invasive and migratory potential (which is characteristic for cells of the aggressive mesenchymal phenotype, with no or a small number of cells expressing E-cadherin).

Referring to the above, the use of the preparation at a dose of 3.2 mcg/ml showed a decrease in the E-cadherin indicators and an increase in the expression of CD44, a stem cell marker, which is indicative of "redistribution" of the adhesive properties from E-cadherin protein to CD44. Analysis of the slug transcription factor responsible for "aggressive"

behavior of tumor cells also shows activity of tumor cells and their characteristics in terms of epithelial-mesenchymal transition. This factor is a marker of mesenchymal (aggressive) cells. It is indicative of high migratory and invasive abilities of cells which and as a result of complication in the disease progression in cancer patients.

Figure 49A:
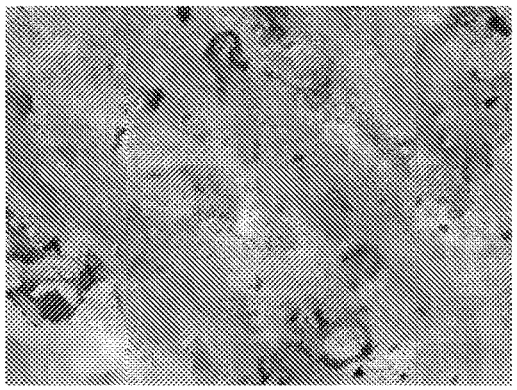
FIGS. 49A-49B illustrate E-cadherin expression in PA cells after the action of $^{64}$Zn-Z2 at doses D2 (A) and D1 (B) (magnification ×100)
Figure 49B:
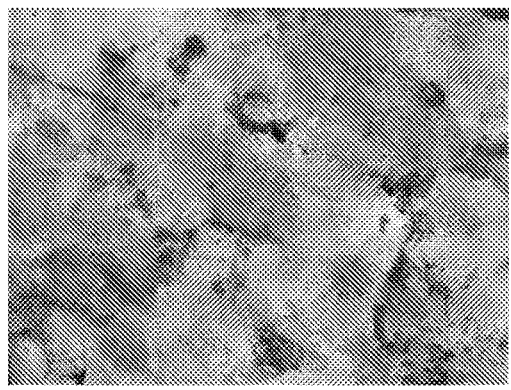
Figure 50A:
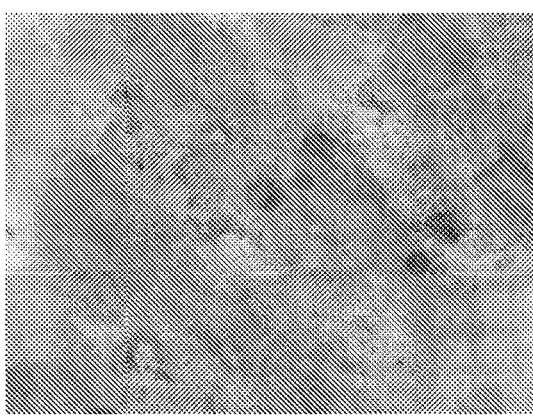
FIGS. 50A-50B illustrate N-cadherin expression in PA cells after the action of $^{64}$Zn-Z2 at doses D2 (A) and D1 (B) (magnification of ×100)
Figure 50B:
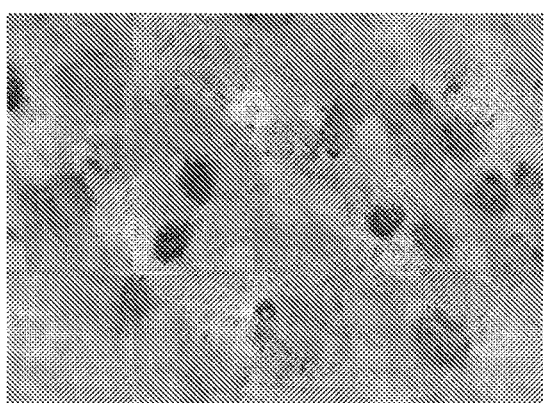
Figure 51A:
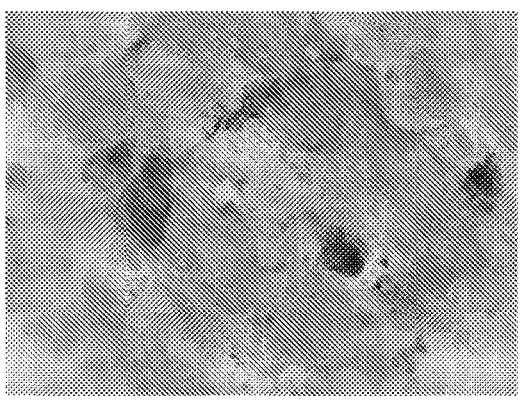
FIGS. 51A-51B illustrate CD44 marker expression in PA cells after the action of $^{64}$Zn-Z2 at doses D2 (A) and D1 (B) (magnification ×100)
Figure 51B:
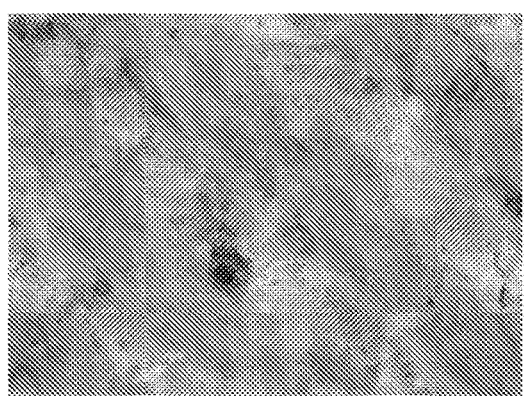
Figure 52A:
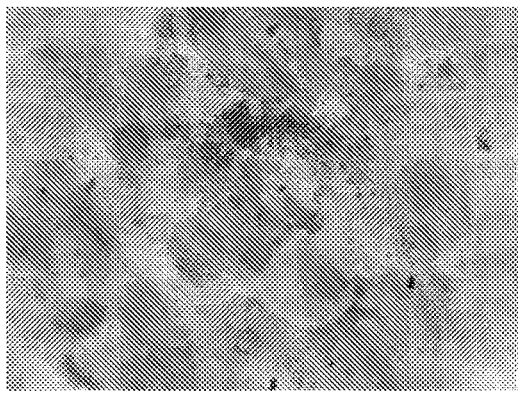
FIGS. 52A-52B illustrate E-cadherin expression in PA cells after the action of $^{24}$Mg at doses D2 (A) and D1 (B) (magnification ×100)
Figure 52B:
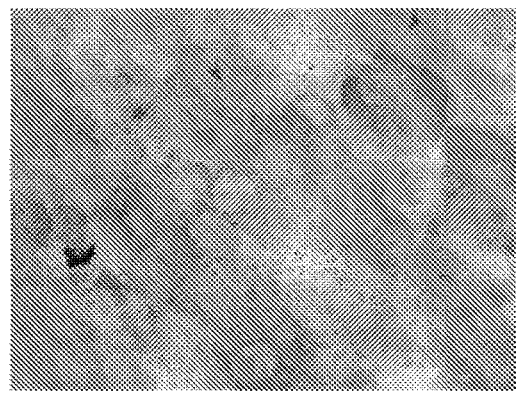
Figure 53A:
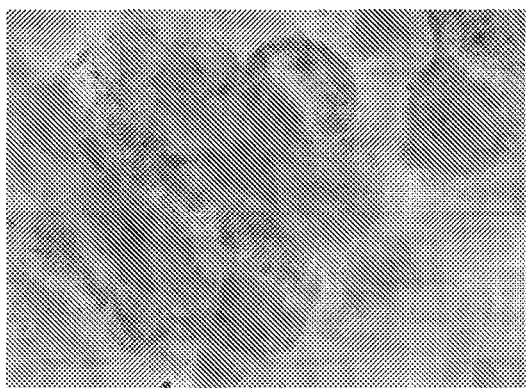
FIGS. 53A-53B illustrate N-cadherin expression in PA cells after the action of $^{24}$Mg at doses D2 (A) and D1 (B) (magnification ×100)
Figure 53B:
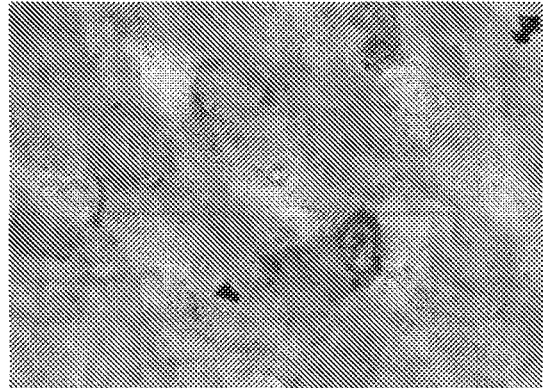
Figure 60A:
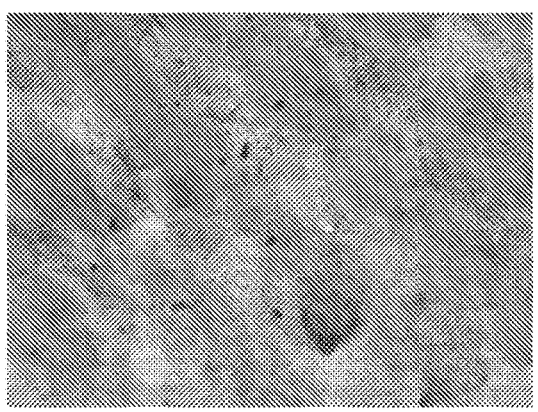
FIGS. 60A-60B illustrate N-cadherin expression in control PA cells not exposed to the action of components (magnification ×100)
Figure 60B:
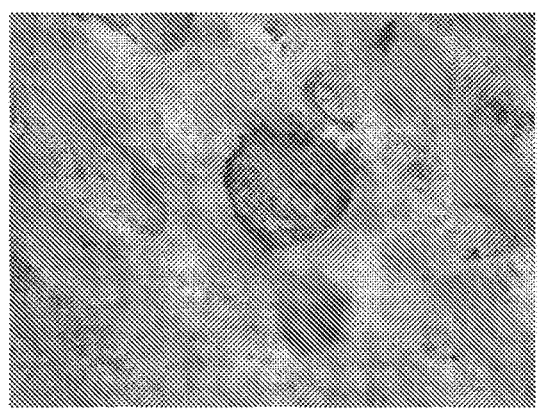
Figure 61A:
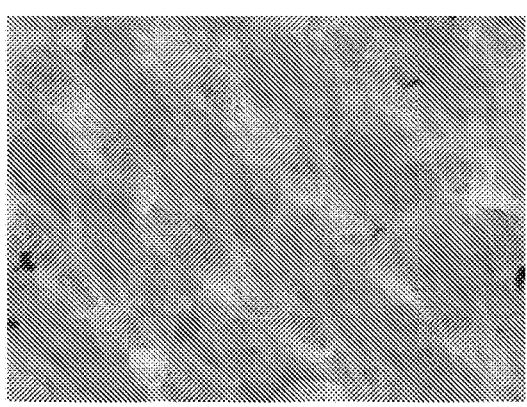
FIGS. 61A-61B illustrate CD44 marker expression in control PA cells not exposed to the action of components (magnification ×100)
Figure 61B:
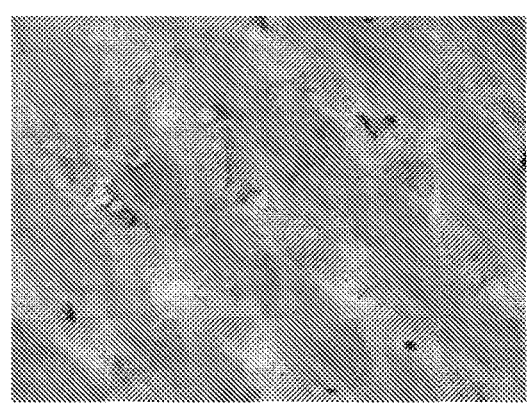
Figure 62:
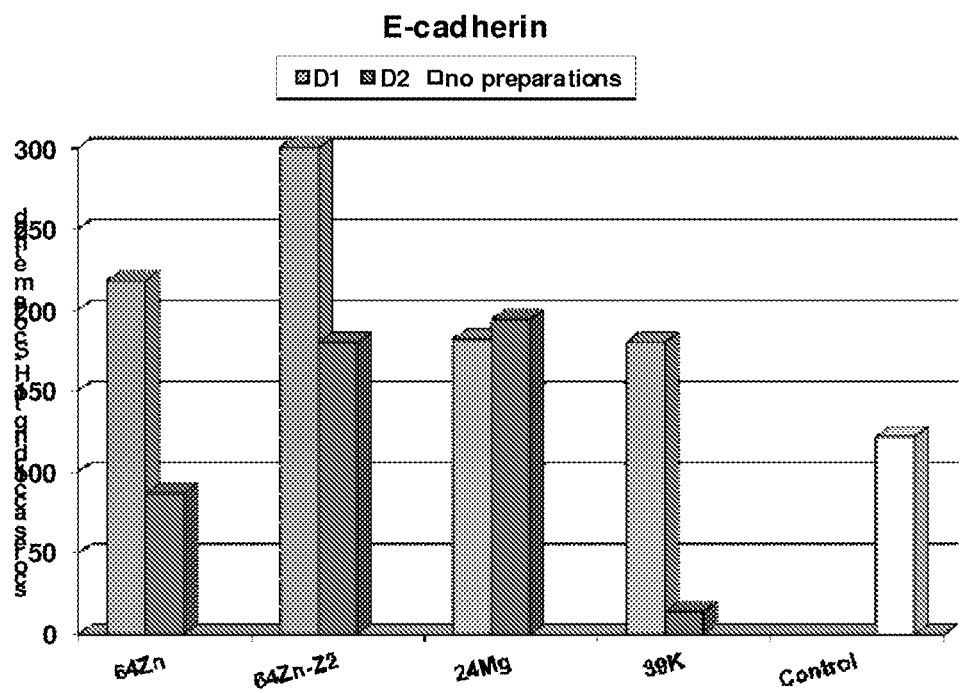
FIG. 62 illustrates comparative expression of E-cadherin in PA cells after the action of light isotopes containing materials.
Figure 63:
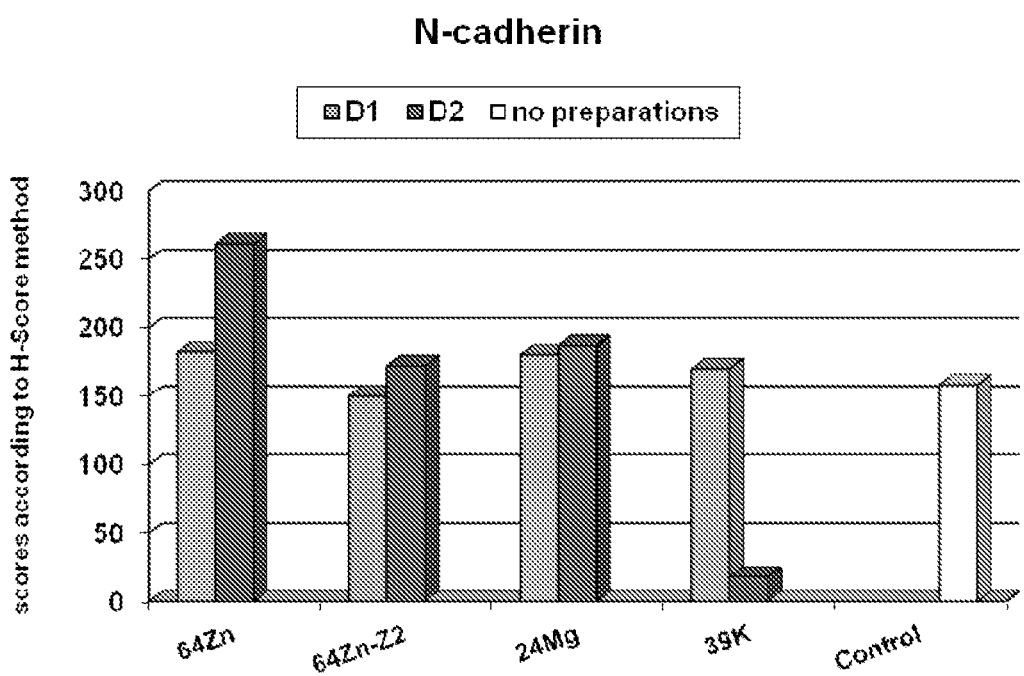
FIG. 63 illustrates comparative expression of N-cadherin in PA cells after the action of light isotopes containing materials.
Figure 64:
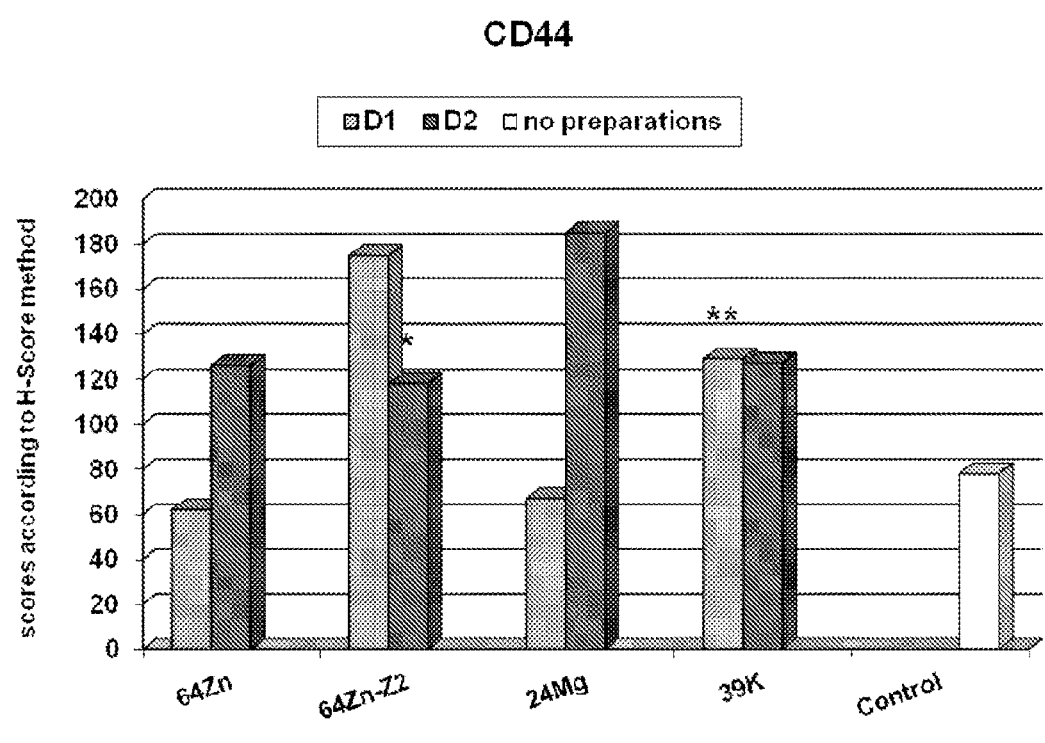
FIG. 64 illustrates comparative expression of CD44 marker in PA cells after the action of light isotopes containing materials (*, ** are the average values of various clonal expression.
Figure 65A:
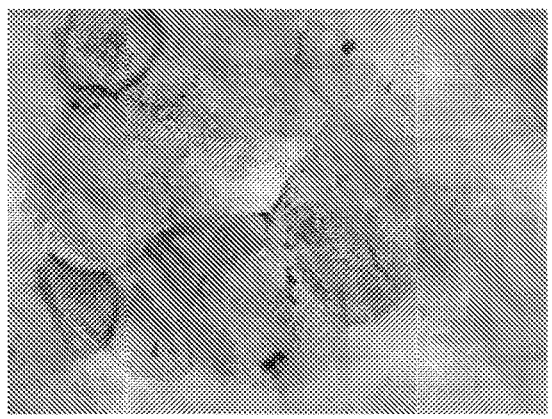
FIGS. 65A-65F illustrate E-cadherin expression in control cells (not exposed to the action of preparations) on cells of A-549 (A, B), MCF-7 (C, D), COLO 205 (E, F) (magnification ×100)
Figure 65B:
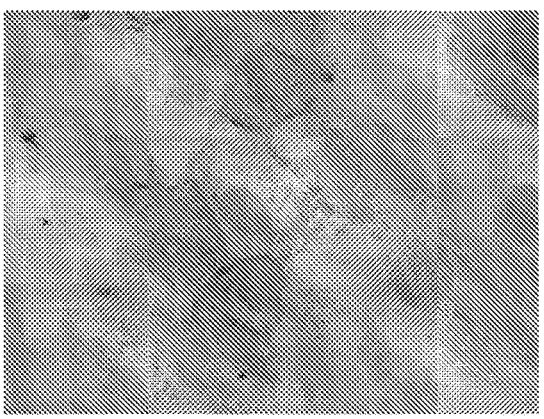
Figure 65C:
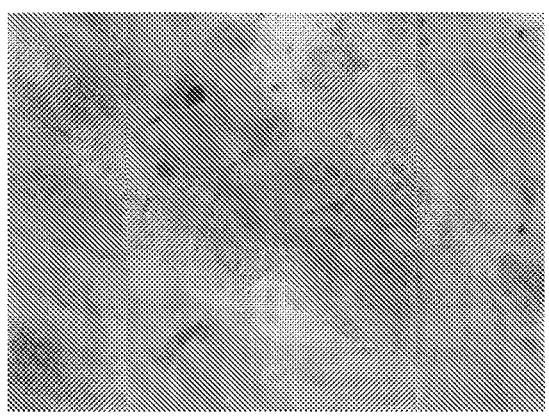
Figure 65D:
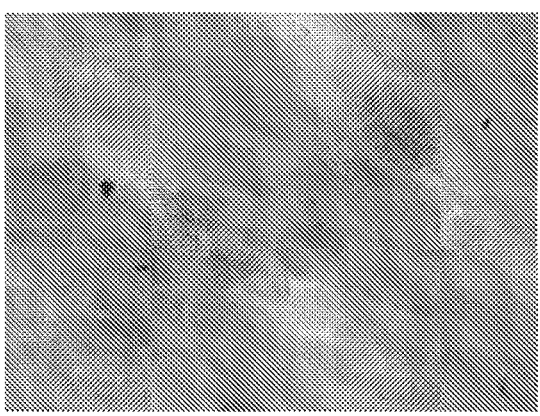
Figure 65E:
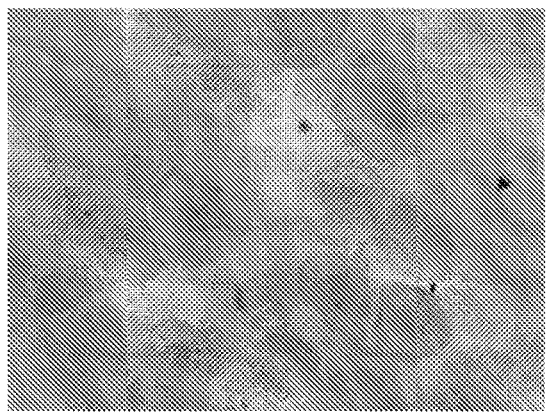
Figure 65F:
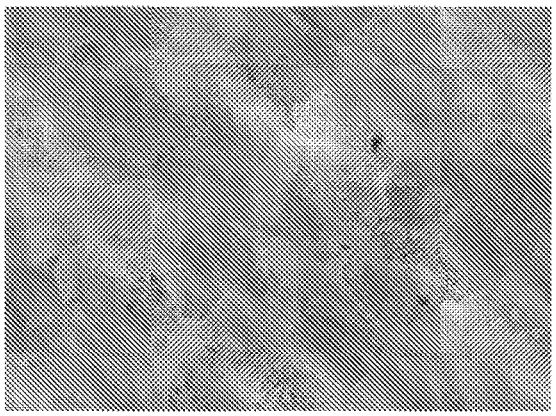
Figure 70A:
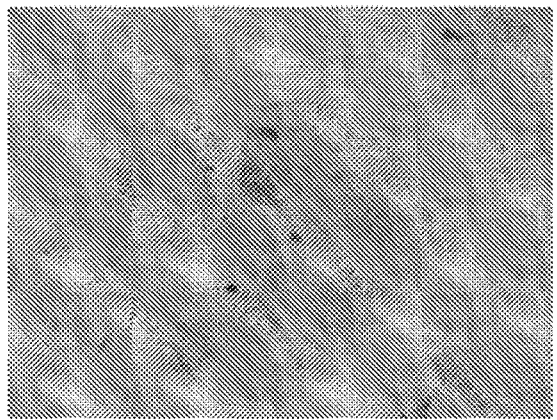
FIGS. 70A-70F illustrate E-cadherin expression in cells after their exposure to the action of $^{64}$Zn: A-549 (A, B), MCF-7 (C, D), COLO 205 (E, F) (magnification ×100)
Figure 70B:
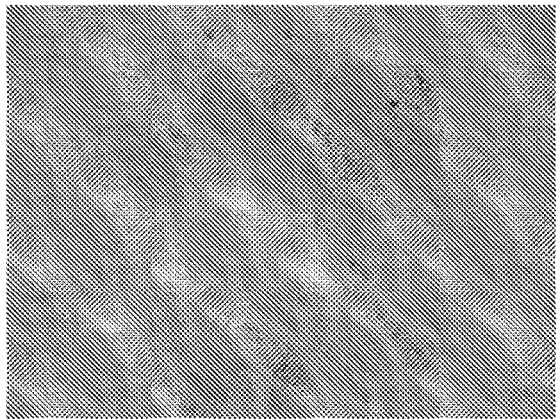
Figure 70C:
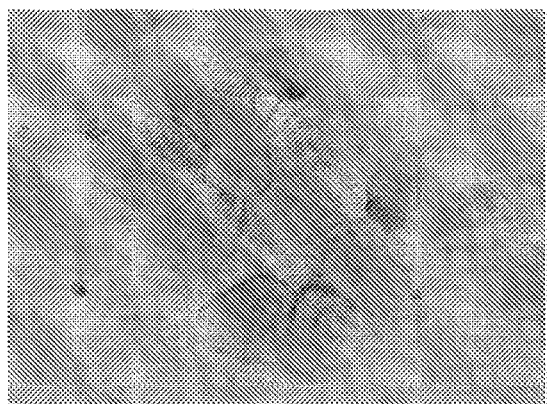
Figure 70D:
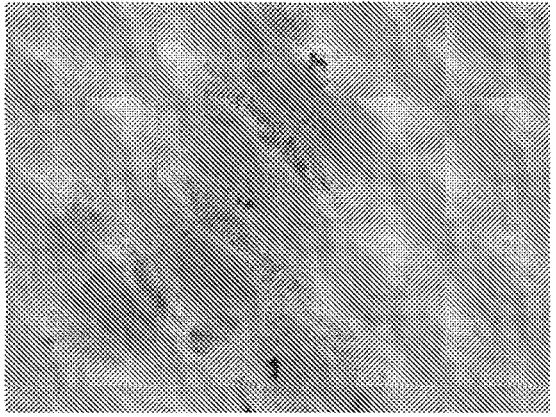
Figure 70E:
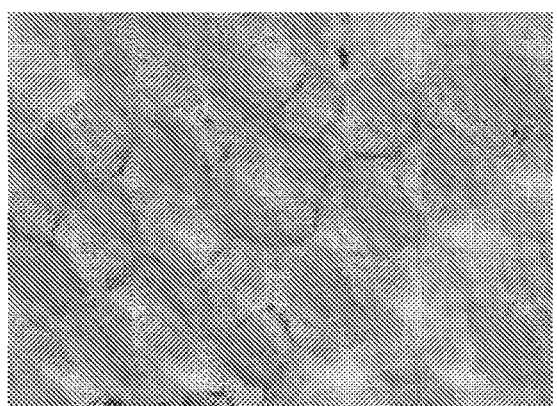
Figure 70F:
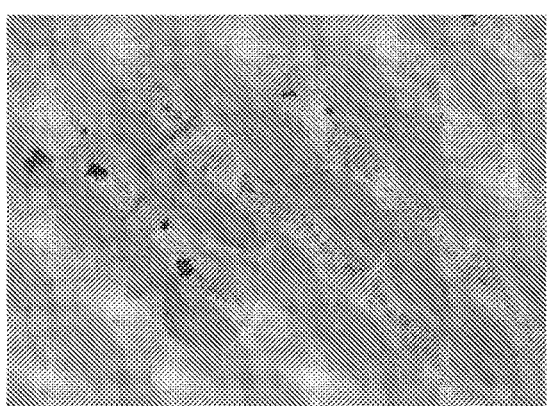
Figure 76:
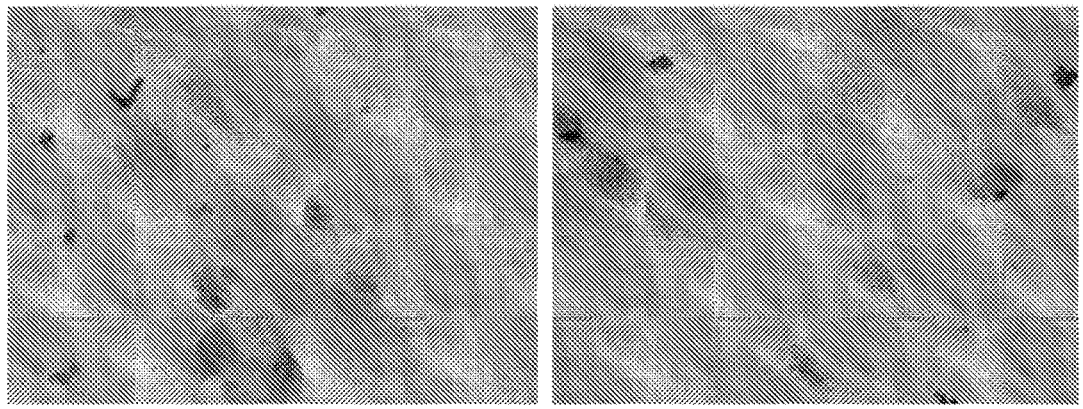
FIG. 76 illustrates E-cadherin expression in NRK cells after their exposure to the action of $^{64}$Zn (magnification ×100)
Figure 77:
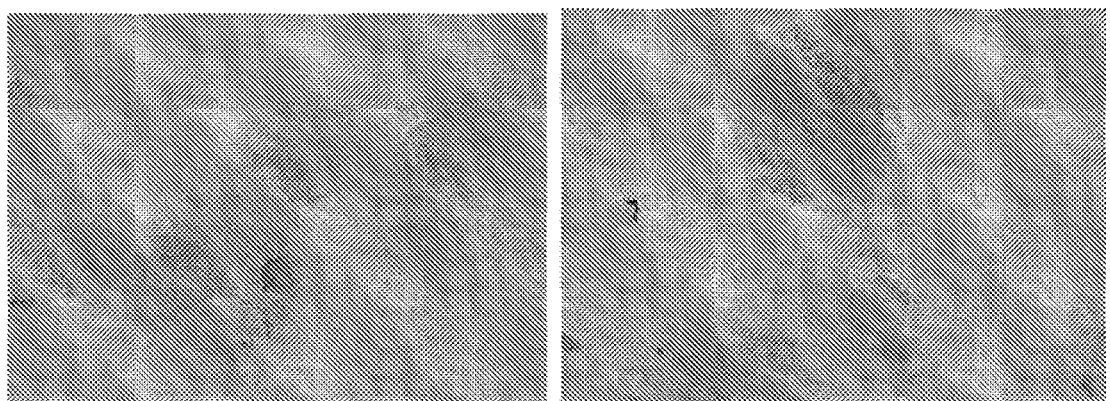
FIG. 77 illustrates CD44 expression in NRK cells after their exposure to the action of $^{64}$Zn (magnification ×100)
Figure 78:
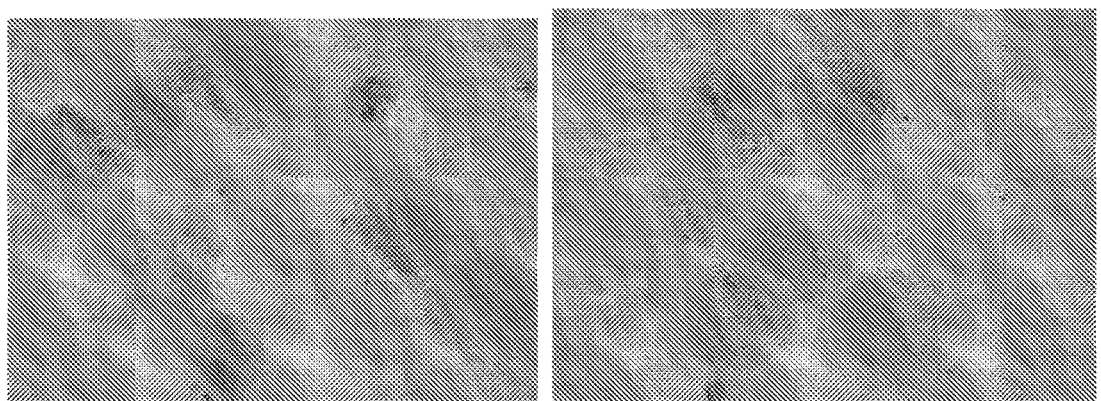
FIG. 78 illustrates E-cadherin expression in NRK cells after their exposure to the action of $^{64}$Zn (magnification ×100)
Figure 79:
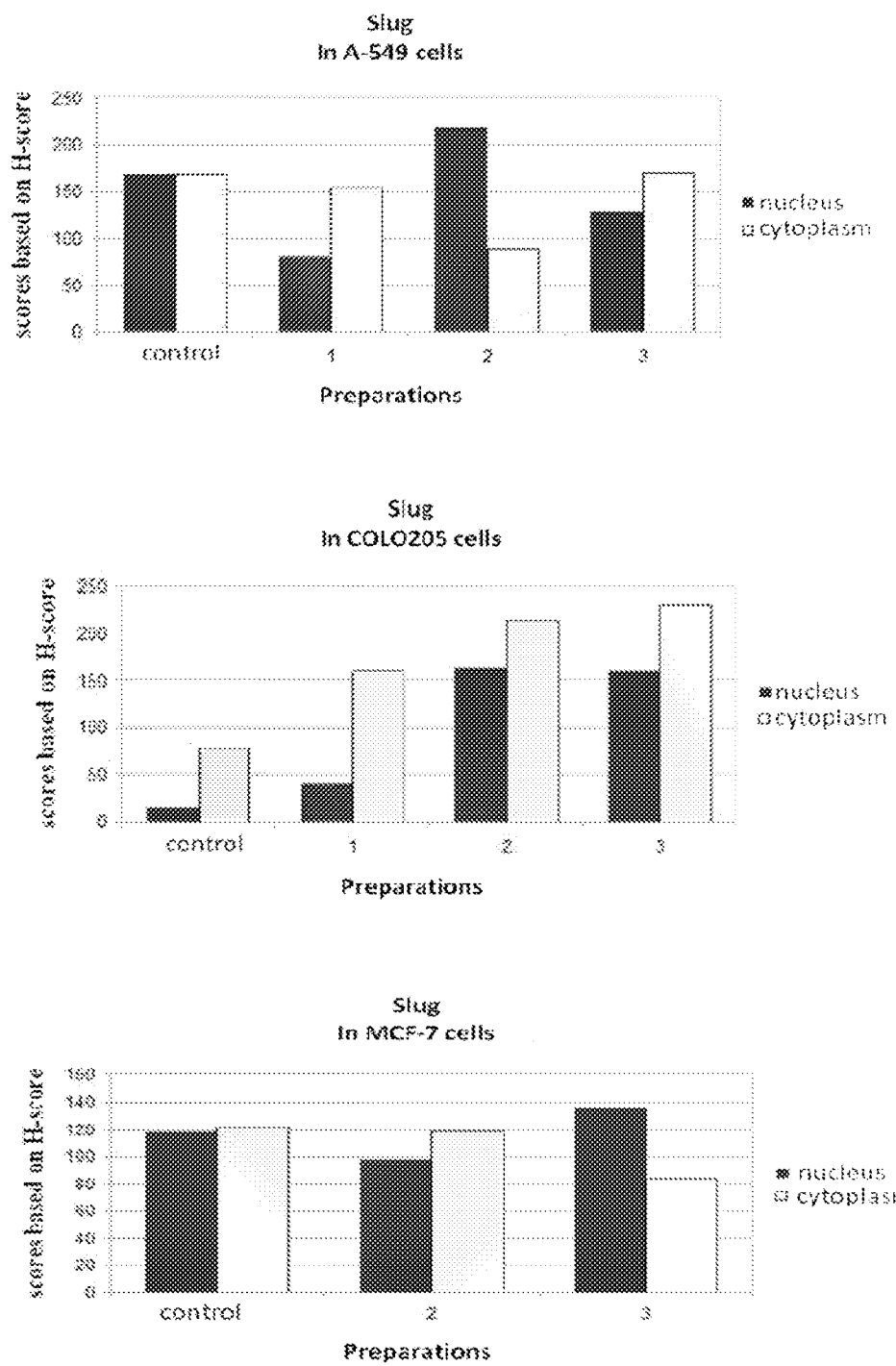
FIG. 79 illustrates results of the study of transcription factor in human tumor cells of different genesis after their exposure to the action of $^{39}$K, (1) $^{64}$Zn, (2) and $^{24}$Mg (3)
Figure 80:
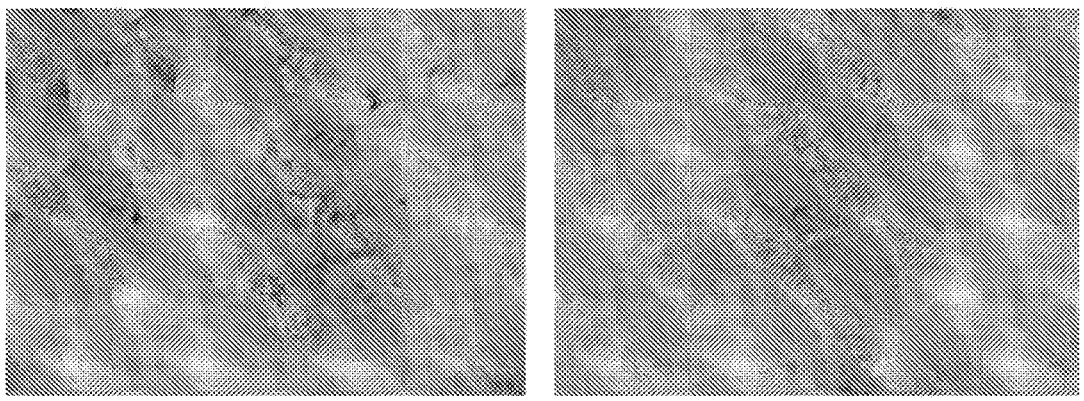
FIG. 80 illustrates A-549 control (no preparations). Slug marker expression (magnification ×100)
Figure 81:
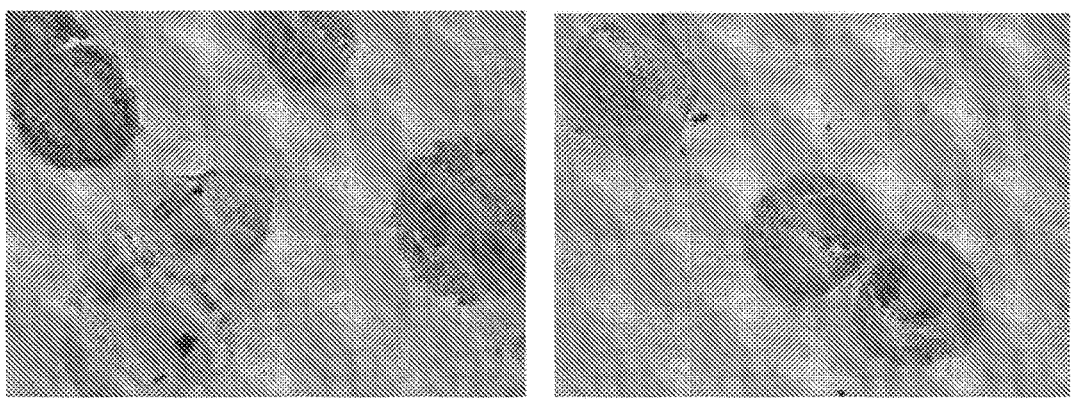
FIG. 81 illustrates slug marker expression in cells of A-549 line after their exposure to the action of $^{39}$K at a dose of IC50 (magnification ×100)
Figure 82:
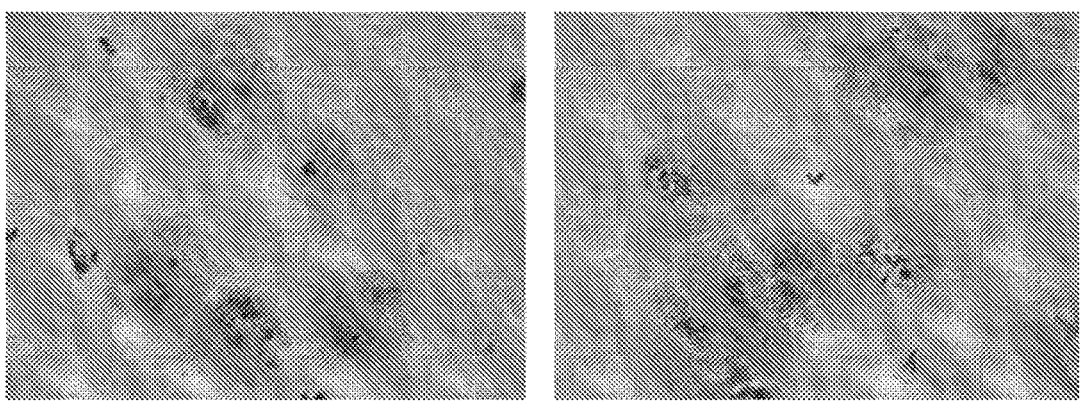
FIG. 82 illustrates slug marker expression in cells of A-549 line after their exposure to the action of $^{64}$Zn at a dose of IC50 (magnification ×100)
Figure 83:
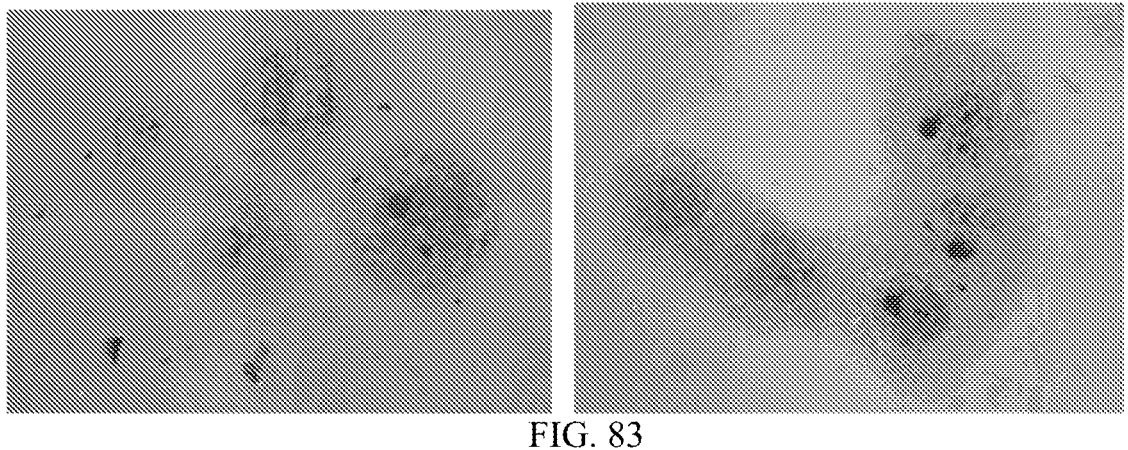
FIG. 83 illustrates slug marker expression in cells of A-549 line after their exposure to the action of $^{24}$Mg at a dose of IC50 (magnification ×100)
Figure 84:
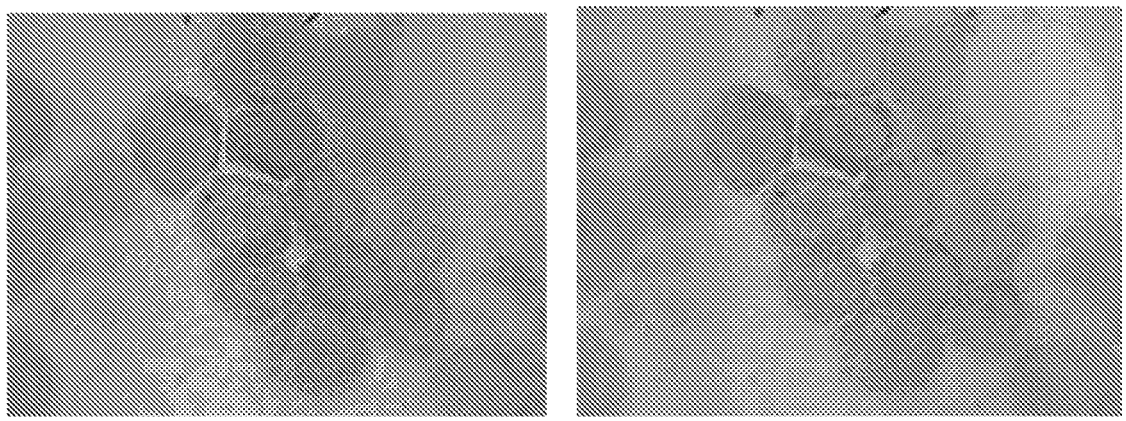
FIG. 84 illustrates COLO 205 control (no preparations). Slug marker expression (magnification ×100)
Figure 85:
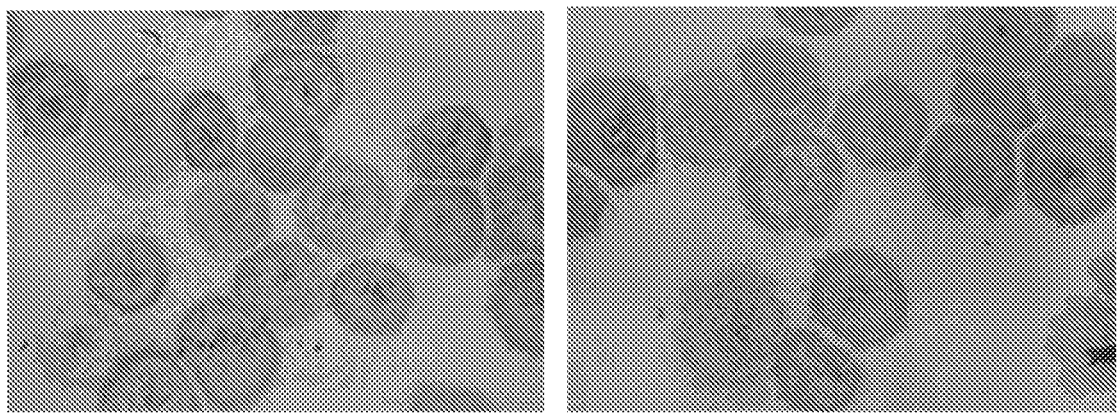
FIG. 85 illustrates slug marker expression in cells of COLO 205 line after their exposure to the action of $^{39}$K at a dose of IC50 (magnification ×100)
Figure 86:
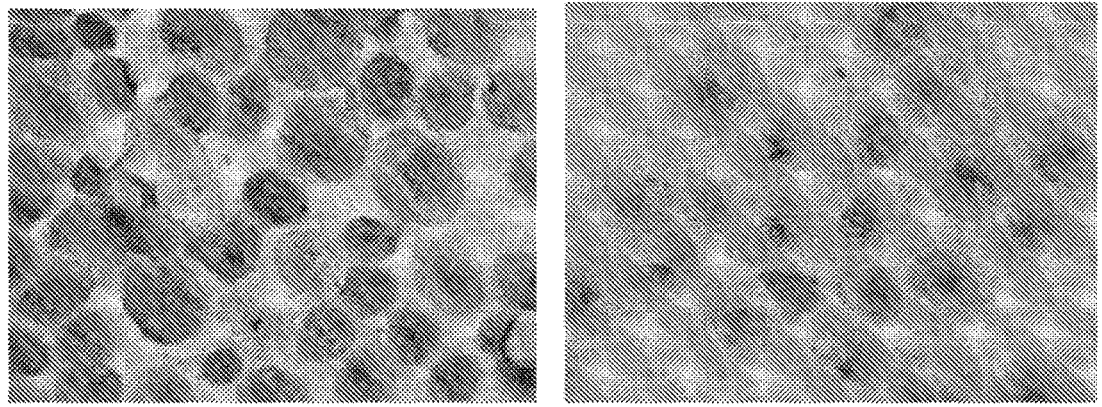
FIG. 86 illustrates slug marker expression in cells of COLO 205 line after their exposure to the action of $^{64}$Zn at a dose of IC50 (magnification ×100)
Figure 87:
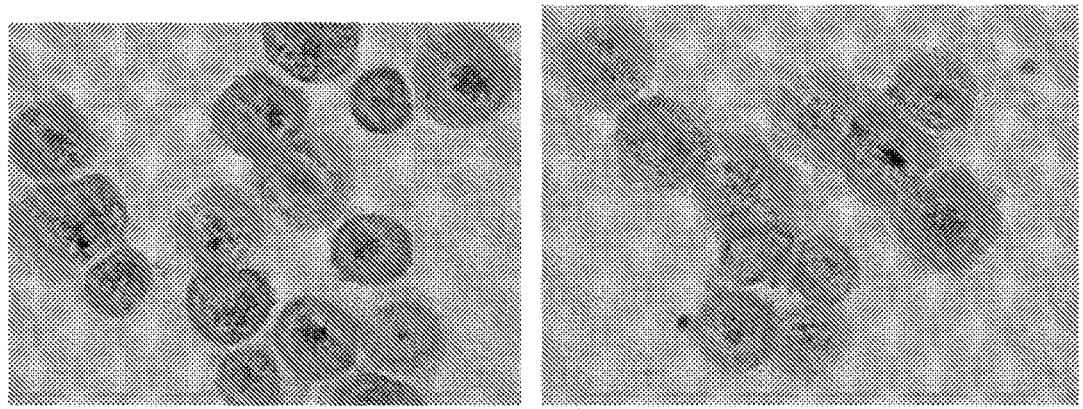
FIG. 87 illustrates slug marker expression in cells of COLO 205 line after their exposure to the action of $^{24}$Mg at a dose of IC50 (magnification ×100)
Figure 88:
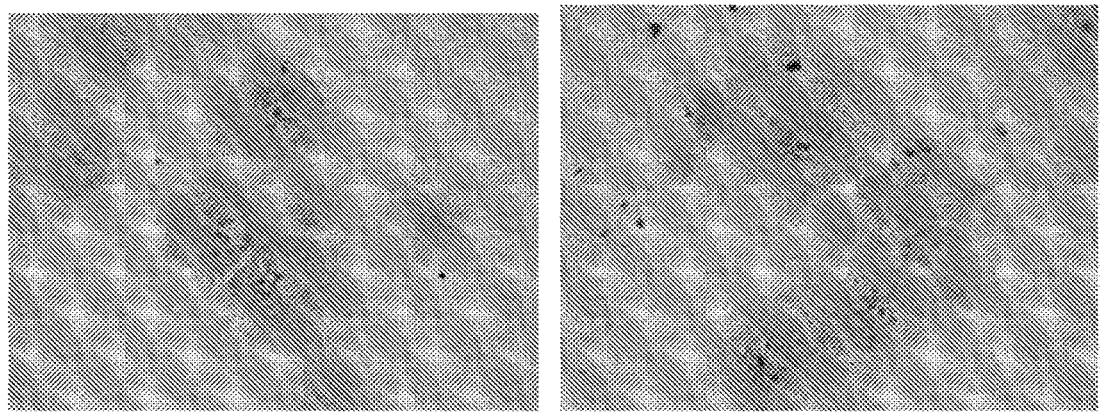
FIG. 88 illustrates MCF-7 control (no preparations). Slug marker expression (magnification ×100)
Figure 92:
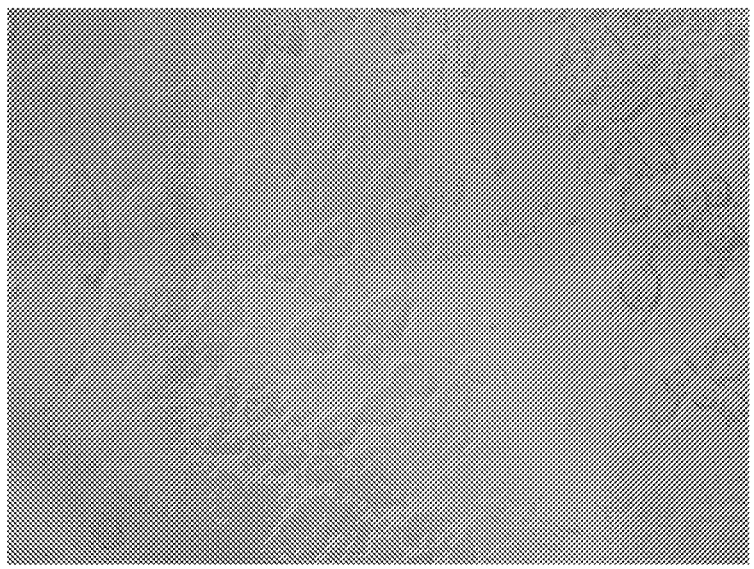
FIG. 92 illustrates primary cells of A-549 line. Human lung cancer Magnification ×400.
Figure 93:
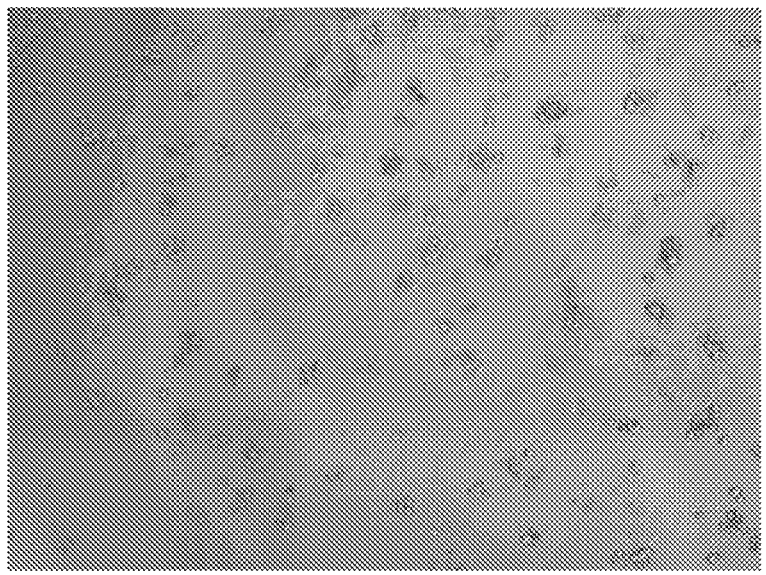
FIG. 93 illustrates an effect of $^{64}$Zn sulphate form diluted in saline with glucose on A-549 cells. About 20% of cells of type A after 24 hours of the experiment Magnification ×100.
Figure 94:
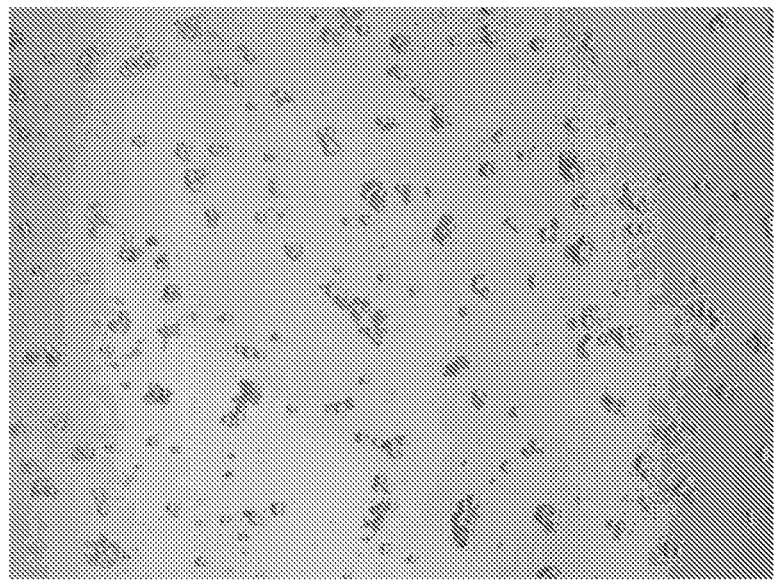
FIG. 94 illustrates an effect of $^{64}$Zn sulphate form diluted in saline with glucose on A-549 cells. About 50% of cells of type A after 28 days of the experiment, Magnification ×100.
Figure 95:
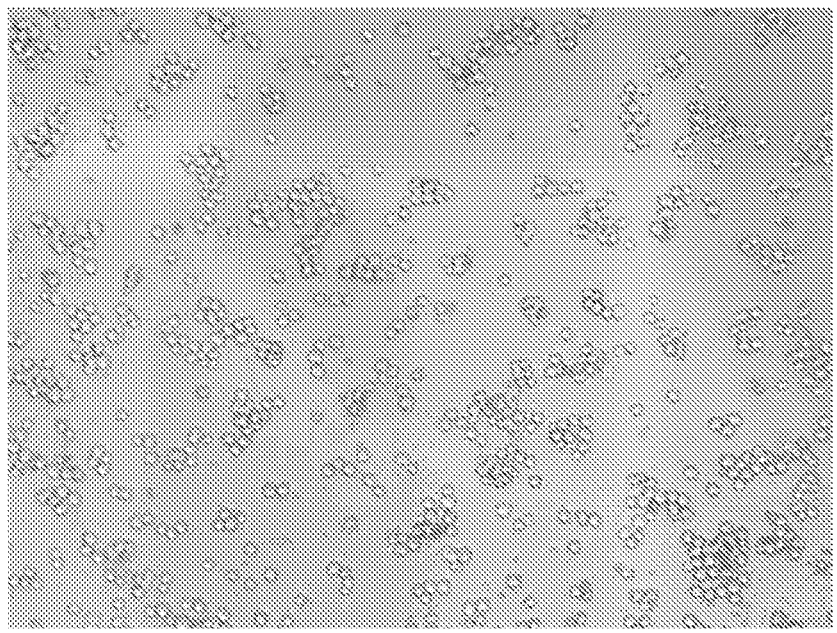
FIG. 95 illustrates an effect of $^{64}$Zn sulphate form diluted in saline with glucose on A-549 cells. About 80% of cells of type A after 60 days of the experiment Magnification ×100.
Figure 96:
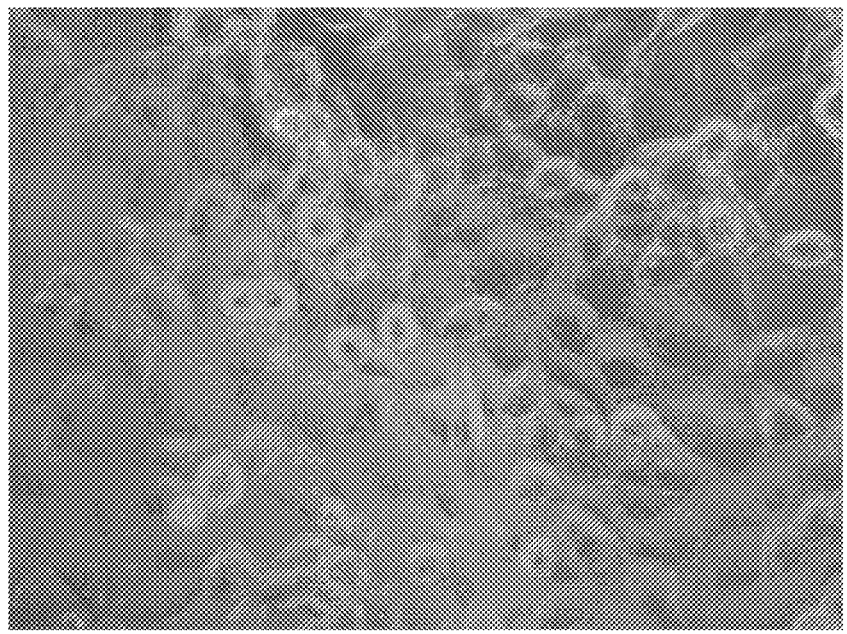
FIG. 96 illustrates an effect of $^{39}$K sulphate form at a dose of 2 mg/ml on A-549 cells after 30 min following the start of the experiment. Cells of type A are light, Magnification ×400.
Figure 97A:
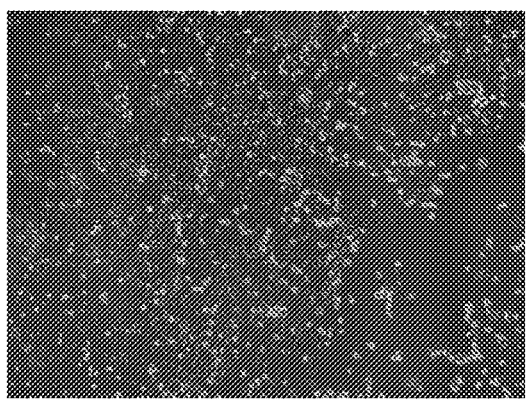
FIGS. 97A-97D illustrate an embryonic cells of a mouse. A, B magnification ×100, C, D—magnification ×400.
Figure 97B:
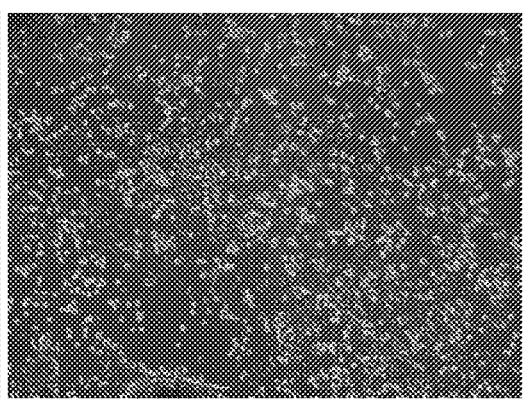
Figure 97C:
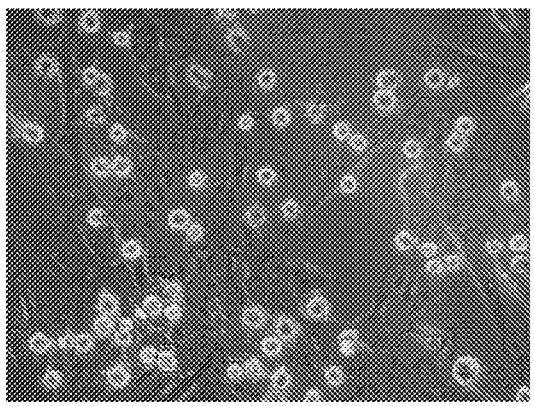
Figure 97D:
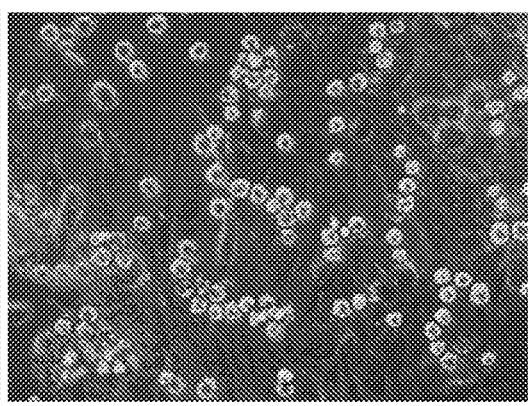

The action of $^{64}$Zn-Z2 component ($^{64}$Zn after 14 days storage at T=+4° C.) on the phenotype of PA tumor cells affects the number of E-cadherin-positive cells for both doses of 3.2 mcg/ml and of 0.128 mcg/ml. Their number grows, especially the number of cells and the expression level that corresponds a dose of 0.128 mcg/ml as shown in FIGS. 45, 49. At the same time the N-cadherin level does not change. The number of cells and their expression level are similar to those of the control cells not exposed to the action of the active component, as shown in FIGS. 45, 60. Thus, a similar phenotypic changes, that were detected under the action of $^{64}$Zn, were also observed under the action of $^{64}$Zn-Z2.

The general criterion of similarity in the effects of sample materials $^{64}$Zn and $^{64}$Zn-Z2 preparation is an increase in the number of E-cadherin-positive cells at dose D1, and the maximum result—300 scores on to the H-Score scale—was obtained with the use of $^{64}$Zn-Z2 component.

The fact that cells are expressing CD 44 stem marker for the $^{64}$Zn-Z2 preparation at a dose of 0.128 mcg/ml is indicative of significantly higher adhesive properties of the cells as compared with a dose of 3.2 mcg/ml. The values of CD44 marker positive cells at a dose of 3.2 mcg/ml for $^{64}$Zn and $^{64}$Zn-Z2 are close with tabulated values of 126 and 118 units on the H-Score scale.

The effect of $^{24}$Mg in 2 doses was an increase in the number of E-cadherin-positive cells and a slight increase in the number of cells, expressing N-cadherin. It indicates domination of epithelial (less malignant) characteristics in these cells after their treatment with $^{24}$Mg containing material. This results in inhibition of their migratory and invasive properties confirmed by scratch assay and analysis of transcription factors which are the key epithelial-mesenchymal transition criteria. The latter are crucial in formation of an aggressive metastatic cell phenotype and plays a key role in the metastasis processes and in the course of a tumor process in general, since acquisition of metastatic and mesenchymal characteristics by cells is indicative of the disease progression.

Figure 54A:
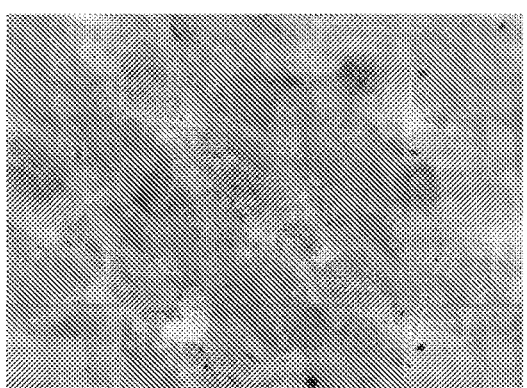
FIGS. 54A-54B illustrate CD44 marker expression in PA cells after the action of $^{24}$Mg at doses D2 (A) and D1 (B) (magnification ×100)
Figure 54B:
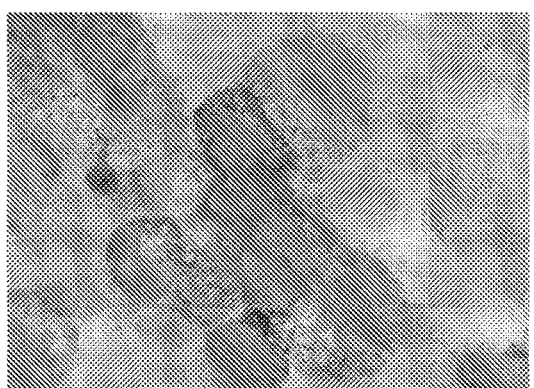
Figure 55A:
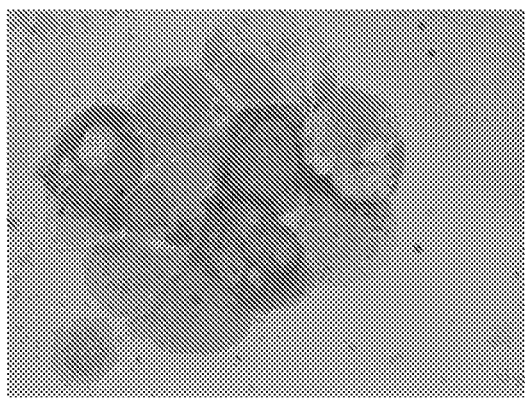
FIGS. 55A-55B illustrate CD44 marker expression in PA cells after the action of $^{24}$Mg at doses D2 (A) and D1 (B) (magnification ×100)
Figure 55B:
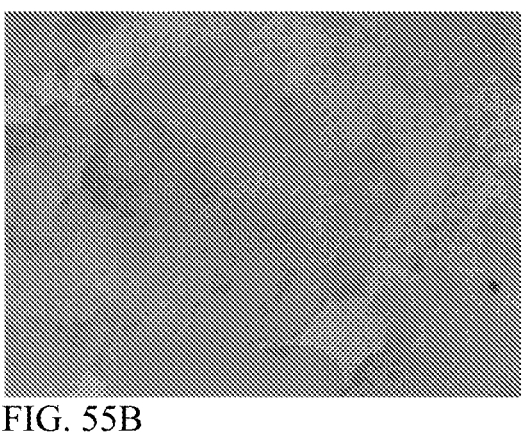

The number of CD44-positive cells after the action of $^{24}$Mg at a dose of 2 mg/ml did not differ from that of control cells. The dose of 3.5 mg/ml causes their number to increase significantly. Besides, a clonal difference in the expression of this protein, which is not only a stem cell marker but also a protein of adhesion and cytoskeleton, was observed in the cell population. Clones with the average number of positive cells and the average level of expression and the clones with more higher characteristics were identified in FIGS. 45, 54.

Figure 56A:
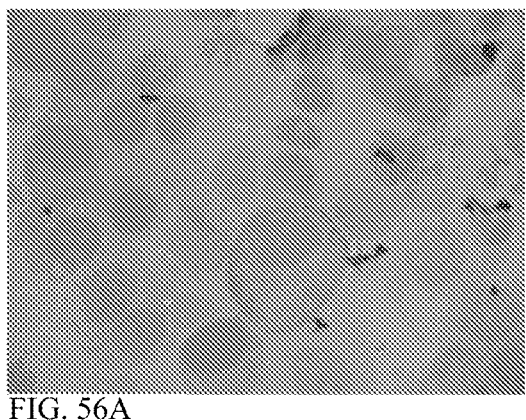
FIGS. 56A-56C illustrate E-cadherin expression in PA cells after the action of $^{39}$K at doses D2 (A) and D1 (B, C) (magnification ×100)
Figure 56B:
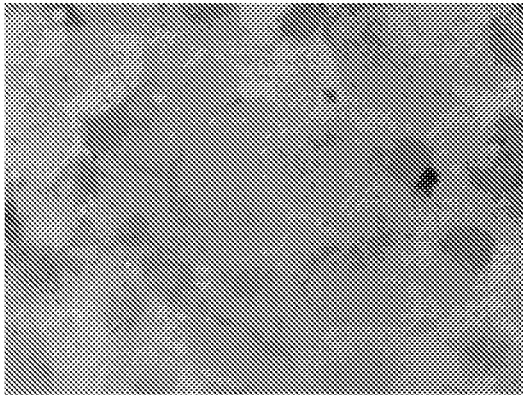
Figure 56C:
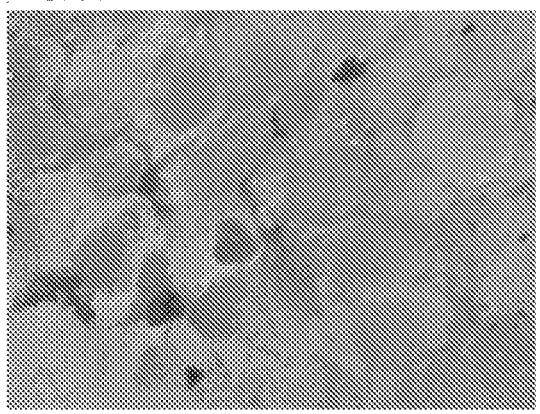

The effect of $^{39}$K on the PA is quite interesting. Dose dependence is significant for this isotope. There is also a possible clonally selective action since different phenotypic manifestations depend on the field visualization were observed in cytospin preparations of cells under the effect of $^{39}$K as shown in FIGS. 45, 56, 58. The ICC analysis showed that the number of E-cadherin-positive cells significantly increased with the action of this preparation at a dose of 0.4 mg/ml and significantly reduced (up to almost complete inhibition) at a dose of 2 mg/ml as shown in FIGS. 45, 56.

Figure 57A:
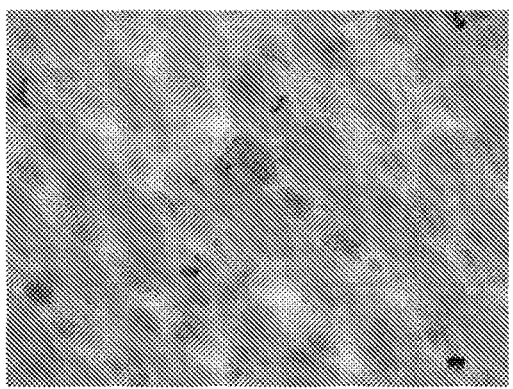
FIGS. 57A-57B illustrate N-cadherin expression in PA cells after the action of $^{39}$K at doses D2 (A) and D1 (B) (magnification ×100)
Figure 57B:
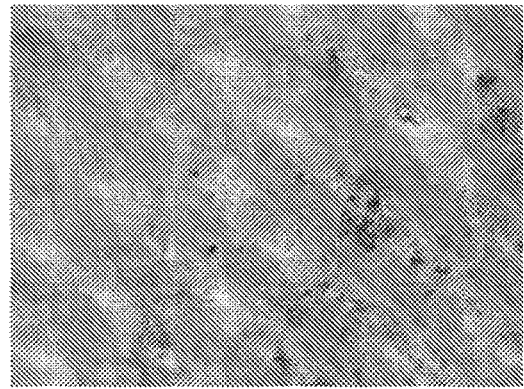
Figure 58A:
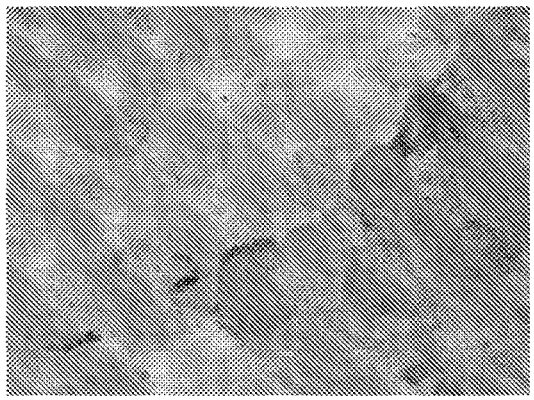
FIGS. 58A-58D illustrate CD44 marker expression in PA cells after the action of $^{39}$K at doses D2 (A) and D1 (B, C, D) (magnification ×100)
Figure 58B:
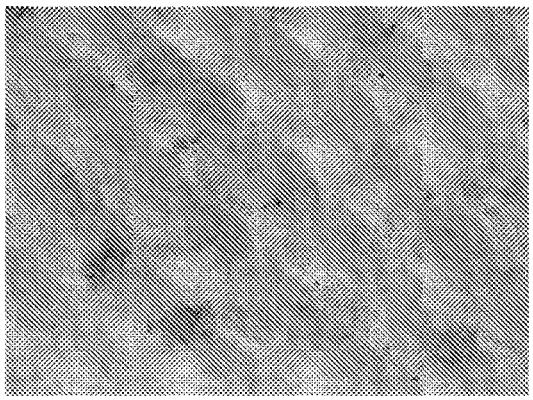
Figure 58C:
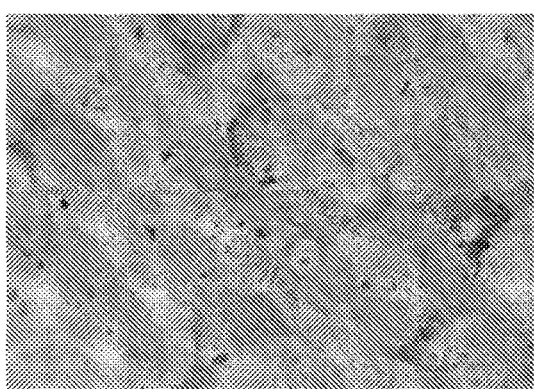
Figure 58D:
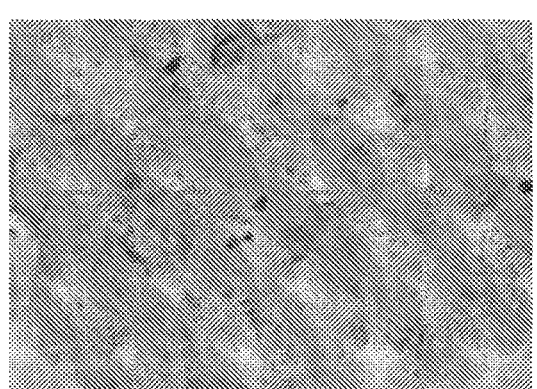
Figure 59A:
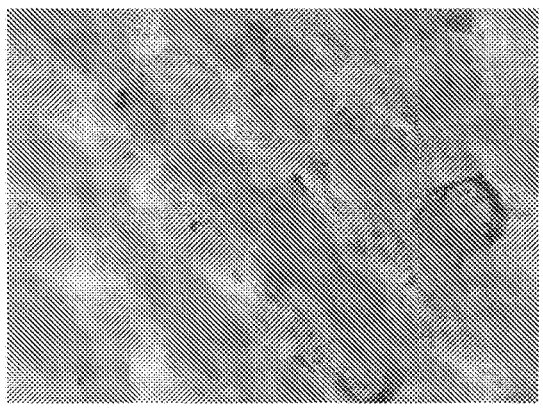
FIGS. 59A-59B illustrate E-cadherin expression in control PA cells not exposed to the action of components (magnification ×100)
Figure 59B:
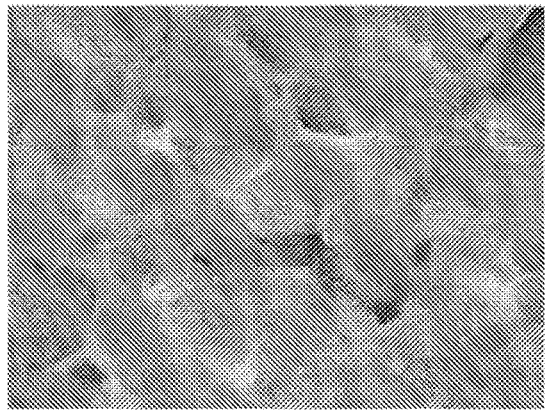

A similar tendency towards almost complete inhibition of another adhesion protein, N-cadherin, was observed under the action of $^{39}$K at dose D2 as shown in FIGS. 45, 57. At the same time the number of CD44-positive cells significantly increased with the action of materials at both doses as shown in FIGS. 45, 58. The observed concentration differences are decisive in clinics when choosing therapeutic dosages. Furthermore, they are potential modifiers of epithelial-mesenchymal transition, as they produce a significant impact on the markers typical for the process which evidences the potential impact on metastatic properties of tumor cells and, accordingly, on the process of metastasis in general. In addition, changes in the expression of the stem cell marker were detected which is also an important element in the characterization of the inhibitory (slowing down the tumor development process) properties of the light isotopes containing materials.

Changes in the expression of markers of epithelial-mesenchymal transition and stem cells are also associated with the sensitivity of tumor cells to therapies and various biologically active agents which makes tumor cells therapeutically more susceptible (open) to the action of light isotope components or other drugs. This enables a comprehensive approach to the treatment of tumors: first component makes the cell more susceptible to further exposure and the following component (light isotope containing one or any other) acts in a much lower dose to achieve the ultimate goal.

A wide range of variations of the values of adhesion markers and stem cells marker characterizes the light isotopes containing materials as efficient modifiers of epithelial-mesenchymal transition with a possibility to control its direction. Increase in the expression level of the adhesion molecules (E, N cadherins) after the action of light isotopes containing materials on tumor cells of PA renal carcinoma evidences blockage for one of the main ways of neoplastic process development—metastasis.

The phenotypic characteristics of cells after exposure to light isotope-containing materials are characterized by epithelial type, i.e., low invasive and migratory potential, which reduces the severity of cancer. $^{64}$Zn-Z2 component after 14 days of storage showed the best result in terms of a number of cadherin-positive cells, assessed on the H-Score scale based on the ratio of the dose-result criteria (the number of cadherin-positive cells). The dose of 0.128 mg/ml showed a score of 300 points on the H-Score.

A comprehensive approach to anti-cancer and anti-tumor therapy consisting of two or more steps can be used. At the first step, by using $^{39}$K (which provided the greatest increase in the number of cells positive to cadherin and CD44-marker at dose D1—0.4 mg/ml), we boost cell adhesion to the maximum and facilitate enhancement of susceptibility of cells to therapy, and at the second stage we act therapeutically on the pre-treated cells by using $^{64}$Zn or $^{64}$Zn-Z2 at dose D1—0.128 mcg/ml (as this concentration is the most rational from the point of view of the dose-effect ratio).

The combined therapy is recommended in combination with surgical treatment: before and after surgical operation on the primary tumor (primary lump or focus) and will contribute to the prevention of possible metastases and occurrence of secondary foci.

Epithelial-mesenchymal transition and a transcription factor as criteria for assessing phenotype in A-549, MCF-7 and COLO 205 human tumor cells and normal rat cells (NRK) after their exposure to the action of components containing $^{39}$K, $^{64}$Zn and $^{24}$Mg. Detection of the effect of cumulation of antitumor properties of light isotopes containing materials on the A-549 cell line. The term "epithelial-mesenchymal transition" (EMT) refers to the definition of the process of reprogramming of epithelial cells which normally occurs during embryonic development or wound healing in the adult organism. Historically the definition of epithelial and mesenchymal cells was based on the difference in their visual characteristics and morphology multicellular structures they form. In particular, it was found that epithelial cells create strong intercellular contacts and form a dense monolayer, which excludes separation of individual cells. Mesenchymal cells, in contrast, do not form any ordered structures and do not create tight intercellular contacts thereby reducing their adhesive properties and increasing their ability to migrate. The phenotype of cells can change under the influence of certain factors and cells can acquire the properties of both types.

Conversion of epithelial cells (less malignant) into mesenchymal (with greater malignancy) is accompanied by changes in their morphology, adhesion and migration ability. There are a lot of markers, that characterize these types of cells at the molecular level. Standard changes during EMT include increased expression of N-cadherin and vimentin, nuclear localization of β-catenin and increased expression of such transcription factors as Slug, Twist and E47, which inhibit the expression of E-cadherin, which in its turn, causes an increased capacity of cells for migration and invasion as well and associated with their resistance to apoptosis.

Thus, in result of EMT in the tumor progression, benign tumor cells acquire capacity for invasion and migration, which in its turn, leads to dissemination of tumors and development of the malignant process. In addition, tumor cells with a predominance of mesenchymal characteristics are less sensitive to anticancer drugs and therefore have a resistant phenotype.

In recent years, we find more and more data about the interrelation of "stem tumor cells" and EMT, in particular. It is reported that these cells appear partly due to EMT. There are data that mesenchymal cells with metastatic phenotype are characterized by the properties of stem cells, namely CD44+CD24− (cells of human breast cancer), and stem cells isolated from normal or tumor breast tissues express some standard EMT markers. That is why a comprehensive study of EMT protein markers, transcription factor and stem cell antigens in tumor cells of a different histogenesis after their exposure to the action of preparations under investigation has become the subject matter of this paper.

Cells of human non-small cell lung cancer (line A-549), human breast cancer (MCF-7 line), human colon adenocarcinoma (COLO 205 line) and normal rat kidney cells (NRK line) (derived from the Bank of Cell Lines from human and animal tissues, R.E. Kavetsky Institute of Experimental Pathology, Oncology and Radiobiology, National Academy of Sciences of Ukraine) were cultured in complete culture medium RPMI 1640 (PAA)/DMEM (PAA), supplemented with 10% newborn/fetal calf serum (depending on the cell type) (PAA) and incubated in 5% $CO_2$ humidified atmosphere at 37° C. The culture medium was replaced in 2 to 3 days.

When making the immunocytochemistry (ICC) assay, cells on microscope glasses (cytospin preparations) were fixed in the solution (methanol+acetone 1:1) for 2 hours at t 20° C. and incubated with 1% solution of bovine serum albumin (BSA) for 20 minutes. Then the monoclonal antibodies—CD44 (Diagnostic BioSystems), E-cadherin (ThermoScientific), N-cadherin (NeoMarker, BioLegend), SLUG (GeneTex)—were applied for the time period specified by the manufacturer (30 to 60 minutes), after which the Poly Vue imaging system conjugated with peroxidase was used and the enzyme activity was detected using diaminobenzidine (ThermoScientific) as a substrate. After the immunocytochemical reaction the preparations were washed with water and counterstained with hematoxylin-eosin (for 15 to 30 seconds).

The results were analyzed by counting cells with expression (brown colored cells) using a light microscope, and were assessed using the classical H-Score method: $S=1\times A+2\times B+3\times C$, where S is the H-Score index giving a range of 0 (protein is not detected) to 300 (high-level expression in 100% of the cells); A is the percentage of weakly staining cells, B is the percentage of moderately staining cells and C is the percentage of strongly staining cells.

Statistical processing of the results was performed using a mathematical biomedical program STATISTISA 6.0. Calculation and comparison of the significance of differences of mean values were performed using the Student's t-test. In our study into antigens associated with epithelial-mesenchymal transition and stem characteristics of tumor cells, we examined cadherins—adhesion and cytoskeleton proteins, CD44 and Slug transcription factor after their exposure to the action of $^{64}Zn$, $^{24}Mg$ and $^{39}K$ containing materials. We studied three types of cells. Cells of human breast cancer—MCF-7 line characterized by epithelial (less malignant) phenotype (i.e., epithelial markers dominate in cell antigens of this line), cells of human non-small cell lung cancer—A 549 line characterized by a mixed phenotype (with markers of both mesenchymal and epithelial cells) and cells of human colon adenocarcinoma—COLO 205 line in which mesenchymal (more malignant) markers dominate.

It has been found that the light isotopes produced the greatest effect on the adhesion protein—E-cadherin—which is a characteristic marker of epithelial cells and its presence is indicative of a less aggressive cellular behavior. The action of $^{39}K$ component resulted in inhibition of a number of cells with the given antigen in the A-549 line, whereas it significantly increased the number of E-cadherin-positive cells in the mesenchymal COLO 205 line which evidences its potential selective effect on cells with a more aggressive mesenchymal phenotype, as well as inhibition of the latter. At the same time, this component acted on another cytoskeletal protein, N-Cadherin, which is a marker of mesenchymal cells, as well as on stem cell marker CD44. The action of $^{64}Zn$ component was characterized by the following results: the number of E-cadherin-positive cells significantly increased in the line with a more aggressive mesenchymal phenotype. Cells with less malignant potential (MCF-7 and A-549) showed smaller values of expression which also characterizes $^{64}Zn$ as a component with a pronounced selective action directed at cells with the mesenchymal (malignant) phenotype. These facts give evidence of strong effects of $^{64}Zn$ on adhesion and cytoskeletal proteins that affect their "malignancy" characteristics as well.

$^{64}Zn$ component virtually had no effect on the expression of CD44 stem cell marker, although interesting was the fact of its intracellular redistribution. This antigen was expressed very specifically and in different ways after the action of $^{64}Zn$, $^{24}Mg$ and $^{39}K$ components. Minor quantitative changes in the components led to redistribution of its expression from the nucleus to the peripheral areas. $^{24}Mg$ component also quite effectively influenced the cells with a more aggressive mesenchymal phenotype (COLO 205) by increasing the number of E-cadherin-positive cells which characterizes its role as an inhibitor of the mesenchymal phenotype.

The data obtained in the study of antigens of immortalized (conditionally normal) cells of a rat (NRK) show that the phenotype of normal cells has not changed after their exposure to the action of $^{64}Zn$ and $^{64}Zn$-Z2 components (which were the most effective in tests both for cancer and for these cells). i.e., these components did not cause any changes in normal cells NRK which is a positive characteristic of the components and indicates that normal cells NRK retain their phenotypic stability. The fact of elocalization (redistribution) of antigens of N-cadherin and CD44 has been observed, which is a very interesting fact and requires further more detailed studies.

In the study of a slug transcription factor, which according to the literary data is a marker of mesenchymal (malignant) phenotype of cells and shows an aggressive metastatic phenotype of tumor cells, interesting facts have been found. Thus, $^{39}$K, $^{64}$Zn and $^{24}$Mg components virtually did not influence manifestation of this factor in cells with epithelial (less aggressive) phenotype. The preparations had multidirectional effects on cells with a mixed phenotype (A-549) with an observed relocalization of the factor from the nucleus to the cytoplasm and vice versa. The number of slug-positive cells with nuclear expression significantly decreased after the action of $^{39}$K component, while after the action of $^{64}$Zn component the decrease in cells with cytoplasmic expression was observed.

In the study of slug transcription factor in COLO 205 cells with the mesenchymal phenotype, $^{39}$K component increased its expression in the cytoplasm, and $^{64}$Zn and $^{24}$Mg components—in the cytoplasm and in the nucleus. Thus it is known from the literature that Slug is a suppressor of E-cadherin, i.e. when it is activated, the number of E-cadherin-positive cells should fall, but we observed a different picture—their number increased, which is an evidence of activation of the epithelial (less malignant) cell phenotype.

Alluding to the above, the effect of accumulation of antitumor properties of light isotopes containing materials on A-549 tumor cell line will now be discussed. When working with the preparations under study, it was noted that the functional activity of certain doses of the components increased over time after preparation of the solution and its subsequent storage at t+4° C. This phenomenon was detected on the A-549 cell line (human lung cancer). Activity of $^{64}$Zn relative to its ability to transform cells from primary tumor cells into cells of type A (similar to stem cells) and of type B (no tumor) differed over time. FIGS. 11 and 12 show the results of quantitative analysis of cells (%) versus control (no preparations) after the action of substances at a dose of 16 mcg/ml dissolved at different times (FIG. 11): 60 days before the experiment, 28 days before the experiment and immediately before the experiment. The preparation was stored at the temperature of +40° C.

Changes in the functional activity of $^{39}$K sulfate form at a dose of 2 mg/ml are shown in FIG. 91. After 20 days of storage of the preparation at T+4° C. the above mentioned dose showed an increase in the component functional activity expressed in a larger number of detected cells of type A. Multiple doses that differed 5 times upward and downward (10 mg/ml and 0.4 mg/ml) did not confirm such effect. $^{39}$K sulfate form at a dose of 10 mg/ml showed no presence of cells of type A on the first and on the 20th day of the experiment, and the dose of 0.4 mg/ml showed identical (in terms of quantity of A cells) results.

Cytogenetic characteristics of A-549, MCF-7 and COLO-205 cell lines after their exposure to the action of materials containing $^{39}$K, $^{64}$Zn and $^{24}$Mg will now be discussed. Advanced Micronucleus Test was used to assess the cytogenetic characteristics of cells after their exposure to the action of the test group of components. The effects of components containing $^{39}$K, $^{64}$Zn and $^{24}$Mg on A-549, COLO-205 and MCF-7 tumor cell lines were assessed both by the number of micronuclei (by fragments of chromosomes or remained chromosomes) and by morphological characteristics, such as internuclear bridges (dicentric chromosomes), nuclear protrusions (gene amplification) (Fenech, 2002) and apoptotic cells.

The effects of materials containing $^{39}$K, $^{64}$Zn and $^{24}$Mg were assessed at the molecular, cellular and chromosomal level depending on the dosage of these components. Cytogenetic analysis was carried out after 48 hours of exposure of the cells to the action of the components. For cytogenetic analysis, the cells were incubated in hypotonic solution KCl (0.54%) (Reahim, Ukraine) for 40 minutes at +37° C. Then they were fixed with a mixture of methyl alcohol (Reahim, Ukraine) and acetic acid (Himlaborreaktiv, Ukraine) (3:1) with replacing the fixative three times. All fixed cell suspensions were applied on cold wet glasses, dried and stained with Giemsa stain (Sigma, Germany). The cytogenetic preparations were analyzed using a binocular microscope Sarl Zeiss, AxioStarPlus (Germany) with magnification of ×1000. The following quantitative characteristics and stages of cell division were analyzed on the preparations: mitoses, cells with premature chromosome condensation (PCC), cells with micronuclei (CMN), apoptotic cells and cells with nuclear protrusions (protrusions) which were calculated for 1000 cells and expressed in per mille (‰).

Doses of the components used and cytogenetic characteristics were $^{39}$K at a dose of 2 mg/ml, $^{64}$Zn at a dose of 20 mcg/ml and $^{24}$Mg at a dose of 4 mg/ml cause inhibition of tumor proliferation (cell division) in the cells of COLO 205 line at the stage of G2/M and significantly increase the number of nuclear shape anomalies. The detected increase in the number of apoptotic cells and protrusions while maintaining the number of micronuclei on the COLO 205 cell line is shown in as shown in FIG. 99.

Formation of the largest number of nuclear protrusions was recorded for A-549 cell line. The maximal effect was observed after the use of the component containing $^{39}$K at a dose of 2 mg/ml. The effect produced by this dose consisted in slowing down proliferation of the tumor cells, formation of micronuclei and various anomalies of the nuclear shape, including shapes of segmented cell destruction. The action of $^{64}$Zn component also led to an increase in micronuclei and nuclear protrusions in comparison with the control cells. The action of $^{64}$Zn at a dose of 20 mcg/ml caused a triple increase in the level of nuclear abnormalities as compared to the dose of 10 mcg/ml and fifty times as high as the baseline (control). A large number of damaged cells of non-apoptotic type, shown in FIG. 100, was observed. The action of $^{24}$Mg was also characterized by accumulation of nuclear anomalies and weakening of the proliferative ability of tumor cells. An increase in the number of apoptotic cells was observed after the action of all three isotopes.

Formation of nuclear protrusions was observed in the cells of MCF-7 line but in an amount smaller than in the previous experiments. The action of $^{64}$Zn in this cell line causes more than a two-fold increase in the level of cells with micronuclei as shown in FIG. 101. An increase in the number of apoptotic cells compared to the control ones was detected.

Figure 102C:
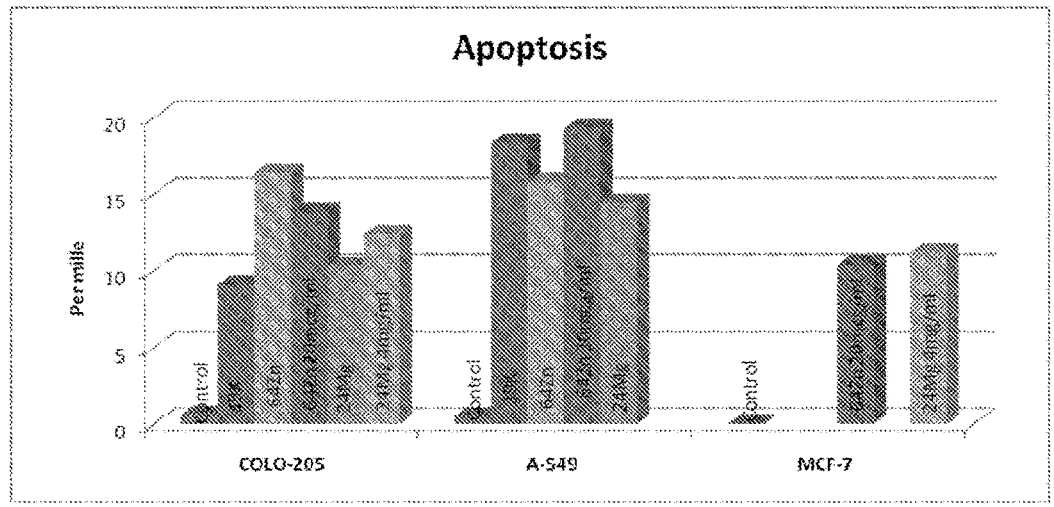
Figure 102D:
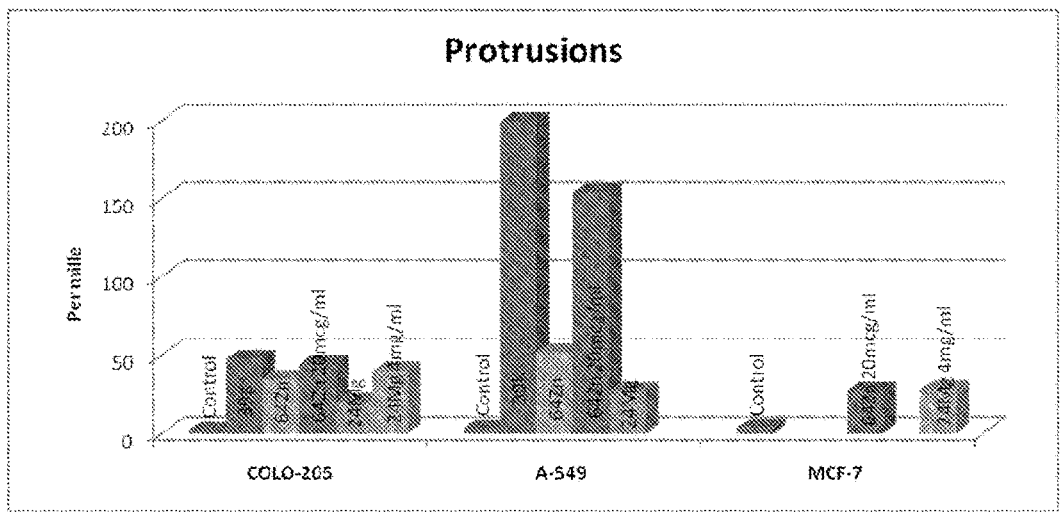

Dose-dependent effects of the isotopes on various cell lines were represented as quantitative characteristics of the degree of abnormality of nuclei. The graphs in FIG. 102 show the quantitative characteristics of nuclear structure abnormalities, such as apoptosis, protrusion and cells with micronuclei. The results are compared with the control group that was not exposed to the isotopes containing materials. The maximum value of the main cell anomalies such as protrusions and apoptosis was recorded on the A-549 cell line for $^{39}K$ at a dose of 2 mg/ml and for $^{64}Zn$ at 2 doses, while the maximum number of protrusions and cells with micronuclei was observed after the action of $^{39}K$ at a dose of 2 mg/ml which is also characterized by reduction of tumor cell proliferation.

Given the similarity of the data about nuclear anomalies (which are expressed in a similar character of cellular abnormalities in all cell lines), one can conclude that a significant number of micronuclei formed in result of nuclear protrusions. Disruptions of the integrity of the nucleus such that the cell loses its ability to further functioning is associated with the beginning of nucleus destruction as shown in FIG. 98.

Major differences in sensitivity of the cell lines were as follows. The COLO 205 cell line showed sensitivity to all the preparations by an increase in the number of cells with abnormal shape of the nucleus, while sensitivity of the MCF-7 line was expressed in a smaller extent and was characterized mainly by the presence of chromosomal aberrations. These disorders are characterized by fragmentation of nuclei in the eukaryotic cell that does not contain the full genome needed for its survival. The component with $^{24}Mg$ on the MCF-7 cell line leads to aneugenic disorders (not associated with the structural damage of chromosomes).

It has been established that all the light isotopes containing materials with $^{64}Zn$, $^{24}Mg$ or $^{39}K$—had the maximal effect on E-cadherin, the marker of epithelial cells, in COLO 205 cells with domination of mesenchymal characteristics. A selective nature of the action of all light isotopes has been shown. An increase in the expression of E-cadherin to the maximum extent occurred on the COLO 205 cell line. The phenotype of these cells was the most malignant of the 3 human cell lines involved in the experiment, namely A-549—non-small cell lung cancer, MCF-7—breast cancer and COLO 205—colon adenocarcinoma. Thus, the effect of the investigated materials was directed to the most malignant cells, and the expression of epithelial E-cadherin indicates inhibition of the malignant properties of cells after their exposure to the action of said materials.

Alluding to the above, $^{39}K$ containing material has shown the best ability to inhibit the mesenchymal (cancerous) phenotype (score 184 on the H-Score scale compared to 87 in the control). This isotope influenced the COLO 205 cells with most aggressive mesenchymal phenotype by significantly increasing the number of E-cadherin-positive cells confirming its role as an inhibitor of the mesenchymal phenotype of tumor cells.

The effects of the materials on CD44 stem cell marker were expressed mainly by its intracellular redistribution. This antigen has not shown any regularity relative to the dose used or cell type. No significant changes in the expression of this marker has been found in all the test tumor cell lines. It has been shown that $^{64}Zn$, $^{24}Mg$ and $^{39}K$ isotopes insignificantly influenced the number of Slug-positive cells (with the transcription factor—a marker of mesenchymal phenotype) in the MCF-7 line with epithelial (less aggressive) phenotype. Their effects on the cells with the lowest malignant potential (of 3 tumor cell lines involved in the experiment) were minimal. The effects of the isotopes on the cells with a mixed phenotype (A-549) were manifested in relocalization of the Slug factor from the nucleus to the cytoplasm and vice versa. The number of Slug-positive cells with nuclear expression significantly decreased after their exposure to $^{39}K$ component, while the action of $^{64}Zn$ resulted in decrease in the number of cells with cytoplasmic expression. The highest expression of Slug transcriptional marker has been observed in the most malignant cell line COLO 205, which indicates that $^{64}Zn$, $^{24}Mg$ and $^{39}K$ isotopes activate an active phase of the epithelial-mesenchymal transition program.

The selective nature of increasing expression of E-cadherin has been found being highest on the COLO 205 cell line and is characterized by an increased adhesion to the matrix. It indicates that the cellular phenotype is directed towards lower malignancy and that the action of the isotopes causes inhibition of malignant properties of cells.

It has been established that $^{39}K$ component increases the expression of Slug transcription factor in the cytoplasm and $^{64}Zn$ and $^{24}Mg$ components—both in the nucleus and in the cytoplasm in COLO 205 cells with mesenchymal phenotype, which in addition to modification of their phenotype towards lower malignancy also indicates a change in their sensitivity to the antitumor agents.

According to the new data in the literature, the transcription factor under study indicates the activation of mesenchymal phenotype. With its stable over-expression an increase in the sensitivity of tumor cells to antitumor agents which are targeted at microtubes of the cellular cytoskeleton and tubulin were observed. This allows to perform gives anti-tumor therapy in two stages. First stage would consist in the action of one of the components on the cell line to increase its sensitivity to anticancer agents. The second stage would consist in the anticancer therapy with reduced dosage due to the high sensitivity of the cells to the action of the administered drugs.

All three isotopes have strong selective effect on the most malignant (mesenchymal) cells. Slug, a marker of malignancy, and cadherins, markers of adhesion, have shown the highest expression in the mesenchymal cell line—COLO 205. The action of all the tested materials on normal rat cells (NRK) did not resulted in any changes in their phenotype. It indicates that normal cells retain their phenotypic stability under the effect of light isotopes.

A cumulative antitumor effect of the $^{64}Zn$ and $^{39}K$ sulfate form has been shown on the example of A-549 cell line. The action of $^{64}Zn$ caused an increase in the number of transformed cells from the primary tumor to cells of type A with the storage of the $^{64}Zn$ sulfate form solution for 60 days. After this period, the number of A cells after the use of $^{64}Zn$ increased up to about 80% compared with 20% recorded at the initial stage of the experiment. A similar result was also found for the $^{39}K$ sulphate form at a dose of 2 mg/ml on the A-549 cell line. The number of cells of type A (after 20 days of storage of the solution) was 2-fold higher than on the first day of control. It should be noted that the observed cumulative property of $^{39}K$ is dose-dependent at it did not manifest itself at 5-fold doses (upward or downward). This property was not manifested at 10 mg/ml and 0.4 mg/ml. 100% transformation of the initial tumor cells to the cells of type A was shown at a dose of 0.4 mg/ml (in both cases), and the dose of 10 mg/ml was not effective and no transformational effect was found.

The action of materials containing isotopes $^{39}K$, $^{64}Zn$ and $^{24}Mg$ on human tumor cells leads to dose-dependent effects which consist in the formation of a large variety of abnormalities of the nucleus, such as protrusions, apoptotic corpuscles and micronuclei. For all the isotopes under study a massive accumulation of cells with protrusions was recorded. Their 15-fold increase under the action of $^{39}K$ component and almost 10-fold increase under the action of $^{64}Zn$ component were observed in the A-549 cell line. A positive correlation between the formation of micronuclei, nuclear protrusions and nucleoplasmic bridges associated with the instability of the genome and gene amplification by initiation of breaking-fusion-bridge cycles was observed under deficiency of folic acid as well as under ionizing radiation used in the radiotherapy treatment of cancer patients.

Processing of cells of the COLO-205 and A-549 cell lines with $^{39}$K, $^{64}$Zn and $^{24}$Mg isotopes resulted in accumulation of cells with premature chromosome condensation. An increase in their number relative to cells in mitosis is indicative of the cell cycle arrest at the G2/M phase. Prolonged mitotic arrest usually leads to DNA damage and induction of p53 and then to apoptosis. A positive correlation between G2/M-arrest and induction of apoptosis was detected in human ovarian cancer cells after their exposure to radiation. Thus, the arrest of the cell cycle in the G2/M phase is an important stage on the way from the genotoxic effects, causing DNA damage, to apoptosis.

The action of $^{39}$K isotopes causes maximal (in comparison with other components) inhibition of cell division at the G2/M stage of the cell cycle. It is known, that the action of some anticancer drugs, such as paclitaxel, is also associated with the phase of premature chromosome condensation. In the case of paclitaxel, its action directed to the induction of apoptosis and the expression of ligands on the cell surface, which in their turn attract K cells for the removal of damaged cells. The effects of $^{39}$K, $^{64}$Zn and $^{24}$Mg isotopes on all cell lines were characterized by an increase in concentration of cells with micronuclei of clastogenic and aneugenic origin.

The A-549 cell line (human lung cancer) has turned to be the most sensitive to all the components under study. Assessment of the effects of $^{39}$K, $^{64}$Zn and $^{24}$Mg on human tumor cells was obtained after 48 hours of interaction of the components with cells. During this time no more than two full cycles of cell division passed. Therefore, the results of the effects of the light isotopes (quantitative characteristics of nuclear abnormalities and proliferative capacity of cells) must be considered in relation to this circumstance. The effects of the isotopes on tumor cells depend on the stage of the cell cycle, and they manifest itself differently at various stages of the cycle. By increasing the time of interaction of $^{39}$K, $^{64}$Zn and $^{24}$Mg with the cell population, we increase the number of contact points in the component cell system (in terms of the full cell cycle) and the number of full cell cycles during which the interaction of the components with cells occurs.

The presence of apoptotic cells (found in a smaller number as compared with protrusions) is associated with a full cycle of cell division during which the isotopes exerted their action during the whole phase of the cell cycle. The presence of protrusions evidences the action of the isotopes, which started at a stage other than the initial stage of cell division. Since the number of cells in the population being at a stage different from the initial stage of division was much larger than the cells at the initial stage, then, accordingly, the number of cells with protrusions was much larger than the cells with apoptosis.

The presence of a sufficiently large number of anomalies in the structure of the cell nucleus which were expressed in the form of protrusions, as well as their character, confirms the presence of classic chromosomal abnormalities (damage of the DNA structure) which in most cases results in the loss of the capacity of cells for replication (doubling) the DNA helix. A similar pattern (in terms of loss of the capacity of cells for further division and multiplication) is observed in the case of programmed cell death—apoptosis. Thus we can conclude that the action of $^{39}$K, $^{64}$Zn and $^{24}$Mg isotopes on human tumor cells analyzed within 1-2 cycles of cell division causes the launch of the mechanism of cell death similar to apoptosis (by the end result—the loss of capacity for further division).

The cell capacity for apoptosis is its natural function and the lack of it is one of the basic features of tumor cells. The results of cytogenetic analysis of tumor cells after their exposure to the isotopes of $^{39}$K, $^{64}$Zn and $^{24}$Mg shows the restoration of a limited number of cycles of cell division which is typical for normal cells.

Figure 103:
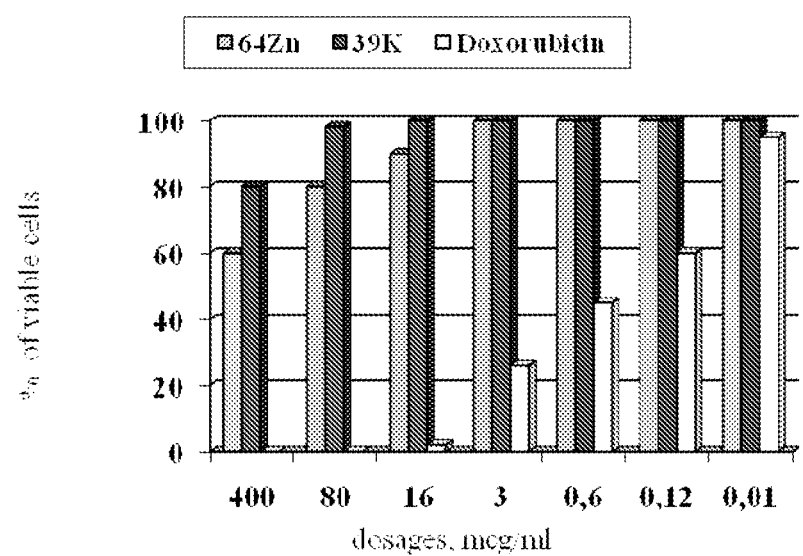
FIG. 103 illustrates quantitative characteristics of normal rat kidney cells NRK after their exposure to the action of anticancer drug Doxorubicin and $^{64}$Zn and $^{39}$K components.
Figure 104:
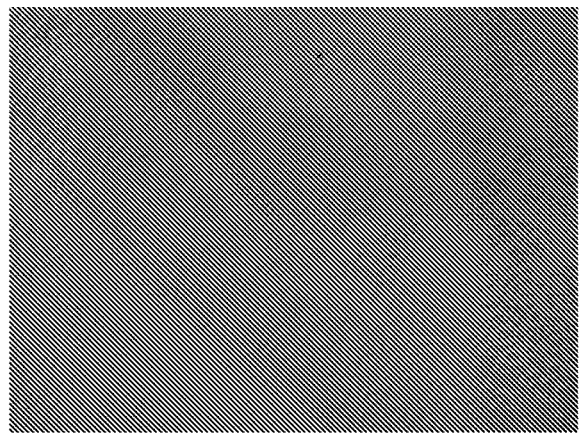
FIG. 104 illustrates an appearance of initial NRK cells before the start of the experiment, Magnification ×100.
Figure 105:
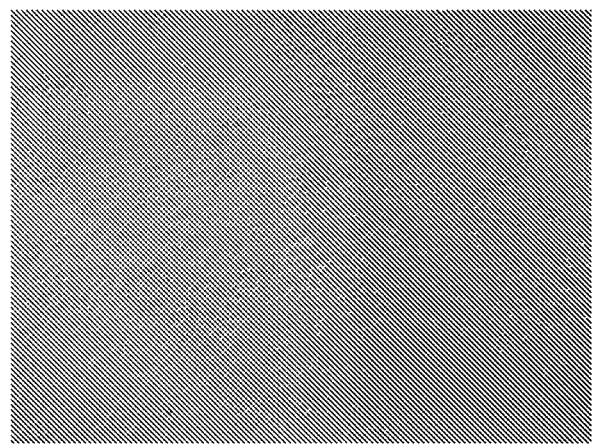
FIG. 105 illustrates an effect of $^{64}$Zn isotopes in the concentration of 16 mcg/ml 30 min after the start of the experiment, Magnification ×100.
Figure 106:
FIG. 106 illustrates an effect of $^{64}$Zn isotopes in the concentration of 16 mcg/ml and cell morphology after 48 hours in a freshly prepared solution, Magnification ×100.
Figure 107:
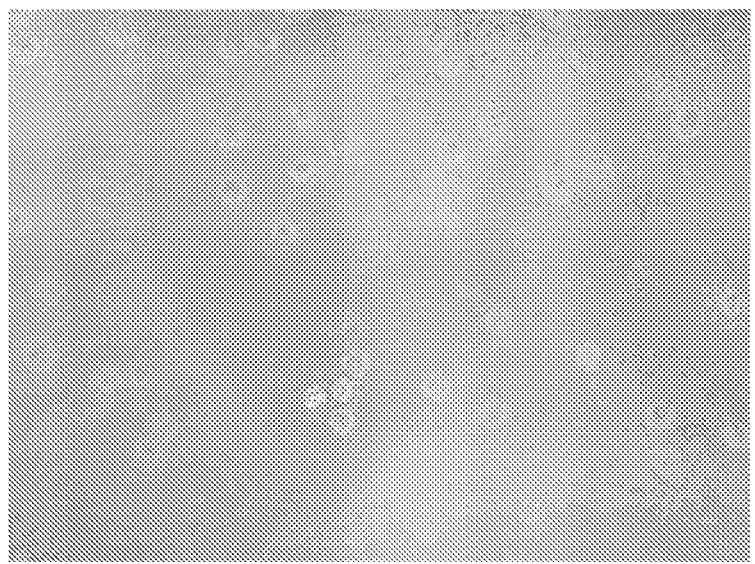
FIG. 107 illustrates an effect of $^{64}$Zn isotopes in the concentration of 16 mcg/ml and cell morphology after 48 hours in a freshly prepared solution, Magnification ×400.
Figure 108:
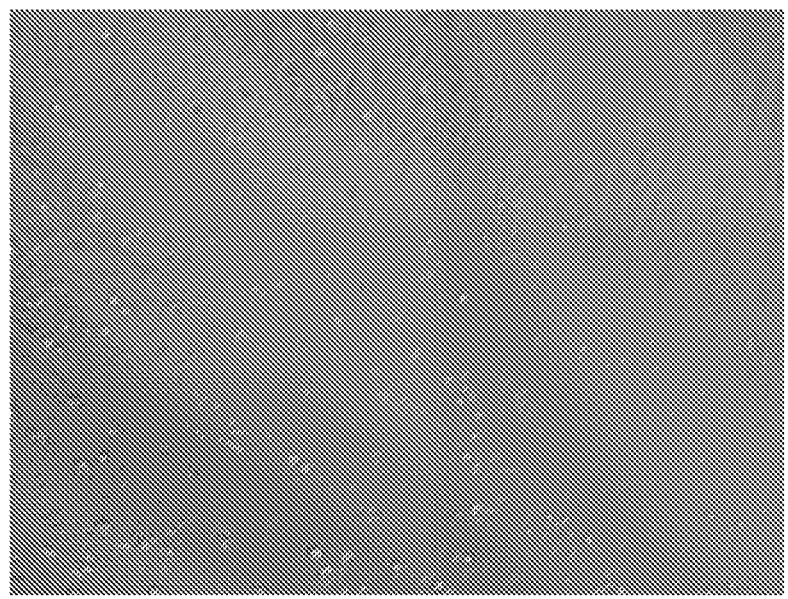
FIG. 108 illustrates an effect of $^{39}$K isotopes in the concentration of 16 mcg/ml 30 min after the start of the experiment, Magnification ×100.
Figure 109:
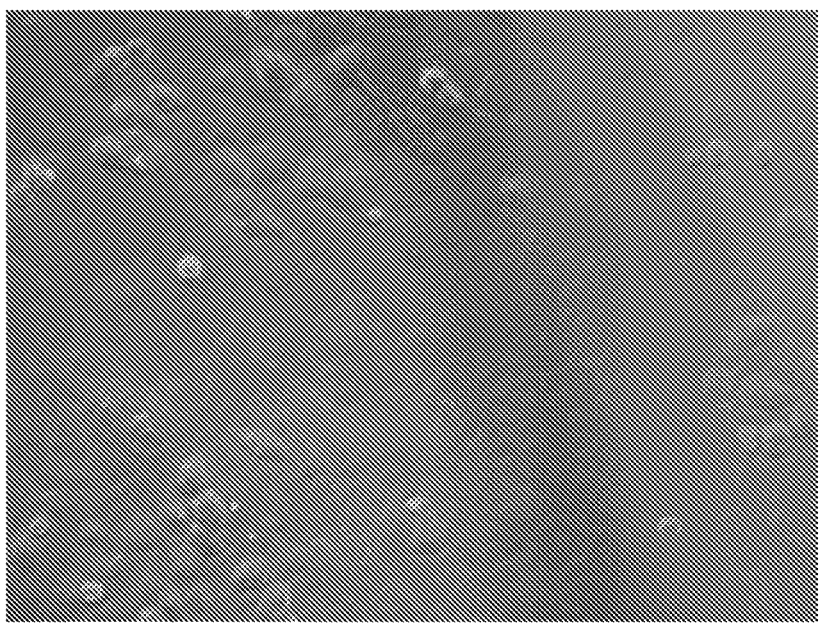
FIG. 109 illustrates an effect of $^{39}$K isotopes in the concentration of 16 mcg/ml 30 min after the start of the experiment, Magnification ×400.
Figure 110:
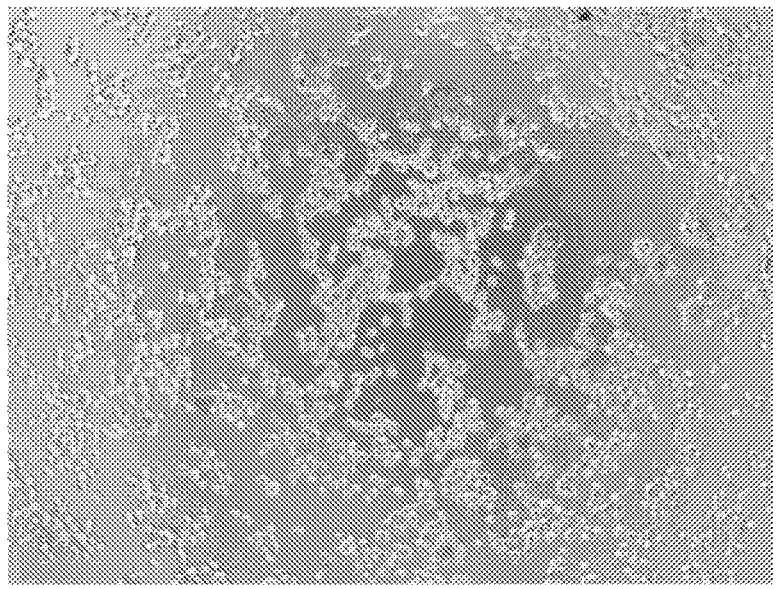
FIG. 110 illustrates an effect of $^{39}$K isotopes in the concentration of 16 mcg/ml and cell morphology after 48 hours in a freshly prepared solution, Magnification ×100.
Figure 111:
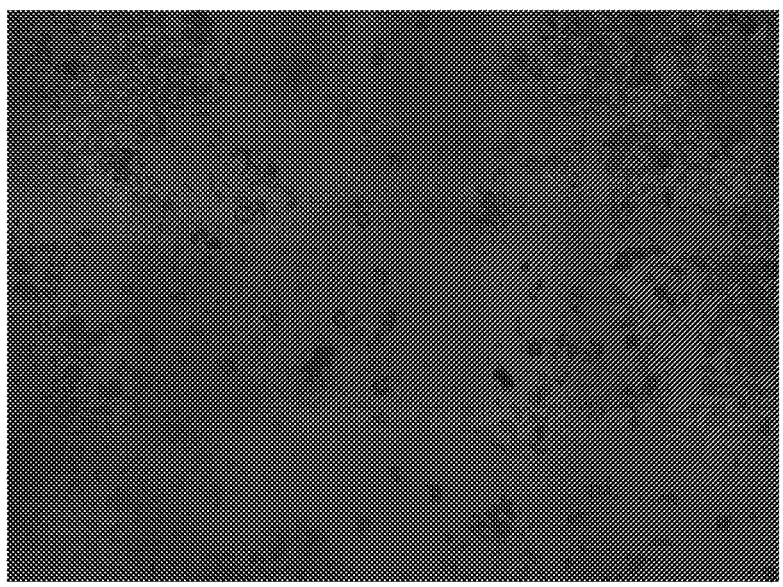
FIG. 111 illustrates an effect of anticancer drug Doxorubicin in the concentration of 16 mcg/ml within 30 min after the start of the experiment, live cells are virtually absent. Magnification ×100.
Figure 112:
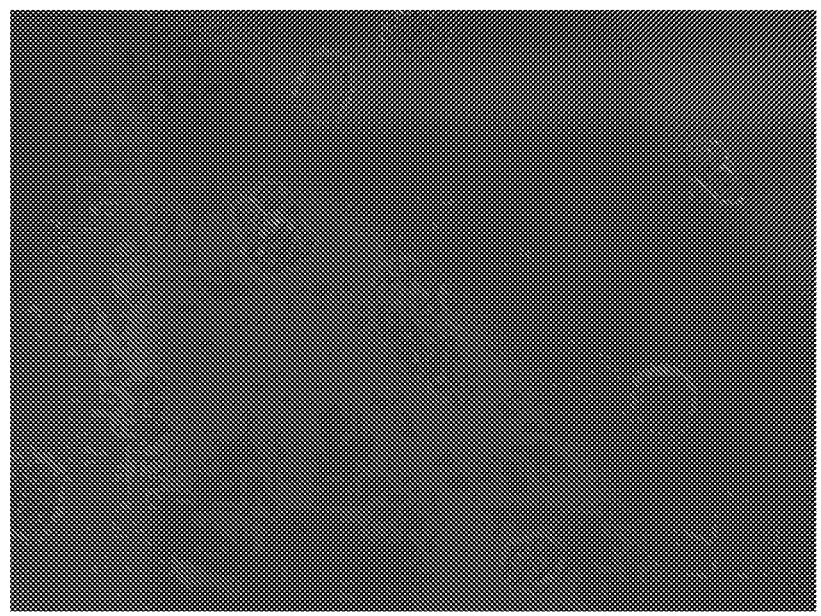
FIG. 112 illustrates an effect of anticancer drug Doxorubicin in the concentration of 16 mcg/ml within 48 hours after the start of the experiment, live cells are absent. Magnification ×400.
Figure 113A:
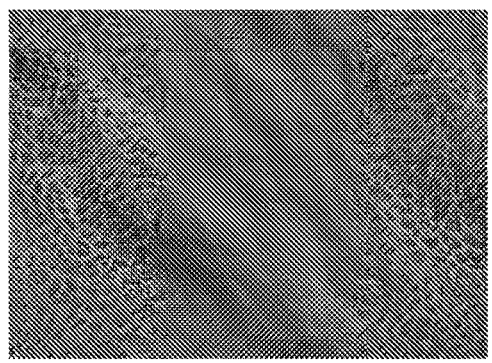
FIGS. 113A-113E illustrate a character of migration of tumor cells of A-549 cell line in the in vitro experiment with $^{39}$K, $^{64}$Zn and $^{24}$Mg components 3 hours following the cell monolayer damage: A. Control group of cells (no preparations) B. A-549+Doxorubicin at the dose of 2 mcg/ml, C. A-549+$^{39}$K preparation (2 mg/ml), D. A-549+$^{64}$Zn preparation (20 meg/nil), E. A-549+$^{24}$Mg preparation (3 mg/ml)
Figure 113B:
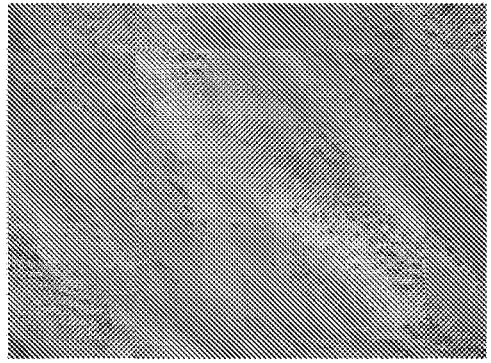
Figure 113C:
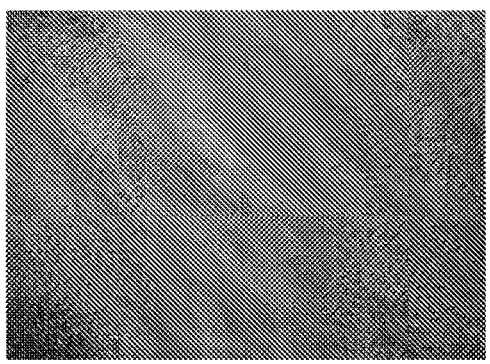
Figure 113D:
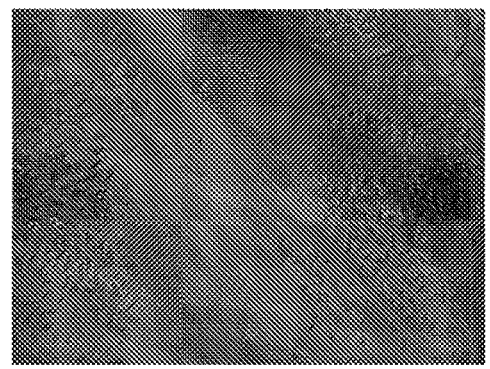
Figure 113E:
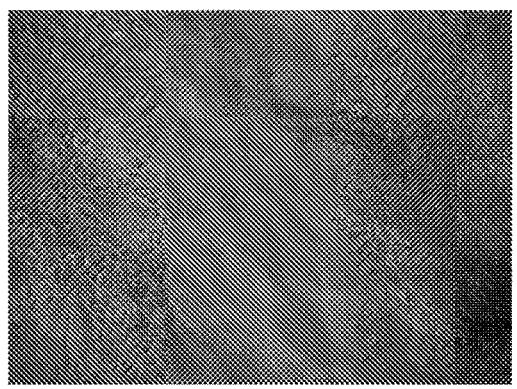

Comparative characteristics of the action of Doxorubicin and the action of components containing $^{39}$K, $^{64}$Zn and $^{24}$Mg on normal rat kidney cells (NRK) and comparative assessment of the effects of $^{39}$K, $^{64}$Zn and $^{24}$Mg vs Doxorubicin on normal rat kidney cells (NRK cell line) will now be discussed. After the data about the effects of $^{64}$Zn, $^{24}$Mg and $^{39}$K components on tumor cells of MCF-7 (human breast cancer), A-549 (human lung cancer) and COLO 205 (human colon adenocarcinoma) cell lines have been obtained, an experiment was conducted to determine the effects of $^{64}$Zn and $^{39}$K components on normal/immortalized rat kidney cells NRK. An immortalized cell line is a stable, capable of unlimited proliferation cell line that consists of cells with a limited lifetime in culture. The action of freshly prepared solutions containing $^{64}$Zn and $^{39}$K isotopes was tested on NRK cells in comparison with doxorubicin as shown in FIG. 103. 0.9% NaCl solution with 5% glucose was used as the solvent for $^{64}$Zn and $^{39}$K. The obtained data and images show that the effects of $^{64}$Zn and $^{39}$K isotopes were associated with the transition of initial NRK cells into cells similar to type A, and the action of anticancer drug Doxorubicin (in concentrations ranging from 400 to 0.01 mcg/ml) shows the number of live and dead cells.

Effect of chemotherapeutic drug Doxorubicin at doses ranging from 400 to 16 mcg/ml during 48 hours on the normal NRK cells resulted in the loss of their mobility, ability to proliferate and complete death. $^{64}$Zn and $^{24}$Mg sulfates at the same concentrations as used for doxorubicine did not affect functional properties of RNK cells. Doxorubicin's ability to inhibit the natural biological properties of normal cells until their death considered as side effect. It significantly reduces its use and concentration range of administration.

In the concentration range from 3 to 0.01 mcg/ml Doxorubicin produces a side effect causing death of normal NRK cells. Reduction in the concentration of doxorubicin increased the number of viable cells. The effects of the sulfate form of $^{64}$Zn and $^{24}$Mg isotopes on the A-549 tumor cell line show signs of similarity of the A-549 cells treated with $^{64}$Zn and $^{39}$K with stem cells of a mouse.

Assessment of migration characteristics of A-549, FC, NRK, HaCaT, A-431 and MM-4 cell lines after their exposure to the materials containing $^{39}$K, $^{64}$Zn and $^{24}$Mg. Analysis of the combined effects of isotopes of $^{39}$K, $^{64}$Zn and $^{24}$Mg and Doxorubicin will now be discussed. Understanding the biological mechanisms of tumor cell migration and search for potential "anti-migration" drugs is an important issue of modern oncology since the cell migration activity is one of the key characteristics of malignancy and an important stage of their metastatic potential.

Today there is no more doubt in the importance of the role of epithelial-mesenchymal transition (EMT) as the main regulator of the metastatic cascade [Raghu Kalluri, Robert A. Weinberg. The basics of epithelial-mesenchymal transition. J. Clin. Invest 2009; 119: 1420-1428, Samy Lamouille, Jian Xu, Rik Derynck. Molecular mechanisms of epithelial-mesenchymal transition. Nature Reviews Molecular Cell Biology 2014; 15: 178-196.]. In modern oncology it is common practice to distinguish steps of the metastatic cascade such as loss of cell adhesion, abnormal motility, invasion, intravasation, survival in the circulation, extravasation, metastatic colonization, and treatment of clinically diagnosed metastasis.

Heterotypic interactions of epithelial and mesenchymal cells are necessary for normal morphogenesis at all stages of embryonic development. During carcinogenesis such interactions provide increased malignant phenotype of cancer cells. The cardinal feature of an epithelial cancer cell is its abnormal mobility and ability to separate and penetrate into the surrounding tissues, i.e., to invasion. Compared with normal epithelium carcinoma, cells are characterized by a progressive decrease in cell adhesion and increase in their migration abilities. In the clinical oncology such notions as "the tumor surface" and "invasive front" of the tumor acquire principal importance as malignant cells leave the primary tumor and enter the blood flow just from the surface of the tumor, from its leading edge. It is at the leading edge where the tumor cells are transformed from epithelial to mesenchymal ones [Kovalev A. A. Metastatic cascade as a therapeutic target. Health of Ukraine.—2011: p. 26-28].

According to the latest data of R. Weinberg (2010), cells in the epithelial-mesenchymal transition state acquire properties of cancer stem cells with the implementation of their main functions—metastasis, colonization and the ability of division in distant organs as well as the possibility of colonization of the primary tumor and stimulation of its growth (self-seeding hypothesis). Many biological processes of tumor growth and metastasis as well as cases of drug resistance and tumor recurrence after treatment are associated with the phenomenon of epithelial-mesenchymal transformation.

Modern approaches in fundamental and clinical studies of the recent years show a clear shift of the scientific interests towards the study of the metastatic properties of cancer cells. According to the generalized statistical data, only 0.1% of circulating tumor cells are able to form metastatic lesions in distant organs showing their invasive properties, and because in most cases in clinical practice a patient's death occurs in connection with an increase in the number of tumor cells, it is the invasive-metastatic cascade that determines the progression of cancer and eventually causes the death of a cancer patient.

Thus the tumor as a heterogeneous biological system that determines the fate of a patient is characterized by a combination of 2 major properties: invasion ability or invasion inability of 0.1% of the tumor cells that left the primary lesion. A vast majority of the remaining cells that left the tumor and died in the systemic circulation through the mechanism of apoptosis or returned to the primary tumor are not a key factor that causes the loss by any organ of its functions or the death of the body.

The rapid and uncontrolled growth of tumor cells with an unlimited number of divisions demonstrates the ability of tumor cells to overcome anatomical and functional barriers formed over millions of years of the biological evolution. According to Charles Darwin, the founder of the Theory of Evolution, it is not the strongest species that survive but those that can better adapt to changing environmental conditions. Understanding the role of each of the participants in this process in terms of genome constancy and chemical bonds that define the implementation of the principle of interaction of circulating tumor cells with the cells of the vascular system (endothelial cells, dendritic cells, macrophages) will make it possible to create "anti-metastatic" drugs of new generation with a possibility to selectively regulate adhesion of cancerous cells in the bloodstream without violating the integrity of physiological hemostasis, i.e., enhance the interaction of tumor cells with the main lesion and reduce the possibility of invasion by circulating cells.

With the progression of a tumor disease doctors are often faced with the tumor resistance to anti-cancer therapeutic agents wherein the cells with low sensitivity are characterized by to most aggressive phenotype. According to the researchers' data there are facts that prove selection of the most aggressive cells with dominating mesenchymal characteristics and, accordingly, increase in their capacity for migration and invasion, which contributes to their dissemination and formation of new metastatic lesions after the selective effects of antitumor drugs.

Therefore, the aim was to study the characteristics of migration of tumor cells under the effect of the well-known anti-cancer drugs and the test substances which characterizes them as modifiers of cellular behavior and potential regulators of cell migration which is an important feature of the metastatic potential of malignant cells. We also paid attention to the effect of the test substances on normal cells for the purpose of their comparative potentially damaging, or vice versa restoring (regenerating), means in therapy.

The most illustrative and effective method for analyzing the migration rate of tumor cells in vitro is the scratch assay which has several advantages. First of all, the migration of cells in vitro most fully reflects the behavior of cells under in vivo conditions. Furthermore, this method can be used to study the mechanisms of regulation of cell migration during the interaction of cells between themselves and with the intercellular matrix [Liang Ch, Park, A Y, Guan, J L In vitro scratch assay: a convenient and inexpensive method for analysis of cell migration in vitro. Nat Protoc 2007; 2: 329-33.].

Alluding to the above, materials, methods, and cell culture will now be discussed. The cells of A-549, A-431, NRK, HaCaT, MM-4, normal fibroblasts (derived from the Bank of Cell Lines from human and animal tissues, R.E. Kavetsky Institute of Experimental Pathology, Oncology and Radiobiology, National Academy of Sciences of Ukraine) were cultured in complete culture medium RPMI 1640/DMEM (PAA, Austria) (depending on the cell type) supplemented with 10% fetal calf serum (PAA, Austria) and incubated in 5% $CO_2$ humidified atmosphere at 37° C. The culture medium was replaced in 2 to 3 days and the cells were passaged in 4 to 5 days.

Analysis of the influence of the components under study on the cell migration rate was performed using the scratch assay method. Cells (5×104/well) were seeded into the wells of a 12-well plate in 2 repeats in RPMI-1640/DMEM culture medium supplemented with 10% PBS, 40 mcg/ml of gentamicin and incubated in 5% $CO_2$ humidified atmosphere at 37° C. for 24 hours.

Then the components under study in different doses (from IC25 to IC50 previously defined as a result of tests on verification of the antiproliferative effects of the components in vitro) and anti-cancer drug Doxorubicin were placed in the respective wells. The plate was incubated in a $CO_2$ incubator for additional 48 hours. After the cells formed a dense monolayer it was damaged (by making a "scratch") and the growth medium was replaced to remove cell debris and smooth the edges of the "scratch." The rate of cell migration was analyzed using an inverted microscope and by photographing cells in the area of injury. The migration activity of cells was fixed at several time points (depending on the cell line analyzed). The microphotomicrographs were analyzed and the cell incubation time needed to restore the monolayer was determined for all experimental groups.

At the first stage of the experiment an assessment of the effects of $^{39}$K, $^{64}$Zn and $^{24}$Mg isotopes on the nature of migration characteristics of tumor cells of the human non-small cell lung cancer of A-549 cell line, immortalized rat kidney cells of NRK cell line and normal rat fibroblasts of RF cell line was carried out. This comparison was made not only for the actual analysis of the potential anti-migration or, on the contrary, restoration effects of the substances under study on cells in vitro but also for the effects of these substances on normal and transformed cells (immortalized or malignant).

A comparative analysis of the photos shown in as shown in FIGS. 113, 114, 115, and 116 characterizes the migration activity of tumor cells of the human non-small cell lung cancer of A-549 cell line in the in vitro experiment using the scratch assay and makes it possible to assess the effect of several doses of $^{39}$K, $^{64}$Zn and $^{24}$Mg isotopes on the process of migration of tumor cells. The following results were obtained after 72 hours of observations of the migration activity of the cells.

All the light isotopes under study, $^{39}$K, $^{64}$Zn and $^{24}$Mg, have shown the ability to slow down the migration ability of tumor cells of the human non-small cell lung cancer of A-549 cell line. The effects of the components under study were assessed by comparing the time of restoration of the monolayer on the control group of cells, on the group of cells exposed to the action of $^{39}$K, $^{64}$Zn and $^{24}$Mg components and on the cells exposed to the action of anti-cancer drug Doxorubicin.

A comparative assessment of the effects of antitumor Doxorubicin as compared to the control group of cells showed that the use of the latter leads to a reduction in the time period of closing up the control gap thereby accelerating the process of migration of tumor cells.

Figure 114:
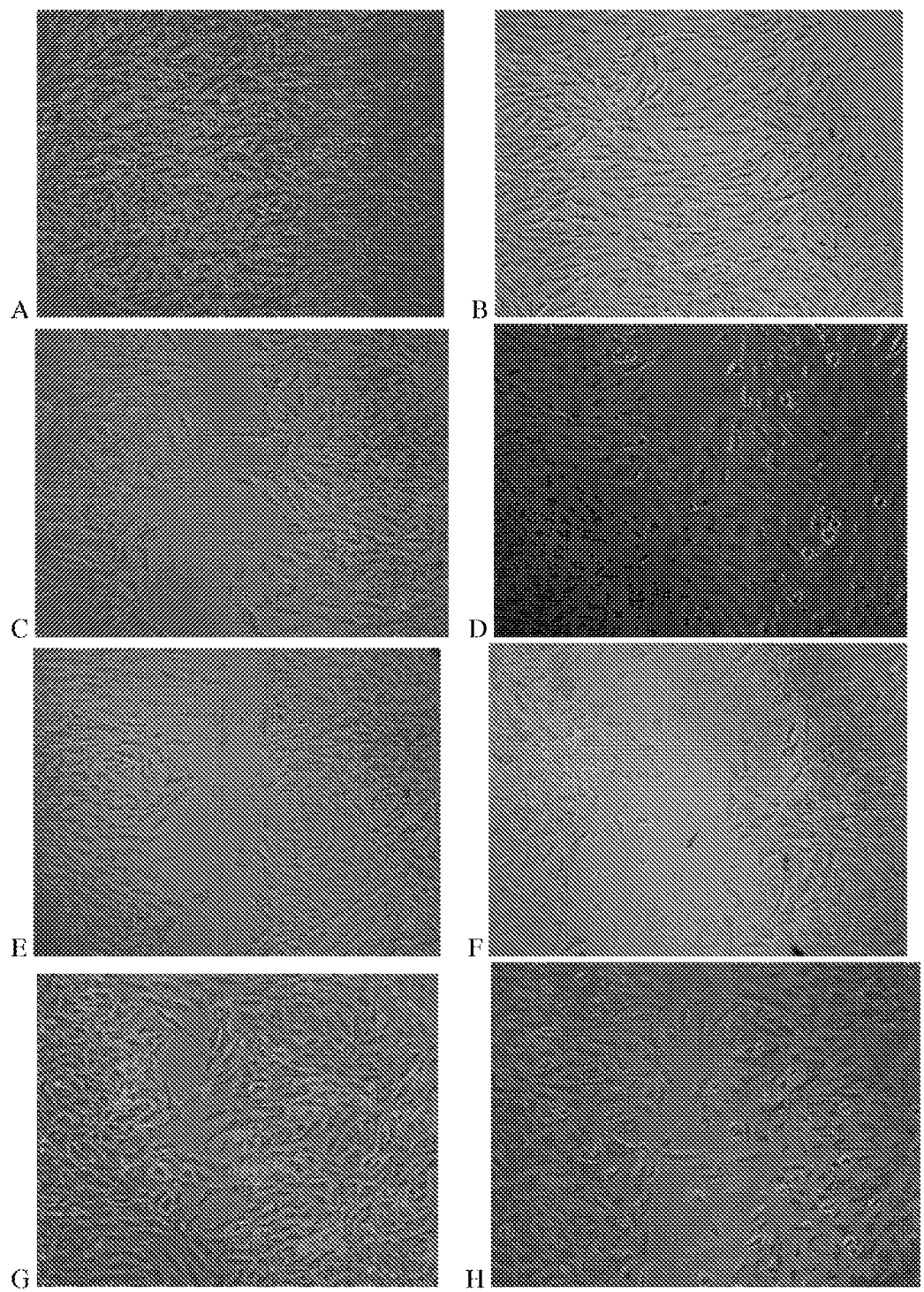
FIGS. 114A-114H illustrate a character of migration of tumor cells of A-549 cell line in the in vitro experiment with $^{39}$K, $^{64}$Zn and $^{24}$Mg components 24 hours following the cell monolayer damage: A. Control, B. A-549+Doxorubicin (2 meg/nil), C. A-549+$^{39}$K preparation (2 mg/ml), D. A-549+$^{39}$K preparation (3 mg/ml), E. A-549+$^{64}$Zn preparation (20 meg/nil), F. A-549+$^{64}$Zn preparation (30 meg/nil), G. A-549+$^{24}$Mg preparation (3 mg/ml), H. A-549+$^{24}$Mg preparation (4 mg/ml)
Figure 115:
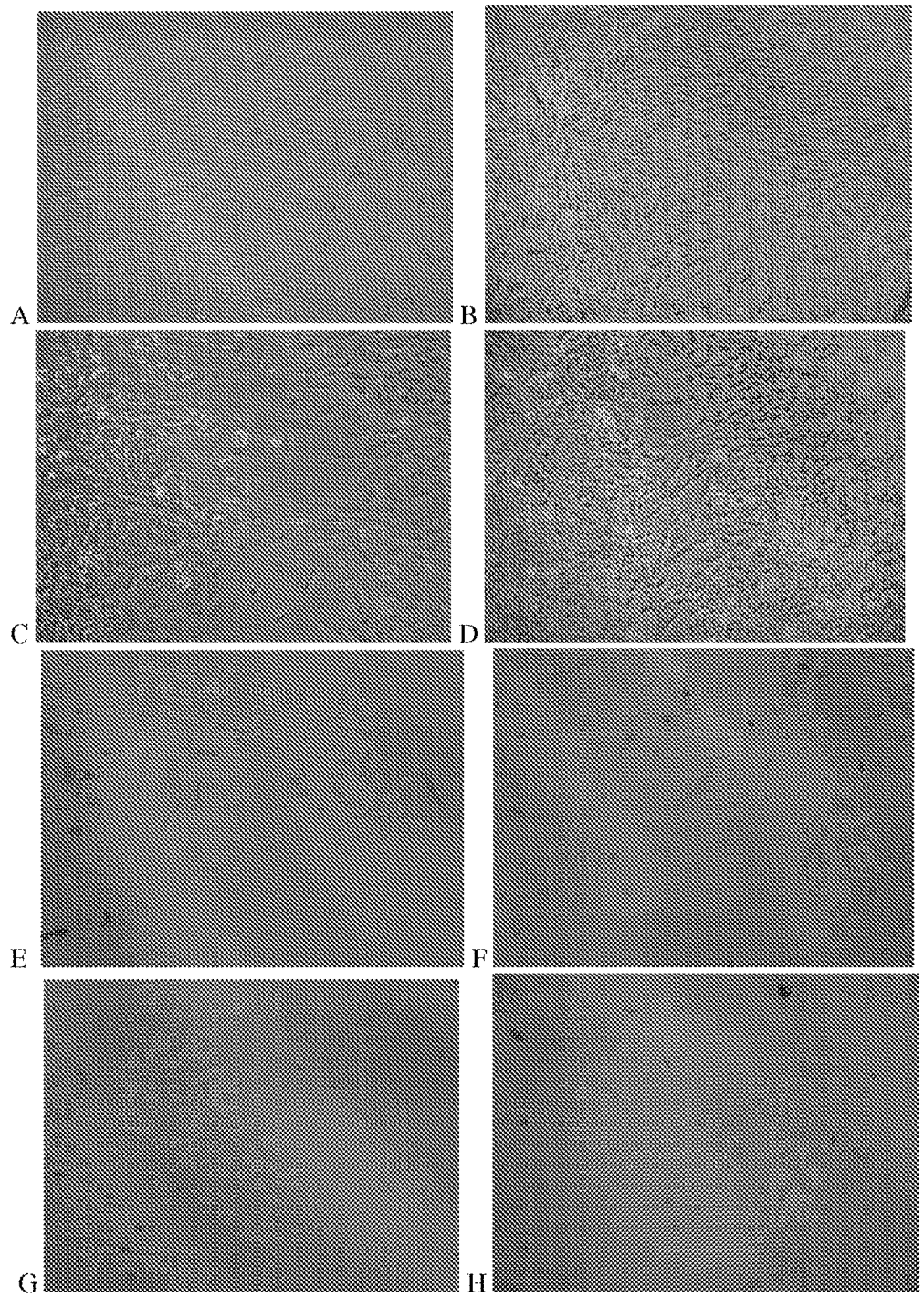
FIGS. 115A-115H illustrate a character of migration of tumor cells of A-549 cell line in the in vitro experiment with $^{39}$K, $^{64}$Zn and $^{24}$Mg components 48 hours following the cell monolayer damage: A. Control, B. A-549+Doxorubicin (2 meg/nil), C. A-549+$^{39}$K preparation (2 mg/ml), D. A-549+$^{39}$K preparation (3 mg/ml), E. A-549+$^{64}$Zn preparation (20 meg/nil), F. A-549+$^{64}$Zn preparation (30 meg/nil), G. A-549+$^{24}$Mg preparation (3 mg/ml), H. A-549+$^{24}$Mg preparation (4 mg/ml)

The effects of different doses of $^{39}$K, $^{64}$Zn and $^{24}$Mg components had the following features. $^{64}$Zn preparation at doses of 20 and 30 mcg/ml as shown in FIGS. 114, 115, 116E, F and $^{39}$K preparation at a dose of 2 mg/ml as shown in FIGS. 114, 115, 116C, D showed the best degree of suppression of the cell migration ability in the experiment with the A 549 tumor cell line. Cells processed with these components in the specified dosages, after 72 hours of their exposure to the action of the preparations under study, showed incomplete (as compared to the control) restoration of the cell monolayer while the control cell monolayer was completely restored already after 24 hours following its damage.

For $^{64}$Zn and $^{24}$Mg components a direct dose-dependent concentration effect was observed and for light isotope $^{39}$K at the doses of 2 mg/ml and 3 mg/ml—a counter effect. $^{39}$K component at the dose of 2 mg/ml showed better ability to suppress the tumor cell migration activity as compared to the dose of 3 mg/ml. The effects of both doses are shown in FIGS. 114, 115, 116C, D at various time intervals of the effects of the preparations.

Anti-cancer drug Doxorubicin showed full restoration of the cell monolayer after 24 hours following the beginning of its action, and at the initial stage of observations (3 hours after the start of the experiment as shown in FIG. 113-B its activity was higher as compared with the control group of cells. This characteristic suggests a conclusion about strengthening of the metastatic potential of tumor cells under the effect of even small doses of Doxorubicin.

According to the collective assessment of the observations made within 72 hours, $^{39}$K at a dose of 2 mg/ml and $^{64}$Zn at the doses of 20 and 30 mcg/ml showed the best results in terms of slowing the migration activity of tumor cells of human non-small cell lung cancer of A-549 cell line.

Figure 119A:
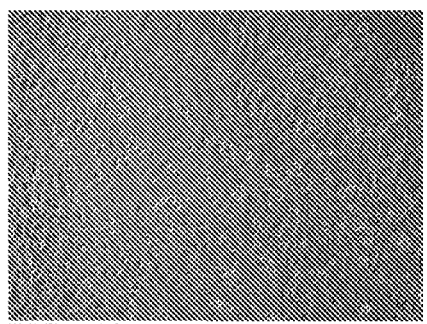
Figure 119B:
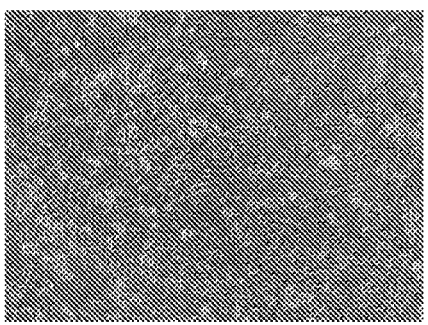
Figure 119C:
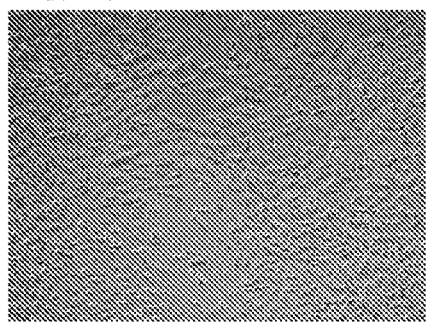
Figure 119D:
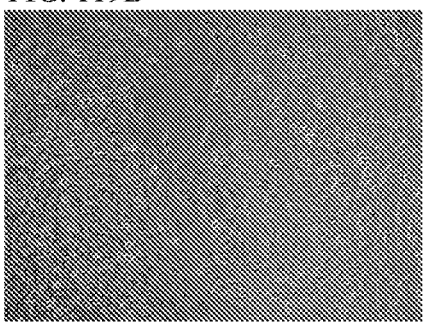
Figure 119E:
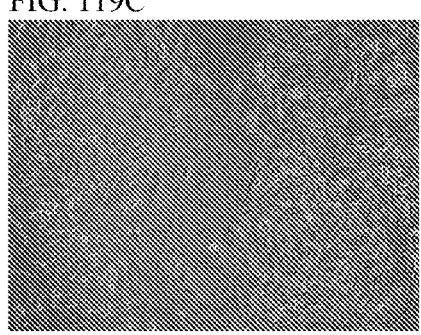

Analysis of the data for the migration activity of A-549 cells showed that $^{64}$Zn preparation at a dose of 20 mg/ml as shown in FIGS. 118, 119D and at a dose of 10 mcg/ml as shown in FIGS. 118, 119E suppresses cell migration of the A 549 line. Cells processed with $^{64}$Zn preparation at a dose of 20 mcg/ml restored the cell monolayer in 72 hours after its damage and those treated with a smaller dose of the same preparation (10 mcg/ml—in approximately 60 hours, whereas the cell monolayer in the control group was completely restored 24 hours after damage.

Figure 119F:
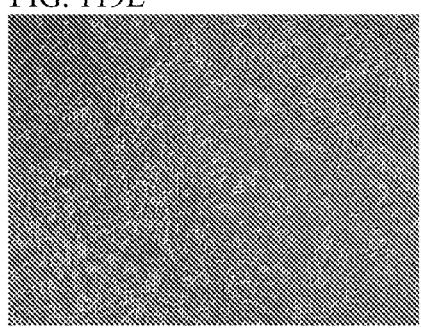
Figure 119G:
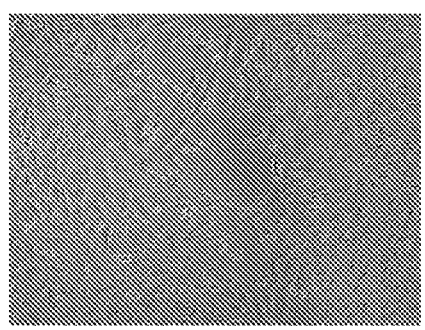
Figure 120:
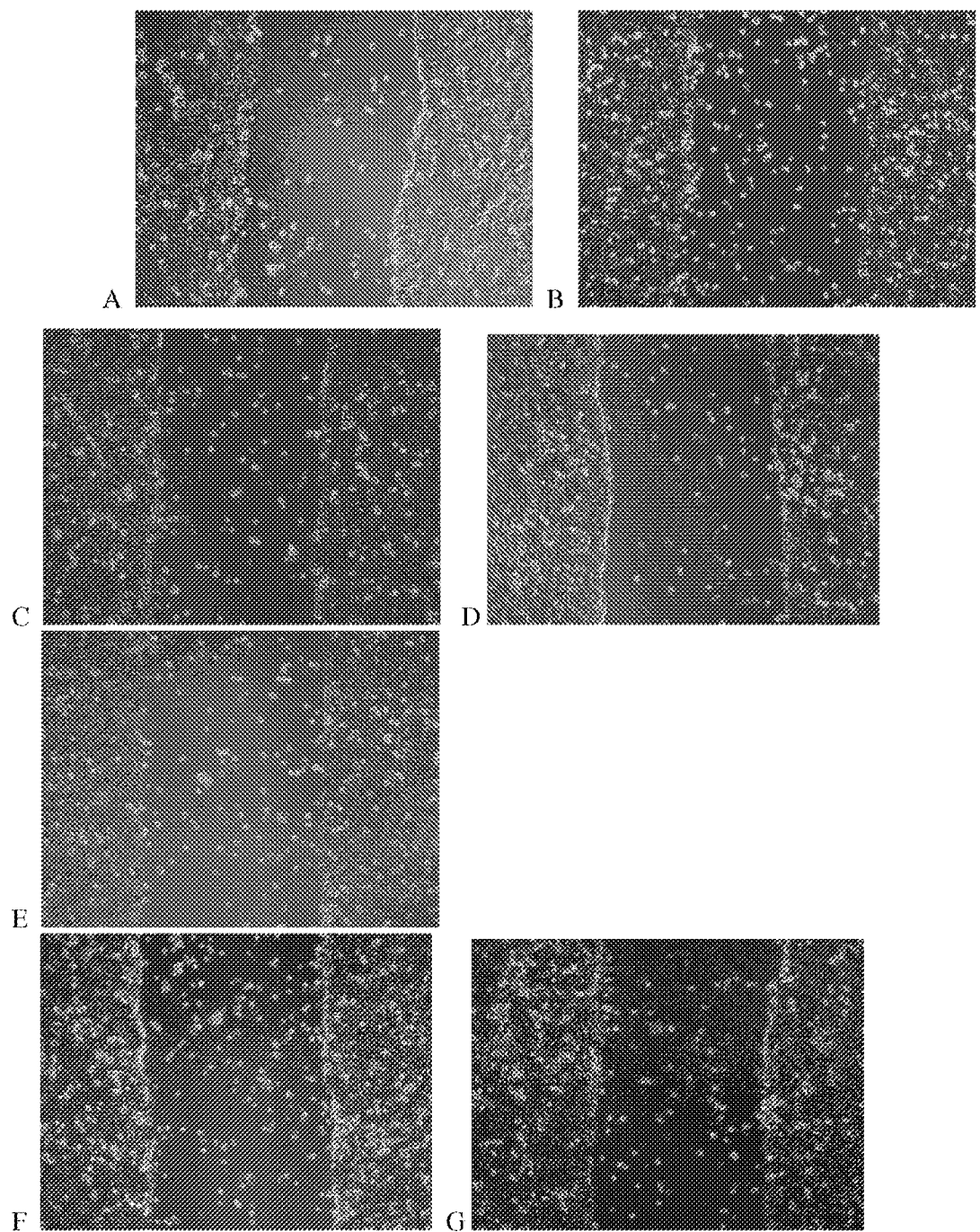
Figure 121:
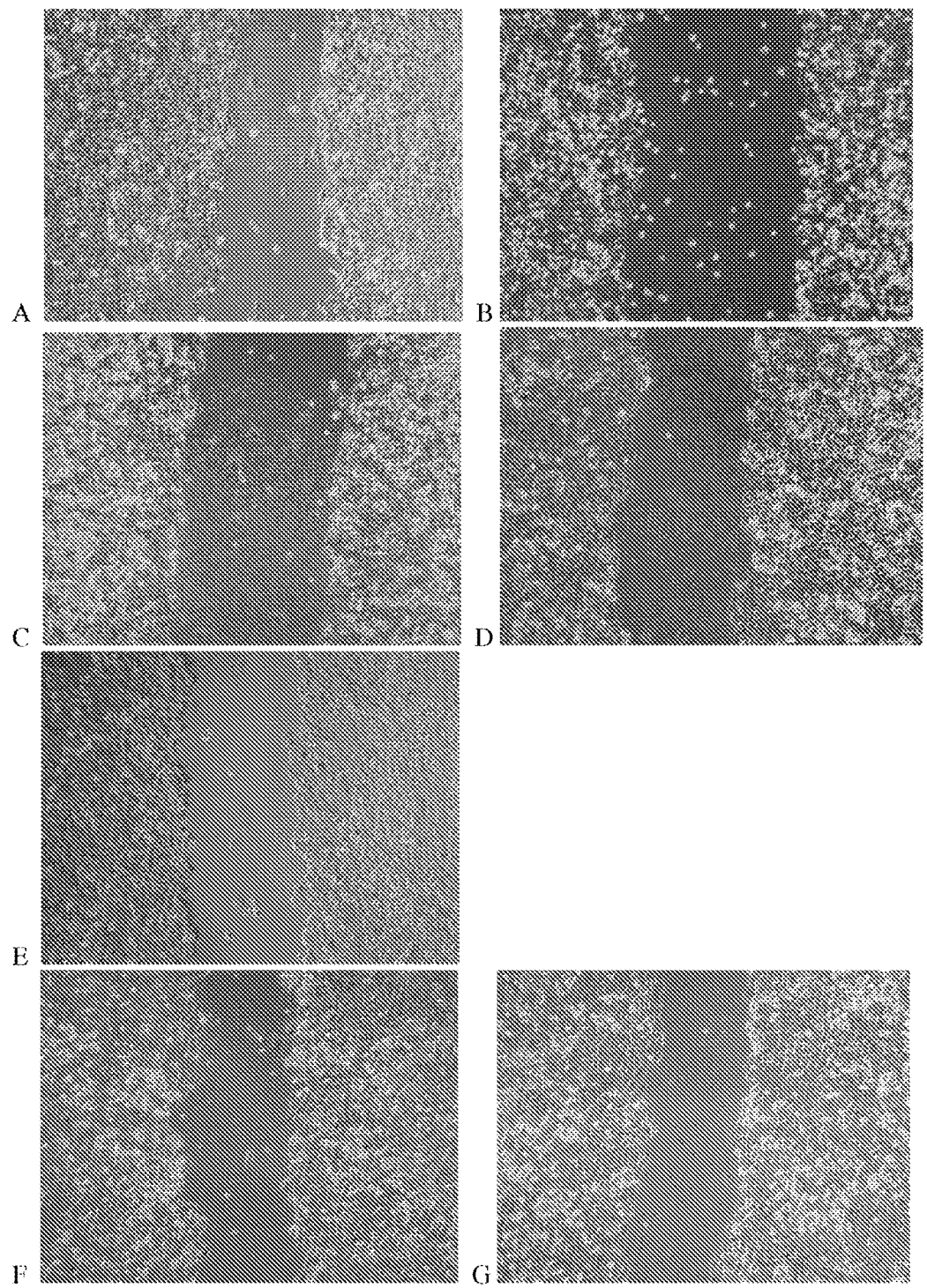

Treatment of cells with the reference drug Doxorubicin at a dose of 0.2 mcg/ml as shown in FIG. 118-B leads to an increase in the migration rate of the cells: restoration of the cell monolayer is observed earlier than 24 hours following its damage. When culturing A-549 cells in the presence of a combination of $^{64}$Zn (10 mcg/ml) and Doxorubicin (0.02 mcg/ml), as well as in the groups where the cells were treated only with $^{64}$Zn at a dose of 10 mcg/ml or only with Doxorubicin at a dose 0.02 mcg/ml, suppression of the migration activity of tumor cells was observed, i.e., the cell monolayer damages were restored in 60 hours following the start of the experiment as shown in FIGS. 118, 119F.

Treatment of A-549 cells with a combination of $^{64}$Zn at a dose of 20 mcg/ml and Doxorubicin at a dose of 0.02 mcg/ml as well as the treatment of these cells with $^{64}$Zn alone at a dose of 20 mcg/ml causes a significant suppression of the cell migration activity. In this case the cells restore the damaged monolayer in 72 hours after the damage took place as shown in FIG. 118, 119E.

Assessment of the effect of $^{39}$K, $^{64}$Zn and $^{24}$Mg on migration characteristics of stem cells derived from rat fibroblasts (RF) will now be discussed. Study of the potential regenerative features of $^{39}$K, $^{64}$Zn and $^{24}$Mg components on the rat stem cells (fibroblasts) in the area of damage to the monolayer has shown that the investigated components did not change any indicators of the restorative properties of the rat stem cells (RF) after the damage of the cell monolayer. The effect of all components consisted in 100% maintenance their restorative features, and no changes in the migration rate within 72 hours were detected. The restorative abilities of both processed and unprocessed (control) cells were the same during this time. Concentration differences among the components within the experiment were within fairly narrow limits. Treatment of RF stem cells with light isotope $^{24}$Mg at doses of 2 and 4 mg/ml showed better result at the dose of 2 mg/ml. The cell monolayer was fully restored in 72 hours after the use of this dose while the dose of 4 mg/ml produced restoration time 10 hours longer and amounted to 82 hours.

Figure 123:
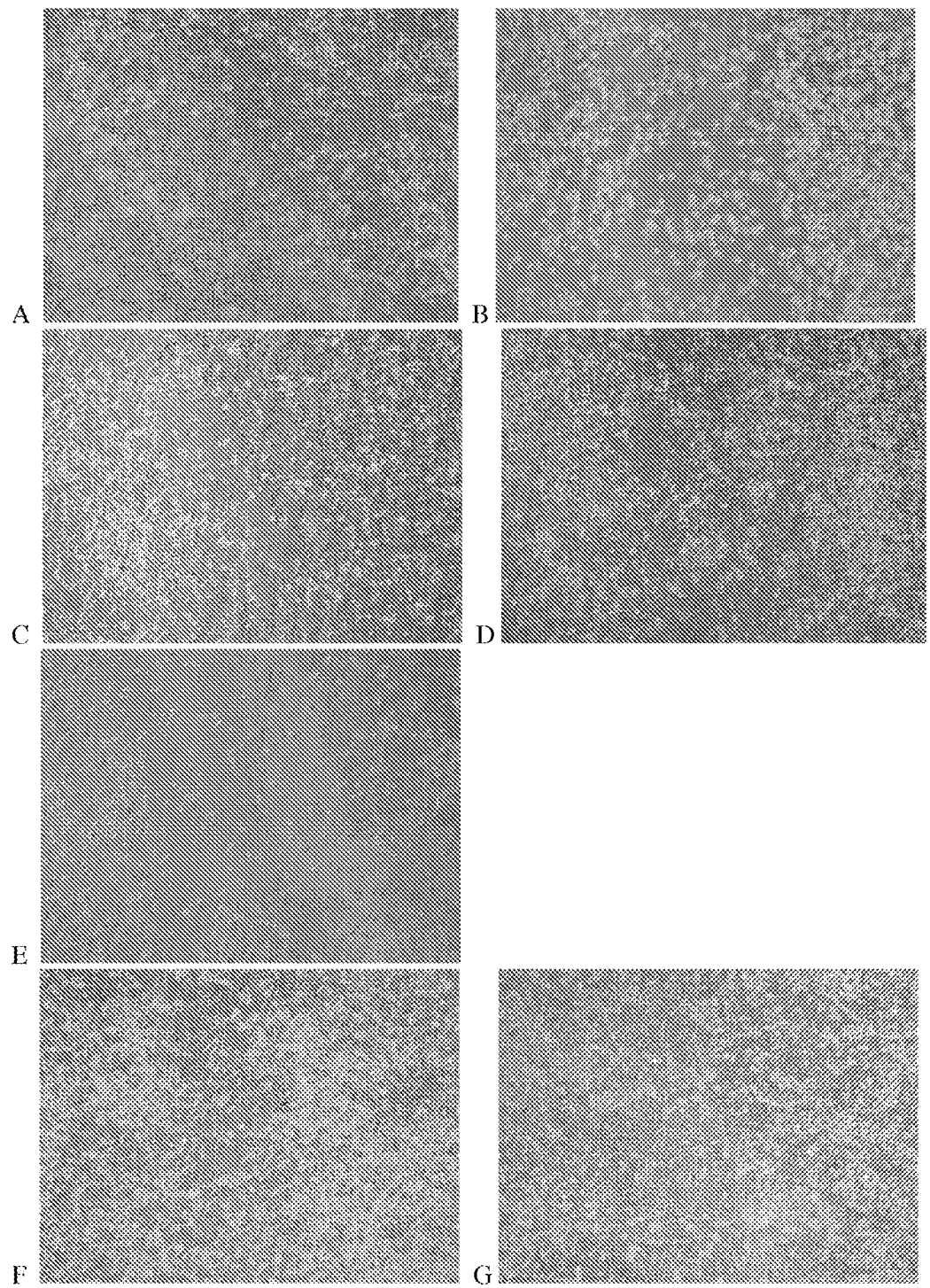

Treatment of stem cells of RF line with $^{39}$K isotopes showed a similar trend. Doses of 1 and 2 mg/ml were tested. Culturing of cells in the presence of $^{39}$K at a dose of 2 mg/ml resulted in complete restoration of the cell monolayer in 96 hours of the control time wherein FIG. 123C shows the result of the action of $^{39}$K at a dose of 2 mg/ml after 72 hours with an incomplete closure of the edges of the scratch during this time. At the dose of 1 mg/ml restoration of the monolayer took 72 hours as shown in FIG. 123D.

Cumulative assessment of the effects of light isotopes $^{39}$K, $^{64}$Zn and $^{24}$Mg on the migration activity of tumor cells of A-549 and RF cell lines showed the following. A possibility of suppression of the migration activity of A-549 tumor cells of human non-small cells lung cancer using $^{39}$K, $^{64}$Zn and $^{24}$Mg components has been discovered. The experiment with tumor cells showed a direct dose-dependent effect for $^{64}$Zn (enhancement of the component effect by increasing its dose), and the effect of $^{39}$K was greater when it was used at a dose of 2 mg/ml compared to that of 3 mg/ml. The concentration characteristic of $^{24}$Mg was expressed by a better effect of the dose of 4 mg/ml compared to that of 3 mg/ml.

$^{64}$Zn isotopes showed the best efficiency both in the experiment with RF stem cells and in the experiment with the tumor cell line. RF stem cells treated with $^{64}$Zn at a dose of 25 mcg/ml as well as the control group of cells (no treatment) completely restored the damaged monolayer within 72 hours after the start of the experiment. The time of restoration of the control monolayer of the A-549 tumor cells (not exposed to the action of isotopes) was 24 hours. The best effect of $^{64}$Zn at the doses of 20 and 30 mcg/ml was in the highest suppression degree of the migration activity of the A-549 tumor cell line in the experiment within 72 hours. This is indicative of an expressed selective effect of $^{64}$Zn specifically on tumor cells which consists in substantial suppression of their migration activity which in its turn is indicative of reduction of their cancerous and metastatic potential. In concurrence with this, an undisturbed restorative potential of the so-called "wound surface" of fibroblasts in the experiment with RF stem cells is indicative of absence of any changes in their restorative characteristics.

The effect of the Doxorubicin has also been tested on stem and tumor cells. As a result of the effect on the tumor cells, they not only failed to lose their migration and metastatic activity but in opposite it increased as compared with the control group of cells. It characterizes Doxorubicin as an agent that increases a malignant potential of a cell and thus the risk of metastases. The effect of this drug on the RF stem cells was expressed by a significant decrease in their overall viability and loss of their restorative function. The cumulative observational data shows the absence of any inhibiting effect on the metastatic potential of the cells of human non-small cell lung cancer with accompanying significant impairment of the functions of RF stem cells.

Morphological characteristics of the 549-A tumor cells after their exposure to Doxorubicin showed changes in the adhesive properties of the cells which were expressed in the change of their shape from predominantly equiaxial as shown in FIG. 114-A towards prolate and oriented in the direction of the migration front as shown in FIG. 114-B, which suggests a change (decrease) in their adhesive properties and adhesive interactions of the cells both with the base and with each other.

In the general case these changes are a result of disruption of the formation of focal contacts and are manifested in a worse adhesion of the cells to the matrix. This leads to changes in the cell activity and the nature of their motion. The observed effect of Doxorubicin is characterized by changes in the factors that stimulate cell movement—motogenic cytokines. By binding to specific receptors on the cell surface, these factors usually cause stimulation of the cell mobility and proliferation thus enhancing the malignant potential of cells.

Analysis of activity of $^{24}$Mg component on the A-549 tumor cells in the concentrations of 3 and 4 mg/ml showed a positive trend towards inhibition (decrease) of the migration activity of the tumor cells of human non-small cell lung cancer. Concentration of 4 mg/ml showed the best result during the observation period. The effect of $^{24}$Mg on the A-549 cells was directly-proportional to the concentration used.

Positive dynamics of the component effect on the RF stem cells was characterized by the less time required for restoration of the monolayer after reducing the dose from 4 mg/ml (and the time of closing the gap in the range of 75 to 82 hours) to 3 mg/ml with the restoration time of 65-72 hours.

Figure 122:
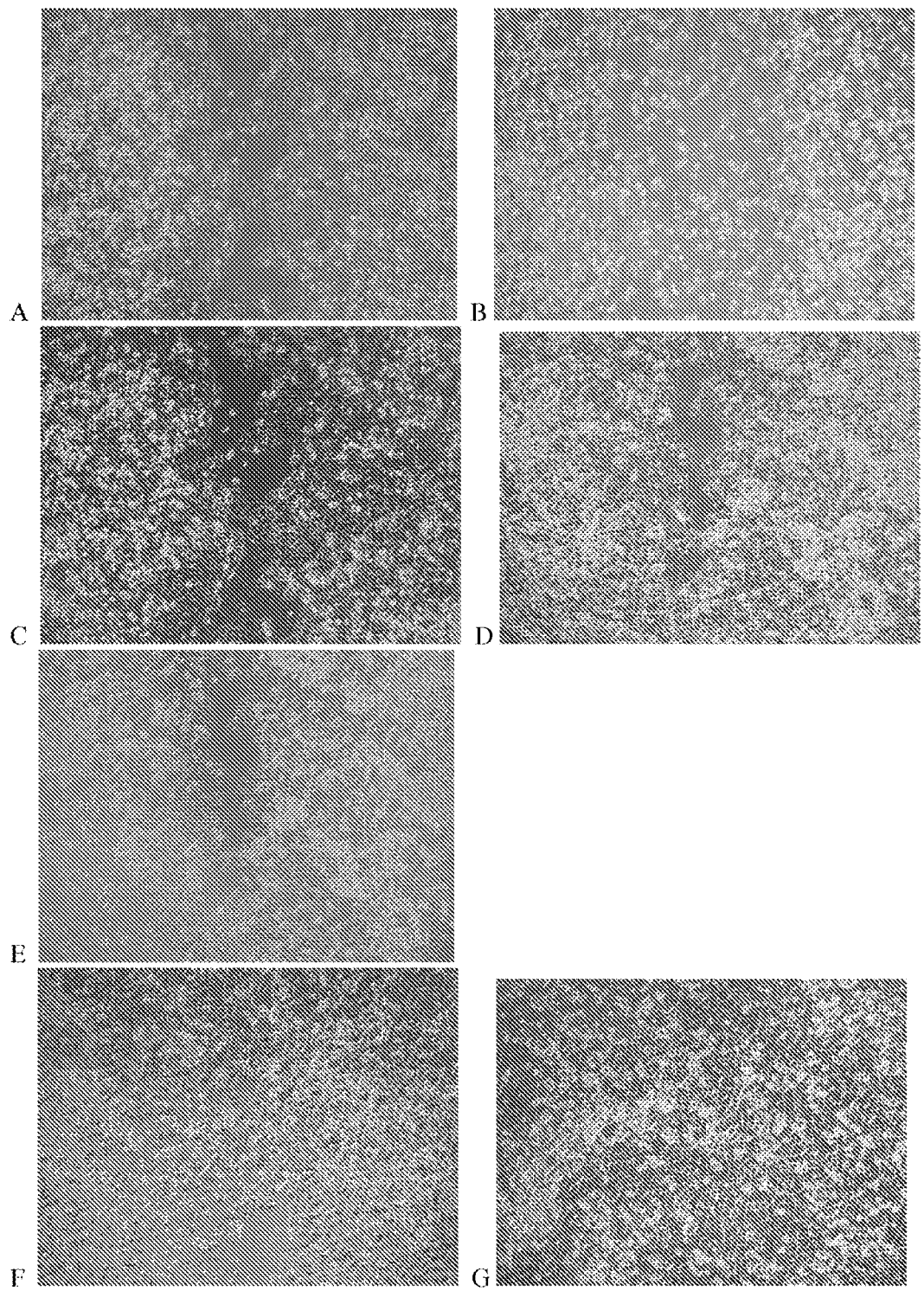

Processing of the RF stem cells with Doxorubicin, a reference drug, at a dose of 15 ng/ml showed the following results. The dose used in this experiment resulted in the irreversible damage of cells, i.e., the cell death, as well as in substantial decrease in the rate of migration of the RF stem cells as shown in FIGS. 122, 123B. Within 96 hours after administration of Doxorubicin, the effect of the drug resulted in the death of 95% of cells, and the monolayer still was not restored during this time.

Combined effect of the component containing $^{64}$Zn and Doxorubicin on stem cells from rat fibroblasts will now be discussed. In the study of the combined effect of the preparations, several changes were made in the protocol of cell processing: cells (5×104/well) were seeded into wells of a 12-well plate in 2 repetitions in DMEM culture medium supplemented with a 10% serum and 40 mcg/ml of gentamicin and incubated in 5% $CO_2$ humidified atmosphere at 37° C. for 24 hours. Then the preparations under study-$^{64}$Zn isotope containing material, Doxorubicin as a reference drug, and a mixture of both components—were added in the appropriate wells in various doses. Then the plate was incubated in a $CO_2$ incubator for another 48 hours.

Next, we used a sampler tip (up to 200 mcl in volume) to damage the monolayer. After that we replaced the medium in each well to remove cellular debris and smooth the edges of the scratch. The rate of cell migration was analyzed using an inverted microscope and the cells were photographed in the region of damage. The migration activity of cells was fixed at several time points (in 1, 24, 48 and 72 hours depending on the test cells) after the monolayer damage. The photographs were analyzed and the cell incubation time needed to restore the monolayer was determined for all experimental groups.

During the study of the drug effect on normal cells (fibroblasts) of the RF line in the region of damage of their monolayer it was found out that $^{64}$Zn component (alone) did not affect the rate of migration of cells of the RF cell line: the cells processed with this preparation at a dose of 25 mcg/ml, as well as the control cells, completely restored the damaged monolayer in 72 hours after the start of the experiment as shown in FIG. 126-D.

Processing of the RF cells with the reference drug Doxorubicin at a dose of 15 ng/ml or 5 ng/ml resulted in a significant decrease in the rate of RF cell migration. The cell interval was not restored within 72 hours of the control time as shown in FIGS. 126-B, C.

The effect of Doxorubicin was also characterized by the death of 95% of cells 48 hours following the monolayer damage (96 hours after administration of Doxorubicin and 48 hours after the drug withdrawal). RF cell culturing in the presence of combination of $^{64}$Zn at a dose of 25 mcg/ml and Doxorubicin at a dose of 15 ng/ml also resulted in the cell death within 48 hours after administration of the preparations. The data with regard to the combined effects of $^{64}$Zn component and Doxorubicin are similar to those produced by Doxorubicin alone.

Migration activity of normal rat kidney cells (NRK cell line) after their exposure to the action of components containing $^{39}$K, $^{64}$Zn and $^{24}$Mg compared to the effect of Doxorubicin will now be discussed. Analysis of migration of cells of the NRK cell line in the region of damage of their monolayer after they were processed with the materials containing $^{39}$K, $^{64}$Zn and $^{24}$Mg and Doxorubicin as a reference drug showed that only Doxorubicin significantly affected (by slowing the activity) the rate of cell migration of the NRK line: cells processed with this drug at a dose of 15 ng/ml restored the damaged monolayer only in 72 hours after the start of experiment as shown in FIGS. 130-A, B. Treatment of NRK cells with $^{39}$K, $^{64}$Zn and $^{24}$Mg isotopes had no effect on their migration activity: in 30 hours after the scratch of the monolayer, as in the control, the NRK cells processed with various doses of the experimental preparations restored the damaged monolayer.

Comparison of the data on the cell migration activity obtained on tumor (A-549), normal (NRK) and stem (RF fibroblasts) cells after their exposure to the action of the preparations under study showed the following. The action of $^{39}$K component on the A-549 tumor cell line as shown in FIGS. 114, 115, 116C, D consisted in suppression of their migration activity within 72 hours (24 hours in the control), and a similar pattern was observed on stem RF fibroblasts: $^{39}$K did not change natural restorative properties of cells and they restored the monolayer in 72 hours (with 72 hours in the control). The action of this component on normal cells (NRK) also caused no changes in time—the control group of cells and cells processed with $^{39}$K restored their monolayer in 30 hours.

The effect of $^{64}$Zn on tumor, normal and stem cells can be characterized by the following. Stem cells (RF), after their exposure to this isotope, fully retained their restorative properties with monolayer restoration time of 72 hours which is the same as in control group of cells. Normal cells (NRK), after being processed with the component, as well as the control cells (no processing) fully restored the damaged monolayer in 30 hours. As a result of effect of $^{64}$Zn on the A-549 tumor cell line the restoration time of the cell monolayer increased to 72 hours compared to 24 hours of restoration of the control monolayer component with no use of isotope. These data demonstrate a selective effect of $^{64}$Zn specifically on tumor cells which consists in substantial suppression of their migration activity which in its turn is indicative of reduction of their metastatic potential. In concurrence with this, an undisturbed restorative potential of the so-called "wound surface" of fibroblasts and normal cells is indicative of absence of any changes in the biological characteristics in normal cells after the effect of $^{64}$Zn component.

$^{24}$Mg isotope at a dose of 4 mg/ml also shows the ability to inhibit the metastatic activity of lung cancer A-549. At the same time processing of the NRK cells with $^{24}$Mg had no effect on their migration activity: within 30 hours after the monolayer violation, as in the control, the NRK cells restored the damaged monolayer maintaining the properties of normal cells. The comparative characteristics of the effect of anticancer drug Doxorubicin on various cell types showed the following. A-549 tumor cells of the human lung cancer not only failed to lose their migration and metastatic activity but on the contrary, the degree of their malignancy after the action of doxorubicin increased with reduction of the time of closing up of the cell gap.

The effect of Doxorubicin on normal kidney cells (NRK) was characterized by suppression of their restorative ability—the cells processed with this drug at a dose of 15 ng/ml restored the damaged monolayer only in 72 hours after the start of the experiment (compared to 30 hours for the control group of cells).

Combined effect of the component containing $^{64}$Zn and Doxorubicin on the migration activity of healthy human skin cells (HaCaT cell line) will now be discussed. The study of migration activity of human keratinocytes of the HaCaT cell line (healthy skin cells) after the combined effect of $^{64}$Zn component and Doxorubicin showed the following results. Separate effect of Doxorubicin was expressed by slowing down the rate of migration of the healthy skin cells as shown in FIGS. 133-B, C. After processing the HaCaT cells with this drug in 2 doses, 15 ng/ml and 5 ng/ml, inhibition of the cell migration rate was observed. The combined action of $^{64}$Zn component and Doxorubicin showed a possibility of restoration of the cell monolayer within 36 hours—time required to restore in control group of cells. Thus one more experimental confirmation of a positive action of light isotope $^{64}$Zn was received on the HaCaT cell line of human keratinocytes—a possibility of reducing negative effect of Doxorubicin on the regenerative function of healthy cells.

Using $^{64}$Zn without Doxorubicin at a dose of 25 mcg/ml made it possible to carry out an assessment of the time of the monolayer healing as compared with the control group of cells. As the experiment showed as shown in FIGS. 133-A, D a separate action of $^{64}$Zn on the HaCaT cell line of human keratinocytes did not affect the time of monolayer healing. It was equal to the time of the control cells monolayer healing—36 hours.

Combined effect of the component containing $^{64}$Zn and Doxorubicin on the migration activity of human epidermoid carcinoma cells (A-431 cell line) will now be discussed. Analysis of the migration activity of the tumor cells of A-431 cell line as shown in FIGS. 134, 135, 136, 137, 138, which were exposed to the combined action of $^{64}$Zn and Doxorubicin showed increase in time for repair of the tumor cells monolayer after the use of light isotope zinc (from 48 hours of control cells repair to 72 hours with $^{64}$Zn) and reduction of the time to close up a cellular gap from 48 to 45 hours after the use of Doxorubicin. The combined effect of $^{64}$Zn and Doxorubicin also did not differ in character from the results obtained earlier. Light isotope neutralized the negative effects of Doxorubicin completely which resulted in healing the cell monolayer in 72 hours and not differ from the result obtained after the action of $^{64}$Zn isotope only. Reduction of the time for the cell monolayer repair from 48 to 45 hours after the use of Doxorubicin was detected at a dose of 0.1 mcg/ml as shown in FIG. 137 Administration of a smaller dose of 0.02 mg/ml showed the result like in control group—48 hours.

Combined effect of the component containing $^{64}$Zn and Doxorubicin on the migration activity of human melanoma tumor cells (MM-4 cell line) will now be discussed. Analysis of a series of photographs, as shown in FIGS. 139, 140, 141, 142, 143, illustrating the process of migration of tumor cells of the MM-4 cell line in the region of damage of their monolayer showed that the combined effect of $^{64}$Zn component, as shown in FIGS. 139, 140, 141D, and Doxorubicin at a dose of 0.1 mcg/ml, as shown in FIGS. 139, 140, 141B, suppress the migration rate of MM-4 melanoma cells.

The closing up time for the control group of cells not exposed to the action of the components was 48 hours. Culturing was carried out using preparations in the following concentrations. Light isotopic $^{64}$Zn was tested separately at a dose of 15 mcg/ml and in a combination with Doxorubicin (15 mg/ml of $^{64}$Zn+0.1 mcg/ml of Doxorubicin and 15 mcg/ml of $^{64}$Zn+0.01 mcg/ml of Doxorubicin), and a separate effect of Doxorubicin was tested in 2 concentrations: 0.1 mcg/ml and 0.01 mcg/ml.

Figure 139:
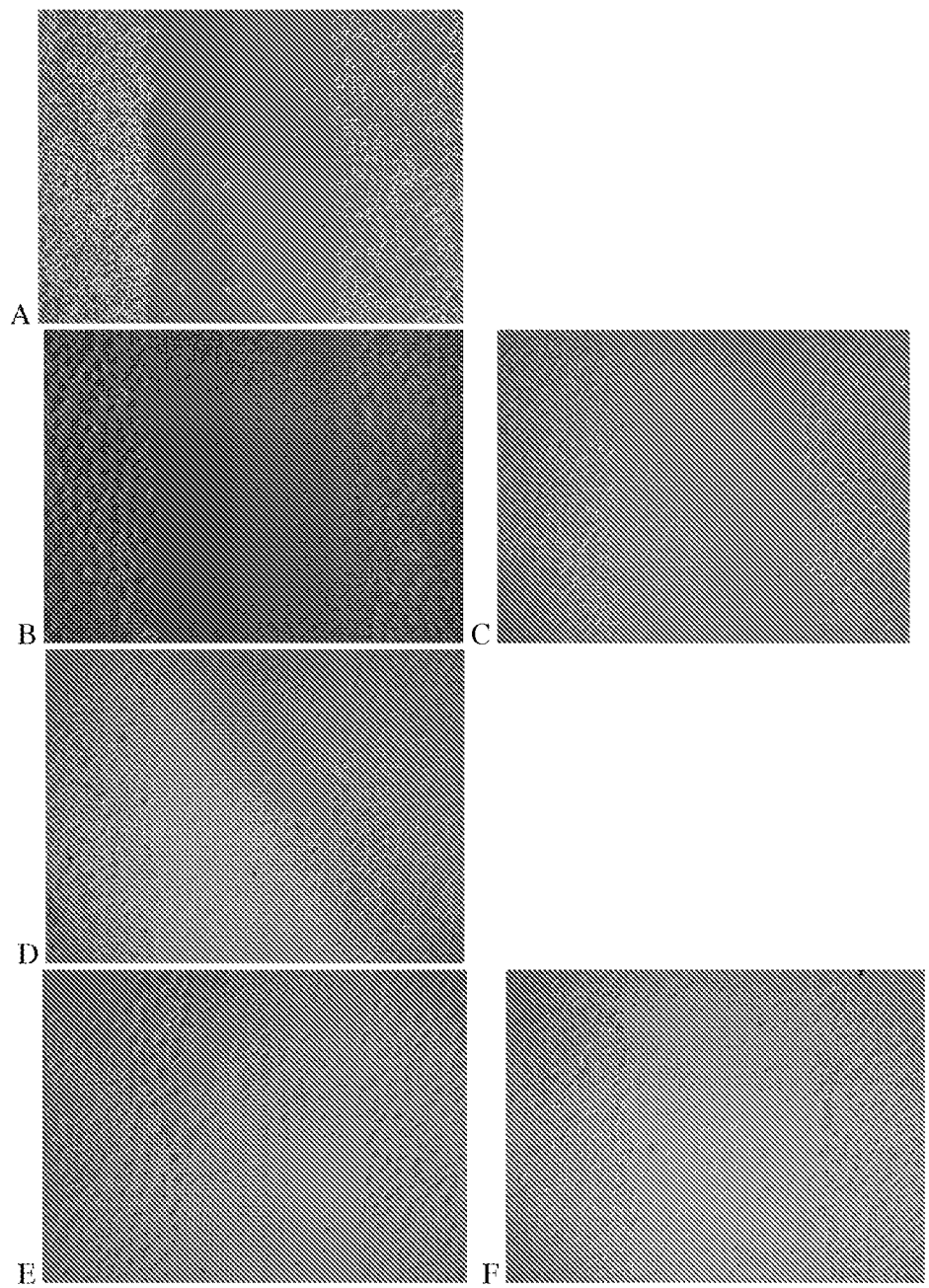
Figure 140:
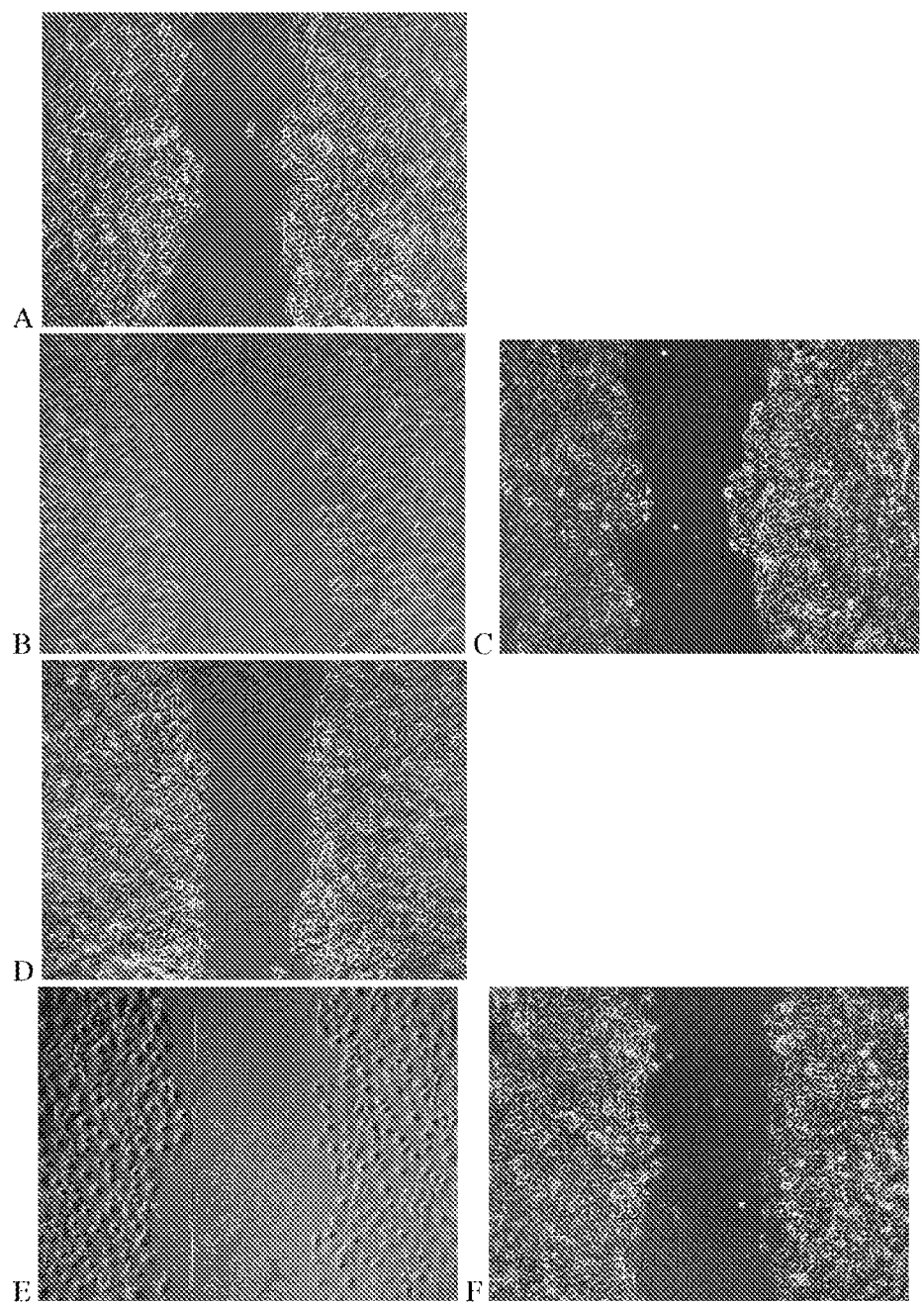
Figure 141:
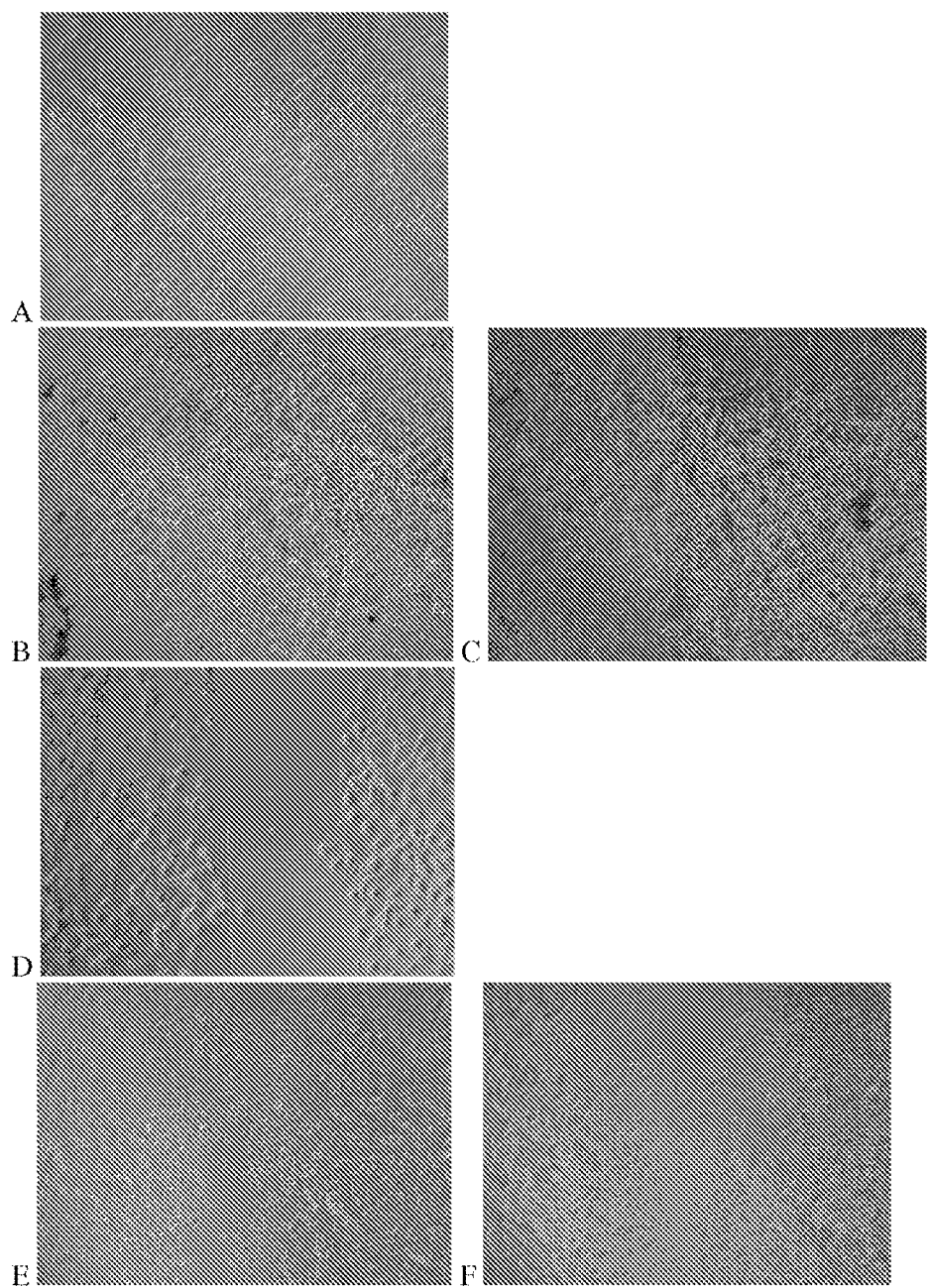

When culturing cells in the presence of both preparations—$^{64}$Zn component+Doxorubicin at a dose of 0.01 mcg/ml, as shown in FIGS. 139, 140, 141E, and $^{64}$Zn component at a dose of 15 mcg/ml+Doxorubicin at a dose of 0.01 mcg/ml, as shown in FIGS. 139, 140, 141F, a significant suppression of migration activity of the MM-4 cells was recorded. The total time of the monolayer restoration after the combined use of $^{64}$Zn component and Doxorubicin (in 2 concentrations) was 70 hours with 48 hours for the control group of cells.

Processing of cells of the MM-4 cell line with Doxorubicin alone showed no statistically significant change in the time of closing of the control monolayer. Observation of the effects of this component at 2 concentrations showed that the period of closing of the gap was 48 hours, which coincides with the time for the control cell monolayer, as shown in FIGS. 141B, C. Thus suppression of the migration activity of tumor cells was recorded after a separate use of light isotope $^{64}$Zn on the MM-4 melanoma cell line (the time of the gap closing amounted to 72 hours vs. 48 hours in the control group). In combination with Doxorubicin the time of the gap closing was equal to 70 hours. The combined use of $^{64}$Zn+Doxorubicin demonstrated effect of neutralization of the negative effects of Doxorubicin. The cell gap was restored in 70 hours versus 72 hours after the use of $^{64}$Zn without Doxorubicin.

Analysis of cellular activity in the Scratch Assay Migrations experiment in which the group of $^{39}$K, $^{64}$Zn and $^{24}$Mg isotopes was used showed a possibility of a delay in the time of restoration of the damaged monolayer of tumor cells and hence the suppression of their migration activity and metastatic potential. A comparative assessment of the time is characterized by 72 hours required for closing the cell gap when $^{39}$K, $^{64}$Zn and $^{24}$Mg isotopes are used separately (on 3 tumor cell lines—A-549, A-431 and MM-4) compared to 24 hours needed to restore the monolayer without the use of the components on the A-549 cell line and 48 hours on the A-431 and MM-4 cell lines.

Assessment of the effects of $^{39}$K, $^{64}$Zn and $^{24}$Mg components on normal (NRK), stem (RF) and skin (normal human keratinocytes HaCaT) cells showed their ability to maintain restorative and regenerating properties of stem cells. The time of restoration of the cell monolayer after the use of $^{39}$K, $^{64}$Zn and $^{24}$Mg components did not differ from the time for control groups of all cell lines (NRK, RF, HaCaT). A positive effect of $^{39}$K, $^{64}$Zn and $^{24}$Mg on normal stem cells expressed in the absence of any contact inhibition effect during the formation of cell monolayer on the NRK, FC, HaCaT cell lines. Activity of the control and experimental groups of cells showed the same results with respect to the time of the cell monolayer restoration which is indicative of the absence of any disturbances of the cell growth mechanisms in the experimental group where $^{39}$K, $^{64}$Zn and $^{24}$Mg were used and of the possibility of maintaining regenerating properties of cells in the presence of light isotopes.

Figure 116:
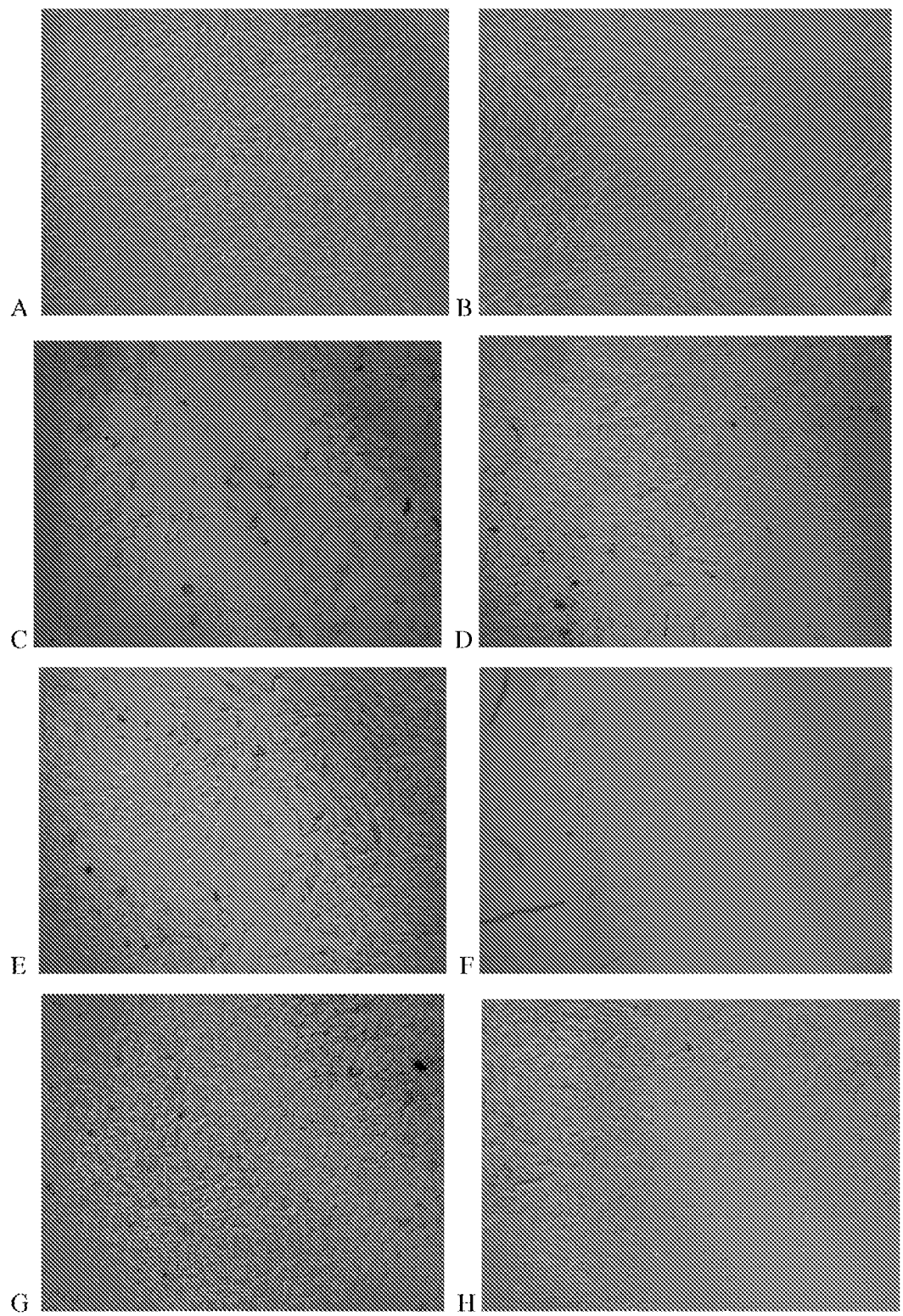
Figure 117A:
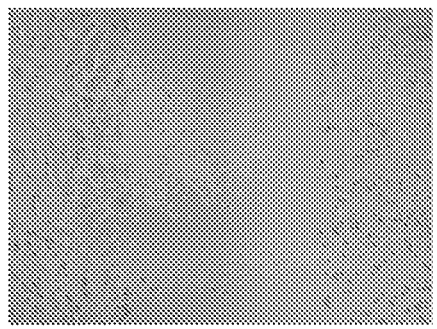
Figure 117B:
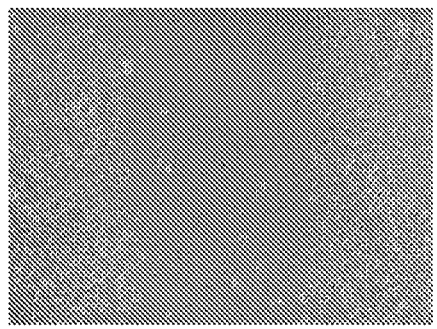
Figure 117C:
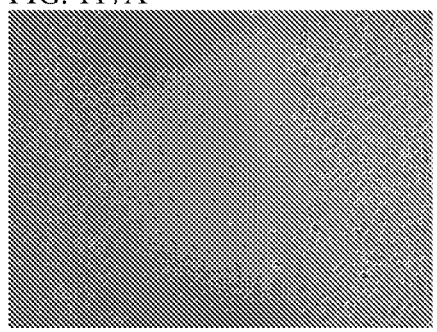
Figure 117D:
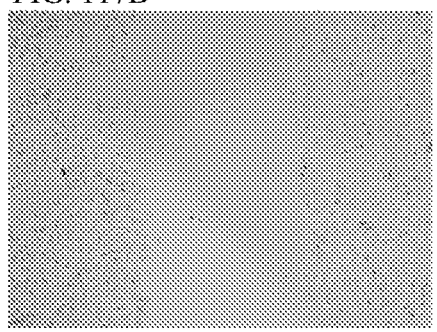
Figure 117E:
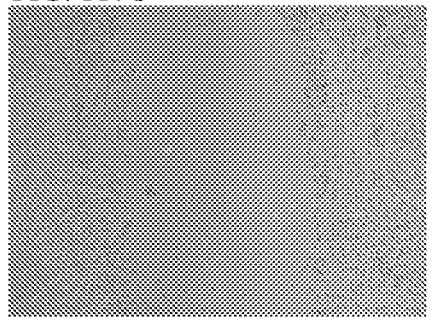
Figure 117F:
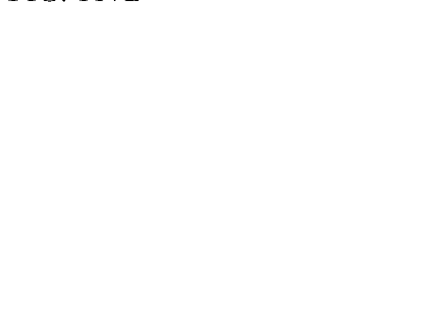
Figure 117G:
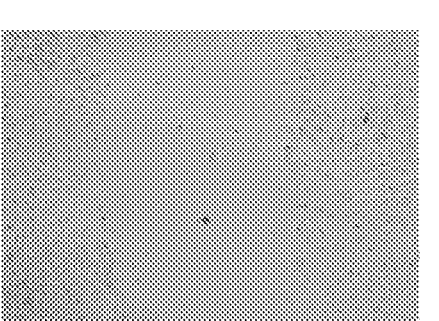
Figure 118A:
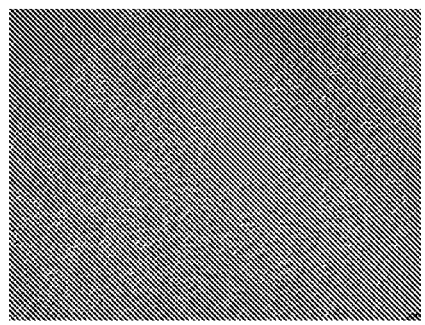
Figure 118B:
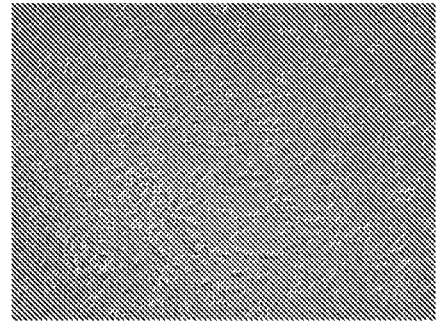
Figure 118C:
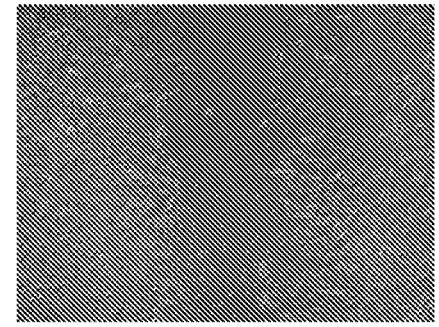
Figure 118D:
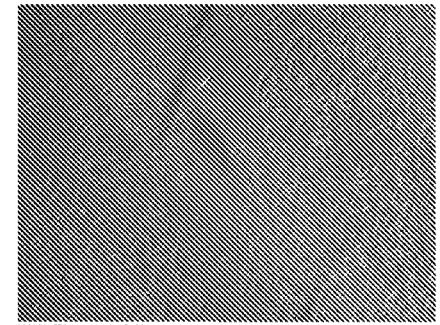
Figure 118E:
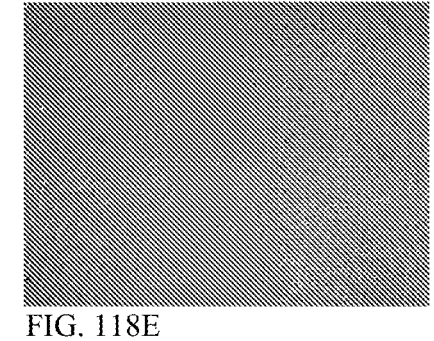
Figure 118F:
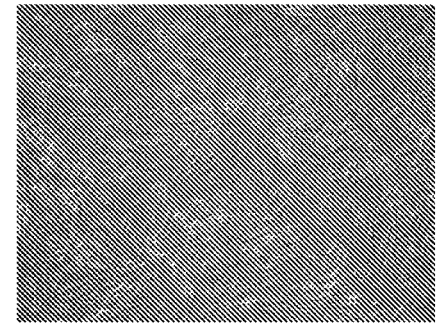
Figure 118G:
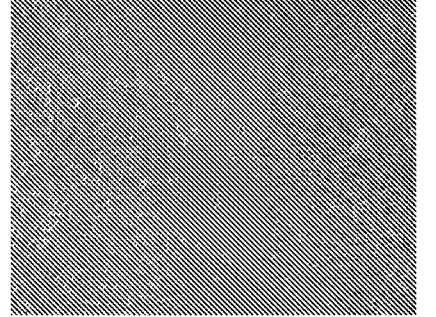

Changes in the morphological characteristics of tumor cells of the A-549 cell line after their exposure to the action of Doxorubicin were detected. They were expressed in the change of their shape from predominantly equiaxial, as shown in FIG. 114-A, towards prolate and oriented in the direction of the migration front, as shown in FIG. 114-B, which suggests a decrease in their adhesive properties and adhesive interactions of the cells both with the base and with each other. Said changes are due to disruption of the formation of focal contacts and are manifested in a worsening adhesion of the cells to the matrix. This leads to changes in the cells activity and the speed of their movement. The observed effect of Doxorubicin is characterized by changes in the factors that stimulate cell movement—motogenic cytokines. By binding to specific receptors on the cell surface, these factors usually cause stimulation of the cell mobility and proliferation thus enhancing the malignant potential of cells. The effects of light isotopes $^{39}$K, $^{64}$Zn and $^{24}$Mg on the A-549 cells after 72 hours is a decrease in the number of unequiaxial cells as shown in FIGS. 116-C, E, G.

The effect of anti-cancer drug Doxorubicin on the migration of the A-549, A-431 and MM-4 tumor cells was characterized by increased cellular activity and reduced time of the cell gap closing as compared to the control groups of cells. It means that Doxorubicin increases metastatic potential of tumor cells. Treatment of stem cells with Doxorubicin at a dose of 15 ng/ml resulted in the cell death. The effect of Doxorubicin on the RF cell line resulted in the death of 95% of cells within 96 hours. The effect of this component on the RF stem cells was a significant reduction in their overall viability and loss of their natural regenerative function.

Action of Doxorubicin on tumor cells is characterized by increased cell activity and, as a result, an increase in their metastatic potential which is manifested in accelerated (as compared to the control group of cells) closing of the cell gap. The action of $^{64}$Zn component, on the contrary, leads to reduction of the tumor and metastatic activity of cells which was manifested in the increase of the time of the cell gap closing as compared to the control group cells.

Comparative assessment of the effects of the pair of $^{64}$Zn—Doxorubicin showed that the combined use of these components on tumor cell lines also reduces migration and tumor cell activity of A-549, A-431 and MM-4 cell lines. This makes it possible to use $^{64}$Zn containing materials both as an independent anti-tumor component, and in the complex schemes of combined therapy aimed to protect organs and tissues from the toxic effects of anti-cancer drugs and their decomposition products (metabolites).

Summarizing the study of the combined effects of $^{64}$Zn and Doxorubicin the following conclusions can be made: $^{64}$Zn isotopes do not affect the rate of migration of normal stem cells which confirms the absence of any negative effects on normal cells. Anti-migration and, as a consequence, anti-metastatic effect of $^{64}$Zn on tumor cells has been observed, which is important, since the degree of migration mobility of malignant cells is the main characteristic of their metastatic and malignant potential. $^{64}$Zn component has an ability to suppress adverse effects of anti-cancer agents, namely inhibit increased migration of tumor cells after the action of antineoplastic Doxorubicin.

Alluding to the above, the aforementioned results prove that it is beneficial to use $^{64}$Zn isotopes in combination with any standard antineoplastic therapy in order to improve its efficiency and reduce the harmful effects of anti-tumor agents. Preparation of samples will now be discussed. Experimental samples obtained by surgery or filtration depends on the objects of investigation (blood, lymph etc.). Said samples having a mass of about 1 gram were quick-frozen by immersion in liquid nitrogen. To reach high rate s of freezing small portions of samples have been used. In ultrafast cooling at a rate of about one hundred degrees in 1 sec., water was transformed into amorphous ice without volumetric expansion.

After that, the amorphous ice was removed from the sample by means of vacuum freeze drying at a low temperature. The ice evaporates and the mineral particles and organic components of the sample remain in the same position in which they were in the initial wet sample, and thus the structure and chemical composition of the sample is preserved. To reduce the drying time of the sample during sublimation, dry nitrogen was fed automatically to the vacuum chamber. This technique increases thermal conductivity of the sample and therefore the convection heat supply accelerates the process of sublimation. The gas feed rate to the vacuum chamber did not exceed 0.1l/min. Samples drying time under these conditions was 10 hours.

At the final stage of preparation of the samples an additional drying under the high vacuum was done. At almost complete (99%) dehydration under the high vacuum, samples were heated to a temperature of 35-40° C. and then have been aged isothermally for about 1 hour under these conditions. Method of secondary ion mass spectrometry with Cameca IMS-4F mass spectrometer was used. Mass spectrometry in the biological samples was performed based on the m/z ratio analysis in the pulse counting mode as well as using results displayed as a mass-spectrum as shown in FIG. 145 or as a profilogram that characterizes distribution of the detected masses along the sample plane as shown in FIG. 147 and in depth as shown in FIG. 146.

The sample prepared for the experiment was placed in a sample holder. After evacuating the system, the probe was calibrated and its mode was stabilized. To prevent the destructive action of the ion beam on the sample and to reduce the amount of static electricity caused by ionization, the analysis was carried out at very low rates of the sample sputtering (less than 104 of the monolayer per second).

A subsequent analysis of the masses obtained in result of the ion beam bombardment of the sample surface was based on the interaction of secondary ions ejected from the sample surface with the electric and magnetic fields of the detectors. Utilization of a double-focusing spectrometer with combination of electric and magnetic fields controls made it possible to maximize the sensitivity of the instrument. For such multistage magnetic spectrometers a background signal resulting from the residuals of the main peaks of the matrix material (wall scattering, on the gas atoms, etc.) can be reduced to a level of less than 10-9 for the general background and only 10-6 for all masses close to the main peak.

To minimize the amount of gases adsorbed on the sample surface ($H_2$, $N_2$, $O_2$, $H_2O$, $CO_2$ and CO) the measurements were performed in an ultrahigh vacuum free of hydrocarbons using cryogenic and getter pumping near the sample. To reduce the formation of positive charge on the surface of the test sample due to electron ionization, the latter was irradiated with electrons emitted by a thermal cathode located nearby. In addition, an electro-conductive additive to the sample increased samples conductivity. Sample dried by sublimation was placed on a metal mesh with a mesh size of 25×25 mm using a pressing technique with the addition of electro-conductive highly dispersed carbon black. The quantitative content of the electro-conductive additive was 0.1% of the sample weight to drain off accumulated charge on the metal mesh.

For the measurement, several methods were applied using Cameca IMS-4F instrument: a) mass spectrometry, b) the method of direct imaging of isotope distribution on the sample surface, c) the method of profilograms, which made it possible to assess a degree of homogeneity of the isotope distribution in the depth of the sample as shown in Figures A vertical line in the middle part corresponds to the natural distribution for each of the detected isotopes. Horizontal yellow and green diagrams characterize deviations from the natural content for each of the said isotopes. Therefore the left side of the graph (with shaded diagram strips) corresponds to an increase in the concentration of isotopes and is represented mainly by heavy isotopes, while the right side (with unshaded diagram strips) on the contrary—a decrease in the percentage of isotopes in relation to the natural content primarily due to light isotopes.

FIG. 148 illustrates the character of distribution of isotopes in the "young" and "old" tissues. We also analyzed the isotopic ratios in pathological (cancer) and healthy tissues of the following chemical elements: magnesium, silicon, sulfur, chlorine, potassium, calcium, chromium, iron, nickel, copper, zinc, bromine, rubidium, molybdenum and silver.

The following types of biological tissues were studied, as shown in FIGS. 155, 156, 157, 158 are biological tissues containing cancerous tumor cells (sample 20 and sample 12) where sample 20 had metastases, normal biological tissues (sample 12 and sample 18). Within each pair of samples (tumor and normal tissue were divided into the following pairs: 12-14 and 18-20), the pairs of samples belonged to the same biological organism. Isotope distribution was studied on the following pairs of samples (see Table 1). Samples 12 and 14, where sample 12 was taken from the central area of the tumor and sample 14 from normal tissue. 2). Samples 18 and 20, where sample 18 was taken from normal tissue and sample 20 from tissue affected by the tumor. Distribution of isotopes detected in samples 12 and 14 is shown in FIG. 8 and in samples 18 and 20 in as shown in FIGS. 159, 160.

Comparative assessment of the experimental results on samples 12 and 14 is shown in as shown in FIGS. 157, 158 and on samples 18 and 20 in as shown in FIGS. 159, 160. Analysis of the obtained data evidences the following pattern of fractionation of the isotopic composition in the tissues affected by the tumor. Tissue samples 20 and 12 characterizing tumor tissues had the following factors of similarity and differences. The similarity consisted in their belonging to the tumor tissues and the difference was in the presence of metastases of poorly differentiated transitional cell carcinoma in sample 20, which characterized this biological sample as an object with a more pronounced degree of damage by cancer.

When analyzing the results of obtained on samples 12 and 14, it can be found that of 20 isotopes detected in these samples represented by magnesium, silicon, potassium, iron, copper, zinc, bromine, rubidium, and silver, the major part, in the amount of 11 isotopes, is characterized as heavy isotopes primarily concentrated in the tissue affected by the tumor (in the "cancer tissue" column in FIG. 157, these isotopes are highlighted in red).

This is in correspondence with the data as shown in FIGS. 155, 157, 158, wherein the content of heavy isotopes in the normal and cancer tissues is shown in red, and the analysis of these results reveals that heavy isotopes is observed in the normal tissue as well. However, the general trend is accumulation of heavy isotopes in the tissue affected by the tumor.

Now let us consider the results obtained on samples 18 and 20. Sample 18 was represented by healthy tissue and sample 20 was a metastasis of poorly differentiated transitional cell carcinoma with extensive necrosis. It should be noted that compared with samples 12 and 14 these samples contained a much larger number of both the elements and isotopes. This can be explained by the man-caused factors of existence of a biological organism as well as by certain selective conditions of accumulation of some elements and their isotopes in a pathological tissue. We have determined that a pair of samples 18 and 20 contained new elements, such as molybdenum, nickel, chromium, chlorine and sulfur, and the list of isotopes found in samples 12 and 14 was considerably expanded and included such isotopes as Zn-68, Zn-64, Fe-57.

If we describe the results obtained on samples 18 and 20 statistically, the following can be concluded. Of the 30 isotopes identified in this pair of samples (which are represented by 11 elements such as magnesium, silicon, sulfur, chlorine, potassium, chromium, iron, nickel, zinc, rubidium, molybdenum) 15 isotopes can be characterized as heavy. According to FIGS. 159, 160, which reflect the results of examination of samples 18 and 20, one can see a predominant increase in the number of heavy isotopes in the tumor tissue affected by metastases as compared to their content in normal tissue. Quantitative assessment of the nature of distribution of light isotopes is bidirectional and consists in the following. A slight increase in the content of light isotopes of such elements as magnesium, sulfur, chlorine, nickel and molybdenum in the healthy tissue relative to their natural distribution (shown in blue) was observed.

As it was noted earlier (in the examination of young and old tissues as well as of samples 12 and 14), an increase in the concentration of heavy isotopes is accompanied by a decrease in the concentration of light isotopes. This is also true for samples 18 and 20. It is important to note a few more facts that characterize the correlation between the concentration of heavy isotopes and a degree of disease of biological tissue. Sample 20 was taken from metastases of poorly differentiated transitional cell carcinoma with extensive necrosis and sample 12—of renal cell carcinoma. From a medical point of view, a metastasis is a recurrence of cancer and it is more dangerous and serious complication for the life of a patient than the primary tumor. The poorly differentiated cancers have the most adverse outcomes. This happens because the tumor overcomes protective barriers and cancer cells get in the lymph and blood stream.

Quantitative assessment of the isotopes detected in samples 12 and 20 indicates an increase in their number (in sample 20) along with an increase in the degree cancer aggressiveness. The range of deviation of isotope concentrations from the one in natural isotope distribution is much higher in sample 20. The maximum deviation from the natural content found on silicon isotopes in sample 20 with an increase in Si29 by 11.6%, while the content of Si28 isotope reduced by 20.6%. Such a difference is expressed less clearly in the pair of samples 12 and 14. The largest increase here was observed in the content of Rb87 isotope which amounted to +8.35% in the tissue affected by tumor, while the largest decrease in the isotopic concentration was found in Mg24 isotope which was −8.1%.

This trend is observed on other elements as well. However, a shift in the distribution towards heavy isotopes is considerably stronger in the pair of samples 18 and 20. Biological tissue affected by cancer cells and metastases has a higher concentration of heavy isotopes while the bordering normal tissue has a lower concentration of light isotopes. Results of mass spectroscopic study of isotopic composition of samples of fungus and cortex. Analysis of the content of trace quantities of isotopes requires prior sample preparation as elements in most objects are in a bound state. They form quite strong organic complexes that prevent accurate and reproducible determination of their content. Therefore, prior to any analysis it is necessary to destroy the organic portion of the sample. Preparation of the samples of fungus and cortex for the analysis was carried out using the dry ashing method. The dry ashing method involves sequential heating of a substance to the ashing temperature in oxygen in a closed system.

Dry ashing of the samples of fungus and cortex was performed in a ceramic crucible placed in a muffle furnace. For the destruction of the organic bond of substances the same quantities of the samples weighed for the analysis (6 grams each) were used. The samples in crucibles were placed in a muffle furnace without protective atmosphere (i.e. in air) at the temperature of 150° C. At this temperature, the samples were heated for one hour and then they were dried step by step by raising the temperature of the furnace by 50° C. every hour. The temperature of the sample was raised in such a mode up to 350° C. (for 4 hours), whereupon it was raised to 360° C. The samples were then held at this temperature for 20 minutes.

Then crucibles with ash were extracted from the furnace and were cooled under the atmospheric conditions to the room temperature. With the same initial masses of fungus and cortex, after completion of the dry ashing procedure the fungus weighed 112 mg while the cortex weighed only 32 mg. The solid residues of the samples of fungus and cortex were pressed in a nickel metal mesh with a mesh size of 50×50 microns. The metal mesh helped to keep the sample material fixed and additionally served as the current collector reducing the amount of static electricity caused by ionization by the ion beam. Information on the isotopic composition of the samples was obtained from the surface area 200×200 mm in size.

Analysis of the samples of fungus and cortex was performed with respect to the following detected elements: magnesium, silicon, potassium, calcium, titanium, iron, copper, zinc, rubidium, strontium. The total number of isotopes found in the samples was 36 isotopes in the 10 detected elements. Quantitative assessment of each isotope was obtained based on the primary analysis of the experimental data characterizing the relationship of mass and impulse response for each of the isotopes.

FIG. 161 show the results of quantitative assessment of the content of isotopes in fungus and birch cortex, and the diagram in FIGS. 161, 162 makes it possible to visually compare the quantitative characteristics of isotopic distribution in fungus and the birch cortex and rings. The following conclusions were made based on the results of our study: In samples from the interior of the tree (birch ring), the natural distribution of isotopes was observed. In the samples prepared from the fungus, the isotopic distribution shifted toward the light isotopes. The concentration of light isotopes was considerably higher and the concentration of heavy isotopes was considerably lower than in the natural distribution.

In the samples prepared from the cortex, surrounding the fungus the isotopic distribution shifted towards an increase in a portion of heavy isotopes and a reduction in the concentration of light isotopes. It should be noted, that the fungus itself is mechanically strong while the cortex around it is in fact quasi-dead tissue with no mechanical strength.

In accordance to modern science, one would never expect any deviations from natural distribution of isotopes for a given element. It does not matter, which object of nature that this element belongs to, and where it is in our universe. For example, potassium is a mixture of two isotopes K-39 (93.3%), K-41 (6.7%) and long-lived radioisotope of K-40 (0.012%). Substitution of one isotope on another may result in the isotope effect—kinetic or magnetic isotope effect, isotopic shift or small variation in the temperature of superconductive transition. Isotope effect should not cause any dramatic changes in chemical properties or structure of materials.

The aforementioned is correct for non-live matter but not for microbes and not for animals and not even for viruses or plants. The results and experimental conditions of detailed study of isotope distribution peculiarities in healthy and pathology affected biological tissues, as well as in "young" and "old" tissues at present stage were obtained on the level of tissue and are not protein or amino acid specific. Never the less said results are very important and allow for new ways of diagnostics, treatment and prevention of irreversible pathologies including cancer and ageing.

Although samples represented different types of cancer or "young" and "old" tissues, the conclusions made have much broader significance, as many pathologies can be discussed in terms of extreme local ageing effects. Notion of immune system should be used not only to describe body's defense against microbes, viruses and other invaders, but also the ability to repair mutation-threatening damage to the most important macromolecules. This function is crucial for irreversible disease prevention and as proved by our data requires uninterrupted critical "spare parts" supply. Said "spare parts" being set of lightest isotopes of vitally important metals. Mass-spectrometry data shows that in healthy tissue of not too young and too old person there is so-called natural distribution of isotopes in complete correspondence with all textbooks. In the tissue from the body of 77 years old, there is a shift in isotope distribution to the side of heavy isotopes.

Concentration of light isotopes in a number of elements is significantly decreased and concentration of heavy isotopes is correspondently increased. Shift of isotope distribution in favor of heavy isotopes was also observed in samples affected by cancer tumor. There is correlation between severity of disease and concentration of heavy isotopes in the tissue. In the sample taken from malignant tumor with well—expressed metastases, concentration of heavy isotopes was much higher and for light isotopes—much lower than in the tissue of malignant tumor without metastases.

In contrast to the "old" and cancer affected samples, in "young" tissue the shift of isotope distribution in the favor of light isotopes was detected with increased concentration of light isotopes and significant decrease in concentration of heavy ones. The difference in concentrations of heavy and light isotopes in healthy and cancer tissues of the same patient depends on progress of the disease and can be higher than tenfold. It is important to notice that as much as light isotopes are spare parts to fix broken chemical bonds back to normal, the heavy isotopes are also spare parts without which dangerous damage to the chemical bonds cannot hold on in time or stabilized and eventually is repaired. It is logical to expect that in right amount light isotopes should be able to rejuvenate biological tissue and transform cells affected by pathology back to normal state. At the same time, one can consider heavy isotopes of the same elements as an efficient and multipotent pathogen or kind of a poison.

At certain concentration, they can cause most of the broken chemical bond to become a source of irreversible pathology. Concentration of light isotopes is also a key to successful treatment of various illnesses. To achieve positive result the amount of "cure" should be much higher than amount of "poison". A lot depends on the damage inflicted by disease. That is why it is inappropriate to speak of one universal dose of "cure" for any disease at any stage. The target is to prevent access of heavy isotopes and provide right amount of light isotopes supply during the treatment time. Otherwise, results will by inconclusive and irreproducible creating uncertainty and confusion. Let us take two examples to demonstrate what happens: one from biotechnology and another from pharmaceutics/folks medicine. First, stem cells treatment. It is proclaimed as possible universal cure and sometime it really helps to some patients with some illnesses. To a few and not always, and no explanation why.

Let us put aside problems related to the reaction of immune system on the alien stem cells infusion. Then stem cells should be able to help healthy organism to become stronger due to the regenerative ability and theoretical possibility to differentiate and substitute damaged cells of various organs. It is necessary to add—given there is sufficient supply of key light isotopes to the tissue or organ under discussion. Otherwise, the lack of light isotopes and excess of heavy ones may cause transformation of stem cells into cancer cells. Stem cells are definitely "young". Therefore, their positive effect can be attributed to the fact that they contain higher that natural concentration of light isotopes.

Here we speak of ratio between light and heavy isotopes. Absolute amount of light isotopes in stem cells is very low. In general, stem cells can be considered as source and carriers of very low quantities of light isotopes. It is better than nothing and sometime even helpful, but it is difficult to predict when. Second example is birch tree mushrooms—"chaga". It is believed to be a "virtual cocktail of antioxidants and phytonutrients" able to bust immune system, reduce inflammation and eliminate cancer. It was used for many centuries as folk medicine with universal properties. Nobel Prize winner Alexander Solzhenitsyn believed he was cured from cancer with chaga and described the story in his famous book "The Cancer Ward". Yet, there is no solid data or statistics to support the legend. They say taking chaga tea over a long period is extremely beneficial. It is probably true. At the same time, nobody dares even to speculate on probability to cure any disease, let alone cancer, with chaga in less than a lifetime.

To figure out the nature of legendary claims on chaga properties we have conducted mass-spectrometry study of samples prepared from chaga mushroom, surrounding bark and birch rings (inner volume of the tree). Results should help to understand real reasons of biological activity for not only chaga, but other folk recipes as well. Chaga mushroom appeared to have a really unique and unheard feature—isotope selectivity. Like in the young human tissue, the isotope distribution is different from the natural one with much higher concentration of light isotopes and lower concentration of heavy isotopes in chaga samples, reverse picture (like in cancer affected tissues) in surrounding bark and natural distribution deep inside birch rings/trunk. They believe that birch tree host gradually dies of due to the mushroom consuming all nutrients from the bark and trunk. At the same time, nothing is preventing additional supply from the root system.

The real problem is the constant excess of heavy isotopes over light ones in the bark and trunk around the mushroom. That is what kills healthy tissue. Chaga contains up to 30% higher concentration of light isotopes of vitally important metals like K, Zn, Mg and Rb. There is a significant shift in isotope distribution but heavy isotopes are still present although in a smaller amounts. We have also discovered that light isotopes spread not equally over the samples. It means that there are areas in mushroom cross-section with no light isotopes at all. Hence, seemingly random biological activity of chaga extracts can be explain by Competition between effects of higher than normal amount of light isotopes and less than normal but still significant presence of heavy isotopes.

Hundreds to thousands times smaller quantities of light isotopes compared to the daily intake of vital elements. Non-homogeneous distribution of chemical elements in the bulk of mushroom. It means that quite often extracts are made from chaga's parts that do not contain any useful elements at all. Chaga's extract consumer should be lucky enough to have multiple random events to coincide to get theoretically possible therapeutic effect.

In Vivo Experiments with Ascites

The term "malignant ascites" is understood as a pathological accumulation of fluid in the peritoneal or pleural cavity, which develops as a result of tumor damage to the peritoneum or lungs. Malignant ascites can be caused by a variety of primary tumors, such as, for example, breast cancer, ovarian cancer or gastrointestinal carcinomas.

The present inventors have unexpectedly found that the agent comprising a light zinc isotope, $^{64}Zn$ in particular, as an aspartate or asparaginate, as well as the method which comprises administration of such agent containing $^{64}Zn$ as an aspartate or asparaginate at doses from 350 μg $^{64}Zn_e$ to 461 μg $^{64}Zn_e$ via intraperitoneal injection, suppress the development of malignant ascites. The intraperitoneal injection of this agent produces a pronounced inhibitory effect on the development of cancers causing ascites, mouse leukemia and mouse breast cancer (Ehrlich ascites carcinoma) in particular, and improves survival in the studies in model mouse systems.

In the experiments on mice, a high antitumor activity of the $^{64}Zn_e$ active ingredient was demonstrated with its direct effect on tumor cells, for example, in ascitic fluid.

Light isotope-enriched elements as enumerated above, including $^{64}Zn_e$, can be formulated in a variety of dosage forms depending on the object of use, in particular as solutions for injections, ointments, and the like. In a preferred embodiment of this invention, the composition for suppression of malignant ascites further comprises agents that promote penetration of the active substance into cells, for example DMSO. According to one preferred embodiment of the method for suppression of the development of the malignant ascites, the composition of the invention, such as one comprising $^{64}Zn_e$, is administered intraperitoneally and/or intravenously. It is preferred that the administration be intraperitoneal.

The studies conducted in mice suggest that the antitumor effect of the $^{64}Zn_e$ compound is probably due not to the direct cytotoxic effect of the drug on tumor cells but indirect one, possibly through the inhibition of proliferation and the activation of nonspecific immunity, as the percentage of dead tumor cells in ascites which were exposed to the action of the agent according to the invention does not exceed 5%. This is also evidenced by a complete absence of acute toxicity for mice with complete inhibition of tumor growth.

The main advantage of the proposed method is that its use does not cause toxic effects, as is characteristic of most methods based on the use of known cytostatic agents, and, due to the important physiological role of the substances used in the method, it, in addition to antitumor activity, provides a number of additional advantages, associated with the optimization of the catalytic, structural and regulatory functions of these elements in the body. It should also be noted that the activity of the $^{64}Zn_e$ compound for suppressing the development of malignant ascites is not inferior to that of known cytostatics.

An aspect of the present invention is described more fully hereinafter by reference to the following examples, which are presented by way of illustration only and should not to be construed to in any way limit the scope of the present invention.

A pilot study to evaluate the efficacy of the light isotope compositions and method of using them to suppress the development and treatment of malignant ascites in humans has also been conducted.

EXAMPLES

Example 6. Zinc (Zn-64) and Aspartic Acid Complex Production Process

Preparation Process of $^{64}Zn_e$ Aspartate $^{64}Zn_e$ aspartate (racemic) having the following formula (in which "$^{64}Zn^{2+}$" refers, in this one instance, to $Zn^{2+}$ enriched for $^{64}Zn$) was prepared in the experiment.

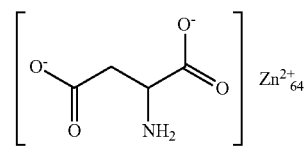

At the first stage, zinc oxide enriched for $^{64}Zn$ was prepared using $^{64}Zn_e$ sulfate as the starting compound.

$$^{64}Zn_eSO_4 + 2NaHCO_3 \rightarrow {}^{64}Zn_eO + Na_2SO_4 + 2CO_2 + H_2O$$

For this purpose, $^{64}Zn_e$ sulfate (zinc was at least 99.9% $^{64}Zn$, although $^{64}Zn_e$ of lower purity may be effective) in an amount of 0.01 mole) was dissolved in 150 ml of water (T=50-70° C.) wherein 1.68 g (0.02 mole) of sodium bicarbonate was added in small portions, to prevent severe foaming, with constant stirring in a magnetic stirrer. After completion of foaming the solution was stirred for another 30 minutes and then left for 1 hour until a white precipitate was formed. During this process, the temperature was maintained at about 60° C. to prevent crystallization of sodium sulfate. The solution with the precipitate, which precipitate was $^{64}Zn_eO$, was then filtered without cooling. The resulting precipitate—$^{64}Zn_eO$—was washed with warm demineralized water (T=40-50° C.) and dried to constant weight in a desiccator over the dehydrating agent phosphorus pentoxide.

After that, 425 ml of demineralized water was poured into a 1 liter flask and heated under reflux to 80° C. 1.33 g (0.01 mole) of aspartic acid was dissolved in water with stirring by a magnetic stirrer. After aspartic acid was completely dissolved, 0.8 g (0.01 mole) of $^{64}Zn_eO$ obtained at the previous stage was added to the clear solution. The mixture was stirred with heating to 80° C. for 1½-2 hours till complete dissolution of $^{64}Zn_eO$. The reaction formula is shown below:

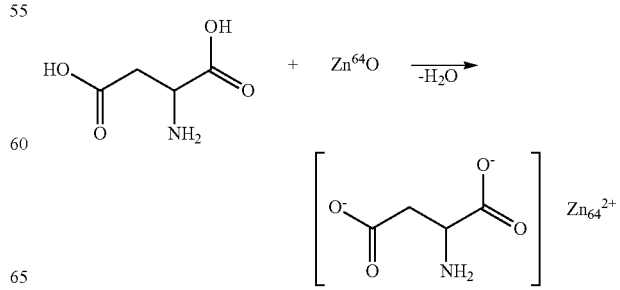

If the precipitate ($^{64}Zn_e$ oxide) was not dissolved completely, the solution was filtered and the undissolved $^{64}Zn_eO$ was collected and dried to its constant weight to determine the $^{64}Zn_e$ complex concentration in the resulting solution. The solution was transferred into a volumetric measure and made up to a volume of 425 ml using demineralized water. 425 ml of $^{64}Zn_e$—aspartic acid complex containing $^{64}Zn_e$ in the amount of approximately 0.0015 g $^{64}Zn_e$ (1.5 mg $^{64}Zn_e$)/ml was thus prepared.

In Vivo Experiments

Unless stated clearly otherwise, in the $^{64}Zn$-enriched zinc aspartate (referred to as "$^{64}Zn_e$ aspartate") that is used in examples 7-9, the zinc is 98.73% $^{64}Zn$. Also, dosage amounts of $^{64}Zn_e$ aspartate expressed in µg/mouse indicates the amount of $^{64}Zn_e$. For example, "75 µg/mouse" of $^{64}Zn_e$ aspartate indicates 75 µg of $^{64}Zn_e$ per mouse. The solutions of $^{64}Zn_e$ aspartate consisted of $^{64}Zn_e$ aspartate dissolved in deuterium-depleted water.

In order to confirm the efficacy of the method of the present invention in suppressing the development of malignant ascites, in vivo studies were performed using a mouse model.

All studies were performed in compliance with the rules of the European Convention for the Protection of Vertebrate Animals Used for Experimental and Scientific purposes [Commission of the European Communities: Council Directive of 18 Dec. 1986 on the Lows, regulating the Application of Principles of Good Laboratory Practice and the Verification of Their Applications for Tests on Chemical Substances (87/18/EEC). The Rules Governing Medicinal Products in the European Community.—1991.—V. 1.—P. 145-146].

The research institution followed the requirements of the plan approved by the Customer and standard operating procedures (SOPs) of the laboratory. The test material was handled in accordance with standard safety rules: the personal protective equipment (gloves, mask and white coat) was worn, the Material Safety Data Sheet (MSDS) was available to the staff and the staff was informed of the potential risks and protective equipment before starting work.

The animals were managed in accordance with the standards set forth in The Guide for Care and Use of Laboratory Animals (ILAR publication, 1996, National Academy Press, 1996). All procedures with experimental animals were reviewed for their compliance with the ethical principles of scientists working with animals and approved by the Bioethics Commission at R.E. Kavetsky IEPOR NAS of Ukraine. The animals were kept in plastic cages with the bedding; the cages were equipped with steel latticed lids and feeding niches. Commercial material, such as ecologically clean hardwood chips, was used as the bedding and the routine checks of the bedding for its compliance with the technical requirements were performed. Characteristics: the chips were of different shapes, 5-20 mm long and 2-1 mm thick, the maximum moisture content was 12%, the chips did not contain any harmful impurities such as heavy metals, pesticides, herbicides or insecticides. A standard pelleted diet for laboratory animals K-12-4 PP "REZON-1", (Ukraine) was used. The diet consisted of basic food ingredients, vitamin and mineral additives. This diet is subject to a regular quality control and the content of food components by the manufacturer. The diet samples were regularly tested for microbiological contamination. The animals were managed under controlled environmental conditions (21-26° C. and the relative humidity in the range of 30 to 60%). The temperature and humidity were constantly monitored. A 12 hour light cycle was maintained in the rooms where the animals were managed. The animals were identified by cage numbers.

Procedure of drug administration: the agent solutions were injected intraperitoneally in the right inguinal region or intravenously in the lateral tail vein using Micro-Fine Plus microinjection syringe (Becton Dickinson). The injection site was pretreated with 96% ethanol.

Clinical observations: daily inspections of all the animals in cages were carried out in order to determine mortality or any signs of deviations in their health status. A thorough examination was performed each time any abnormalities were detected. All deviations were recorded. The tumor size was measured every 2 days (3 times a week) after the start of visible ascites/tumor node growth (the $8^{th}$ day after tumor cell inoculation).

Terminal procedures and pathomorphology: if an animal died in the studies, the time of its death was determined and recorded, the animal was weighed and subjected to necropsy (without organ retrieval). Dying animals were euthanized, weighed and necropsied.

Descriptive statistics was applied to all the quantitative data: the mean value and standard error of the mean were calculated which are, along with the N value, shown in the summary tables. To determine the reliability of the inter-group differences, the data were analyzed by parametric or nonparametric tests depending on the quantitative data distribution type. The differences were determined at 0.05 significance point.

Example 7. Studies Supporting the Efficacy of a Light Isotope-Enriched Compound and Method Performed in In Vivo Experiments Using a Mouse Model of Breast Cancer (Ehrlich Ascites Carcinoma)

10 male outbred mice (5 mice per group) at the age of 10 weeks, weighing 19-23 g were used in Ehrlich ascites carcinoma (EAC) model. Before the experiment, all the animals were healthy, with normal behavioral performance. During the experiment, the animals were kept in plastic cages under natural light illumination, on a standard diet with free access to food and water. An ascites strain of mouse breast cancer (EAC) maintained in outbred mice was used in the experiment. To inoculate the strain, the tumor cells derived from the ascitic fluid were placed in saline solution. The suspension cellularity was evaluated in the hemocytometer and adjusted to a concentration of $1 \times 10^6$ cells/ml with saline solution. The tumor was transplanted by injecting 250 µl of the tumor cell suspension ($0.25 \times 10^6$ cells/mouse) into the abdominal cavity of the animals.

The animals were divided into groups as follows:

Group No 1—control group, mice with EAC+solvent (deuterium-depleted water (this water contains deuterium at a level of 10 ppm));

Group No 2—mice with EAC+$^{64}Zn_e$ aspartate.

The solution comprising $^{64}Zn_e$ aspartate was injected intraperitoneally using a microinjection syringe at a dose of 0.075 mg (75 µg)/mouse every other day (5 times during 10 days) starting from the first day after injection in a volume of 0.5 ml/mouse. The dynamics of tumor growth in the experimental animals was observed for 13 days following the i.p. inoculation of tumor cells (by the volume of ascites in the peritoneal cavity). On the 13th day after i.p. inoculation of tumor cells, the whole ascites fluid was recovered from the animals and the total number of live/dead cells in each mouse was determined. Deuterium-depleted water alone was used instead of a solution of $^{64}Zn_e$ aspartate as control in the experiment.

The dynamics of formation of ascites in the control and experimental groups was assessed visually using a 10-point scale (one point was 0.46 cm of the mean diameter of the mouse abdomen filled with ascites).

In addition, on the 13$^{th}$ day after intraperitoneal inoculation of tumor cells, all ascetic fluid was removed from the abdomens in all animals from each group by washing their peritoneal cavities with saline solution and live and dead tumor cells were counted using the traditional vital dye trypan blue (HyClon, USA) and a hemocytometer.

The number of cells was determined using the following formula:

$$X = ((a)/80) \times 10^6,$$

where X is the number of cells in 1 ml and a is the number of cells counted in 80 small squares of the hemocytometer.

The data on the dynamics of accumulation of ascites in the experimental animals and lifespan of mice in the in vivo experiment were used to assess anticancer activity of $^{64}Zn_e$ aspartate against mouse model of breast cancer. The results of the studies are presented in Tables 1-2.

TABLE 1

Ehrlich carcinoma growth dynamics (analysis of changes in the volumes of ascites in laboratory animals)

| Group of experimental animals | Day after inoculation of tumor cells | | | |
|---|---|---|---|---|
| | 7 | 9 | 11 | 13 |
| | Volume of ascites in mice (points) | | | |
| EAC control | 2.8 ± 0.6 | 6.3 ± 0.5 | 8.1 ± 1.1 | 9.4 ± 0.6 |
| EAC + $^{64}Zn_e$ aspartate | 0* | 0** | 0* | 0** |

*p < 0.02,
**p < 0.002 as compared with the control group

The data analysis shows that the agent according to the invention containing $^{64}$Zn-enriched zinc as aspartate exhibits significant antitumor activity against Ehrlich ascites carcinoma in mice. Thus a series of 5 i.p. injections of the agent at a dose of 75 µg/mouse statistically reliably suppressed the growth of ascites in animals, in comparison with the control group.

The data on counting the number of live and dead cells in the ascites of the experimental animals correlated with the results described above. Thus, at day 13 of the experiment, the absence of ascitic fluid was noted in the abdominal cavities of the animals of the therapeutic group, in contrast to the control (4±0.9 ml) (Table 2). The absence of live tumor cells in the abdominal cavities of the mice of the experimental group was also noted (Table 2).

TABLE 2

Total number of cells in the ascites at day 13 after inoculation of EAC cells

| Group of experimental animals | Number of live cells/mouse (M ± m) | Number of dead cells/mouse | Volume of ascites (M ± m), ml/mouse |
|---|---|---|---|
| EAC control | 1.05 ± 0.2 × 10$^9$ | Less than 2% | 4 ± 0.9 |
| EAC + 64Zne aspartate, 75 µg/mouse | 0* | 0 | 0* |

*p < 0.05 as compared with the control group

The data show that the composition comprising $^{64}Zn_e$ aspartate suppressed the growth of Ehrlich ascites carcinoma in the experimental mice by 100%, after 5 injections of the agent. Thus, at day 13 of the experiment, the absence of ascitic fluid was noted in the abdominal cavities of the animals of the therapeutic group, in contrast to the control (4±0.9 ml) (Table 2). The absence of live tumor cells in the abdominal cavities of the mice of the experimental group was also noted (Table 2).

This indicates that the agent comprising $^{64}Zn_e$ aspartate, as well as the method that provides five-time intraperitoneal administration of the said agent, ensures complete suppression of the growth of the experimental ascetic tumor in the in vivo experiment on EAC model.

Example 8. Toxicological Study of the Agent According to the Invention for Acute Toxicity In the experiment, the acute toxicity effects of the $^{64}Zn_e$ composition were assessed and the tolerated dose of the $^{64}Zn_e$ compound included in the composition was determined.

To this end, the effects of the agent according to the invention on the basic physiological functions of healthy animals were studied. 70 male $C_{57}Bl/6J$ mice at the age of 7-8 weeks, weighing 18-23 g were used in the experiment. The animals were taken from R.E. Kavetsky IEPOR NASU Vivarium. Before the experiment, all the animals were healthy, with normal behavioral performance. During the experiment, the animals were kept in plastic cages under natural light illumination, on a standard diet with free access to food and water.

Clinical observations were carried out by daily examination of all animals kept in cages to identify mortality or any signs of a deviation in health status. When revealing deviations, a thorough examination was carried out. All deviations were recorded. The size of the tumors was measured every 2 days (3 times a week) after the apparent onset of ascites/tumor node growth (at day 8 after the inoculation of tumor cells). Dying animals were euthanized, weighed and necropsied. The decision to euthanize such animals was taken jointly with the research supervisor and veterinarian. The animals were subjected to complete necrosis, which included examination of the external surface of the body, all passages, cranial, thoracic, abdominal cavities and their contents.

In the experiment, the animals were administered the solution comprising $^{64}Zn_e$ aspartate intraperitoneally at doses of 120 µg/mouse, 80 µg/mouse, 50 µg/mouse and 25 µg/mouse, and intravenously at doses of 50 µg/mouse, 25 µg/mouse and 12.5 µg/mouse. The agent was dissolved in deuterium-depleted water and injected 7 times every other day for 14 days in a volume of 0.5 ml/mouse for intraperitoneal injection and in a volume of 0.2 ml for intravenous injection with the agent. In order to determine the maximum tolerated dose of $^{64}Zn_e$ aspartate included in the composition of the agent according to the invention, the laboratory mice were injected with the $^{64}Zn_e$ aspartate solution using a series of injections (7 injections) and different routes of administration (i.p. or i.v.). The animals were observed during 24 days after the first administration of the agent (14 days for a series of injections of the $^{64}Zn_e$ compound and 10 days after the last administration of the agent). The overall health of the animals, state of coat and mucous membranes, their behavior, reflexes, and basic functions of the gastrointestinal tract were evaluated. The data obtained are presented in Table 3.

TABLE 3

Assessment of the overall health of the experimental animals during 24 days of the experiment

| Group of experimental animals | General condition of the experimental animals |
|---|---|
| Control | 100% of the animals in the group are alive. Locomotor activity is normal. Behavioral reactions are normal. No signs of lethargy, weakness, convulsions, paralysis, cyanosis, hypersalivation, diarrhea, vomiting, bleeding, urination disorders are observed. Condition of the coat and visible mucous membranes is normal. Respiratory activity is not impaired. |
| +$^{64}Zn_e$ aspartate administered i.p. at a dose of 120 μg/mouse | 100% of the animals in the group died within 48 hours after the first injection. Locomotor activity was impaired. Lethargy, weakness, convulsions, paralysis were observed. Respiratory activity was impaired. |
| +$^{64}Zn_e$ aspartate administered i.p. at a dose of 80 μg/mouse | 80% of the animals in the group are alive. Some changes in the behavior of animals, such as flaccidity, were observed during 60 min. after each injection of the agent. Later the general condition of mice returned to normal. Further, the behavioral responses were normal: no signs of lethargy, weakness, convulsions, paralysis, cyanosis, hypersalivation, vomiting, bleeding or urination disorders were observed. Locomotor activity was normal. Condition of the coat and visible mucous membranes was normal. Respiratory activity was not impaired. It should be noted that a short-lasting diarrhea was observed in 40% of the animals in the group 18-24 hours after administration of the agent. 20% of the animals in the group died after 4 or 5 injections with $^{64}Zn_e$ aspartate (on the $8^{th}$ or $10^{th}$ day after the first injection). |
| +$^{64}Zn_e$ aspartate administered i.p. at a dose of 50 μg/mouse | 100% of the animals in the group are alive. Locomotor activity is normal. Behavioral reactions are normal. No signs of lethargy, weakness, convulsions, paralysis, cyanosis, hypersalivation, diarrhea, vomiting, bleeding, urination disorders are observed. Condition of the coat and visible mucous membranes is normal. Respiratory activity is not impaired. |
| +$^{64}Zn_e$ aspartate administered i.p. at a dose of 25 μg/mouse | 100% of the animals in the group are alive. Locomotor activity is normal. Behavioral reactions are normal. No signs of lethargy, weakness, convulsions, paralysis, cyanosis, hypersalivation, diarrhea, vomiting, bleeding, urination disorders are observed. Condition of the coat and visible mucous membranes is normal. Respiratory activity is not impaired. |
| +$^{64}Zn_e$ aspartate administered i.v. at a dose of 50 μg/mouse | 100% of the animals in the group died within 10-20 minutes after the first injection. Locomotor activity was impaired. Lethargy, weakness, convulsions, paralysis were observed. Respiratory activity was impaired. |
| +$^{64}Zn_e$ aspartate administered i.v. at a dose of 25 μg/mouse | 100% of the animals in the group are alive. Locomotor activity is normal. Behavioral reactions are normal. No signs of lethargy, weakness, convulsions, paralysis, cyanosis, hypersalivation, diarrhea, vomiting, bleeding, urination disorders are observed. Condition of the coat and visible mucous membranes is normal. Respiratory activity is not impaired. |
| +$^{64}Zn_e$ aspartate administered i.v. at a dose of 12.5 μg/mouse | 100% of the animals in the group are alive. Locomotor activity is normal. Behavioral reactions are normal. No signs of lethargy, weakness, convulsions, paralysis, cyanosis, hypersalivation, diarrhea, vomiting, bleeding, urination disorders are observed. Condition of the coat and visible mucous membranes is normal. Respiratory activity is not impaired. |

As a result, the maximum tolerated doses of the $^{64}Zn_e$ aspartate composition for different routes of administration were selected when 100% of the animals remained alive for 24 days (from the moment of the first administration of the agent) showing no signs of intoxication. The maximum tolerated dose of the composition comprising $^{64}Zn_e$ aspartate administered intravenously was 25 μg/mouse while for intraperitoneal administration it was 80 μg/mouse.

During the study of tolerability of the doses of the agent comprising $^{64}Zn_e$ aspartate used in the experiment, the effect of the injected agent on the weight of the laboratory mice was also assessed. The data are presented in Table 4.

TABLE 4

Changes in the weight of experimental animals after administration of the agent comprising $^{64}Zn_e$ compounds

| | Day of experiment | | | | | | | |
|---|---|---|---|---|---|---|---|---|
| Group | 0 | 2 | 4 | 8 | 11 | 15 | 19 | 24 |
| Control | 21.8 ± 0.3 | 20.8 ± 0.4 | 20.3 ± 0.5 | 21.1 ± 0.5 | 21.3 ± 0.6 | 20.8 ± 0.6 | 21 ± 0.5 | 21.2 ± 0.4 |
| +$^{64}Zn_e$ | 21.4 ± 0.4 | 20.5 ± 0.5 | 17.3 ± 0.2** | 17.5 ± 0.1*** | 17.3 ± 0.1*** | 16.5 ± 0.1*** | 17.2 ± 0.2*** | 17.6 ± 0.1*** |

TABLE 4-continued

Changes in the weight of experimental animals after administration of the agent comprising $^{64}Zn_e$ compounds

| Group | Day of experiment | | | | | | | |
|---|---|---|---|---|---|---|---|---|
| | 0 | 2 | 4 | 8 | 11 | 15 | 19 | 24 |
| aspartate administered i.p. at a dose of 80 μg/mouse | | | | | | | | |
| +$^{64}Zn_e$ aspartate administered i.p. at a dose of 50 μg/mouse | 21.3 ± 0.5 | 20.4 ± 0.4 | 19.2 ± 0.6 | 19.8 ± 0.7 | 19.5 ± 0.8 | 19 ± 0.6 | 19.2 ± 0.7 | 20 ± 0.5 |
| +$^{64}Zn_e$ aspartate administered i.p. at a dose of 25 μg/mouse | 21.1 ± 0.5 | 20.1 ± 0.3 | 18.3 ± 0.7 | 18.4 ± 1 | 18.2 ± 0.9* | 19.2 ± 0.5 | 19.8 ± 0.4 | 20.5 ± 0.6 |
| +$^{64}Zn_e$ aspartate administered i.v. at a dose of 25 μg/mouse | 21.8 ± 0.3 | 21.3 ± 0.5 | 20.8 ± 0.5 | 21.4 ± 0.5 | 21.4 ± 0.5 | 21.3 ± 0.6 | 21.7 ± 0.4 | 21.6 ± 0.5 |
| +$^{64}Zn_e$ aspartate administered i.v. at a dose of 12.5 μg/mouse | 21.1 ± 0.4 | 20.9 ± 0.3 | 20.2 ± 0.5 | 20.6 ± 0.9 | 20.6 ± 1 | 20.9 ± 0.9 | 21 ± 0.7 | 21.1 ± 0.8 |

*$p < 0.05$,
**$p < 0.005$,
***$p < 0.001$ as compared with the control group.

The data in Table 4 show that administration of the agent comprising $^{64}Zn_e$ isotope as aspartate resulted in insignificant changes in weight of the experimental animals. At the same time, there is a statistically significant ($p<0.001$) tendency to loss in the full body weight of the animals that received i.p. treatment with $^{64}Zn_e$ aspartate at a dose of 80 μg/mouse. In this group, the body weight loss by 15-20%, compared to the control figures, was observed in the mice already on the 4$^{th}$ day after the first injection with the agent. It can be assumed that administration of $^{64}Zn_e$ aspartate at a dose of 80 μg/mouse leads to disruption of certain biochemical processes in mice.

Example 9. Studies Supporting the Efficacy of the $^{64}Zn_e$ Aspartate Composition and Method Performed in In Vivo Experiments Using Mouse L1210 Leukemia Model The efficacy of the $^{64}Zn_e$ aspartate composition with respect to growth and metastatic activity of the experimental tumor (strain of mouse L1210 leukemia) was assessed in the experiment. Ascitic leukemic cells, strain L1210, obtained from Bank of Cell Lines from Human and Animal Tissues, R.E. Kavetsky IEPOR NAS of Ukraine, and maintained in DBA$_2$ mice were used in the experiment. To inoculate the strain, tumor cells derived from ascitic fluid were placed in normal saline solution, the cellularity of suspension was determined using a hemocytometer and adjusted to a concentration of 1×10$^6$ cells/ml with saline solution. The tumor was transplanted by injecting 250 μl of the tumor cell suspension (0.25×10$^6$ cells/mouse) into abdominal cavities of the animals.

80 male BDF$_1$ mice at the age of 8-10 weeks, weighing 18-22 g were used in the experiment. The animals were taken from R.E. Kavetsky IEPOR NASU Vivarium. Before the experiment, all the animals were healthy, with normal behavioral performance. During the experiment, the animals were kept in plastic cages under natural light illumination, on a standard diet with free access to food and water.

In the experiment, 0.25×10$^6$ cells of mouse L1210 leukemia in 0.3 ml of saline solution were injected in the peritoneal cavities of the BDF$_1$ mice. The agent according to the invention was dissolved in deuterium-depleted water (deuterium-depleted water Langvey) and given to the experimental animals from the first day after the inoculation of the tumor cells. The solution composition comprising $^{64}Zn_e$ aspartate and deuterium-depleted water was injected intraperitoneally using a microinjection syringe at doses of 25 μg/mouse, 50 μg/mouse and 75 μg/mouse every other day (7 times during 14 days) in a volume of 0.5 ml/mouse. The said agent was also injected intravenously at a dose of 25 μg/mouse every other day (7 times during 14 days) in a volume of 0.2 ml/mouse. The dynamics of tumor growth in the experimental animals was observed for 60 days (by the volume of ascites in the peritoneal cavity). At day 8, 13 and 18 after i.p. inoculation of tumor cells, the whole ascites fluid was recovered from the animals and the total number of live/dead cells in each mouse was determined. Some mice were also used to evaluate their average life span in the experiment.

Clinical observations were carried out as described in Example 7.

The animals were divided into groups as follows (16 mice per group):

1. Group No 1: control group, L1210+solvent (deuterium-depleted water);
2. Group No 2: L1210+$^{64}$Zn$_e$ aspartate administered i.v. at a dose of 25 μg/mouse;
3. Group No 3: L1210+$^{64}$Zn$_e$ aspartate administered i.p. at a dose of 25 μg/mouse;
4. Group No 4: L1210+$^{64}$Zn$_e$ aspartate administered i.p. at a dose of 50 μg/mouse;
5. Group No 5: L1210+$^{64}$Zn$_e$ aspartate administered i.p. at a dose of 75 μg/mouse.

$^{64}$Zn$_e$ aspartate was diluted in deuterium-depleted water and injected, starting from the first day of the tumor transplantation, 7 times every other day during 14 days in a volume of 0.5 ml/mouse using an i.p. route of administration and in a volume of 0.2 ml/mouse using an i.v. route of administration. The animals of the control group received intraperitoneal injections with 0.5 ml/mouse of deuterium-depleted water.

The dynamics of tumor growth in the experimental animals was observed for 60 days following the inoculation of tumor cells (by the volume of ascites in the peritoneal cavity). The dynamics of formation of ascites in the control and experimental groups was assessed visually using a 10-point scale (one point was 0.5 cm of the mean diameter of the mouse abdomen filled with ascites).

In addition, at 8, 13 and 18 days after the mice were inoculated with the tumor cells, all ascitic fluid was removed from the abdomens in all animals from each group by washing their peritoneal cavities with saline solution and live and dead tumor cells were counted using the traditional vital dye trypan blue (HyClon, USA) and a hemocytometer. The number of cells was determined using the following formula:

$$X = ((a)/80) \times 10^6,$$

where X is the number of cells in 1 ml and a is the number of cells counted in 80 small squares of the hemocytometer.

50% of the mice in each group were used to assess their average length of survival in the experiment. The percentage change in the lifespan of the experimental animals was calculated using the following formula: $(c-d)/c \times 100$, where: c is the average lifespan in the experimental group and d is the average lifespan in the control group. The total time of observation of the lifespan of the experimental animals was 60 days after the tumor inoculation.

To assess the significance levels of differences in average values between the groups, the Student's t-test and non-parametric Mann-Whitney U test were applied. Calculations were performed using Statistica 6.0 software package.

As a result of in vivo experiment on the assessment of antitumor activity of the solution of $^{64}$Zn$_e$ aspartate in deuterium-depleted water, the following data on the dynamics of ascites growth in experimental animals were obtained in the mouse L1210 leukemia model:

TABLE 5

Dynamics of L1210 leukemia growth (analysis of changes in the volumes of ascites in laboratory animals)

| Group of experimental animals | Day after inoculation of tumor cells (Volume of ascites in mice, points) | | | | | | | | |
|---|---|---|---|---|---|---|---|---|---|
| | 8 | 10 | 13 | 15 | 18 | 20 | 22 | 26 | 28 |
| L1210 control | 2.5 | 4.7 ± 0.2 | 8.6 ± 0.3 | 10 | — | — | — | — | — |
| L1210 + $^{64}$Zn$_e$ aspartate administered i.v. at a dose of 25 μg/mouse | 3.3 ± 0.3** | 4.7 ± 0.4 | 7.7 ± 0.4 | 9.7 ± 0.3 | 8 ± 0.9 | 10 | — | — | — |
| L1210 + $^{64}$Zn$_e$ aspartate administered i.p. at a dose of 25 μg/mouse | 0.6 ± 0.3* | 1.1 ± 0.5* | 2.5 ± 0.6* | 4.1 ± 1.1* | 4.8 ± 1.4 | 4.6 ± 1.8 | 3.5 ± 2.2 | 2.5 ± 2.5 | 0 |
| L1210 + $^{64}$Zn$_e$ aspartate administered i.p. at a dose of 50 μg/mouse | 0* | 0* | 0.4 ± 0.2* | 1.3 ± 0.7* | 1.1 ± 1.1 | 0 | 0 | 0 | 0 |
| L1210 + $^{64}$Zn$_e$ aspartate administered i.p. at a dose of 75 μg/mouse | 0* | 0* | 0.4 ± 0.4* | 1 ± 1* | 1.1 ± 1.1 | 0 | 0 | 0 | 0 |

*$p < 0.001$,
**$p < 0.02$ as compared with the control group.

The analysis of data in Table 5 shows that the solution comprising $^{64}$Zn$_e$ aspartate and deuterium-depleted water, at dosages selected for the study, suppresses L1210 leukemia cell growth significantly only when administered intraperitoneally. A series of intravenous injections with the same $^{64}$Zn$_e$ aspartate solution produced no effect on the growth of mouse leukemia L1210 cells. It should be noted that both in the control and in the experimental groups, where animals received i.v. or i.p. injections with a $^{64}$Zn$_e$ aspartate at a dose of 25 μg/mouse, the growth of tumor cells was already recorded at day 8 after the tumor inoculation. However, in the groups where mice were injected with 50 μg/mouse or 75 μg/mouse of the agent, the ascites growth was recorded only on the 13$^{th}$ day in the experiment (Table 5).

It was also shown that increasing the dose of the $^{64}$Zn$_e$ aspartate led to enhancement of its antitumor activity (Table 5). Thus at day 15 after the tumor inoculation, while the amount of ascites in all mice in the control group reached the maximum value (10 points), in the group where mice received i.p. treatment with $^{64}Zn_e$ aspartate at a dose of 25 µg/mouse the amount of ascites was 60% (4.1 points) less, and in the groups where the experimental animals were injected with 50 µg and 75 µg of the $^{64}Zn_e$ aspartate solution, the amount of ascites was 87% (1.3 points) and 90% (1 point) less respectively.

The data on the number of live and dead cells in the ascites harvested from the peritoneal cavities of the experimental animals were correlated with the described above results. Thus at day 8 and day 13 after the inoculation of tumor cells, no ascites in the peritoneal cavities of animals in the therapeutic group treated with the agent comprising $^{64}Zn_e$ aspartate at the doses of 50 µg/mouse or 75 µg/mouse was observed, in contrast to the control group (Tables 6, 7). Moreover, the absence of live tumor cells in the peritoneal cavities of mice of these experimental groups was recorded (Tables 6, 7). It should be noted that the data presented in Table 6 show that the composition comprising $^{64}Zn_e$ aspartate suppresses the growth of L1210 leukemia cells after 3 injections, as a statistically significant decrease in the number of live cells, by 100%, in the peritoneal cavities of mice in the experimental group where animals received the agent comprising $^{64}Zn_e$ aspartate at the doses of 50 µg/mouse or 75 µg/mouse was observed.

TABLE 6

Total number of cells in the ascites at day 8 after inoculation of L1210 cells

| Group of experimental animals | Number of live cells/mouse (M ± m) | Number of dead cells/mouse (M ± m), % | Volume of ascites (M ± m), ml/mouse | Remarks |
|---|---|---|---|---|
| L1210 control | 659.4 ± 37.8 × $10^6$ | below 2 | 1.5 ± 0.3 | — |
| L1210 + $^{64}Zn_e$ aspartate administered i.v. at a dose of 25 µg/mouse | 902 ± 169 × $10^6$ | below 2 | 1.2 ± 0.3 | — |
| L1210 + $^{64}Zn_e$ aspartate administered i.p. at a dose of 25 µg/mouse | 335.8 ± 335.8 × $10^6$ | below 2 | 0.8 ± 0.8 | Of 2 mice in this experimental group from which ascites was removed, the presence of fluid with tumor cells was observed in one mouse. Moreover, the number of cells in the ascites of this mouse was at the level of control indicators (671.6 × $10^6$). No fluid or tumor cells in the peritoneal cavity of the other mouse were observed. |
| L1210 + $^{64}Zn_e$ aspartate administered i.p. ata dose of 50 µg/mouse | 0** | 0 | 0* | — |
| L1210 + $^{64}Zn_e$ aspartate administered i.p. at a dose of 75 µg/mouse | 0** | 0 | 0* | — |

*$p < 0.05$,
**$p < 0.005$ as compared with the control group

TABLE 7

Total number of cells in the ascites at day 13 after inoculation of L1210 cells

| Group of experimental animals | Number of live cells/mouse (M ± m) | Number of dead cells/mouse (M ± m), % | Volume of ascites (M ± m), ml/mouse | Remarks |
|---|---|---|---|---|
| L1210 control | 1403 ± 108 × $10^6$ | below 3 | 4 ± 0.4 | — |
| L1210 + $^{64}Zn_e$ aspartate administered i.v. at a dose of 25 µg/mouse | 1322 ± 557 × $10^6$ | below 3 | 6 ± 1.5 | — |
| L1210 + $^{64}Zn_e$ aspartate administered i.p. at | 532.7 ± 363.8 × $10^6$ | below 3 | 1.9 ± 1.5 | Of 3 mice in this experimental group from which ascites was removed, |

TABLE 7-continued

Total number of cells in the ascites at day 13 after inoculation of L1210 cells

| Group of experimental animals | Number of live cells/mouse (M ± m) | Number of dead cells/mouse (M ± m), % | Volume of ascites (M ± m), ml/mouse | Remarks |
|---|---|---|---|---|
| a dose of 25 µg/mouse | | | | the presence of fluid with tumor cells was observed in two mice. Moreover, the number of cells in the ascites of the first mouse was at the level of control indicators (1228.2 × 10$^6$) and in the second mouse it was 3.8 times smaller (370 × 10$^6$). No fluid or tumor cells in the peritoneal cavity of the third mouse were observed. |
| L1210 + $^{64}$Zn$_e$ aspartate administered i.p. at a dose of 50 µg/mouse | 0** | 0 | 0* | — |
| L1210 + $^{64}$Zn$_e$ aspartate administered i.p. at a dose of 75 µg/mouse | 0** | 0 | 0* | — |

*p < 0.005,
**p < 0.001 as compared with the control group

A realistic assessment of antitumor activity of the agent comprising $^{64}$Zn$_e$ aspartate and deuterium-depleted water in the therapeutic groups was performed by counting the number of tumor-free mice (Table 8).

The data presented in Table 8 show that a series of 7 i.p. injections with the solution comprising $^{64}$Zn$_e$ aspartate at the dose of 75 µg/mouse suppresses the growth of tumor cells in the experimental animals by 93.8%, at the dose of 50 µg/mouse by 68.8% and at the dose of 25 µg/mouse by 31.2%, compared with the control group.

TABLE 8

Suppression of the growth of L1210 leukemic cells after their exposure to the action of the solution comprising $^{64}$Zn$_e$ aspartate

| Group of experimental animals | Number of animals in the group with tumor, pc | Number of animals in the group without tumor, pc | Tumor-free animals, % |
|---|---|---|---|
| L1210 control | 16 | 0 | 0 |
| L1210 + $^{64}$Zn$_e$ aspartate administered i.v. at a dose of 25 µg/mouse | 16 | 0 | 0 |
| L1210 + $^{64}$Zn$_e$ aspartate administered i.p. at a dose of 25 µg/mouse | 11 | 5 | 31.2 |
| L1210 + $^{64}$Zn$_e$ aspartate administered i.p. at a dose of 50 µg/mouse | 5 | 11 | 68.8 |
| L1210 + $^{64}$Zn$_e$ aspartate administered i.p. at a dose of 75 µg/mouse | 1 | 15 | 93.8 |

Therapeutic effects of the composition comprising $^m$Zn$_e$ aspartate on the mouse L1210 leukemia model were also assessed taking into account the average lifespan of the experimental animals. The following results were obtained:

TABLE 9

Increase in the lifespan of experimental animals treated with the solution comprising $^{64}$Zn$_e$ aspartate

| Group of experimental animals | Average lifespan of animals (M ± m), days | Increase in the lifespan of experimental animals, % |
|---|---|---|
| L1210 control | 16.5 ± 0.8 | — |
| L1210 + $^{64}$Zn$_e$ aspartate administered i.v. at a dose of 25 µg/mouse | 16.9 ± 1.3 | 2.4 |
| L1210 + $^{64}$Zn$_e$ aspartate administered i.p. at a dose of 25 µg/mouse | 28.1 ± 4.7* | 41.3 |
| L1210 + $^{64}$Zn$_e$ aspartate administered i.p. at a dose of 50 µg/mouse | 41.6 ± 8.7* | 60.3 |
| L1210 + $^{64}$Zn$_e$ aspartate administered i.p. at a dose of 75 µg/mouse | 55 ± 5** | 70 |

*p < 0.05,
**p < 0.001 as compared with the control group

The data analysis shows that the agent comprising $^{64}$Zn$_e$ aspartate administered intraperitoneally statistically significantly increases the average lifespan of the experimental mice (FIG. 1). Thus, compared with the control group (16.5±0.8 days), the average lifespan of mice that were injected with the agent comprising $^{64}$Zn$_e$ aspartate at the dose of 25 µg/mouse increased by 41.3% (28.1±4.7 days), in the group where mice received the agent at the dose of 50 µg/mouse the average lifespan increased by 60.3% (41.6±8.7 days) and in the group "L1210 $^{64}$Zn$_e$ aspartate administered i.p. at a dose of 75 µg/mouse" this figure increased by 70% (55±5 days) (Table 9).

Thus the applicant demonstrated the in vivo antitumor activity of the $^{64}$Zn$_e$ isotope as aspartate against the models of mouse breast cancer (Ehrlich ascites carcinoma) and mouse leukemia (L1210 strain). A series of i.p. injections with the agent according to the invention significantly suppressed the growth of experimental tumors, by 31 to 94% depending on the dosages of the agent comprising $^{64}Zn_e$ aspartate, and increased the average lifespan of experimental animals by 70% (in the case of administering the agent to mice at a dose of 75 µg/mouse).

An antitumor action of the solution comprising $^{64}Zn_e$ aspartate is probably attributable not to direct but to mediated cytotoxic effect of the drug on the tumor cells which is manifested by inhibition of their proliferation and activation of nonspecific immunity, as the percentage of dead tumor cells in the ascites treated with the agent comprising $^{64}Zn_e$ aspartate did not exceed 5%. This is also evidenced by the total absence of acute toxicity in mice with complete inhibition of tumor growth.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A therapeutic composition comprising at least one excipient and an effective amount of $^{64}Zn$-enriched zinc, wherein the $^{64}Zn$-enriched zinc is present as a chelate of an amino acid, wherein the $^{64}Zn$-enriched zinc is at least 80% $^{64}Zn$.

2. The composition of claim 1, wherein the $^{64}Zn$-enriched zinc is at least 90% $^{64}Zn$.

3. A therapeutic composition comprising $^{64}Zn$-enriched zinc wherein the $^{64}Zn$-enriched zinc is at least 90% $^{64}Zn$ and is present as a chelate of an amino acid, and the composition contains between 0.6 mg and 330 mg of $^{64}Zn$.

4. The composition of claim 3, wherein the composition contains between about 2 mg and about 110 mg of $^{64}Zn$.

5. The composition of claim 3 wherein the $^{64}Zn$-enriched zinc is present as a chelate of asparaginate.

6. The composition of claim 3 wherein the $^{64}Zn$-enriched zinc is present as a chelate of aspartate.

7. The composition of claim 3 wherein the $^{64}Zn$-enriched zinc is present as a chelate of glutamate.

8. A method of treating cancer in a patient in need of such treatment comprising the step of administering a composition of claim 1 to the patient.

9. A method of treating cancer in a patient in need of such treatment comprising the step of administering a composition of claim 3 to the patient.

10. A therapeutic composition comprising $^{64}Zn$-enriched zinc present as a chelate of an amino acid, wherein the $^{64}Zn$-enriched zinc is at least 90% $^{64}Zn$ and the composition contains between 0.6 mg and 330 mg of $^{64}Zn$ and further contains at least one excipient selected from an emulsifier, a detergent, a surfactant, a preservative, and DMSO.

* * * * *